(12) United States Patent
Jayasinghe et al.

(10) Patent No.: US 11,078,530 B2
(45) Date of Patent: Aug. 3, 2021

(54) ENZYME-PORE CONSTRUCTS

(71) Applicant: Oxford Nanopore Technologies Ltd., Oxford (GB)

(72) Inventors: Lakmal Jayasinghe, Oxford (GB); John Hagan Pryce Bayley, Oxford (GB); Stephen Cheley, East Lansing, MI (US); Brian McKeown, Middle Barton Oxon (GB); James White, Oxford (GB); James Anthony Clarke, Oxford (GB)

(73) Assignee: Oxford Nanopore Technologies Ltd., Oxford (GB)

( * ) Notice: Subject to any disclaimer, the term of this patent is extended or adjusted under 35 U.S.C. 154(b) by 0 days.

(21) Appl. No.: 16/129,693

(22) Filed: Sep. 12, 2018

(65) Prior Publication Data
US 2019/0002972 A1 Jan. 3, 2019

Related U.S. Application Data

(60) Continuation of application No. 14/858,138, filed on Sep. 18, 2015, now Pat. No. 10,077,471, which is a division of application No. 14/455,394, filed on Aug. 8, 2014, now Pat. No. 9,885,078, which is a division of application No. 13/002,709, filed as application No. PCT/GB2009/001679 on Jul. 6, 2009, now abandoned.

(60) Provisional application No. 61/078,695, filed on Jul. 7, 2008.

(51) Int. Cl.
| | |
|---|---|
| *C12Q 1/6869* | (2018.01) |
| *C12N 9/12* | (2006.01) |
| *C12N 9/22* | (2006.01) |
| *C12N 9/52* | (2006.01) |
| *C07K 14/31* | (2006.01) |
| *C12N 9/16* | (2006.01) |
| *C12N 9/90* | (2006.01) |
| *C12N 9/96* | (2006.01) |

(52) U.S. Cl.
CPC .......... *C12Q 1/6869* (2013.01); *C07K 14/31* (2013.01); *C12N 9/127* (2013.01); *C12N 9/1247* (2013.01); *C12N 9/1252* (2013.01); *C12N 9/1276* (2013.01); *C12N 9/16* (2013.01); *C12N 9/22* (2013.01); *C12N 9/52* (2013.01); *C12N 9/90* (2013.01); *C12N 9/96* (2013.01)

(58) Field of Classification Search
CPC ...... C12N 9/96; C12N 9/1247; C12N 9/1252; C12N 9/16; C12N 9/90; C12N 9/127; C12N 9/1276; C12N 9/22; C12N 9/52
See application file for complete search history.

(56) References Cited

U.S. PATENT DOCUMENTS

| | | | |
|---|---|---|---|
| 5,496,009 A | 3/1996 | Farrell et al. | |
| 5,561,043 A | 10/1996 | Cantor et al. | |
| 5,771,935 A | 6/1998 | Myers | |
| 5,777,078 A | 7/1998 | Bayley et al. | |
| 5,795,782 A | 8/1998 | Church et al. | |
| 5,817,771 A | 10/1998 | Bayley et al. | |
| 5,985,834 A | 11/1999 | Engel et al. | |
| 6,015,714 A | 1/2000 | Baldarelli et al. | |
| 6,087,099 A | 7/2000 | Gupte et al. | |
| 6,123,819 A | 9/2000 | Peeters | |
| 6,127,166 A | 10/2000 | Bayley et al. | |
| 6,251,610 B1 | 6/2001 | Gupte et al. | |
| 6,362,002 B1 | 3/2002 | Denison et al. | |
| 6,426,231 B1 | 7/2002 | Bayley et al. | |
| 6,451,563 B1 | 9/2002 | Wittig et al. | |
| 6,627,067 B1 | 9/2003 | Branton et al. | |
| 6,824,659 B2 | 11/2004 | Bayley et al. | |
| 6,863,833 B1 | 3/2005 | Bloom et al. | |
| 6,916,665 B2 | 7/2005 | Bayley et al. | |
| 6,927,070 B1 | 8/2005 | Bayley et al. | |
| 7,087,729 B1 | 8/2006 | Prive | |
| 7,189,503 B2 | 3/2007 | Akeson et al. | |
| 7,360,556 B2 | 4/2008 | Mijers | |
| 7,361,466 B2 | 4/2008 | Korlach et al. | |
| 7,766,028 B2 | 8/2010 | Massengale et al. | |
| 8,105,846 B2 | 1/2012 | Bayley et al. | |
| 8,162,006 B2 | 4/2012 | Guala | |
| 8,652,779 B2 | 2/2014 | Turner et al. | |
| 8,785,211 B2 | 7/2014 | Bayley et al. | |
| 8,822,160 B2 | 9/2014 | Bayley et al. | |
| 8,828,208 B2 | 9/2014 | Canas et al. | |
| 8,828,700 B2 | 9/2014 | Lee et al. | |

(Continued)

FOREIGN PATENT DOCUMENTS

| | | |
|---|---|---|
| CH | 344883 A | 2/1960 |
| CN | 101224320 A | 7/2008 |
| DE | 202004009831 | 8/2004 |
| DE | 202007012680 | 1/2008 |
| EP | 247824 | 12/1987 |

(Continued)

OTHER PUBLICATIONS

Ngo et al. in The Protein Folding Problem and Tertiary Structure Prediction, 1994, Merz et al. (ed.), Birkhauser, Boston, MA, pp. 433 and 492-495.*

(Continued)

*Primary Examiner* — Richard G Hutson
(74) *Attorney, Agent, or Firm* — Wolf, Greenfield & Sacks, P.C.

(57) ABSTRACT

The invention relates to constructs comprising a transmembrane protein pore subunit and a nucleic acid handling enzyme. The pore subunit is covalently attached to the enzyme such that both the subunit and enzyme retain their activity. The constructs can be used to generate transmembrane protein pores having a nucleic acid handling enzyme attached thereto. Such pores are particularly useful for sequencing nucleic acids. The enzyme handles the nucleic acid in such a way that the pore can detect its component nucleotides by stochastic sensing.

20 Claims, 11 Drawing Sheets

Specification includes a Sequence Listing.

(56) References Cited

U.S. PATENT DOCUMENTS

| | | |
|---|---|---|
| 9,057,102 B2 | 6/2015 | Turner et al. |
| 9,127,313 B2 | 9/2015 | Brown et al. |
| 9,222,082 B2 | 12/2015 | Jayasinghe et al. |
| 9,447,152 B2 | 9/2016 | Clarke et al. |
| 9,546,400 B2 | 1/2017 | Turner et al. |
| 9,556,480 B2 | 1/2017 | Turner et al. |
| 9,562,887 B2 | 2/2017 | Maglia et al. |
| 9,678,056 B2 | 6/2017 | Turner et al. |
| 9,732,381 B2 | 8/2017 | Stoddart et al. |
| 9,738,929 B2 | 8/2017 | Turner et al. |
| 9,885,078 B2 | 2/2018 | Jayasinghe et al. |
| 10,077,471 B2 | 9/2018 | Jayasinghe et al. |
| 2002/0028458 A1 | 3/2002 | Lexow |
| 2002/0094526 A1 | 7/2002 | Bayley et al. |
| 2002/0098530 A1 | 7/2002 | Pfeifer et al. |
| 2002/0197618 A1 | 12/2002 | Sampson |
| 2003/0027194 A1 | 2/2003 | Kurz et al. |
| 2003/0044816 A1 | 3/2003 | Denison et al. |
| 2003/0059778 A1 | 3/2003 | Berlin et al. |
| 2003/0087232 A1 | 5/2003 | Christians et al. |
| 2003/0099951 A1 | 5/2003 | Akeson et al. |
| 2003/0108902 A1 | 6/2003 | Abarzua |
| 2003/0118595 A1 | 6/2003 | Niemeyer et al. |
| 2003/0134807 A1 | 7/2003 | Hardin et al. |
| 2003/0166137 A1 | 9/2003 | Zuker et al. |
| 2003/0211502 A1 | 11/2003 | Sauer et al. |
| 2003/0215881 A1 | 11/2003 | Bayley et al. |
| 2004/0180412 A1 | 9/2004 | Liu et al. |
| 2004/0214177 A1 | 10/2004 | Bension |
| 2004/0229315 A1 | 11/2004 | Lee et al. |
| 2005/0053961 A1 | 3/2005 | Akeson et al. |
| 2005/0142559 A1 | 6/2005 | Makrigiorgos |
| 2005/0221316 A1 | 10/2005 | Pedersen et al. |
| 2005/0260655 A1 | 11/2005 | Liu et al. |
| 2006/0051807 A1 | 3/2006 | Fuller |
| 2006/0063171 A1 | 3/2006 | Akeson et al. |
| 2007/0015182 A1 | 1/2007 | Abarzua |
| 2007/0048748 A1 | 3/2007 | Williams et al. |
| 2007/0122885 A1 | 5/2007 | Reeves et al. |
| 2007/0163656 A1 | 7/2007 | Mijers |
| 2008/0166724 A1 | 7/2008 | Gerber et al. |
| 2008/0206252 A1 | 8/2008 | Pennica et al. |
| 2008/0311582 A1 | 12/2008 | Bayley et al. |
| 2009/0087850 A1 | 4/2009 | Eid et al. |
| 2009/0167288 A1 | 7/2009 | Reid et al. |
| 2009/0256116 A1 | 10/2009 | Shumaker-Parry et al. |
| 2009/0298075 A1 | 12/2009 | Travers et al. |
| 2010/0221212 A1 | 9/2010 | Stagliano et al. |
| 2011/0019186 A1 | 1/2011 | Himmelhaus et al. |
| 2011/0108147 A1 | 5/2011 | Carmody et al. |
| 2011/0177498 A1 | 7/2011 | Clarke et al. |
| 2011/0229877 A1 | 9/2011 | Jayasinghe et al. |
| 2011/0281768 A1 | 11/2011 | Travers et al. |
| 2011/0311965 A1 | 12/2011 | Maglia et al. |
| 2012/0058468 A1 | 3/2012 | Mckeown |
| 2012/0064599 A1 | 3/2012 | Jayasinghe et al. |
| 2012/0100530 A1 | 4/2012 | Moysey et al. |
| 2012/0107802 A1 | 5/2012 | Stoddart et al. |
| 2013/0143802 A1 | 6/2013 | Chilkoti |
| 2013/0149769 A1 | 6/2013 | Kizaki et al. |
| 2013/0195908 A1 | 8/2013 | Leonetti et al. |
| 2013/0264207 A1 | 10/2013 | Ju et al. |
| 2014/0051069 A1 | 2/2014 | Jayasinghe et al. |
| 2014/0206842 A1 | 7/2014 | Majeed et al. |
| 2015/0008126 A1 | 1/2015 | Maglia et al. |
| 2015/0031020 A1 | 1/2015 | Jayasinghe et al. |
| 2015/0175663 A1 | 6/2015 | Yokoi et al. |
| 2016/0076092 A1 | 3/2016 | Jayasinghe et al. |
| 2017/0335384 A1 | 11/2017 | Jayasinghe et al. |

FOREIGN PATENT DOCUMENTS

| | | |
|---|---|---|
| EP | 934757 | 8/1999 |
| EP | 1640168 | 3/2006 |
| EP | 1946793 | 7/2008 |
| GB | 2130219 | 5/1984 |
| GB | 2443260 | 4/2008 |
| GB | 2453377 | 4/2009 |
| GB | 2474073 | 4/2011 |
| JP | 11-137260 | 5/1999 |
| WO | WO 1999/05167 | 2/1999 |
| WO | WO 2000/028312 | 5/2000 |
| WO | WO 2001/040516 | 6/2001 |
| WO | WO 2001/042782 | 6/2001 |
| WO | WO 2001/059453 | 8/2001 |
| WO | WO 2002/042496 | 5/2002 |
| WO | WO 2003/012146 | 2/2003 |
| WO | WO 2003/017020 | 2/2003 |
| WO | WO 2003/095669 | 11/2003 |
| WO | WO 2005/056750 | 6/2005 |
| WO | WO 2005/124888 | 12/2005 |
| WO | WO 2006/020775 | 2/2006 |
| WO | WO 2006/028508 | 3/2006 |
| WO | WO 2006/100484 | 9/2006 |
| WO | WO 2007/057668 | 5/2007 |
| WO | WO 2007/075987 | 7/2007 |
| WO | WO 2007/084103 | 7/2007 |
| WO | WO 2007/146158 | 12/2007 |
| WO | WO 2008/008974 | 1/2008 |
| WO | WO 2008/045575 | 4/2008 |
| WO | WO 2008/083554 | 7/2008 |
| WO | WO 2008/102120 | 8/2008 |
| WO | WO 2008/102121 | 8/2008 |
| WO | WO 2008/124107 | 10/2008 |
| WO | WO 2009/035647 | 3/2009 |
| WO | WO 2009/077734 | 6/2009 |
| WO | WO 2010/004265 | 1/2010 |
| WO | WO 2010/004273 | 1/2010 |
| WO | WO 2010/034018 | 3/2010 |
| WO | WO 2010/086603 | 8/2010 |
| WO | WO 2010/086622 | 8/2010 |
| WO | WO 2010/109197 | 9/2010 |
| WO | WO 2010/122293 | 10/2010 |
| WO | WO 2011/067559 | 6/2011 |
| WO | WO 2012/042226 | 4/2012 |

OTHER PUBLICATIONS

Tominaga et al., Biomacromolecules, vol. 6, pp. 2299-2304, 2005.*
Akeson, Microsecond Time-Scale Discrimination Among Polycytidylic Acid, Polyadenylic Acid, and Polyuridylic Acid as Homopolymers or as Segments Within Single RNA Molecules, Biophysical Journal, vol. 77:3227-3233 (1999).
Amblard et al., The Cu(I)-catalyzed Huisgen azide-alkyne 1,3-dipolar cycloaddition reaction in nucleotide and oligonucleotide chemistry, Chem. Rev., vol. 109(9):4207-4220 (2009).
Ashkenasy et al., Recognizing a Single Base in an Individual DNA Strand: A Step Toward DNA Sequencing in Nanopores, Angew. Chem. Int. Ed., vol. 44:1401-1404 (2005).
Ashkenasy, Nurit et al., Single Nucleobase Sensitivity of a-Hemolysin (a-HL) Transmembrane Protein Pore: Toward Single DNA Sequencing, ACS National Meeting, vol. 45(13), Abstract No. 74 (2005).
Astier et al., Toward Single Molecule DNA Sequencing: Direct Identification of Ribonucleoside and Deoxyribonucleoside 5'-Monophosphates by Using an Engineered Protein Nanopore Equipped with a Molecular Adapter, J. Am. Chem. Soc., vol. 128:1705-1710 (2006).
Astier. Yann et al., Stochastic Detection of Motor Protein-RNA Complexes by Single-Channel Current Recording, ChemPhysChem, vol. 8:2189-2194 (2007).
Avrameas et al., The Cross-Linking of Proteins with Glutaraldehyde and its use for the Preparation of Immunoadsorbants. Immunochemistry. 6:43-53 (1969).
Bayley, Hagan et al., Stochastic sensors inspired by biology, Nature, vol. 413:226-230 (2001).

(56) References Cited

OTHER PUBLICATIONS

Bayley, Hagan, Sequencing single molecules of DNA, Current Opinion in Chemical Biology, vol. 10:628-637 (2006.
Benner, Seico et al., Sequence-specific detection of individual DNA polymerase complexes in real time using a nanopore, Nature Nanotechnology, vol. 2:718-724 (2007).
Bittker et al., Recent advances in the in vitro evolution of nucleic acids, Current Opinions in Chemical Biology 6 :367 (2002).
Bowie, James U. et al., Deciphering the Message in Protein Sequences: Tolerance to Amino Acid Substitutions, Science, vol. 247:1306-1310 (1990.
Braha, Orit et al., Carriers versus Adapters in Stochastic Sensing, ChemPhysChem, vol. 6:889-892 (2005).
Braha, Orit et al., Designed protein pores as components for biosensors, Chemistry & Biology, vol. 4:497-505 (1997).
Branton, Daniel et al., The potential and challenges of nanopore sequencing, Nat. Biotechnol., vol. 26 (10):1146-1153 (2008).
Braslavsky, Ido et al., Sequence information can be obtained from single DNA molecules, PNAS, vol. 100 (7):3960-3964 (2003).
Bu Dan Ova, Natalia et al., Heptakis(6-amino-6-deoxy)-beta-cyclodextrin as a chiral selector for the separation of anionic analyle enantiomers by capillary electrophoresis, Electrophoresis, vol. 25:2795-2800 (2004).
Burgess, Wilson H. et al., Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue, The Journal of Cell Biology, vol. 111 :2129-2138 (1990).
Busam, Robert D., Structure of *Escherichia coli* exonuclease I in complex with thymidine 5'-monophosphate, Acta Cryst., vol. D64:206-210 (2008).
Butler, Tom Z. et al., Determination of RNA Orientation during Translocation through a Biological Nanopore, Biophysical Journal, vol. 90:190-199 (2006.
Butler, Tom Z. et al., Single-molecule DNA detection with an engineered MspA protein nanopore, PNAS, vol. 105 (52):20647-20652 (2008).
Calderone et al., Directing Otherwise Incompatible Reactions in a Single Solution by Using DNA-Templated Organic Synthesis, Agnew Chem. Int. Ed.41 (21) :4104 (2002).
Case 1:17-cv-00275-LPS Document 18. Notice of subsequent events relating to Oxford's motion to dismiss (D.I. 9). Oct. 18, 2017.
Case 1:17-cv-00275-LPS Document 19. Oxford Nanopore Technologies, Inc.'s response to Pacific Biosciences of California, Inc.'s notice of subsequent events. Oct. 24, 2017.
Case 1:17-cv-00275-RGA Document 10. Oxford's opening brief in support of its motion to dismiss PacBio's complaint for patent infringement. May 8, 2017.
Case 1:17-cv-00275-RGA Document 14. PacBio's response to Oxford's motion to dismiss. Jun. 5, 2017.
Case 1:17-cv-00275-RGA Document 16. Oxford's reply brief in support of its motion to dismiss PacBio's complaint for patent infringement. Jun. 26, 2017.
Case 1:17-cv-01353-LPS Document 13. First Amended Complaint for Patent Infringement. Nov. 30, 2017.
Case 1:17-cv-01353-LPS Document 15. Plaintiff's response to Oxford Nanopore Techologies, Inc.'s Motion to Dismiss and Request for Scheduling Conference. Nov. 30, 2017.
Case 1:17-cv-01353-RGA Document 10. Oxford's opening brief in support of its motion to partially dismiss Pacbio's complaint for patent infringement. Nov. 16, 2017.
Chan, Eugene Y., Advances in sequencing technology, Mutation Research, vol. 573:13-40 (2005.
Cheley, Stephen et al., A functional protein pore with a 'retro' transmembrane domain, Protein Science, vol. 8:1257-1267 (1999).
Cheley, Stephen et al., A Genetically Encoded Pore for the Stochastic Detection of a Protein Kinase, ChemBioChem, vol. 7:1923-1927 (2006).
Cheley, Stephen et al., Spontaneous oligomerization of a staphylococcal alpha-hemolysin conformationally constrained by removal of residues that form the transmembrane beta-barrel, Protein Engineering, vol. 10 (12):1433-1443 (1997).
Cheley, Stephen et al., Stochastic Sensing of Nanomolar Inositol 1,4,5-Triphosphate with an Engineered Pore, Chemistry & Biology, vol. 9:829-838 (2002).
Chen, Min et al., Outer membrane protein G: Engineering a quiet pore for biosensing, PNAS, vol. 105 (17):6272-6277 (2008).
Chen, Peng et al., Atomic Layer Deposition to Fine-Tune the Surface Properties and Diameters of Fabricated Nanopores, Nano Letters, vol. 4(7):1333-1337 (2004).
Clarke, James et al., Continuous base identification for single-molecule nanopore DNA sequencing, Nature Nanotechnology, vol. 4:265-270 (2009).
Cockroft, Scott L. et al., A Single-Molecule Nanopore Device Detects DNA Polymerase Activity with Single- Nucleotide Resolution, J.Am. Chem. Soc., vol. 130:818-820 (2008).
Comai, Massimiliano et al., Protein engineering modulates the transport properties and ion selectivity of the pores formed by staphylococcal y-haemolysins in lipid membranes, Molecular Microbiology, vol. 44(5):1251-1267 (2002).
Cudic, Predrag et al., Binding of Nucleotides in Water by Phenathridinium Bis(intercaland) Receptor Molecules, J. Chem. Soc., Chem. Commun., pp. 1073-1075 (1995).
Dapprich, Johannes, Single-Molecule DNA Digestion by Lambda-Exonuclease, Cytometry, vol. 36:163-168 (1999).
Davidson et al., Insertion of the T3 DNA polymerase thioredoxin binding domain enhances the processivity and fidelity of Taq DNA polymerase. Nucleic Acids Res. Aug. 15, 2003;31(16):4702-9.
Deamer, David W. et al., Characterization of Nucleic Acids by Nanopore Analysis, Ac. Chem. Res., vol. 35:817-825 (2002).
Deamer, David W. et al., Nanopores and nucleic acids: prospects for ultrarapid sequencing, Tibtech, vol. 18:147-151 (2000).
Dorre, Klaus et al., Techniques for single molecule sequencing, Bioimaging, vol. 5:139-152 (1997).
Eid, John et al., Real-Time DNA Sequencing from Single Polymerase Molecules, Science, vol. 323:133-138 (2009).
Eliseev et al., Aminocyclodextrins as Selective Hosts with Several Binding Sites for Nucleotides, Angew. Chem. Int. Ed. Engl., vol. 32(9):1331-1333 (1993).
Eliseev, Alexey V. et al., Molecular Recognition of Nucleotides, Nucleosides, and Sugars by Aminocyclodextrins, J. Am. Chem. Soc., vol. 116:6081-6088 (1994).
Erie, Dorothy et al., A Dumbell-Shaped, Double-Hairpin Structure of DNA: A Thermodynamic Investigation, Biochemistry, vol. 26:7150-7159 (1987).
Flomembom, 0. et al., Single stranded DNA translocation through a nanopore: A master equation approach, Physical Review E, vol. 68:041910, DOI: 10.1103/PhysRevE.68.041910, 7 pages, (2003).
Flusberg, Benjamin A. et al., Direct detection of DNA methylation during single-molecule, real-time sequencing, Nature Methods, vol. 7(6):461-465 (2010).
Fuller et al., Real-time single-molecule electronic DNA sequencing by synthesis using polymer-tagged nucleotides on a nanopore array, Proc Natl Acad Sci US A. May 10, 2016;113(19):5233-8. Epub Apr. 18, 2016.
Gartner et al., Multistep Small-Molecule Synthesis Programmed by DNA Templates, JACS 124: 10,304 (2002).
Gartner et al., The Generality of DNA-Templated Synthesis as a Basis for Evolving Non-Natural Small Molecules, JACS 123 :6961 (2001).
Genschel, Jochen et al., Interaction of *E.coli* Single-Stranded DNA Binding Protein (SSB) with Exonuclease I. The Carboxy-Terminus of SSB Is the Recognition Site fo the Nuclease, Biol. Chem., vol. 381 :183-192 (2000.
Gershow, Marc et al., Recapturing and trapping single molecules with a solid-state nanopore, Nature Nanotechnology, vol. 2:775-779 (2007).
Ghosal, Sandip, Electrokinetic-ftow-induced viscous drag on a tethered DNA inside a nanopore, Physical Review E, vol. 76:061916, DOI: 10.1103/PhysRevE.76.061916, 3 pages, (2007.
Gu, Li-Oun et al., Electroosmotic enhancement of the binding of a neutral molecule to a transmembrane pore, PNAS, vol. 100(26):15498-15503 (2003).

(56) References Cited

OTHER PUBLICATIONS

Gu, Li-Oun et al., Reversal of charge selectivity in transmembrane protein pores by using noncovalent molecular adapters, PNAS, vol. 97(8):3959-3964 (2000).
Gu, Li-Qun et al., Stochastic sensing of organic analytes by a pore-forming protein containing a molecular adapter, Nature, vol. 398:686-690 (1999).
Gu. Li-Oun et al., Capture of a Single Molecule in a Nanocavity, Science, vol. 291 :636-640 (2001).
Gu. Li-Oun et al., Prolonged Residence Time of a Noncovalent Molecular Adapter, beta-Cyclodextrin, within the Lumen of Mutant alpha-Hemolysin Pores, J. Gen. Physiol., vol. 118:481-493 (2001).
Guan, Xiyun et al., Stochastic Sensing of TNT with a Genetically Engineered Pore, ChemBioChem., vol. 6:1875-1881 (2005).
Han, Eugene S. et al., RecJ exonuclease: substrates, products and interaction with SSB, Nucleic Acids Research, vol. 34(4):1084-1091 (2006).
Han, Jongyoon et al., Characterization and Optimization of an Entropic Trap for DNA Separation, Anal. Chem., vol. 74:394-401 (2002).
Hein, Christopher D. et al., Click Chemistry, a Powerful Tool for Pharmaceutical Sciences, Pharm. Res., vol. 25 (10):2216-2230 (2008).
Henrickson, Sarah E. et al., Driven DNA Transport into an Asymmetric Nanometer-Scale Pore, Physical Review Letters, vol. 85(14):3057-3060 (2000).
Heyman et al., SP1 as a novel scaffold building block for self-assembly nanofabrication of submicron enzymatic structures. Nano Lett. Jun. 2007;7(6):1575-9. Epub May 26, 2007.
Hogrefe et al., Long-range PCR with a DNA polymerase fusion. Methods Mol Biol. 2011;687:17-23. doi: 10.1007/978-1-60761-944-4_2.
Holden, Matthew A. et al., Direct Introduction of Single Protein Channels and Pores into Lipid Bilayers, J. Am. Chem. Soc., vol. 127:6502-6503 (2005).
Holden, Matthew A. et al., Functional Bionetworks from Nanoliter Water Droplets, J. Am. Chem. Soc., vol. 129:8650-8655 (2007).
Hornblower, Breton et al., Single-molecule analysis of DNA-protein complexes using nanopores, Nature Methods, vol. 4(4):315-317 (2007).
Howarka. Stefan et al., Probing Distance and Electrical Potential within a Protein Pore with Tethered DNA, Biophysical Journal, vol. 83:3202-3210 (2002).
Howorka, S. et al., Improved Protocol for High-Throughput Cysteine Scanning Mutagenesis, Biotechniques, vol. 25(5):764-766 (1998).
Howorka, Stefan et al., DNA Duplex Formation of Individual DNA Strands within a Single Protein Pore, Biophysical Journal, vol. 82{1, pt. 2):508a, No. 2482-Plat (2002).
Howorka, Stefan et al., Kinetics of duplex formation for individual DNA strands within a single protein nanopore, PNAS, vol. 98(23):12996-13001 (2001).
Howorka, Stefan et al., Sequence-specific detection of individual DNA strands using engineered nanopores, Nature Biotechnology, vol. 19:636-639 (2001).
Hu, Tao et al., Theory of DNA translocation through narrow ion channels and nanopores with charged walls, Physical Review E, 78:032901, DOI: 10.1103/PhysRevE.78.032901, 3 pages, (2008).
Hwang, William L. et al., Electrical Behavior of Droplet Interface Bilayer Networks: Experimental Analysis and Modeling, J. Am. Chem. Soc., vol. 129:11854-11864 (2007).
International Preliminary Report on Patentability and Written Opinion for Appliction No. PCT/GB2009/001690, 9 pages, dated Jan. 11, 2011.
International Preliminary Report on Patentability for Application No. PCT/GB2006/004265, 7 pages, dated May 20, 2008.
International Preliminary Report on Patentability for Application No. PCT/GB2008/003372, 6 pages, dated Apr. 7, 2010.
International Search Report for Application No. PCT/GB2009/001679, 3 pages, dated Nov. 5, 2009.
International Search Report for Application No. PCT/GB2009/001690, 3 pages, dated Oct. 13, 2009.
Jayasinghe et al., Role of the amino latch of staphylococcal alpha-hemolysin in pore formation: a co-operative interaction between the N terminus and position 217. J Biol Chem. Jan. 27, 2006;281(4):2195-204. Epub Oct. 14, 2005.
Jayasinghe, Lakmal et al., The leukocidin pore: Evidence for an octamer with four LukF subunits and four LukS subunits alternating around a central axis, Protein Science, vol. 14:2550-2561 (2005).
Johnson et al., A covalent linkage between the gene 5 DNA polymerase of bacteriophage T7 and *Escherichia coli* thioredoxin, the processivity factor: fate of thioredoxin during DNA synthesis. J Biol Chem. Jun. 27, 2003;278(26):23762-72. Epub Apr. 11, 2003.
Jung, Yuni et al., The Internal Cavity of the Staphylococcal alpha-Hemolysin Pore Accommodates -175 Exogenous Amino Acid Residues, Biochemistry, vol. 44(25):8919-8929 (2005).
Kalisch et al., Covalently linked sequencing primer linkers (splinkers) for sequence analysis of restriction fragments (Recombinant DNA; hairpin ligation; synthetic oligodeoxynucleotides; dideoxynucleotides), Gene, vol. 44:263-270(1986).
Kanan et al. Reaction discovery enabled by DNA-templated synthesis and in vitro selection. Nature 431 : 545 (2004).
Kang, Xiao-feng et al., Single Protein Pores Containing Molecular Adapters at High Temperatures, Angew. Chem. Int. Ed., vol. 44:1495-1499 (2005).
Kasianowicz, John J. et al., Characterization of individual polynucleotide molecules using a membrane channel, Proc. Natl. Acad. Sci. USA, vol. 93:13770-13773 (1996).
Khulbe, Pramod K. et al., DNA translocation through a-hemolysin nanopores with potential application to macromolecular data storage, Journal of Applied Physics, vol. 97(104317):1-7 (2005).
Kocalka, Petr et al., Rapid and Efficient DNA Strand Cross-Linking by Click Chemistry, ChemBioChem, vol. 9:1280-1285 (2008).
Kolb et al., Click Chemistry: Diverse Chemical Function from a Few Good Reactions, Angew. Chem. Int. Ed., vol. 40:2004-2021 (2001).
Kovall, Rhett et al., Toroidal Structure of Lambda-Exonuclease, Science, vol. 277:1824-1827 (1997).
Kumar et al., PEG-Labeled Nucleotides and Nanopore Detection for Single Molecule DNA Sequencing by Synthesis, Scientific Reports 2, Article No. 684 (2012), Sep. 21, 2012.
Lazar, Eliane et al., Transforming Growth Factor alpha: Mutation of Aspartic Acid 47 and Leucine 48 Results in Different Biological Activities, Molecular and Cellular Biology, vol. 8(3):1247-1252 (1988).
Lemon et al., Localization of bacterial DNA polymerase: evidence for a factory model of replication. Science. Nov. 20, 1998;282(5393):1516-9.
Li, Jiali et al., DNA molecules and configurations in a solid-state nanopore microscope, Nature, vol. 2:611-615 (2003.
Lovett, Susan T. et al., Identification and purification of a single-stranded-DNA-specific exonuclease encoded by the recJ gene of *Escherichia coli*, Proc. Natl. Acad. Sci. USA, vol. 86:2627-2631 (1989).
Lovrinovic et al., Rapid synthesis of DNA-cysteine conjugates for expressed protein ligation, Biochemical and Biophysical Research Communications, vol. 335:943-948 (2005).
Luo, Kaifu et al., Influence of Polymer-Pore Interactions on Translocation, Physical Review Letters, vol. 99:148102, DOI: 10.1103/PhysRev Lett. 99.148102, 4 pages, (2007.
Lutz et al., Efficient construction of therapeutics, bioconjugates, biomaterials and bioactive surfaces using azide-alkyne 'click' chemistry, Advanced Drug Delivery Reviews, vol. 60:958-970 (2008).
Maglia et al., Enhanced translocation of single DNA molecules through alpha-hemolysin nanopores by manipulation of internal charge, PNAS, vol. 105(50):19720-19725 (2008).
Martin, Hugh et al., Nanoscale Protein Pores Modified with PAMAM Dendrimers, J. Am. Chem. Soc., vol. 129:9640-9649 (2007).
Martinez et al., The mRNA Cap Structure Stimulates Rate of Poly(A) Removal and Amplifies Processivity of Degradation, The Journal of Biological Chemistry, vol. 276(30):27923-27929 (2001).
Marziali, Andre et al., New DNA Sequencing Methods, Annu. Rev. Biomed. Eng., vol. 3:195-223 (2001).

(56) References Cited

OTHER PUBLICATIONS

Mathe, Jerome et al., Orientation discrimination of a single-stranded DNA inside the a-hemolysin membrane channel, PNAS, vol. 102(35):12377-12382 (2005).

Matsuura. Shun-ichi et al.. Real-time observation of a single DNA digestion by I exonuclease under a fluorescence microscope field. Nucleic Acids Research, vol. 29(16):1-5 (2001)

Meller et al., Single molecule measurements of DNA transport through a nanopore, Electrophoresis, vol. 23: 2583-2591 (2002.

Meller, Amit et al., Rapid nanopore discrimination between single polynucleotide molecules, PNAS, vol. 97 (3):1079-1084 (2000).

Meller, Dynamics of polynucleotide transport through nanometre-scale pores, Journal of Physics: Condensed Matter, vol. 15:R581-R607 (2003.

Merzlyak et al., Conductance and Ion Selectivity of a Mesoscopic Protein Nanopore Probed with Cysteine Scanning Mutagenesis, Biophysical Journal, vol. 89:3059-3070 (2005).

Mitchell, Nick et al., Chemical Tags Facilitate the Sensing of Individual DNA Strands with Nanopores, Angew. Chem. Int. Ed., vol. 47:5565-5568 (2008.

Mohammad. Mohammad M. et al., Controlling a Single Protein In a Nanopore through Electrostatic Traps, J. Am. Chem. Soc., vol. 130:4081-4088 (2008).

Mol, Clifford D. et al., Structure and function of the multifunctional DNA-repair enzyme exonuclease 111, Nature, vol. 374:381-386 (1995).

Motré et al., Enhancing helicase-dependent amplification by fusing the helicase with the DNA polymerase. Gene. Aug. 15, 2008;420(1):17-22. doi:10.1016/j.gene.2008.04.017. Epub May 8, 2008.

Movileanu, Liviu et al., Location of a Construction in the Lumen of a Transmembrane Pore by Targeted Covalent Attachment of Polymer Molecules, J. Gen. Physiol., vol. 117:239-251 (2001).

Movileanu, Llviu et al., Detecting protein analytes that modulate transmembrane movement of a polymer chain within a single protein pore, Nature Biotechnology, vol. 18:1091-1095 (2001).

Muller et al., DNA-directed assembly of artificial multienzyme complexes, Biochemical and Biophysical Research Communications, vol. 377:62-67 (2008).

Nakane et al., A Nanosensor for Transmembrane Capture and Identification of Single Nucleic Acid Molecules, Biophysical Journal, vol. 87:615-621 (2004.

Nakane et al., Nanopore sensors for nucleic acid analysis, J. Phys.: Condens. Matter, vol. 15: R 1365-R1393 (2003).

Niemeyer et al., DNA-Directed Assembly of Bienzymic Complexes from In Vivo Biotinylated Nad(P)H: FMN Oxidoreductase and Luciferase, ChemBioChem., vol. 3:242-245 (2002).

Nwe, Kido et al., Growing Applications of 'Click Chemistry' for Bioconjugation in Comtemporary Biomedical Research, Cancer Biotherapy and Radiopharmaceuticals, vol. 24(3):289-302 (2009).

Paner et al., Studies of DNA Dumbells. VI. Analysis of Optical Melting Curves of Dumbells with a Sixteen-Base Pair Duplex Stem and End-Loops of Variable Size and Sequence, Biopolymers, vol. 39:779-793 (1996).

Paner, Teodoro M. et al., Studies of DNA Dumbells. III. Theoretical Analysis of Optical Melting Curves of Dumbells with a 16 Base-Pair Duplex Stem and Tn End Loops (n=2, 3, 4, 5, 6, 8, 10, 14), Biopolymers, vol. 32(7):881-892 (1992). cited byapplicant.

Phoenix et al., OmpF-LPP Signal Sequence Mutants with Varying Charge Hydrophobicity Ratios Provide Evidence for a Phosphatidylglycerol-Signal Sequence Interaction during Protein Translocation across the *Escherichia coli* Inner Membrane, The Journal of Biological Chemistry, vol. 268(23):17069-17073 (1993).

Purnell et al., Nucleotide Identificaiton and Orientation Discrimination of DNA Homopolymers Immobilized in a Protein Nanopore, Nano Letters, vol. 8(9):3029-3034 (2008).

Sanchez-Quesada et al., Cyclic Peptides as Molecular Adapters for a Pore-Forming Protein, Journal of the American Chemical Society, vol. 122(48):11757-11766 (2000).

Sanchez-Quesada, Jorge et al., Single DNA Rotaxanes of a Transmembrane Pore Protein, Angew. Chem. Int. Ed., vol. 43:3063-3067 (2004).

Sanderson, Katherine, Standard and Pores. Could the next generation of genetic sequencing machines be built froma collection of miniscule holes? Nature News, vol. 456(7218):23-25 (2008).

Sauer-Budge, Alexis F. et al., Unzipping Kinetics of Double-Stranded DNA in a Nanopore, Phys. Rev. Letters, vol. 90(23):238101-1-238101-4 (2003).

Seeman, Nucleic Acid Junctions and Lattices, J. theor. Biol., vol. 99:237-247 (1982).

Seo et al., Click Chemistry to Construct Fluorescent Oligonucleotides for DNA Sequencing, J. Org. Chem., vol. 68:609-612 (2003).

Seol, Stretching of Homopolymeric RNA Reveals Single-Stranded Helices and Base-Stacking, Physical Review Letters, vol. 98:158103, DOI:10.1103/PhysRevLett.98.158103, 4 pages, (2007).

Shank, Lalida P. et al., Redesigning Channel-Forming Peptides: Amino Acid Substitutions that Enhance Rates of Supramolecular Self-Assembly and Raise Ion Transport Activity, Biophysical Journal, vol. 90:2138-2150 (2006).

Shin, Seong-Ho et al., Kinetics of a Reversible Covalent-Bond-Forming Reaction Observed at the Single-Molecule Level, Angew. Chem. Int. Ed., vol. 41(19):3707-3709 (2002).

Smeets, Ralph M.M. et al., Salt Dependence of Ion Transport and DNA Translocation through Solid-State Nanopores, Nano Letters, vol. 6(1):89-95 (2006).

Song, Langzhou et al., Structure of Staphylococcal alpha-Hemolysin, a Heptameric Transmembrane Pore, Science, vol. 274:1859-1866 (1996).

Stoddart, David et al., Multiple base-recognition sites in a biological nanopore—two heads are better than one, Angew. Chem. Int. Ed. Engl., vol. 49(3):556-559 (2010).

Stoddart, David et al., Single-nucleotide discrimination in immobilized DNA oligonucleotides with a biological nanopore, PNAS, vol. 106(19):7702-7707 (2009).

Stranges et al., Design and characterization of a nanopore-coupled polymerase for single-molecule DNA : sequencing by synthesis on an electrode array, Proc Natl Acad Sci US A. Nov. 1, 2016 ;113(44):E6749-E6756. Epub Oct. 11, 2016.

Sutherland, Todd C. et al., An analysis of mismatched duplex DNA unzipping through a bacterial nanopore, Biochem. Cell Biol., 82:407-412 (2004).

Tadey, Tanya et al., Capillary electrophoretic separation of nucleotide isomers via complexation with cyclodextrin and borate, Journal of Chromatography B, vol. 657:365-372 (1994).

Thomas, Kirk R. et al., Processivity of DNA Exonucleases, The Journal of Biological Chemistry, vol. 253(2):424-429 (1978).

Toh Da, Koji et al., Channel Mimetic Sensing Membranes for Nucleotides Based on Multitopic Hydrogen Bonding, Israel Journal of Chemistry, vol. 37:267-275 (1997).

Travers et al., A flexible and efficient template format for circular consensus sequencing and SNP detection, Nucleic Acids Research, vol. 38(15):e159, doi:10.1093/nar/gkq543 (2010).

Tung, Ching-Hsuan, Preparation and Applications of Peptide-Oligonucleotide Conjugates, Bioconjugate Chemistry, vol. 11(5):605-618 (2000).

United States District Court for the District of Delaware Order. *Pacific Biosciences of California, Inc.* v. *Oxford Nanopore Technolgoies, Inc.* Civil Action No. 17-275-RGA. Nov. 9, 2017.

Van De Goor, Tom A., Nanopore Detection: Threading DNA Through a Tiny Hole, PharmaGenomics, vol. 4 (3):28-30 (2004).

Walker, Barbara et al., Key Residues for Membrane Binding, Oligomerization and Pore Forming Activity of Staphylococcal alpha-Hemolysin Identified by Cysteine Scanning Mutagenesis and Targeted Chemical Modification, The Journal of Biological Chemistry, vol. 270 (39):23065-23071 (1995).

Wang et al., A novel strategy to engineer DNA polymerases for enhanced processivity and improved performance in vitro. Nucleic Acids Res. Feb. 18, 2004;32(3):1197-207. Print 2004.

Wang, Hui et al., Nanopores with a spark for single-molecule detection, Nature Biotechnology, vol. 19:622-623 (2001).

(56) References Cited

OTHER PUBLICATIONS

Wang, Qian et al., Bioconjugation by Copper(I)-Catalyzed Azide-Alkyne [3+2] Cycloaddition, J. Am. Chem. Soc., vol. 125:3192-3193 (2003).

Wanunu, Meni et al., DNA Translocation Governed by Interactions with Solid-State Nanopores, Biophysical Journal, vol. 95:4716-4725 (2008).

Wemmer, David E. et al., Preparation and melting of single strand circular DNA loops, Nucleic Acids Research, vol. 13(23):8611-8621 (1985).

Winters-Hilt, Stephen et al., Highly Accurate Classification of Watson-Crick Basepairs on Termini of Single DNA Molecules, Biophysical Journal, vol. 84:967-976 (2003).

Wolfe, Aaron J. et al., Catalyzing the Translocation of Polypeptides through Attractive Interactions, J. Am. Chem. Soc., vol. 129:14034-14041 (2007).

Wong et al., Polymer capture by electro-osmotic flow of oppositely charged nanopores, The Journal of Chemical Physics, vol. 126:164903-1-164903-6 (2007.

Wu et al., Protein Nanopores with Covalently Attached Molecular Adapters, J. Am. Chem. Soc. 2007;129:16142-16148.

Xie, Hongzhi et al., Single-Molecule Observation of the Catalytic Subunit of cAMP-Dependent Protein Kinase Binding to an Inhibitor Peptide, Chemistry & Biology, vol. 12:109-120 (2005).

Yamagata et al., Overexpression, purification and characterization of RecJ protein from Thermus thermophilus HB8 and its core domain, Nucleic Acids Research, vol. 29(22):4617-4624 (2001).

\* cited by examiner

ENZYME-PORE CONSTRUCTS

RELATED APPLICATIONS

This application is a continuation of U.S. patent application Ser. No. 14/858,138, filed Sep. 18, 2015, which is a divisional of U.S. patent application Ser. No. 14/455,394 filed Aug. 8, 2014, now U.S. Pat. No. 9,885,078, which is a divisional of U.S. patent application Ser. No. 13/002,709, filed May 13, 2011, now abandoned, which is a 35 U.S.C. 371 national stage filing of International Application No. PCT/GB2009/001679 filed Jul. 6, 2009, which claims the benefit under 35 U.S.C. § 119(e) to U.S. Provisional Patent Application No. 61/078,695 filed Jul. 7, 2008. The contents of the above referenced applications are incorporated herein by reference in their entireties.

FIELD OF THE INVENTION

The invention relates to constructs comprising a transmembrane protein pore subunit and a nucleic acid handling enzyme. The pore subunit is covalently attached to the enzyme such that both the subunit and enzyme retain their activity. The constructs can be used to generate transmembrane protein pores having a nucleic acid handling enzyme attached thereto. Such pores are particularly useful for sequencing nucleic acids. The enzyme handles the nucleic acid in such a way that the pore can detect each of its component nucleotides by stochastic sensing.

BACKGROUND OF THE INVENTION

Stochastic detection is an approach to sensing that relies on the observation of individual binding events between analyte molecules and a receptor. Stochastic sensors can be created by placing a single pore of nanometer dimensions in an insulating membrane and measuring voltage-driven ionic transport through the pore in the presence of analyte molecules. The frequency of occurrence of fluctuations in the current reveals the concentration of an analyte that binds within the pore. The identity of an analyte is revealed through its distinctive current signature, notably the duration and extent of current block (Braha, O., Walker, B., Cheley, S., Kasianowicz, J. J., Song, L., Gouaux, J. E., and Bayley, H. (1997) Chem. Biol. 4, 497-505; and Bayley, H., and Cremer, P. S. (2001) Nature 413, 226-230).

Engineered versions of the bacterial pore forming toxin α-hemolysin (α-HL) have been used for stochastic sensing of many classes of molecules (Bayley, H., and Cremer, P. S. (2001) Nature 413, 226-230; Shin, S., H., Luchian. T., Cheley, S., Braha, P., and Bayley, H. (2002) Angew. Chem. Int. Ed. 41, 3707-3709; and Guan, X., Gu, L.-Q., Cheley, S., Braha, O., and Bayley, H. (2005) ChemBioChem 6, 1875-1881). In the course of these studies, it was found that attempts to engineer α-HL to bind small organic analytes directly can prove taxing, with rare examples of success (Guan, X., Gu. L.-Q., Cheley, S., Braha, O., and Bayley, H. (2005) ChemBioChem 6, 1875-1881). Fortunately, a different strategy was discovered, which utilized non-covalently attached molecular adaptors, notably cyclodextrins (Gu, L.-Q., Braha, O., Conlan, S., Cheley, S., and Bayley, H. (1999) Nature 398, 686-690), but also cyclic peptides (Sanchez-Quesada, J., Ghadiri, M. R., Bayley, H., and Braha, O. (2000) J. Am. Chem. Soc. 122, 11758-11766) and cucurbiturils (Braha. O., Webb, J., Gu, L.-Q., Kim, K., and Bayley, H. (2005) ChemPhysChem 6, 889-892). Cyclodextrins become transiently lodged in the α-HL pore and produce a substantial but incomplete channel block. Organic analytes, which bind within the hydrophobic interiors of cyclodextrins, augment this block allowing analyte detection (Gu, L.-Q., Braha, O., Conlan, S., Cheley, S., and Bayley, H. (1999) Nature 398, 686-690).

There is currently a need for rapid and cheap DNA or RNA sequencing technologies across a wide range of applications. Existing technologies are slow and expensive mainly because they rely on amplification techniques to produce large volumes of nucleic acid and require a high quantity of specialist fluorescent chemicals for signal detection. Stochastic sensing has the potential to provide rapid and cheap DNA sequencing by reducing the quantity of nucleotide and reagents required.

SUMMARY OF THE INVENTION

The inventors have surprisingly demonstrated that covalent attachment of a transmembrane protein pore subunit to a nucleic acid handling enzyme results in a construct that is capable of both forming a pore and handling nucleic acids. The inventors have also surprisingly demonstrated that the construct can be used to generate a transmembrane protein pore that is capable of both handling a nucleic acid and sequencing the nucleic acid via stochastic sensing. The fixed nature and close proximity of the enzyme to the pore means that a proportion of the nucleotides in a target nucleic acid will interact with the pore and affect the current flowing through the pore in a distinctive manner. As a result, transmembrane protein pores comprising such constructs are useful tools for stochastic sensing and especially for sequencing nucleic acids.

Accordingly, the invention provides a construct comprising a transmembrane protein pore subunit and a nucleic acid handling enzyme, wherein the subunit is covalently attached to the enzyme, wherein the subunit retains its ability to form a pore and wherein the enzyme retains its ability to handle nucleic acids. The invention also provides:

a polynucleotide sequence which encodes a construct of the invention;

a modified pore for use in sequencing nucleic acids, comprising at least one construct of the invention;

a kit for producing a modified pore for use in sequencing nucleic acids, comprising:
(a) at least one construct of the invention; and
(b) any remaining subunits needed to form a pore;

a kit for producing a modified pore for use in sequencing nucleic acids, comprising:
(b) at least one polynucleotide of the invention; and
(c) polynucleotide sequences encoding any remaining subunits needed to form a pore;

a method of producing a construct of the invention, comprising:
(a) covalently attaching a nucleic acid handling enzyme to a transmembrane protein pore subunit; and
(b) determining whether or not the resulting construct is capable of forming a pore and handling nucleic acids;

a method of producing a modified pore of the invention, comprising:
(a) covalently attaching a nucleic acid handling enzyme to a transmembrane protein pore; and
(b) determining whether or not the resulting pore is capable of handling nucleic acids and detecting nucleotides;

method of producing a modified pore of the invention, comprising:

(a) allowing at least one construct of the invention to form a pore with other suitable subunits; and
(b) determining whether or not the resulting pore is capable of handling nucleic acids and detecting nucleotides.

a method of purifying a transmembrane pore comprising at least one construct of the invention, comprising:
(a) providing the at least one construct and the other subunits required to form the pore:
(b) oligomerising the at least one construct and other subunits on synthetic lipid vesicles; and
(c) contacting the vesicles with a non-ionic surfactant; and
(d) recovering the oligomerised pore;

a method of sequencing a target nucleic acid sequence, comprising:
(a) contacting the target sequence with a pore of the invention, which comprises an exonuclease, such that the exonuclease digests an individual nucleotide from one end of the target sequence;
(b) contacting the nucleotide with the pore so that the nucleotide interacts with the adaptor;
(c) measuring the current passing through the pore during the interaction and thereby determining the identity of the nucleotide; and
(d) repeating steps (a) to (c) at the same end of the target sequence and thereby determining the sequence of the target sequence; and a method of sequencing a target nucleic acid sequence, comprising:
(a) contacting the target sequence with a pore of the invention so that the enzyme pushes or pulls the target sequence through the pore and a proportion of the nucleotides in the target sequence interacts with the pore; and
(b) measuring the current passing through the pore during each interaction and thereby determining the sequence of the target sequence.

DESCRIPTION OF THE SEQUENCE LISTING

Figure 1:
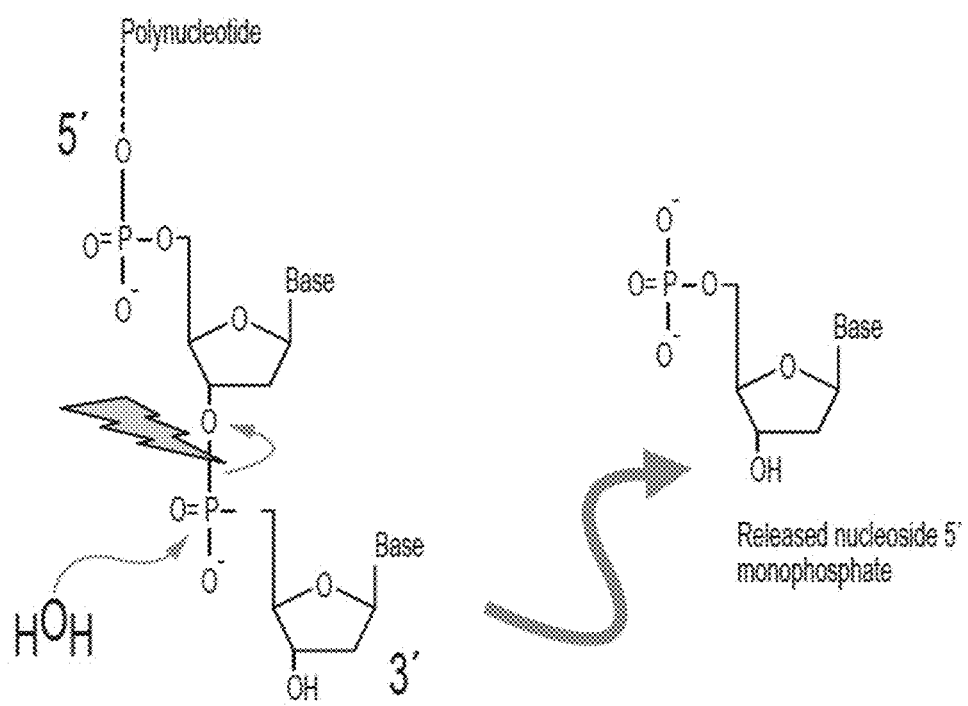
FIG. 1 shows how exonuclease enzymes catalyse the hydrolysis of phosphodiester bonds. Within the active site of the exonuclease, a water molecule is enabled to react with the phosphate of the 3' end of the polynucleotide (DNA). Cleavage of the bond between the phosphate and the sugar towards the 5' end releases a monophosphate (deoxy)nucleoside.

SEQ ID NO: 1 shows the polynucleotide sequence encoding one subunit of wild-type α-hemolysin (α-HL).

SEQ ID NO: 2 shows the amino acid sequence of one subunit of wild-type α-HL. Amino acids 2 to 6, 73 to 75, 207 to 209, 214 to 216 and 219 to 222 form α-helices. Amino acids 22 to 30, 35 to 44, 52 to 62, 67 to 71, 76 to 91, 98 to 103, 112 to 123, 137 to 148, 154 to 159, 165 to 172, 229 to 235, 243 to 261, 266 to 271, 285 to 286 and 291 to 293 form β-strands. All the other non-terminal amino acids, namely 7 to 21, 31 to 34, 45 to 51.63 to 66, 72, 92 to 97, 104 to 111, 124 to 136, 149 to 153, 160 to 164, 173 to 206, 210 to 213, 217, 218, 223 to 228, 236 to 242, 262 to 265, 272 to 274 and 287 to 290 form loop regions. Amino acids 1 and 294 are terminal amino acids.

SEQ ID NO: 3 shows the polynucleotide sequence encoding one subunit of α-HL M113R/N139Q (HL-RQ).

SEQ ID NO: 4 shows the amino acid sequence of one subunit of α-HL M113R/N139Q (HL-RQ). The same amino acids that form α-helices, β-strands and loop regions in wild-type α-HL form the corresponding regions in this subunit.

SEQ ID NO: 5 shows the pT7 α-HL BspEI knockout polynucleotide sequence (pT7-SC1_BspEI-KO). The α-HL encoding sequence is between nucleotides 2709 and 3593. The BspEI remnant is at nucleotides 3781 and 3782.

SEQ ID NO: 6 shows the polynucleotide sequence encoding one subunit of wild-type α-hemolysin containing a BspEI cloning site at position 1 (L1).

SEQ ID NO: 7 shows the polynucleotide sequence encoding one subunit of wild-type α-hemolysin containing a BspEI cloning site at position 2 (L2a).

SEQ ID NO: 8 shows the polynucleotide sequence encoding one subunit of wild-type α-hemolysin containing a BspEI cloning site at position 2 (L2b).

SEQ ID NO: 9 shows the codon optimized polynucleotide sequence derived from the xthA gene from E. coli. It encodes the exonuclease III enzyme from E. coli.

SEQ ID NO: 10 shows the amino acid sequence of the exonuclease II enzyme from E. coli. This enzyme performs distributive digestion of 5' monophosphate nucleosides from one strand of double stranded DNA (dsDNA) in a 3'-5' direction. Enzyme initiation on a strand requires a 5' overhang of approximately 4 nucleotides. Amino acids 11 to 13, 15 to 25, 39 to 41, 44 to 49, 85 to 89, 121 to 139, 158 to 160, 165 to 174, 181 to 194, 198 to 202, 219 to 222, 235 to 240 and 248 to 252 form α-helices. Amino acids 2 to 7, 29 to 33, 53 to 57, 65 to 70, 75 to 78, 91 to 98, 101 to 109, 146 to 151, 195 to 197, 229 to 234 and 241 to 246 form 1-strands. All the other non-terminal amino acids, 8 to 10, 26 to 28, 34 to 38, 42, 43, 50 to 52, 58 to 64, 71 to 74, 79 to 84, 90, 99, 100, 110 to 120, 140 to 145, 152 to 157, 161 to 164, 175 to 180, 203 to 218, 223 to 228, 247 and 253 to 261, form loops. Amino acids 1, 267 and 268 are terminal amino acids. The enzyme active site is formed by loop regions connecting β$_1$-α$_1$, β$_3$-β$_4$, β$_5$-β$_6$, β$_{III}$-α$_I$, β$_{IV}$-α$_{II}$ and β$_V$-β$_{VI}$ (consisting of amino acids 8-10, 58-64, 90, 110-120, 152-164, 175-180, 223-228 and 253-261 respectively). A single divalent metal ion is bound at residue E34 and aids nucleophilic attack on the phosphodiester bond by the D229 and H259 histidineaspartate catalytic pair.

SEQ ID NO: 11 shows the codon optimized polynucleotide sequence derived from the sbcB gene from E. coli. It encodes the exonuclease I enzyme (EcoExoI from E. coli.

SEQ ID NO: 12 shows the amino acid sequence of exonuclease I enzyme (EcoExoI) from E. coli. This enzyme performs processive digestion of 5' monophosphate nucleosides from single stranded DNA (ssDNA) in a 3'-5' direction. Enzyme initiation on a strand requires at least 12 nucleotides. Amino acids 60 to 68, 70 to 78, 80 to 93, 107 to 119, 124 to 128, 137 to 148, 165 to 172, 182 to 211, 213 to 221, 234 to 241, 268 to 286, 313 to 324, 326 to 352, 362 to 370, 373 to 391, 401 to 454 and 457 to 475 form α-helices. Amino acids 10 to 18, 28 to 26, 47 to 50, 97 to 101, 133 to 136, 229 to 232, 243 to 251, 258 to 263, 298 to 302 and 308 to 311 form β-strands. All the other non-terminal amino acids, 19 to 27, 37 to 46, 51 to 59, 69, 79, 94 to 96102 to 106, 120 to 123, 129 to 132, 149 to 164, 173 to 181, 212, 222 to 228 233, 242, 252 to 257, 264 to 267, 287 to 297, 303 to 307, 312, 325, 353 to 361, 371, 372, 392 to 400455 and 456, form loops. Amino acids 1 to 9 are terminal amino acids. The overall fold of the enzyme is such that three regions combine to form a molecule with the appearance of the letter C, although residues 355-358, disordered in the crystal structure, effectively convert this C into an O-like shape. The amino terminus (1-206) forms the exonuclease domain and has homology to the DnaQ superfamily, the following residues (202-354) form an SH3-like domain and the carboxyl domain (359-475) extends the exonuclease domain to form the C-like shape of the molecule. Four acidic residues of EcoExoI are conserved with the active site residues of the DnaQ superfamily (corresponding to D15, E17, D108 and D186). It is suggested a single metal ion is bound by residues D15 and 108. Hydrolysis of DNA is likely catalyzed by attack of the scissile phosphate with an activated water molecule, with H181 being the catalytic residue and aligning the nucleotide substrate.

SEQ ID NO: 13 shows the codon optimized polynucleotide sequence derived from the recJ gene from T. thermophilus. It encodes the RecJ enzyme from T. thermophilus (TthRecJ-cd).

SEQ ID NO: 14 shows the amino acid sequence of the RecJ enzyme from T. thermophilus (TthRecJ-cd). This enzyme performs processive digestion of 5' monophosphate nucleosides from ssDNA in a 5'-3' direction. Enzyme initiation on a strand requires at least 4 nucleotides. Amino acids 19 to 33, 44 to 61, 80 to 89, 103 to 111, 136 to 140, 148 to 163, 169 to 183, 189 to 202, 207 to 217, 223 to 240, 242 to 252, 254 to 287, 302 to 318, 338 to 350 and 365 to 382 form α-helices. Amino acids 36 to 40, 64 to 68, 93 to 96, 116 to 120, 133 to 135, 294 to 297, 321 to 325, 328 to 332, 352 to 355 and 359 to 363 form β-strands. All the other non-terminal amino acids, 34, 35, 41 to 43, 62, 63, 69 to 79, 90 to 92, 97 to 102, 112 to 115, 121 to 132, 141 to 147, 164 to 168, 184 to 188203 to 206, 218 to 222, 241, 253, 288 to 293, 298 to 301, 319, 320, 326, 327, 333 to 337, 351 to 358 and 364, form loops. Amino acids 1 to 18 and 383 to 425 are terminal amino acids. The crystal structure has only been resolved for the core domain of RecJ from Thermus thermophilus (residues 40-463). To ensure initiation of translation and in vivo expression of the RecJ core domain a methionine residue was added at its amino terminus, this is absent from the crystal structure information. The resolved structure shows two domains, an amino (2-253) and a carboxyl (288-463) region, connected by a long α-helix (254-287). The catalytic residues (D46, D98, H122, and D183) co-ordinate a single divalent metal ion for nucleophilic attack on the phosphodiester bond. D46 and H120 proposed to be the catalytic pair, however, mutation of any of these conserved residues in the E. coli RecJ was shown to abolish activity.

SEQ ID NO: 15 shows the codon optimized polynucleotide sequence derived from the bacteriphage lambda exo (redX) gene. It encodes the bacteriphage lambda exonuclease.

SEQ ID NO: 16 shows the amino acid sequence of the bacteriphage lambda exonuclease. The sequence is one of three identical subunits that assemble into a trimer. The enzyme performs highly processive digestion of nucleotides from one strand of dsDNA, in a 3'-5' direction. Enzyme initiation on a strand preferentially requires a 5' overhang of approximately 4 nucleotides with a 5' phosphate. Amino acids 3 to 10, 14 to 16, 22 to 26, 34 to 40, 52 to 67, 75 to 95, 135 to 149, 152 to 165 and 193 to 216 form α-helices. Amino acids 100 to 101, 106 to 107, 114 to 116, 120 to 122, 127 to 131, 169 to 175 and 184 to 190 form β-strands. All the other non-terminal amino acids, 11 to 13, 17 to 21, 27 to 33, 41 to 51, 68 to 74, 96 to 99, 102 to 105, 108 to 113, 117 to 119, 123 to 126, 132 to 134, 150 to 151, 166 to 168, 176 to 183, 191 to 192, 217 to 222, form loops. Amino acids 1, 2 and 226 are terminal amino acids. Lambda exonuclease is a homo-trimer that forms a toroid with a tapered channel through the middle, apparently large enough for dsDNA to enter at one end and only ssDNA to exit at the other. The catalytic residues are undetermined but a single divalent metal ion appears bound at each subunit by residues D119, E129 and L130.

SEQ ID NO: 17 shows the polynucleotide sequence encoding HL-wt-EcoExoIII-L1-H6 used in the Example.

SEQ ID NO: 18 shows the amino acid sequence of one subunit of HL-wt-EcoExoIII-L1-H6 used in the Example.

SEQ ID NO: 19 shows the polynucleotide sequence encoding HL-RQC-EcoExoIII-L1-H6 used in the Example.

SEQ ID NO: 20 shows the amino acid sequence of one subunit of HL-RQC-EcoExoIII-L1-H6 used in the Example.

SEQ ID NO: 21 shows the polynucleotide sequence encoding HL-RQC-EcoExoI-L1-H6 used in the Example.

SEQ ID NO: 22 shows the amino acid sequence of one subunit of HL-RQC-EcoExoI-L1-H6 used in the Example.

SEQ ID NO: 23 shows the polynucleotide sequence encoding HL-RQC-TthRecJ-L1-H6 used in the Example.

SEQ ID NO: 24 shows the amino acid sequence of one subunit of HL-RQC-TthRecJ-L1-H6 used in the Example.

SEQ ID NO: 25 shows the polynucleotide sequence encoding HL-RQC-EcoExoIII-L2-D45-N47Δ-H6 used in the Example.

SEQ ID NO: 26 shows the amino acid sequence of one subunit of HL-RQC-EcoExoIII-L2-D45-N47Δ-H6 used in the Example.

SEQ ID NO: 27 shows the polynucleotide sequence encoding HL-RQC-EcoExoI-Cter-{SG}8-H6 used in the Example.

SEQ ID NO: 28 shows the amino acid sequence of one subunit of HL-RQC-EcoExoI-Cter-{SG}8-H6 used in the Example.

SEQ ID NO: 29 shows the polynucleotide sequence encoding HL-RQC-EcoExoI-Cter-DG{SG}8-H6 used in the Example.

SEQ ID NO: 30 shows the amino acid sequence of one subunit of HL-RQC-EcoExoI-Cter-DG{SG}8-H6 used in the Example.

SEQ ID NOs: 31 and 32 show the oligonucleotide sequences used in the exonuclease assay of the Example.

DETAILED DESCRIPTION OF THE INVENTION

It is to be understood that different applications of the disclosed products and methods may be tailored to the specific needs in the art. It is also to be understood that the terminology used herein is for the purpose of describing particular embodiments of the invention only, and is not intended to be limiting.

In addition as used in this specification and the appended claims, the singular forms "a", "an", and "the" include plural referents unless the content clearly dictates otherwise. Thus, for example, reference to "a construct" includes "constructs", reference to "a transmembrane protein pore" includes two or more such pores, reference to "a molecular adaptor" includes two or more such adaptors, and the like.

All publications, patents and patent applications cited herein, whether supra or infra, are hereby incorporated by reference in their entirety.

Constructs

The present invention provides constructs that are useful for sequencing nucleic acids. The constructs comprise a transmembrane protein pore subunit and a nucleic acid handling enzyme. The subunit is covalently attached to the enzyme. The constructs of the invention are useful tools for forming pores that are capable of sequencing nucleic acids by stochastic sensing. The constructs of the invention are particularly useful for generating transmembrane protein pores that can both handle a target nucleic acid sequence and discriminate between the different nucleotides in the target sequence. As described in more detail below, the enzyme handles a target nucleic acid in such a way that the pore can identify nucleotides in the target sequence and thereby sequence the target sequence.

The subunit retains its ability to form a pore. The ability of a construct to form a pore can be assayed using any method known in the art. For instance, the construct may be inserted into a membrane along with other appropriate subunits and its ability to oligomerize to form a pore may be determined. Methods are known in the art for inserting constructs and subunits into membranes, such as lipid bilayers. For example, constructs and subunits may be suspended in a purified form in a solution containing a lipid bilayer such that it diffuses to the lipid bilayer and is inserted by binding to the lipid bilayer and assembling into a functional state. Alternatively, constructs and subunits may be directly inserted into the membrane using the "pick and place" method described in M. A. Holden, H. Bayley. J. Am. Chem. Soc. 2005, 127, 6502-6503 and International Application No. PCT/GB2006/001057 (published as WO 2006/100484). The ability of a construct to form a pore is typically assayed as described in the Examples.

The enzyme retains its ability to handle nucleic acids. This allows the construct to form a pore that may be used to sequence nucleic acids as described below. The ability of a construct to handle nucleic acids can be assayed using any method known in the art. For instance, construct or pores formed from the constructs can be tested for their ability to handle specific sequences of nucleic acids. The ability of a construct or a pore to handle nucleic acids is typically assayed as described in the Examples.

A construct of the invention may form part of a pore. Alternatively, a construct may be isolated, substantially isolated, purified or substantially purified. A construct is isolated or purified if it is completely free of any other components, such as lipids or other pore monomers. A construct is substantially isolated if it is mixed with carriers or diluents which will not interfere with its intended use. For instance, a construct is substantially isolated or substantially purified if it present in a form that comprises less than 10%, less than 5%, less than 2% or less than 1% of other components, such as lipids or other pore monomers. A construct of the invention may be present in a lipid bilayer.

Attachment

The subunit is covalently attached to the enzyme. The subunit may be attached to the enzyme at more than one, such as two or three, points. Attaching the subunit to the enzyme at more than one point can be used to constrain the mobility of the enzyme. For instance, multiple attachments may be used to constrain the freedom of the enzyme to rotate or its ability to move away from the subunit.

The subunit may be in a monomeric form when it is attached to the enzyme (post expression modification). Alternatively, the subunit may be part of an oligomeric pore when it is attached to an enzyme (post oligomerisation modification).

The subunit can be covalently attached to the enzyme using any method known in the art. The subunit and enzyme may be produced separately and then attached together. The two components may be attached in any configuration. For instance, they may be attached via their terminal (i.e. amino or carboxy terminal) amino acids. Suitable configurations include, but are not limited to, the amino terminus of the enzyme being attached to the carboxy terminus of the subunit and vice versa. Alternatively, the two components may be attached via amino acids within their sequences. For instance, the enzyme may be attached to one or more amino acids in a loop region of the subunit. In a preferred embodiment, terminal amino acids of the enzyme are attached to one or more amino acids in the loop region of a subunit. Terminal amino acids and loop regions are discussed above.

In one preferred embodiment, the subunit is genetically fused to the enzyme. A subunit is genetically fused to an enzyme if the whole construct is expressed from a single polynucleotide sequence. The coding sequences of the subunit and enzyme may be combined in any way to form a single polynucleotide sequence encoding the construct.

The subunit and enzyme may be genetically fused in any configuration. The subunit and enzyme may be fused via their terminal amino acids. For instance, the amino terminus of the enzyme may be fused to the carboxy terminus of the subunit and vice versa. The amino acid sequence of the enzyme is preferably added in frame into the amino acid sequence of the subunit. In other words, the enzyme is preferably inserted within the sequence of the subunit. In such embodiments, the subunit and enzyme are typically attached at two points, i.e. via the amino and carboxy terminal amino acids of the enzyme. If the enzyme is inserted within the sequence of the subunit, it is preferred that the amino and carboxy terminal amino acids of the enzyme are in close proximity and are each attached to adjacent amino acids in the sequence of the subunit or variant thereof. In a preferred embodiment, the enzyme is inserted into a loop region of the subunit.

In another preferred embodiment, the subunit is chemically fused to the enzyme. A subunit is chemically fused to an enzyme if the two parts are chemically attached, for instance via a linker molecule.

The subunit may be transiently attached to the enzyme by a hex-his tag or Ni-NTA. The subunit and enzyme may also be modified such that they transiently attach to each other.

The construct retains the pore forming ability of the subunit. The pore forming ability of the subunit is typically provided by its α-helices and β-strands. β-barrel pores comprise a barrel or channel that is formed from β-strands, whereas α-helix bundle pores comprise a barrel or channel that is formed from α-helices. The α-helices and β-strands are typically connected by loop regions. In order to avoid affecting the pore forming ability of the subunit, the enzyme is preferably genetically fused to a loop region of the subunit or inserted into a loop region of the subunit. The loop regions of specific subunits are discussed in more detail below.

Similarly, the construct retains the nucleic acid handling ability of the enzyme, which is also typically provided by its secondary structural elements (α-helices and β-strands) and tertiary structural elements. In order to avoid affecting the nucleic acid handling ability of the enzyme, the enzyme is preferably genetically fused to the subunit or inserted into the subunit via residues or regions that does not affect its secondary or tertiary structure.

The subunit may be attached directly to the enzyme. The subunit is preferably attached to the enzyme using one or more, such as two or three, linkers. The one or more linkers may be designed to constrain the mobility of the enzyme. The linkers may be attached to one or more reactive cysteine residues, reactive lysine residues or non-natural amino acids in the subunit and/or enzyme. Suitable linkers are well-known in the art. Suitable linkers include, but are not limited to, chemical crosslinkers and peptide linkers. Preferred linkers are amino acid sequences (i.e. peptide linkers). The length, flexibility and hydrophilicity of the peptide linker are typically designed such that it does not to disturb the functions of the subunit and enzyme. Preferred flexible peptide linkers are stretches of 2 to 20, such as 4, 6, 8, 10 or 16, serine and/or glycine amino acids. More preferred flexible linkers include $(SG)_1$, $(SG)_2$, $(SG)_3$, $(SG)_4$, $(SG)_5$ and $(SG)_8$ wherein S is serine and G is glycine. Preferred rigid linkers are stretches of 2 to 30, such as 4, 6, 8, 16 or 24, proline amino acids. More preferred rigid linkers include $(P)_{12}$ wherein P is proline.

Linkers may be attached to the subunit first and then the enzyme, the enzyme first and then the subunit or the enzyme and subunit at the same time. When the linker is attached to the subunit, it may be a monomeric subunit, part of an oligomer of two or more monomers or part of complete oligomeric pore. It is preferred that the linker is reacted before any purification step to remove any unbound linker.

A preferred method of attaching the subunit to the enzyme is via cysteine linkage. This can be mediated by a bi-functional chemical linker or by a polypeptide linker with a terminal presented cysteine residue. α-HL (SEQ ID NO: 2) lacks native cysteine residues so the introduction of a cysteine into the sequence of SEQ ID NO: 2 enables the controlled covalent attachment of the enzyme to the subunit. Cysteines can be introduced at various positions, such as position K8, T9 or N17 of SEQ ID NO: 2 or at the carboxy terminus of SEQ ID NO: 2. The length, reactivity, specificity, rigidity and solubility of any bi-functional linker may designed to ensure that the enzyme is positioned correctly in relation to the subunit and the function of both the subunit and enzyme is retained. Suitable linkers include bismaleimide crosslinkers, such as 1,4-bis(maleimido)butane (BMB) or bis(maleimido)hexane. One draw back of bi-functional linkers is the requirement of the enzyme to contain no further surface accessible cysteine residues, as binding of the bi-functional linker to these cannot be controlled and may affect substrate binding or activity. If the enzyme does contain several accessible cysteine residues, modification of the enzyme may be required to remove them while ensuring the modifications do not affect the folding or activity of the enzyme. In a preferred embodiment, a reactive cysteine is presented on a peptide linker that is genetically attached to the enzyme. This means that additional modifications will not necessarily be needed to remove other accessible cysteine residues from the enzyme. The reactivity of cysteine residues may be enhanced by modification of the adjacent residues, for example on a peptide linker. For instance, the basic groups of flanking arginine, histidine or lysine residues will change the pKa of the cysteines thiol group to that of the more reactive S group. The reactivity of cysteine residues may be protected by thiol protective groups such as dTNB. These may be reacted with one or more cysteine residues of the enzyme or subunit, either as a monomer or part of an oligomer, before a linker is attached.

Cross-linkage of subunits or enzymes to themselves may be prevented by keeping the concentration of linker in a vast excess of the subunit and/or enzyme. Alternatively, a "lock and key" arrangement may be used in which two linkers are used. Only one end of each linker may react together to form a longer linker and the other ends of the linker each react with a different part of the construct (i.e. subunit or monomer).

The site of covalent attachment is selected such that, when the construct is used to form a pore, the enzyme handles a target nucleic acid sequence in such a way that a proportion of the nucleotides in the target sequence interacts with the pore. Nucleotides are then distinguished on the basis of the different ways in which they affect the current flowing through the pore during the interaction.

There are a number of ways that pores can be used to sequence nucleic acid molecules. One way involves the use of an exonuclease enzyme, such as a deoxyribonuclease. In this approach, the exonuclease enzyme is used to sequentially detach the nucleotides from a target nucleic strand. The nucleotides are then detected and discriminated by the pore in order of their release, thus reading the sequence of the original strand. For such an embodiment, the exonuclease enzyme is preferably attached to the subunit such that a proportion of the nucleotides released from the target nucleic acid is capable of entering and interacting with the barrel or channel of a pore comprising the construct. The exonuclease is preferably attached to the subunit at a site in close proximity to the part of the subunit that forms the opening of the barrel of channel of the pore. The exonuclease enzyme is more preferably attached to the subunit such that its nucleotide exit trajectory site is orientated towards the part of the subunit that forms part of the opening of the pore.

Another way of sequencing nucleic acids involves the use of an enzyme that pushes or pulls the target nucleic acid strand through the pore. In this approach, the ionic current fluctuates as a nucleotide in the target strand passes through the pore. The fluctuations in the current are indicative of the sequence of the strand. For such an embodiment, the enzyme is preferably attached to the subunit such that it is capable of pushing or pulling the target nucleic acid through the barrel or channel of a pore comprising the construct and does not interfere with the flow of ionic current through the pore. The enzyme is preferably attached to the subunit at a site in close proximity to the part of the subunit that forms part of the opening of the barrel of channel of the pore. The enzyme is more preferably attached to the subunit such that its active site is orientated towards the part of the subunit that forms part of the opening of the pore.

A third way of sequencing a nucleic acid strand is to detect the bi-products of a polymerase in close proximity to a pore detector. In this approach, nucleoside phosphates (nucleotides) are labelled so that a phosphate labelled species is released upon the addition of a polymerase to the nucleotide strand and the phosphate labelled species is detected by the pore. The phosphate species contains a specific label for each nucleotide. As nucleotides are sequentially added to the nucleic acid strand, the bi-products of the base addition are detected. The order that the phosphate labelled species are detected can be used to determine the sequence of the nucleic acid strand.

The enzyme is preferably attached to a part of the subunit that forms part of the cis side of a pore comprising the construct. In electrophysiology, the cis side is the grounded side. If a hemolysin pore is inserted correctly into an electrophysiology apparatus, the Cap region is on the cis side. It is well known that, under a positive potential, nucleotides will migrate from the cis to the trans side of pores used for stochastic sensing. Positioning the enzyme at the cis side of a pore allows it to handle the target nucleic acid such that a proportion of the nucleotides in the sequence enters the barrel or channel of the pore and interacts with it. Preferably, at least 20%, at least 40%, at least 50%, at least 80% or at least 90% of the nucleotides in the sequence enters the barrel or channel of the pore and interacts with it.

The site and method of covalent attachment is preferably selected such that mobility of the enzyme is constrained. This helps to ensure that the enzyme handles the target nucleic acid sequence in such a way that a proportion of the nucleotides in the target sequence interacts with the pore. For instance, constraining the ability of enzyme to move means that its active site can be permanently orientated towards the part of the subunit that forms part of the opening of the barrel of channel of the pore. The mobility of the enzyme may be constrained by increasing the number of points at which the enzyme is attached to the subunit and/or the use of specific linkers.

Subunit

The constructs of the invention comprise a subunit from a transmembrane protein pore. A transmembrane protein pore is a polypeptide or a collection of polypeptides that permits ions driven by an applied potential to flow from one side of a membrane. The pore preferably permits nucleotides to flow from one side of a membrane to the other along the applied potential. The pore preferably allows a nucleic acid, such as DNA or RNA, to be pushed or pulled through the pore.

The subunit is part of a pore. The pore may be a monomer or an oligomer. The subunit preferably forms part of a pore made up of several repeating subunits, such as 6, 7 or 8 subunits. The subunit more preferably forms part of a heptameric pore. The subunit typically forms part of a barrel or channel through which the ions may flow. The subunits of the pore typically surround a central axis and contribute strands to a transmembrane β barrel or channel or a transmembrane α-helix bundle or channel. When part of a construct of the invention, the subunit may be a monomer or part of an oligomeric pore.

The subunit typically forms part of a pore whose barrel or channel comprises amino acids that facilitate interaction with nucleotides or nucleic acids. These amino acids are preferably located near the constriction of the barrel or channel. The subunit typically comprises one or more positively charged amino acids, such as arginine, lysine or histidine. These amino acids typically facilitate the interaction between the pore and nucleotides or nucleic acids by interacting with the phosphate groups in the nucleotides or nucleic acids or by π-cation interaction with the bases in the nucleotides or nucleic acids. The nucleotide detection can be facilitated with an adaptor.

Subunits for use in accordance with the invention can be derived from β-barrel pores or α-helix bundle pores. β-barrel pores comprise a barrel or channel that is formed from β-strands. Suitable β-barrel pores include, but are not limited to, β-toxins, such as α-hemolysin and leukocidins, and outer membrane proteins/porins of bacteria, such as outer membrane porin F (OmpF), outer membrane porin G (OmpG), outer membrane phospholipase A and Neisseria autotransporter lipoprotein (NalP). α-helix bundle pores comprise a barrel or channel that is formed from α-helices. Suitable α-helix bundle pores include, but are not limited to, inner membrane proteins and α outer membrane proteins, such as WZA.

The subunit is preferably derived from α-hemolysin (α-HL). The wild-type α-HL pore is formed of seven identical monomers or subunits (i.e. it is heptameric). The sequence of one wild-type monomer or subunit of α-hemolysin is shown in SEQ ID NO: 2. The subunit in the constructs of the invention preferably comprises the sequence shown in SEQ ID NO: 2 or a variant thereof. Amino acids 1, 7 to 21, 31 to 34, 45 to 51, 63 to 66, 72, 92 to 97, 104 to 111, 124 to 136, 149 to 153, 160 to 164, 173 to 206, 210 to 213, 217, 218, 223 to 228, 236 to 242, 262 to 265, 272 to 274, 287 to 290 and 294 of SEQ ID NO: 2 form loop regions. The enzyme is preferably attached to one or more of amino acids 8, 9, 17, 18, 19, 44, 45, 50 and 51 of SEQ ID NO: 2. The enzyme is more preferably inserted between amino acids, 18 and 19, 44 and 45 or 50 and 51 of SEQ ID NO: 2.

A variant of SEQ ID NO: 2 is a subunit that has an amino acid sequence which varies from that of SEQ ID NO: 2 and which retains its pore forming ability. The ability of the variant to form pores can be assayed as described above. The variant may include modifications that facilitate covalent attachment to or interaction with the nucleic acid handling enzyme. The variant preferably comprises one or more reactive cysteine residues that facilitate attachment to the enzyme. For instance, the variant may include a cysteine at one or more of positions 8, 9, 17, 18, 19, 44, 45, 50 and 51 and/or on the amino or carboxy terminus of SEQ ID NO: 2. Preferred variants comprise a substitution of the residue at position 8, 9 or 17 of SEQ ID NO: 2 with cysteine (K8C, T9C or N17C).

The variant may be modified to facilitate genetic fusion of the enzyme. For instance, one or more residues adjacent to the insertion site may be modified, such as deleted, to facilitate insertion of the enzyme and/or linkers. If the enzyme is inserted into loop 2 of SEQ ID NO: 2, one or more of residues D45, K46, N47. H48, N49 and K50 of SEQ ID NO: 2 may be deleted. A preferred construct containing such a deletion comprises the sequence shown in SEQ ID NO: 26 or a variant thereof.

The variant may also include modifications that facilitate any interaction with nucleotides or facilitate orientation of a molecular adaptor as discussed below. The variant may also contain modifications that facilitate covalent attachment of a molecular adaptor.

The subunit may be any of the variants of SEQ ID NO: 2 described in a co-pending International application claiming priority from US Application No. 61/078,687 and being filed simultaneously with this application [J A Kemp & Co Ref: N. 104403A; Oxford Nanolabs Ref: ONL IP 004]. All the teachings of that application may be applied equally to the present invention. In particular, the variant preferably has a glutamine at position 139 of SEQ ID NO: 2. The variant preferably has an arginine at position 113 of SEQ ID NO: 2. The variant preferably has a cysteine at position 119, 121 or 135 of SEQ ID NO: 2. Any of the variants of SEQ ID NO: 2 shown in SEQ ID NOs: 4, 6, 8, 10, 12 and 14 of the co-pending application may be used to form a construct of the invention.

The subunit may be a naturally occurring variant which is expressed by an organism, for instance by a Staphylococcus bacterium. Variants also include non-naturally occurring variants produced by recombinant technology. Over the entire length of the amino acid sequence of SEQ ID NO: 2, a variant will preferably be at least 50% homologous to that sequence based on amino acid identity. More preferably, the subunit polypeptide may be at least 55%, at least 60%, at least 65%, at least 70%, at least 75%, at least 80%, at least 85%, at least 90% and more preferably at least 95%, 97% or 99% homologous based on amino acid identity to the amino acid sequence of SEQ ID NO: 2 over the entire sequence. There may be at least 80%, for example at least 85%, 90% or 95%, amino acid identity over a stretch of 200 or more, for example 230, 250, 270 or 280 or more, contiguous amino acids ("hard homology").

Amino acid substitutions may be made to the amino acid sequence of SEQ ID NO: 2 in addition to those discussed above, for example up to 1, 2, 3, 4, 5, 10, 20 or 30 substitutions. Conservative substitutions may be made, for example, according to Table 1 below.

TABLE 1

Conservative substitutions
Amino acids in the same block in the second column and preferably in the same line in the third column may be substituted for each other.

| NON-AROMATIC | Non-polar | G A P |
| --- | --- | --- |
| | | I L V |
| | Polar - uncharged | C S T M |
| | | N Q |
| | Polar - charged | D E |
| | | H K R |
| AROMATIC | | H F W Y |

One or more amino acid residues of the amino acid sequence of SEQ ID NO: 2 may additionally be deleted from the polypeptides described above. Up to 1, 2, 3, 4, 5, 10, 20 or 30 residues may be deleted, or more.

Variants may fragments of SEQ ID NO: 2. Such fragments retain pore forming activity. Fragments may be at least 50, 100, 200 or 250 amino acids in length. A fragment preferably comprises the pore forming domain of SEQ ID NO: 2. Fragments typically include residues 119, 121, 135, 113 and 139 of SEQ ID NO: 2.

One or more amino acids may be alternatively or additionally added to the polypeptides described above. An extension may be provided at the amino terminus or carboxy terminus of the amino acid sequence of SEQ ID NO: 2 or a variant or fragment thereof. The extension may be quite short, for example from 1 to 10 amino acids in length. Alternatively, the extension may be longer, for example up to 50 or 100 amino acids. A carrier protein may be fused to a subunit or variant.

As discussed above, a variant of SEQ ID NO: 2 is a subunit that has an amino acid sequence which varies from that of SEQ ID NO: 2 and which retains its ability to form a pore. A variant typically contains the regions of SEQ ID NO: 2 that are responsible for pore formation. The pore forming ability of α-HL, which contains a 1-barrel, is provided by β-strands in each subunit. A variant of SEQ ID NO: 2 typically comprises the regions in SEQ ID NO: 2 that form β-strands. The amino acids of SEQ ID NO: 2 that form β-strands are discussed above. One or more modifications can be made to the regions of SEQ ID NO: 2 that form β-strands as long as the resulting variant retains its ability to form a pore. Specific modifications that can be made to the 1-strand regions of SEQ ID NO: 2 are discussed above.

A variant of SEQ ID NO: 2 preferably includes one or more modifications, such as substitutions, additions or deletions, within its α-helices and/or loop regions. Amino acids that form α-helices and loops are discussed above.

Standard methods in the art may be used to determine homology. For example the UWGCG Package provides the BESTFIT program which can be used to calculate homology, for example used on its default settings (Devereux et al (1984) *Nucleic Acids Research* 12, p 387-395). The PILEUP and BLAST algorithms can be used to calculate homology or line up sequences (such as identifying equivalent residues or corresponding sequences (typically on their default settings)), for example as described in Altschul S. F. (1993) J Mol Evol 36:290-300; Altschul, S. F et al (1990) J Mol Biol 215:403-10.

Software for performing BLAST analyses is publicly available through the National Center for Biotechnology Information (http://www.ncbi.nlm.nih.gov/). This algorithm involves first identifying high scoring sequence pair (HSPs) by identifying short words of length W in the query sequence that either match or satisfy some positive-valued threshold score T when aligned with a word of the same length in a database sequence. T is referred to as the neighbourhood word score threshold (Altschul et al, supra). These initial neighbourhood word hits act as seeds for initiating searches to find HSP's containing them. The word hits are extended in both directions along each sequence for as far as the cumulative alignment score can be increased. Extensions for the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program uses as defaults a word length (W) of 11, the BLOSUM62 scoring matrix (see Henikoff and Henikoff (1992) *Proc. Natl. Acad. Sci. USA* 89: 10915-10919) alignments (B) of 50, expectation (E) of 10, M=5, N=4, and a comparison of both strands.

The BLAST algorithm performs a statistical analysis of the similarity between two sequences; see e.g., Karlin and Altschul (1993) *Proc. Natl. Acad. Sci. USA* 90: 5873-5787. One measure of similarity provided by the BLAST algorithm is the smallest sum probability (P(N)), which provides an indication of the probability by which a match between two amino acid sequences would occur by chance. For example, a sequence is considered similar to another sequence if the smallest sum probability in comparison of the first sequence to the second sequence is less than about 1, preferably less than about 0.1, more preferably less than about 0.01, and most preferably less than about 0.001.

The variant may be modified for example by the addition of histidine or aspartic acid residues to assist its identification or purification or by the addition of a signal sequence to promote their secretion from a cell where the polypeptide does not naturally contain such a sequence.

The subunit may be labelled with a revealing label. The revealing label may be any suitable label which allows the pore to be detected. Suitable labels include, but are not limited to, fluorescent molecules, radioisotopes, e.g. $^{125}$I, $^{35}$S, enzymes, antibodies, antigens, polynucleotides and ligands such as biotin.

The subunit may be isolated from a pore producing organism, such as *Staphylococcus aureus*, or made synthetically or by recombinant means. For example, the subunit may be synthesized by in vitro translation and transcription. The amino acid sequence of the subunit may be modified to include non-naturally occurring amino acids or to increase the stability of the subunit. When the subunit is produced by synthetic means, such amino acids may be introduced during production. The subunit may also be altered following either synthetic or recombinant production.

The subunit may also be produced using D-amino acids. For instance, the pores may comprise a mixture of L-amino acids and D-amino acids. This is conventional in the art for producing such proteins or peptides.

The subunit may also contain other non-specific chemical modifications as long as they do not interfere with its ability to form a pore. A number of non-specific side chain modifications are known in the art and may be made to the side chains of the pores. Such modifications include, for example, reductive alkylation of amino acids by reaction with an aldehyde followed by reduction with $NaBH_4$, amidination with methylacetimidate or acylation with acetic anhydride. The modifications to the subunit can be made after expression of the subunit or construct or after the subunit has been used to form a pore.

The subunit can be produced using standard methods known in the art. Polynucleotide sequences encoding a subunit may be isolated and replicated using standard methods in the art. Such sequences are discussed in more detail below. Polynucleotide sequences encoding a subunit may be expressed in a bacterial host cell using standard techniques in the art. The subunit may be produced in a cell by in situ expression of the polypeptide from a recombinant expression vector. The expression vector optionally carries an inducible promoter to control the expression of the polypeptide.

A subunit may be produced in large scale following purification by any protein liquid chromatography system from pore producing organisms or after recombinant expression as described below. Typical protein liquid chromatography systems include FPLC, AKTA systems, the Bio-Cad system, the Bio-Rad BioLogic system and the Gilson HPLC system.

Nucleic Acid Handling Enzyme

The constructs of the invention comprise a nucleic acid handling enzyme. A nucleic acid handling enzyme is a polypeptide that is capable of interacting with and modifying at least one property of a nucleic acid. The enzyme may modify the nucleic acid by cleaving it to form individual nucleotides or shorter chains of nucleotides, such as di- or trinucleotides. The enzyme may modify the nucleic acid by orienting it or moving it to a specific position.

A nucleic acid is a macromolecule comprising two or more nucleotides. The nucleic acid handled by the enzyme may comprise any combination of any nucleotides. The nucleotides can be naturally occurring or artificial. A nucleotide typically contains a nucleobase, a sugar and at least one phosphate group. The nucleobase is typically heterocyclic. Nucleobases include, but are not limited to, purines and pyrimidines and more specifically adenine, guanine, thymine, uracil and cytosine. The sugar is typically a pentose sugar. Nucleotide sugars include, but are not limited to, ribose and deoxyribose. The nucleotide is typically a ribonucleotide or deoxyribonucleotide. The nucleotide typically contains a monophosphate, diphosphate or triphosphate. Phosphates may be attached on the 5' or 3' side of a nucleotide.

Nucleotides include, but are not limited to, adenosine monophosphate (AMP), adenosine diphosphate (ADP), adenosine triphosphate (ATP), guanosine monophosphate (GMP), guanosine diphosphate (GDP), guanosine triphosphate (GTP), thymidine monophosphate (TMP), thymidine diphosphate (TDP), thymidine triphosphate (TTP), uridine monophosphate (UMP), uridine diphosphate (UDP), uridine triphosphate (UTP), cytidine monophosphate (CMP), cytidine diphosphate (CDP), cytidine triphosphate (CTP), cyclic adenosine monophosphate (cAMP), cyclic guanosine monophosphate (cGMP), deoxyadenosine monophosphate (dAMP), deoxyadenosine diphosphate (dADP), deoxyadenosine triphosphate (dATP), deoxyguanosine monophosphate (dGMP), deoxyguanosine diphosphate (dGDP), deoxyguanosine triphosphate (dGTP), deoxythymidine monophosphate (dTMP), deoxythymidine diphosphate (dTDP), deoxythymidine triphosphate (dTTP), deoxyuridine monophosphate (dUMP), deoxyuridine diphosphate (dUDP), deoxyuridine triphosphate (dUTP), deoxycytidine monophosphate (dCMP), deoxycytidine diphosphate (dCDP) and deoxycytidine triphosphate (dCTP). The nucleotides are preferably selected from AMP, TMP, GMP, UMP, dAMP, dTMP, dGMP or dCMP.

The nucleic acid handled by the enzyme is preferably double stranded, such as DNA. The nucleic acid handled by the enzyme may be single stranded, such as cDNA or RNA. Enzymes that handle single stranded nucleic acids may be used to sequence double stranded DNA as long as the double stranded DNA is chemically or thermally dissociated into a single strand before it is handled by the enzyme.

It is preferred that the tertiary structure of the nucleic acid handling enzyme is known. Knowledge of the three dimensional structure of the enzyme allows modifications to be made to the enzyme to facilitate its function in the construct or pore of the invention.

The enzyme may be any size and have any structure. For instance, the enzyme may be an oligomer, such as a dimer or trimer. The enzyme is preferably a small, gloubular polypeptide formed from one monomer. Such enzymes are easy to handle and are less likely to interfere with the pore forming ability of the subunit, particularly if fused to or inserted into the sequence of the subunit.

The amino and carboxy termini of the enzyme are preferably in close proximity. The amino and carboxy termini of the enzyme are more preferably presented on same face of the enzyme. Such embodiments facilitate insertion of the enzyme into the sequence of the subunit. For instance, if the amino and carboxy termini of the enzyme are in close proximity, each can be attached by genetic fusion to adjacent amino acids in the sequence of the subunit.

It is also preferred that the location and function of the active site of the enzyme is known. This prevents modifications being made to the active site that abolish the activity of the enzyme. It also allows the enzyme to be attached to the subunit so that the enzyme handles the target nucleic acid sequence in such a way that a proportion of the nucleotides in the target sequence interacts with the pore. It is beneficial to position the active site of the enzyme as close as possible to the part of the subunit that forms part of the opening of the barrel of channel of the pore, without the enzyme itself presenting a block to the flow of current. Knowledge of the way in which an enzyme may orient nucleic acids also allows an effective construct to be designed.

As discussed in more detail below, it may be necessary to purify the construct of the invention. It is preferred that the enzyme is capable of withstanding the conditions used to purify the construct.

The constructs of the invention are useful for forming pores. Such pores may be used to sequence nucleic acids. In order that most of the nucleotides in the target nucleic acid are correctly identified by stochastic sensing, the enzyme must handle the nucleic acid in a buffer background which is compatible with discrimination of the nucleotides. The enzyme preferably has at least residual activity in a salt concentration well above the normal physiological level, such as from 100 mM to 500 mM. The enzyme is more preferably modified to increase its activity at high salt concentrations. The enzyme may also be modified to improve its processivity, stability and shelf life.

Suitable modifications can be determined from the characterisation of nucleic acid handling enzymes from extremophiles such as halophilic, moderately halophilic bacteria, thermophilic and moderately thermophilic organisms, as well as directed evolution approaches to altering the salt tolerance, stability and temperature dependence of mesophilic or thermophilic exonucleases.

The enzyme also preferably retains at least partial activity at room temperature. This allows pores formed from the construct to sequence nucleic acids at room temperature.

The nucleic acid handling enzyme is preferably a nucleolytic enzyme. The nucleic acid handling enzyme is more preferably member of any of the Enzyme Classification (EC) groups 3.1.11, 3.1.13, 3.1.14, 3.1.15, 3.1.16, 3.1.21, 3.1.22, 3.1.25, 3.1.26, 3.1.27, 3.1.30 and 3.1.31. The nucleic acid handling enzyme is more preferably any one of the following enzymes:

3.1.11.—Exodeoxyribonucleases producing 5'-phosphomonoesters.
   3.1.11.1 Exodeoxyribonuclease I.
   3.1.11.2 Exodeoxyribonuclease III.
   3.1.11.3 Exodeoxyribonuclease (lambda-induced).
   3.1.11.4 Exodeoxyribonuclease (phage SP3-induced).
   3.1.11.5 Exodeoxyribonuclease V.
   3.1.11.6 Exodeoxyribonuclease VII.
3.1.13.—Exoribonucleases producing 5'-phosphomonoesters.
   3.1.13.1 Exoribonuclease II.
   3.1.13.2 Exoribonuclease H.
   3.1.13.3 Oligonucleotidase.
   3.1.13.4 Poly(A)-specific ribonuclease.
   3.1.13.5 Ribonuclease D.
3.1.14.—Exoribonucleases producing 3'-phosphomonoesters.
   3.1.14.1 Yeast ribonuclease.
3.1.15.—Exonucleases active with either ribo- or deoxyribonucleic acid producing 5' phosphomonoesters
   3.1.15.1 Venom exonuclease.
3.1.16.—Exonucleases active with either ribo- or deoxyribonucleic acid producing 3' phosphomonoesters
   3.1.16.1 Spleen exonuclease.
3.1.21.—Endodeoxyribonucleases producing 5'-phosphomonoesters.
   3.1.21.1 Deoxyribonuclease 1.
   3.1.21.2 Deoxyribonuclease IV (phage-T(4)-induced).
   3.1.21.3 Type I site-specific deoxyribonuclease.
   3.1.21.4 Type II site-specific deoxyribonuclease.
   3.1.21.5 Type III site-specific deoxyribonuclease.
   3.1.21.6 CC-preferring endodeoxyribonuclease.
   3.1.21.7 Deoxyribonuclease V.

3.1.22.—Endodeoxyribonucleases producing other than 5'-phosphomonoesters.
   3.1.22.1 Deoxyribonuclease II.
   3.1.22.2 *Aspergillus* deoxyribonuclease K(1).
   3.1.22.3 Transferred entry: 3.1.21.7.
   3.1.22.4 Crossover junction endodeoxyribonuclease.
   3.1.22.5 Deoxyribonuclease X.
3.1.25.—Site-specific endodeoxyribonucleases specific for altered bases.
   3.1.25.1 Deoxyribonuclease (pyrimidine dimer).
   3.1.25.2 Transferred entry: 4.2.99.18.
3.1.26.—Endoribonucleases producing 5'-phosphomonoesters.
   3.1.26.1 Physarum polycephalum ribonuclease.
   3.1.26.2 Ribonuclease alpha.
   3.1.26.3 Ribonuclease III.
   3.1.26.4 Ribonuclease H.
   3.1.26.5 Ribonuclease P.
   3.1.26.6 Ribonuclease IV.
   3.1.26.7 Ribonuclease P4.
   3.1.26.8 Ribonuclease M5.
   3.1.26.9 Ribonuclease (poly-(U)-specific).
   3.1.26.10 Ribonuclease IX.
   3.1.26.11 Ribonuclease Z.
3.1.27.—Endoribonucleases producing other than 5'-phosphomonoesters.
   3.1.27.1 Ribonuclease T(2).
   3.1.27.2 *Bacillus subtilis* ribonuclease.
   3.1.27.3 Ribonuclease T(1).
   3.1.27.4 Ribonuclease U(2).
   3.1.27.5 Pancreatic ribonuclease.
   3.1.27.6 *Enterobacter* ribonuclease.
   3.1.27.7 Ribonuclease F.
   3.1.27.8 Ribonuclease V.
   3.1.27.9 tRNA-intron endonuclease.
   3.1.27.10 rRNA endonuclease.
3.1.30.—Endoribonucleases active with either ribo- or deoxyribonucleic producing 5' phospomonoesters
   3.1.30.1 *Aspergillus* nuclease S(1).
   3.1.30.2 *Serratia marcescens* nuclease.
3.1.31.—Endoribonucleases active with either ribo- or deoxyribonucleic producing 3' phosphomonoesters
   3.1.31.1 Micrococcal nuclease.

The enzyme is most preferably an exonuclease, such as a deoxyribonuclease, which cleave nucleic acids to form individual nucleotides. The advantages of exodeoxyribonucleases are that they are active on both single stranded and double stranded DNA and hydrolyse bases either in either the 5'-3' or 3'-5' direction.

An individual nucleotide is a single nucleotide. An individual nucleotide is one which is not bound to another nucleotide or nucleic acid by a nucleotide bond. A nucleotide bond involves one of the phosphate groups of a nucleotide being bound to the sugar group of another nucleotide. An individual nucleotide is typically one which is not bound by a nucleotide bond to another nucleic acid sequence of at least 5, at least 10, at least 20, at least 50, at least 100, at least 200, at least 500, at least 1000 or at least 5000 nucleotides.

Preferred enzymes for use in the method include exonuclease III enzyme from *E. coli* (SEQ ID NO: 10), exonuclease I from *E. coli* (SEQ ID NO: 12), RecJ from *T. thermophilus* (SEQ ID NO: 14) and bacteriophage lambda exonuclease (SEQ ID NO: 16) and variants thereof. The exonuclease enzyme preferably comprises any of the sequences shown in SEQ ID NOs: 10, 12, 14 and 16 or a variant thereof. Three identical subunits of SEQ ID NO: 16 interact to form a trimer exonuclease. A variant of SEQ ID NO: 10, 12, 14 or 16 is an enzyme that has an amino acid sequence which varies from that of SEQ ID NO: 10, 12, 14 or 16 and which retains nucleic acid handling ability. The enzyme may include modifications that facilitate handling of the nucleic acid and/or facilitate its activity at high salt concentrations and/or room temperature. The enzyme may include modifications that facilitate covalent attachment to or its interaction with the subunit. As discussed above, accessible cysteines may be removed from the enzyme to avoid non-specific reactions with a linker. Alternatively, one or more reactive cysteines may be introduced into the enzyme, for instance as part of a genetically-fused peptide linker, to facilitate attachment to the subunit.

Variants may differ from SEQ ID NO: 10, 12, 14 and 16 to the same extent as variants of SEQ ID NO: 2 differ from SEQ ID NO: 2 as discussed above.

A variant of SEQ ID NO: 10, 12, 14 or 16 retains its nucleic acid handling activity. A variant typically contains the regions of SEQ ID NO: 10, 12, 14 or 16 that are responsible for nucleic acid handling activity. The catalytic domains of SEQ ID NOs: 10, 12, 14 and 16 are discussed above. A variant of SEQ ID NO: 10, 12, 14 or 16 preferably comprises the relevant catalytic domain. A variant SEQ ID NO: 10, 12, 14 or 16 typically includes one or more modifications, such as substitutions, additions or deletions, outside the relevant catalytic domain.

Preferred enzymes that are capable of pushing or pulling the target nucleic acid sequence through the pore include polymerases, exonucleases, helicases and topoisomerases, such as gyrases. The polymerase is preferably a member of any of the Enzyme Classification (EC) groups 2.7.7.6, 2.7.7.7, 2.7.7.19, 2.7.7.48 and 2.7.7.49. The polymerase is preferably a DNA-dependent DNA polymerase, an RNA-dependent DNA polymerase, a DNA-dependent RNA polymerase or an RNA-dependent RNA polymerase. The helicase is preferably a member of any of the Enzyme Classification (EC) groups 3.6.1.- and 2.7.7.-. The helicase is preferably an ATP-dependent DNA helicase (EC group 3.6.1.8), an ATP-dependent RNA helicase (EC group 3.6.1.8) or an ATP-independent RNA helicase. The topoisomerase is preferably a member of any of the Enzyme Classification (EC) groups 5.99.1.2 and 5.99.1.3.

The enzyme may be labelled with a revealing label. The revealing label may be any of those described above.

The enzyme may be isolated from an enzyme-producing organism, such as *E. coli*, *T. thermophilus* or bacteriophage, or made synthetically or by recombinant means. For example, the enzyme may be synthesized by in vitro translation and transcription as described above and below. The enzyme may be produced in large scale following purification as described above.

Preferred Constructs

Preferred constructs of the invention comprise the sequence shown in any one of SEQ ID NOs: 18, 20, 22, 24, 26, 28 and 30 or a variant thereof. Variants of SEQ ID NO: 18, 20, 22, 24, 26, 28 or 30 must retain their pore forming ability and nucleic acid handling ability. Variants may differ from SEQ ID NOs: 18, 20, 22, 24, 26, 28 and 30 to the same extent and in the same way as discussed above for variants of SEQ ID NO: 2 and variants of SEQ ID NO: 10, 12, 14 or 16.

Polynucleotide Sequences

The present invention also provides polynucleotide sequences which encode a construct in which the enzyme is genetically fused to the subunit or is inserted into the sequence of the subunit. It is straightforward to generate such polynucleotide sequences using standard techniques. A polynucleotide sequence encoding the enzyme is either fused to or inserted into a polynucleotide sequence encoding the subunit. The fusion or insertion is typically in frame. If a polynucleotide sequence encoding the enzyme is inserted into a polynucleotide sequence encoding the subunit, the sequence encoding the enzyme is typically flanked at both ends by restriction endonuclease sites, such as those recognized by BspE1. It may also be flanked at both ends by polynucleotide sequences encoding linkers, such as 5 to 10 codons each encoding serine or glycine.

The polynucleotide sequence preferably encodes a construct comprising SEQ ID NO: 10, 12, 14 or 16 or a variant thereof genetically fused to or inserted into SEQ ID NO: 2 or a variant thereof. The variants of SEQ ID NO: 2, 10, 12, 14 or 16 may be any of those discussed above. SEQ ID NO: 10, 12, 14 or 16 or a variant thereof may be genetically fused to or inserted into SEQ ID NO: 2 or a variant thereof as described above.

The polynucleotide sequence preferably comprises SEQ ID NO: 9, 11, 13 or 15 or a variant thereof genetically fused to or inserted into SEQ ID NO: 1 or a variant thereof. SEQ ID NO: 9, 11, 13 or 15 or a variant thereof is preferably inserted into SEQ ID NO: 1 or a variant thereof between nucleotides 2765 and 2766, 2843 and 2844 or 2861 and 2862 of SEQ ID NO: 1. The polynucleotide sequence more preferably comprises the sequence shown in SEQ ID NO: 17, 19, 21, 23, 25, 27 or 29 or a variant thereof.

Variants of SEQ ID NOs: 1, 9, 11, 13, 15, 17, 19, 21, 23, 25, 27 or 29 are sequences that are at least 50%, 60%, 70%, 80%, 90% or 95% homologous based on nucleotide identity to sequence of SEQ ID NO: 1, 9, 11, 13, 15, 17, 19, 21, 23, 25, 27 or 29 over the entire sequence. There may be at least 80%, for example at least 85%, 90% or 95% nucleotide identity over a stretch of 600 or more, for example 700, 750, 850 or 900 or more, contiguous nucleotides ("hard homogly"). Homology may be calculated as described above. The polynucleotide sequence may comprise a sequence that differs from SEQ ID NO: 1, 9, 11, 13, 15, 17, 19, 21, 23, 25, 27 or 29 on the basis of the degeneracy of the genetic code.

Polynucleotide sequences may be isolated and replicated using standard methods in the art. Chromosomal DNA may be extracted from a pore producing organism, such as *Staphylococcus aureus*, and/or an enzyme producing organism, such as *E. coli, T. thermophilus* or bacteriophage. The gene encoding the subunit and enzyme may be amplified using PCR involving specific primers. The amplified sequences may then be incorporated into a recombinant replicable vector such as a cloning vector. The vector may be used to replicate the polynucleotide in a compatible host cell. Thus polynucleotide sequences encoding a subunit and/or enzyme may be made by introducing a polynucleotide encoding a subunit and/or enzyme into a replicable vector, introducing the vector into a compatible host cell, and growing the host cell under conditions which bring about replication of the vector. The vector may be recovered from the host cell. Suitable host cells for cloning of polynucleotides are known in the art and described in more detail below.

The polynucleotide sequence may be cloned into suitable expression vector. In an expression vector, the polynucleotide sequence encoding a construct is typically operably linked to a control sequence which is capable of providing for the expression of the coding sequence by the host cell. Such expression vectors can be used to express a construct.

The term "operably linked" refers to a juxtaposition wherein the components described are in a relationship permitting them to function in their intended manner. A control sequence "operably linked" to a coding sequence is ligated in such a way that expression of the coding sequence is achieved under conditions compatible with the control sequences. Multiple copies of the same or different polynucleotide may be introduced into the vector.

The expression vector may then be introduced into a suitable host cell. Thus, a construct can be produced by inserting a polynucleotide sequence encoding a construct into an expression vector, introducing the vector into a compatible bacterial host cell, and growing the host cell under conditions which bring about expression of the polynucleotide sequence. The recombinantly-expressed construct may self-assemble into a pore in the host cell membrane. Alternatively, the recombinant construct produced in this manner may be isolated from the host cell and inserted into another membrane. When producing an oligomeric pore comprising a construct of the invention and at least one different subunit, the construct and different subunits may be expressed separately in different host cells as described above, removed from the host cells and assembled into a pore in a separate membrane, such as a rabbit cell membrane.

The vectors may be for example, plasmid, virus or phage vectors provided with an origin of replication, optionally a promoter for the expression of the said polynucleotide sequence and optionally a regulator of the promoter. The vectors may contain one or more selectable marker genes, for example an ampicillin resistance gene. Promoters and other expression regulation signals may be selected to be compatible with the host cell for which the expression vector is designed. A T7, trc, lac, ara or $\lambda_L$ promoter is typically used.

The host cell typically expresses the construct at a high level. Host cells transformed with a polynucleotide sequence encoding a construct will be chosen to be compatible with the expression vector used to transform the cell. The host cell is typically bacterial and preferably *E. coli*. Any cell with a λ DE3 lysogen, for example C41 (DE3), BL21 (DE3), JM109 (DE3), B834 (DE3), TUNER. Origami and Origami B, can express a vector comprising the T7 promoter.

Modified Pores

The present invention also provides modified pores for use in sequencing nucleic acids. The pores comprise at least one construct of the invention. The pores may comprise more than one, such as 2, 3 or 4, constructs of the invention.

A pore of the invention may be isolated, substantially isolated, purified or substantially purified. A pore of the invention is isolated or purified if it is completely free of any other components, such as lipids or other pores. A pore is substantially isolated if it is mixed with carriers or diluents which will not interfere with its intended use. For instance, a pore is substantially isolated or substantially purified if it present in a form that comprises less than 10%, less than 5%, less than 2% or less than 1% of other components, such as lipids or other pores. Alternatively, a pore of the invention may be present in a lipid bilayer or in a surfactant micelle.

The enzyme attached to the construct handles a target nucleic acid sequence in such a way that a proportion of the nucleotide in the target sequence interacts with the pore, preferably the barrel or channel of the pore. Nucleotides are then distinguished on the basis of the different ways in which they affect the current flowing through the pore during the interaction.

The fixed nature of the enzyme means that a target nucleic acid sequence is handled by the pore in a specific manner. For instance, each nucleotide may be digested from one of the target sequence in a processive manner or the target sequence may be pushed or pulled through the pore. This ensures that a proportion of the nucleotides in the target nucleic acid sequence interacts with the pore and is identified. The lack of any interruption in the signal is important when sequencing nucleic acids. In addition, the fixed nature of the enzyme and the pore means they can be stored together, thereby allowing the production of a ready-to-use sensor.

In a preferred embodiment, an exonuclease enzyme, such as a deoxyribonuclease, is attached to the pore such that a proportion of the nucleotides is released from the target nucleic acid and interacts with the barrel or channel of the pore. In another preferred embodiment, an enzyme that is capable of pushing or pulling the target nucleic acid sequence through the pore is attached to the pore such that the target nucleic acid sequence is pushed or pulled through the barrel or channel of the pore and a proportion of the nucleotides in the target sequence interacts with the barrel or channel. In this embodiment, the nucleotides may interact with the pore in blocks or groups of more than one, such as 2, 3 or 4. Suitable enzymes include, but are not limited to, polymerases, exonucleases, helicases and topoisomerases, such as gyrases. In each embodiment, the enzyme is preferably attached to the pore at a site in close proximity to the opening of the barrel of channel of the pore. The enzyme is more preferably attached to the pore such that its active site is orientated towards the opening of the barrel of channel of the pore. This means that a proportion of the nucleotides of the target nucleic acid sequence is fed in the barrel or channel. The enzyme is preferably attached to the cis side of the pore.

The modified pore may be based on any of the transmembrane protein pores discussed above, including the β-barrel pores and α-helix bundle pores.

For constructs comprising the sequence shown in SEQ ID NO: 2 or a variant thereof, the pore typically comprises an appropriate number of additional subunits comprising the sequence shown in SEQ ID NO: 2 or a variant thereof. A preferred pore of the invention comprises one construct comprising the sequence shown in SEQ ID NO: 2 or a variant thereof and six subunits comprising the sequence shown in SEQ ID NO: 2 or a variant thereof. The pore may comprise one or more subunits comprising the sequence shown in SEQ ID NO: 4 or a variant thereof. SEQ ID NO: 4 shows the sequence of SEQ ID NO: 2 except that it has an arginine at position 113 (M113R) and a glutamine at position 139 (N139Q). A variant of SEQ ID NO: 4 may differ from SEQ ID NO: 4 in the same way and to the same extent as discussed for SEQ ID NO: 2 above. A preferred pore of the invention comprises one construct comprising the sequence shown in SEQ ID NO: 2 or a variant thereof and six subunits comprising the sequence shown in SEQ ID NO: 4 or a variant thereof.

The pores may comprise a molecular adaptor that facilitates the interaction between the pore and the nucleotides or the target nucleic acid sequence. The presence of the adaptor improves the host-guest chemistry of the pore and nucleotides released from or present in the target nucleic acid sequence. The principles of host-guest chemistry are well-known in the art. The adaptor has an effect on the physical or chemical properties of the pore that improves its interaction with nucleotides. The adaptor typically alters the charge of the barrel or channel of the pore or specifically interacts with or binds to nucleotides thereby facilitating their interaction with the pore.

The adaptor mediates the interaction between nucleotides released from or present in the target nucleic acid sequence and the pore. The nucleotides preferably reversibly bind to the pore via or in conjunction with the adaptor. The nucleotides most preferably reversibly bind to the pore via or in conjunction with the adaptor as they pass through the pore across the membrane. The nucleotides can also reversibly bind to the barrel or channel of the pore via or in conjunction with the adaptor as they pass through the pore across the membrane. The adaptor preferably constricts the barrel or channel so that it may interact with the nucleotides.

The adaptor is typically cyclic. The adaptor preferably has the same symmetry as the pore. An adaptor having seven-fold symmetry is typically used if the pore is heptameric (e.g. has seven subunits around a central axis that contribute 14 strands to a transmembrane β barrel). Likewise, an adaptor having six-fold symmetry is typically used if the pore is hexameric (e.g. has six subunits around a central axis that contribute 12 strands to a transmembrane β barrel, or is a 12-stranded β barrel). Any adaptor that that facilitates the interaction between the pore and the nucleotide can be used. Suitable adaptors include, but are not limited to, cyclodextrins, cyclic peptides and cucurbiturils. The adaptor is preferably a cyclodextrin or a derivative thereof. The adaptor is more preferably heptakis-6-amino-β-cyclodextrin ($am_7$-βCD), 6-monodeoxy-6-monoamino-β-cyclodextrin ($am_1$-βCD) or heptakis-(6-deoxy-6-guanidino)-cyclodextrin ($gu_7$-βCD). Table 2 below shows preferred combinations of pores and adaptors.

TABLE 2

Suitable combinations of pores and adaptors

| Pore | Number of strands in the transmembrane β-barrel | Adaptor |
| --- | --- | --- |
| Leukocidin | 16 | γ-cyclodextrin (γ-CD) |
| OmpF | 16 | γ-cyclodextrin (γ-CD) |
| α-hemolysin (or a variant thereof discussed above) | 14 | β-cyclodextrin (β-CD) 6-monodeoxy-6-monoamino-β-cyclodextrin ($am_1$β-CD) heptakis-6-amino-β-cyclodextrin ($am_7$-β-CD) heptakis-(6-deoxy-6-guanidino)-cyclodextrin ($gu_7$-β-CD) |
| OmpG | 14 | β-cyclodextrin (β-CD) 6-monodeoxy-6-monoamino-β-cyclodextrin ($am_1$β-CD) heptakis-6-amino-β-cyclodextrin ($am_7$-β-CD) heptakis-(6-deoxy-6-guanidino)-cyclodextrin ($gu_7$-β-CD) |
| NalP | 12 | α-cyclodextrin (α-CD) |
| OMPLA | 12 | α-cyclodextrin (α-CD) |

The adaptor is preferably covalently attached to the pore. The adaptor can be covalently attached to the pore using any method known in the art. The adaptor may be attached directly to the pore. The adaptor is preferably attached to the pore using a bifunctional crosslinker. Suitable crosslinkers are well-known in the art. Preferred crosslinkers include 2,5-dioxopyrrolidin-1-yl 3-(pyridin-2-yldisulfanyl)propanoate, 2,5-dioxopyrrolidin-1-yl 4-(pyridin-2-yldisulfanyl)butanoate and 2,5-dioxopyrrolidin-1-yl 8-(pyridin-2-yldisulfanyl)octananoate. The most preferred crosslinker is succinimidyl 3-(2-pyridyldithio)propionate (SPDP). Typically, the adaptor is covalently attached to the bifunctional crosslinker before the adaptor/crosslinker complex is covalently attached to the pore but it is also possible to covalently attach the bifunctional crosslinker to the pore before the bifunctional crosslinker/pore complex is attached to the adaptor.

The site of covalent attachment is selected such that the adaptor facilitates interaction of nucleotides released from or present in the target nucleic acid sequence with the pore and thereby allows detection of nucleotides. This can be done as explained in the co-pending International application claiming priority from U.S. Application No. 61/078,687 and being filed simultaneously with this application [J A Kemp & Co Ref: N. 104403A; Oxford Nanolabs Ref: ONL IP 004].

For pores based on α-HL, the correct orientation of the adaptor within the barrel or channel of the pore and the covalent attachment of adaptor to the pore can be facilitated as described in the co-pending International application claiming priority from U.S. Application No. 61/078,687 and being filed simultaneously with this application [J A Kemp & Co Ref: N.104403A; Oxford Nanolabs Ref: ONL IP 004]. Any of the specific modifications to SEQ ID NO: 2 disclosed in the co-pending application are equally applicable to the pores of this invention. In particular, every subunit of the pore, including the construct(s), preferably has a glutamine at position 139 of SEQ ID NO: 2. One or more of the subunits of the pore, including the construct(s), may have an arginine at position 113 of SEQ ID NO: 2. One or more of the subunits of the pore, including the construct(s), may have a cysteine at position 119, 121 or 135 of SEQ ID NO: 2. Any of the variants of SEQ ID NO: 2 shown in SEQ ID NOs: 4, 6, 8, 10, 12 and 14 of the co-pending application may be used to form a modified pore of the invention.

Preferred modified pores of the invention comprise:

(a) a construct comprising the sequence shown in SEQ ID NO: 18, 20, 22, 24, 26, 28 or 30 or a variant thereof and six subunits of α-HL M113R/N139Q shown in SEQ ID NO: 4;

(b) a construct of the invention comprising the sequence shown in SEQ ID NO: 2 or a variant thereof, five subunits of α-HL M113R/N139Q shown in SEQ ID NO: 4 or a variant thereof and one subunit of α-HL M113R/N139Q/G119C-D8 shown in SEQ ID NO: 10 of the co-pending application;

(c) a a construct of the invention comprising the sequence shown in SEQ ID NO: 2 or a variant thereof, five subunits of α-HL M113R/N139Q shown in SEQ ID NO: 4 or a variant thereof and one subunit of α-HL M113R/N139Q/N121C-D8 shown in SEQ ID NO: 12 of the co-pending application; or (d) a construct of the invention comprising the sequence shown in SEQ ID NO: 2 or a variant thereof, five subunits of α-HL M113R/N139Q shown in SEQ ID NO: 4 or a variant thereof and and one subunit of α-HL M113R/N139Q/L135C-D8 shown in SEQ ID NO: 14 of the co-pending application.

Methods of Producing Constructs of the Invention

The invention also provides methods of producing a construct of the invention. The methods comprise covalently attaching a nucleic acid handling enzyme to a transmembrane protein pore subunit. Any of the subunits and enzymes discussed above can be used in the methods. The site of and method of covalent attachment are selected as discussed above.

The methods also comprise determining whether or not the construct is capable of forming a pore and handling nucleic acids. Assays for doing this are described above. If a pore can be formed and nucleic acids can be handled, the subunit and enzyme have been attached correctly and a construct of the invention has been produced. If a pore cannot be formed or nucleic acids cannot be handled, a construct of the invention has not been produced.

Methods of Producing Modified Pores

The present invention also provides methods of producing modified pores of the invention. The modified pore may be formed by allowing at least one construct of the invention to form a pore with other suitable subunits or by covalently attaching an enzyme to a subunit in an oligomeric pore. Any of the constructs, subunits, enzymes or pores discussed above can be used in the methods. The site of and method of covalent attachment are selected as discussed above.

The methods also comprise determining whether or not the pore is capable of handling nucleic acids and detecting nucleotides. The pore may be assessed for its ability to detect individual nucleotides or short chains of nucleotides, such as di- or trinucleotides. Assays for doing this are described above and below. If the pore is capable of handling nucleic acids and detecting nucleotides, the subunit and enzyme have been attached correctly and a pore of the invention has been produced. If a pore cannot be handle nucleic acids and detect nucleotides, a pore of the invention has not been produced.

In a preferred embodiment, a heteroheptamer of seven subunits comprising the sequence shown in SEQ ID NO: 2 or a variant thereof and containing one cysteine in an appropriate place is reacted with a bifunctional cross-linker. The pore may be reacted with the linker before or after it has been purified, typically by SDS PAGE. The pore/linker construct is then reacted with an enzyme containing at least one reactive cysteine, for instance on a genetically-fused peptide linker. After the coupling reaction, the modified pore of the invention is removed from any unreacted enzyme or pore/linker construct.

Method of Purifying Pores

The present invention also provides methods of purifying modified pores of the invention. The methods allow the purification of pores comprising at least one construct of the invention. The methods do not involve the use of anionic surfactants, such as sodium dodecyl sulphate (SDS), and therefore avoid any detrimental effects on the enzyme part of the construct. The methods are particularly good for purifying pores comprising a construct of the invention in which the subunit and enzyme have been genetically fused.

The methods involve providing at least one construct of the invention and any remaining subunits required to form a pore of the invention. Any of the constructs and subunits discussed above can be used. The construct(s) and remaining subunits are inserted into synthetic lipid vesicles and allowed to oligomerise. Methods for inserting the construct(s) and remaining subunits into synthetic vesicles are well known in the art.

The synthetic vesicles should have similar properties to rabbit cell membranes, but should lack the rabbit cell membrane proteins. The vesicles may comprise any components and are typically made of a blend of lipids. Suitable lipids are well-known in the art. The synthetic vesicles preferably comprise 30% cholesterol, 30% phosphatidylcholine (PC), 20% phosphatidylethanolamine (PE), 10% sphingomyelin (SM) and 10% phosphatidylserine (PS).

The vesicles are then contacting with a non-ionic surfactant or a blend of non-ionic surfactants. The non-ionic surfactant is preferably an Octyl Glucoside (OG) or DoDecyl Maltoside (DDM) detergent. The oligomerised pores are then purified, for example by using affinity purification based on his-tag or Ni-NTA.

Methods of Sequencing Nucleic Acids

The present invention also provides methods of sequencing a target nucleic acid sequence. In one embodiment, the method comprises (a) contacting the target sequence with a pore of the invention, which comprises an exonuclease, such that the exonuclease digests an individual nucleotide from one end of the target sequence; (b) contacting the nucleotide with the pore so that the nucleotide interacts with the adaptor, (c) measuring the current passing through the pore during the interaction and thereby determining the identity of the nucleotide; and (d) repeating steps (a) to (c) at the same end of the target sequence and thereby determining the sequence of the target sequence. Hence, the method involves stochastic sensing of a proportion of the nucleotides in a target nucleic acid sequence in a successive manner in order to sequence the target sequence. Individual nucleotides are described above.

In another embodiment, the method comprises (a) contacting the target sequence with a pore of the invention so that the target sequence is pushed or pulled through the pore and a proportion of the nucleotides in the target sequence interacts with the pore and (b) measuring the current passing through the pore during each interaction and thereby determining the sequence of the target sequence. Hence, the method involves stochastic sensing of a proportion of the nucleotides in a target nucleic acid sequence as the nucleotides pass through the barrel or channel in a successive manner in order to sequence the target sequence.

Pores comprising a construct of the invention are particularly suited to these methods. In order to effectively sequence the nucleic acid, it is important to ensure that a proportion of the nucleotides in the nucleic acid is identified in a successive manner. The fixed nature of the enzyme means that a proportion of the nucleotides in the target sequence affects the current flowing through the pore.

The whole or only part of the target nucleic acid sequence may be sequenced using this method. The nucleic acid sequence can be any length. For example, the nucleic acid sequence can be at least 10, at least 50, at least 100, at least 150, at least 200, at least 250, at least 300, at least 400 or at least 500 nucleotides in length. The nucleic acid sequence can be naturally occurring or artificial. For instance, the method may be used to verify the sequence of a manufactured oligonucleotide. The methods are typically carried out in vitro.

The methods may be carried out using any suitable membrane/pore system in which a pore comprising a construct of the invention is inserted into a membrane. The methods are typically carried out using (i) an artificial membrane comprising a pore comprising a construct of the invention, (ii) an isolated, naturally occurring membrane comprising a pore comprising a construct of the invention, or (iii) a cell expressing a pore comprising a construct of the invention. The methods are preferably carried out using an artificial membrane. The membrane may comprise other transmembrane and/or intramembrane proteins as well as other molecules in addition to the pore of the invention.

The membrane forms a barrier to the flow of ions, nucleotides and nucleic acids. The membrane is preferably a lipid bilayer. Lipid bilayers suitable for use in accordance with the invention can be made using methods known in the art. For example, lipid bilayer membranes can be formed using the method of Montal and Mueller (1972). Lipid bilayers can also be formed using the method described in International Application No. PCT/GB08/000563.

The methods of the invention may be carried out using lipid bilayers formed from any membrane lipid including, but not limited to, phospholipids, glycolipids, cholesterol and mixtures thereof. Any of the lipids described in International Application No. PCT/GB08/000563 may be used.

Methods are known in the art for inserting pores into membranes, such as lipid bilayers. Some of those methods are discussed above.

Interaction Between the Pore and Nucleotides

The nucleotide or nucleic acid may be contacted with the pore on either side of the membrane. The nucleotide or nucleic acid may be introduced to the pore on either side of the membrane. The nucleotide or nucleic acid is typically contacted with the side of the membrane on which the enzyme is attached to the pore. This allows the enzyme to handle the nucleic acid during the method.

A proportion of the nucleotides of the target nucleic acid sequence interacts with the pore and/or adaptor as it passes across the membrane through the barrel or channel of the pore. Alternatively, if the target sequence is digested by an exonuclease, the nucleotide may interact with the pore via or in conjunction with the adaptor, dissociate from the pore and remain on the same side of the membrane. The methods may involve the use of pores in which the orientation of the adaptor is fixed. In such embodiments, the nucleotide is preferably contacted with the end of the pore towards which the adaptor is oriented. Most preferably, the nucleotide is contacted with the end of the pore towards which the portion of the adaptor that interacts with the nucleotide is orientated.

The nucleotides may interact with the pore in any manner and at any site. As discussed above, the nucleotides preferably reversibly bind to the pore via or in conjunction with the adaptor. The nucleotides most preferably reversibly bind to the pore via or in conjunction with the adaptor as they pass through the pore across the membrane. The nucleotides can also reversibly bind to the barrel or channel of the pore via or in conjunction with the adaptor as they pass through the pore across the membrane.

During the interaction between a nucleotides and the pore, the nucleotide affects the current flowing through the pore in a manner specific for that nucleotide. For example, a particular nucleotide will reduce the current flowing through the pore for a particular mean time period and to a particular extent. In other words, the current flowing through the pore is distinctive for a particular nucleotide. Control experiments may be carried out to determine the effect a particular nucleotide has on the current flowing through the pore. Results from carrying out the method of the invention on a test sample can then be compared with those derived from such a control experiment in order to identify a particular nucleotide.

Apparatus

The methods may be carried out using any apparatus that is suitable for investigating a membrane/pore system in which a pore comprising a construct of the invention is inserted into a membrane. The methods may be carried out using any apparatus that is suitable for stochastic sensing. For example, the apparatus comprises a chamber comprising an aqueous solution and a barrier that separates the chamber into two sections. The barrier has an aperture in which the membrane containing the pore is formed. The nucleotide or nucleic acid may be contacted with the pore by introducing the nucleic acid into the chamber. The nucleic acid may be introduced into either of the two sections of the chamber, but is preferably introduced into the section of the chamber containing the enzyme.

The methods may be carried out using the apparatus described in International Application No. PCT/GB08/000562.

The methods involve measuring the current passing through the pore during interaction with the nucleotides. Therefore the apparatus also comprises an electrical circuit capable of applying a potential and measuring an electrical signal across the membrane and pore. The methods may be carried out using a patch clamp or a voltage clamp. The methods preferably involves the use of a voltage clamp.

Conditions

The methods of the invention involve the measuring of a current passing through the pore during interaction with nucleotides in a target nucleic acid sequence. Suitable conditions for measuring ionic currents through transmembrane protein pores are known in the art and disclosed in the Examples. The method is carried out with a voltage applied across the membrane and pore. The voltage used is typically from −400 mV to +400 mV. The voltage used is preferably in a range having a lower limit selected from −400 mV, −300 mV, −200 mV, −150 mV, −100 mV, −50 mV, −20 mV and 0 mV and an upper limit independently selected from +10 mV, +20 mV, +50 mV, +100 mV, +150 mV, +200 mV, +300 mV and +400 mV. The voltage used is more preferably in the range 120 mV to 170 mV. It is possible to increase discrimination between different nucleotides by a pore of the invention by using an increased applied potential.

The methods are carried out in the presence of any alkali metal chloride salt. In the exemplary apparatus discussed above, the salt is present in the aqueous solution in the chamber. Potassium chloride (KCl), sodium chloride (NaCl) or caesium chloride (CsCl) is typically used. KCl is preferred. The salt concentration is typically from 0.1 to 2.5M, from 0.3 to 1.9M, from 0.5 to 1.8M, from 0.7 to 1.7M, from 0.9 to 1.6M or from 1M to 1.4M. High salt concentrations provide a high signal to noise ratio and allow for currents indicative of the presence of a nucleotide to be identified against the background of normal current fluctuations. However, lower salt concentrations are preferably used so that the enzyme is capable of functioning. The salt concentration is preferably from 150 to 500 mM. Good nucleotide discrimination at these low salt concentrations can be achieved by carrying out the method at temperatures above room temperature, such as from 30° C. to 40° C.

The methods are typically carried out in the presence of a buffer. In the exemplary apparatus discussed above, the buffer is present in the aqueous solution in the chamber. Any buffer may be used in the methods. One suitable buffer is Tris-HCl buffer. The methods are typically carried out at a pH of from 4.0 to 10.0, from 4.5 to 9.5, from 5.0 to 9.0, from 5.5 to 8.8, from 6.0 to 8.7 or from 7.0 to 8.8 or 7.5 to 8.5. The pH used is preferably about 7.5.

The methods are typically carried out at from 0° C. to 100° C., from 15° C. to 95° C., from 16° C. to 90° C., from 17° C. to 85° C., from 18° C. to 80° C., 19° C. to 70° C., or from 20° C. to 60° C. The methods may be carried out at room temperature. The methods are preferably carried out at a temperature that supports enzyme function, such as about 37° C. Good nucleotide discrimination can be achieved at low salt concentrations if the temperature is increased.

In addition to increasing the solution temperature, there are a number of other strategies that can be employed to increase the conductance of the solution, while maintaining conditions that are suitable for enzyme activity. One such strategy is to use the lipid bilayer to divide two different concentrations of salt solution, a low salt concentration of salt on the enzyme side and a higher concentration on the opposite side. One example of this approach is to use 200 mM of KCl on the cis side of the membrane and 500 mM KCl in the trans chamber. At these conditions, the conductance through the pore is expected to be roughly equivalent to 400 mM KCl under normal conditions, and the enzyme only experiences 200 mM if placed on the cis side. Another possible benefit of using asymmetric salt conditions is the osmotic gradient induced across the pore. This net flow of water could be used to pull nucleotides into the pore for detection. A similar effect can be achieved using a neutral osmolyte, such as sucrose, glycerol or PEG. Another possibility is to use a solution with relatively low levels of KCl and rely on an additional charge carrying species that is less disruptive to enzyme activity.

Exonuclease-Based Methods

In one embodiment, the method of sequencing a target nucleic acid sequence involves contacting the target sequence with a pore having an exonuclease enzyme, such as deoxyribonuclease, attached thereto. The constructs needed to make such pores are discussed above. Any of the exonuclease enzymes discussed above may be used in the method. The exonuclease releases individual nucleotides from one end of the target sequence. Exonucleases are enzymes that typically latch onto one end of a nucleic acid sequence and digest the sequence one nucleotide at a time from that end. The exonuclease can digest the nucleic acid in the 5' to 3' direction or 3' to 5' direction. The end of the nucleic acid to which the exonuclease binds is typically determined through the choice of enzyme used and/or using methods known in the art. Hydroxyl groups or cap structures at either end of the nucleic acid sequence may typically be used to prevent or facilitate the binding of the exonuclease to a particular end of the nucleic acid sequence.

The method involves contacting the nucleic acid sequence with the exonuclease so that the nucleotides are digested from the end of the nucleic acid at a rate that allows identification of a proportion of nucleotides as discussed above. Methods for doing this are well known in the art. For example, Edman degradation is used to successively digest single amino acids from the end of polypeptide such that they may be identified using High Performance Liquid Chromatography (HPLC). A homologous method may be used in the present invention.

The rate at which the exonuclease functions is typically slower than the optimal rate of a wild-type exonuclease. A suitable rate of activity of the exonuclease in the method of sequencing involves digestion of from 0.5 to 1000 nucleotides per second, from 0.6 to 500 nucleotides per second, 0.7 to 200 nucleotides per second, from 0.8 to 100 nucleotides per second, from 0.9 to 50 nucleotides per second or 1 to 20 or 10 nucleotides per second. The rate is preferably 1., 10, 100, 500 or 1000 nucleotides per second. A suitable rate of exonuclease activity can be achieved in various ways. For example, variant exonucleases with a reduced optimal rate of activity may be used in accordance with the invention.

Pushing or Pulling DNA Through the Pore

Strand sequencing involves the controlled and stepwise translocation of nucleic acid polymers through a pore. The majority of DNA handling enzymes are suitable for use in this application provided they hydrolyse, polymerise or process single stranded DNA or RNA. Preferred enzymes are polymerases, exonucleases, helicases and topoisomerases, such as gyrases. The enzyme moiety is not required to be in as close a proximity to the pore lumen as for individual nucleotide sequencing as there is no potential for disorder in the series in which nucleotides reach the sensing moiety of the pore.

The two strategies for single strand DNA sequencing are the translocation of the DNA through the nanopore, both cis to trans and trans to cis, either with or against an applied potential. The most advantageous mechanism for strand sequencing is the controlled translocation of single strand DNA through the nanopore with an applied potential. Exonucleases that act progressively or processively on double stranded DNA can be used on the cis side of the pore to feed the remaining single strand through under an applied potential or the trans side under a reverse potential. Likewise, a helicase that unwinds the double stranded DNA can also be used in a similar manner. There are also possibilities for sequencing applications that require strand translocation against an applied potential, but the DNA must be first "caught" by the enzyme under a reverse or no potential. With the potential then switched back following binding the strand will pass cis to trans through the pore and be held in an extended conformation by the current flow. The single strand DNA exonucleases or single strand DNA dependent polymerases can act as molecular motors to pull the recently translocated single strand back through the pore in a controlled stepwise manner, trans to cis, against the applied potential.

Kits

The present invention also provides kits for producing a modified pore for use in sequencing nucleic acids. In one embodiment, the kits comprise at least one construct of the invention and any remaining subunits need to form a pore. The kits may comprise enough constructs of the invention to form a complete pore (i.e. a homo-oligomer). The kits may comprise any of the constructs and subunits discussed above. A preferred kit comprises (i) a construct comprising a subunit comprising the sequence shown in SEQ ID NO: 2 or a variant thereof and (ii) six subunits comprising the sequence shown in SEQ ID NO: 2 or a variant thereof. A more preferred kit comprises (i) a construct comprising the sequence shown in SEQ ID NO: 18, 20, 22, 24, 26, 28 or 30 or a variant thereof and (ii) six subunits comprising the sequence shown in SEQ ID NO: 2 or a variant thereof.

In another embodiment, the kits comprise at least one polynucleotide sequence of the invention and polynucleotide sequences encoding any remaining subunits needed to form a pore. The kit may comprise enough polynucleotides of the invention to encode a complete pore (i.e. a homo-oligomer). The kits may comprise any of the polynucleotides described above. A preferred kit comprises (i) a polynucleotide sequence encoding a construct, which comprises a subunit comprising the sequence shown in SEQ ID NO: 2 or a variant thereof and (ii) six polynucleotide sequences each encoding a subunit comprising the sequence shown in SEQ ID NO: 2 or a variant thereof. A more preferred kit comprises (i) a polynucleotide sequence encoding a construct comprising the sequence shown in SEQ ID NO: 18, 20, 22, 24, 26, 28 or 30 or a variant thereof and (ii) six polynucleotide sequences each encoding a subunit comprising the sequence shown in SEQ ID NO: 2 or a variant thereof.

The kits of the invention may additionally comprise one or more other reagents or instruments which enable any of the embodiments mentioned above to be carried out. Such reagents or instruments include one or more of the following: suitable buffer(s) (aqueous solutions), means to obtain a sample from a subject (such as a vessel or an instrument comprising a needle), means to amplify and/or express polynucleotide sequences, a membrane as defined above or voltage or patch clamp apparatus. Reagents may be present in the kit in a dry state such that a fluid sample resuspends the reagents. The kit may also, optionally, comprise instructions to enable the kit to be used in the method of the invention or details regarding which patients the method may be used for. The kit may, optionally, comprise nucleotides.

The following Example illustrates the invention:

Example

1 Materials and Methods
1.1 Bacterial Strains and Growth Conditions

The bacterial strains used in this work were *E. coli* strains XL-10 Gold and BL21 DE3 pLysS (Stratagene). *E. coli* strains were grown at 370C either in Luria-Bertani Broth (LB), Terrific Broth at 225 rpm, Luria-Bertani agar (LA) or tryptone-yeast extract agar (TY) (Bertani. G. (1951). Studies on lysogenesis. I. The mode of phage liberation by lysogenic *Escherichia coli. Journal of Bacteriology.* 62, 293-300; Beringer, J. (1974). R factor transfer in *Rhizobium leguminosarum. Journal of General Microbiology.* 84, 188-98; and Tartoff, K. and Hobbs, C. (1987). Improved media for growing plasmid and cosmid clones. *Bethesda Research Labs Focus.* 9, 12). Antibiotics were used at the following concentrations: Ampicillin 100 µg ml$^{-1}$; chloramphenicol 30 µg ml$^{-1}$.

1.2 Genetic Manipulations

All general DNA cloning was performed as adapted methods of that previously described (Sambrook, J. and Russell, D. (2001). Molecular Cloning: A Laboratory Manual, 3rd Edition. Cold Spring Harbor Laboratory Press, Cold Spring Harbor, N.Y.). DNA polymerases, restriction endonucleases, exonuclease, ligases and phosphatases were all obtained from New England Biolabs. Exonuclease genes were manufactured by GenScript Corporation and received as fragments cloned into pT7-SC1, by BspEI or NdeI/HindIII. All mutations and fusion constructs were assembled in the expression vector pT7-SC1 (Cheley, S., Malghani, M., Song, L., Hobaugh, M., Gouaux, E., Yang, J. and Bayley, H. (1997). Spontaneous oligomerization of a staphylococcal alpha-hemolysin conformationally constrained by removal of residues that form the transmembrane beta-barrel. *Protein Engineering.* 10, 1433-43) and verified by sequencing using either the T7 forward or reverse primers, EcoExoIII_seq and EcoExoI_seq.

Site directed mutagenesis of the αHL gene was performed by in vivo homologous recombination of PCR products (Jones, D. (1995) PCR mutagenesis and recombination in vivo. In PCR primer: a laboratory manual. In: Dveksler, C. (ed). Cold Spring Harbor Laboratory Press, Cold Spring Harbor, N.Y.). Amplification of two halves of the target plasmid with complimentary primer pairs generates two PCR products with complimentary sequences at both the 5' and 3' ends. Transformation of both products into chemically competent *E. coli* allows in vivo homologous recombination. For all mutagenesis SC46 was used as the antisense primer for amplification of product 1 and SC47 as the sense primer for amplification of product 2. These complementary primer binding sites are within the β-lactamase gene of pT7-SC1. Colonies recovered on LA 100 ng µl$^{-1}$ ampicillin therefore indicated successful homologous recombination.

PCR was conducted in 50 µl reactions using 1 unit Phusion™ DNA polymerase, 0.2 mM dNTPs, 1 µM primers and 4 ng BamHI/HindIII or NdeI/EcoNI digested plasmid DNA. Reactions were cycled as follows: 1 cycle of 98° C. for 2 min; 30 cycles of 98° C. for 15 s, 57° C. for 30 s and 72° C. for 45 s; and a final extension of 72° C. for 5 min. 2.5 µl of each pair of PCR products were mixed and used to transform chemically competent *E. coli* (XL-10 Gold).

1.3 Rapid In Vitro Transcription Translation

[$^{35}$S]L-methionine labelled proteins were generated by coupled in vitro transcription and translation (IVTT) using an *E. coli* T7-S30 extract system for circular DNA (Promega). The complete amino acid mixture (1 mM) minus cysteine and the complete amino acid mixture (1 mM) minus methionine, supplied in the kit, were mixed in equal volumes to obtain the working amino acid solution required to generate high concentrations of the protein. Reactions were scaled up or down based on the following, for a 50 µl reaction volume: 20 µl S30 Premix solution; 5 µl amino acid mix; 1 µl [$^{35}$S]L-methionine (MP Biomedicals. 1175 Ci mmol$^{-1}$, 10 mCi ml$^{-1}$), 1 µl rifampicin (0.8 mg ml$^{-1}$), 8 µl plasmid DNA (400 ng µl$^{-1}$) and 15 µl. T7 S30 extract. Synthesis was carried out for 1.5 hours at 37° C. to produce 50 µl of radiolabelled IVTT protein. Different proteins were also co-expressed in one reaction as for coupled transcription, translation and oligomerisation. The reaction components remained the same except the DNA concentration was divided accordingly for each plasmid encoding each protein. Protein samples were centrifuged at 14,000 rpm for 10 minutes to separate insoluble debris of IVTT reactions.

1.4 In Vivo Protein Expression

Wild-type α-hemolysin and fusion constructs were cloned into the expression vector pT7-SC1, under the control of the inducible T7 promoter, and expressed in *E. coli* (BL21 DE3 pLysS. Stratagene) as soluble proteins. Cultures were grown to a high $OD_{600}$ (approximately 1.5-2) at 37° C. and 240 rpm in Terrific broth medium (100 µg µl$^{-1}$ ampicillin and 30 µg l$^{-1}$ chloramphenicol). The temperature was reduced to 18° C. and cultures left for 30 minutes to equilibrate. Over expression of the target protein was induced by addition of IPTG to the medium (0.2 mM). After 18 hours cells were pelleted at 10,000 rpm for 30 minutes at 4° C. Cells were resuspended and lysed by the addition of BugBuster (Novagen) supplemented with the addition of benzonase, EDTA-free proteinase inhibitors (Roche) and to 50 mM $MgCl_2$. Cell debris was pelleted by centrifugation at 10.000 rpm for 30 minutes at 4° C. and polyethyleneimine (PEI) added to the supernatant. The recovered supernatant was incubated for 30 mins at 4° C. after which precipitate was removed by centrifugation at 10,000 rpm for 30 minutes at 4° C. Clarified lysate was filtered and adjusted to pH 8.0, 500 mM NaCl, 10 mM Imidazole.

His-tagged proteins were purified as standard practice by Ni-NTA affinity chromatography and gel filtration. Non-tagged α-hemolysin subunits were purified as standard practice by cation exchange followed by gel filtration.

1.4.1 Affinity Purification (His-Tag)

Clarified lysate was filtered and adjusted to pH 8.0, 500 mM NaCl, 10 mM Imidazole before loading onto a His-Trap crude column (GE Healthcare) and eluted with 300 mM Imidazole. Fractions containing the protein of interest were combined and applied to a gel filtration column equilibrated with 10 mM TRIS pH 8.0, 100 mM NaCl, 1 mM DTT. Eluted protein was evaluated by SDS-PAGE.

1.4.2 Ion Exchange

Clarified lysate was filtered and adjusted to 10 mM MES pH 6.0 before loading onto a cation exchange column (GE Healthcare) and eluting with 0-500 mM NaCl. Fractions containing the protein of interest were combined and applied to a gel filtration column. Eluted protein was evaluated by SDS-PAGE.

To maintain the reactivity of engineered cysteine residues in α-Hemolysin derivatives, required as sites for chemical modification, proteins were purified using the same buffers but supplemented to 1 mM DTT. Exonucleases or exonuclease fusion proteins were purified using the same buffers supplemented to 1 mM $MgCl_2$.

1.5 Oligomerisation on Red Blood Cell Membranes

α-Hemolysin monomers were mixed in various molar ratios and allowed to oligomerise on rabbit erythrocyte membranes (2.5 mg protein ml$^{-1}$) for 1 hour at either room temperature, 30° C., 37° C. (or 42° C. After the incubation, reaction mixture was centrifuged at 14.000 rpm for 10 minutes and supernatant discarded. Membrane pellet was washed by resuspension in 200 µl MBSA (10 mM MOPS, 150 mM NaCl, pH 7.4 containing 1 mg ml$^{-1}$ bovine serum albumin) and centrifuging again at 14,000 rpm for 10 minutes. After discarding the supernatant, membrane pellet was dissolved in 75 µl of IX Laemmli sample buffer, with the addition of β-mercaptoethanol. The entire sample was loaded into a single well of a 5% SDS-polyacrylamide gel and elelctrophoresed for ~18 hours at 50 V, with 0.01 mM sodium thioglycolate included in the running buffer. Gel was vacuum-dried onto a Whatman 3 mm filter paper at 50° C. for about three hours and exposed to an X-ray film overnight (Kodak). The oligomer band was excised from the gel, using the autoradiogram as template, and the gel slice rehydrated in 300 µl TE buffer (10 mM Tris, 1 mM EDTA, pH 8.0) containing 2 mM DT. After removing the Whatman filter paper slice, gel piece was crushed using a sterile pestle. Oligomer protein was separated from gel debris by centrifuging through 0.2 UM cellulose acetate microfilterage tubes (Rainin) at 14.000 rpm for 30 min. Filtrate was stored in aliquots at −80° C.

1.6 Oligomerisation on Synthetic Lipid Vesicles

Synthetic lipid vesicles composed of: 30% cholesterol; 30% phosphatidylcholine (PC); 20% phosphatidylethanolamine (PE); 10% sphingomyelin (SM); 10% phosphatidylserine (PS); were prepared by bath sonication for 15 minutes at room temperature. Organic solvent is evaporated by a gentle stream of nitrogen until a dry film is produced. Deionised water added to give a required concentration of 2.5 mg ml$^{-1}$ and mixture bath sonicated again for 15 minutes. Wild-type α-hemolysin and fusion monomers were mixed in various molar ratios and allowed to oligomerise on synthetic lipid vesicles (2.5 mg ml$^{-1}$ for every 1 mg α-hemolysin monomer) for 1 hour at either room temperature, 30° C., 37° C. or 42° C. and 350 rpm. To pellet lipid associated proteins samples were centrifuged at 14,000 rpm for 10 minutes. Pellet was washed once in MBSA (10 mM MOPS, 150 mM NaCl, pH 7.4 containing 1 mg ml$^{-1}$ bovine serum albumin) and lipids were dissolved by addition of 0.1-1% n-Dodecyl-D-maltopyranoside (DDM), for 1 hour at either 4° C. or room temperature. To purify the fusion homo and heteroheptamers away from wild-type homoheptamer 300 µl of Ni-NTA agarose (Qiagen) was added and left overnight at 4° C. and 350 rpm. Affinity bound heptamer was pelted with Ni-NTA agarose by centrifugation at 14,000 rpm for 10 minutes. The Ni-NTA agarose beads were washed twice in 500 µl wash buffer (10 mM Tris, 10 mM Imidazole, 500 mM NaCl, pH 8.0) for 10 minutes and recovered by centrifugation. Purified heteroheptamer was eluted in 500 µl elution buffer (10 mM Tris, 250 mM Imidazole. pH 8.0) for 1 hour at 4° C. The Ni-NTA agarose was removed by centrifugation and the supernatant containing the eluted purified fusion heptamers removed. Eluted heptamers were de-salted by passage through a buffer exchange column (NAP-5, GE Healthcare), equilibrated with 10 mM Tris pH 8.0.

1.7 Exonuclease Fluorescence Assay

Recombinant *E. coli* Exonuclease III was purchased from New England Biolabs (100 units µl$^{-1}$). Double stranded DNA template labelled with a 5' fluorophore (5HEX) on the sense strand and a 3' black hole quencher (BHQ-2a-Q) on the antisense strand was obtained from Operon.

The oligo sequences are given below along with the respective fluorophore and quencher pair:

(SEQ ID NO: 31)
5'[5HEX]GCAACAGAGCTGATGGATCAAATGCATTAGGTAAACATGTTA
CGTCGTAA 3'

(SEQ ID NO: 32)
5'CGATCTTACGACGTAACATGTTTACCTAATGCATTTGATCCATCAGCT
CTGTTGC[BHQ2a]3'

The substrate dsDNA has a 5 bp overhang at the 5' end of the antisense strand, enabling initiation of exonuclease III on the 3' end of the sense strand.

Fluorescence measurements were taken using a Cary Eclipse (Varian) with an excitation and emission wavelength of 535 and 554 nm respectively and an excitation and emission slit of 5 nm. Measurements were taken every 4 seconds for 60 minutes. 40 µl reactions were performed at 37° C. and consisted of: 200 nm substrate dsDNA; 25 mM Tris pH 7.5; 1 mM MgCl$_2$; 100 mM KCl; 0.001 units Exo III; unless otherwise stated.

1.8 Planar Bilayer Recordings

All bilayers were formed by apposition of two monolayers of 1,2-diphytanoyl-sn-glycero-3-phosphocholine (Avanti Polar Lipids) across a 60-150 µm diameter aperture in Teflon film (25 µm thickness from Goodfellow, Malvern, Pa.), which divided a chamber into two buffer compartments (cis and trans) each with a volume of 1 ml. Bilayers were formed across the aperture by consecutively raising the buffer level in each compartment until a high resistance seal was observed (≥10 GΩ). Unless otherwise stated, fusion heptamers and DNA or dNMPs were added to the cis compartment, which was connected to ground. The adapter molecule am7βCD or am6-amPDP1-βCD was added to the trans compartment if required, which was connected to the headstage of the amplifier. Unless stated otherwise, experiments were carried out in 25 mM Tris.HCl, 400 mM KCl pH 8.0, at 22° C.

1.9 Exonucleases

Exonucleases, such as deoxyribonucleases, are a subgroup of the EC 3.1 enzymes. They catalyse the hydrolysis of the phosphodiester bond between adjacent bases in a DNA strand to release individual nucleoside 5' mono-phosphates (FIG. 1). Attractive activities catalyse the cleavage of this bond (through nucleophilic attack of an activated water molecule upon the phosphorus) as shown.

There are a limited number of distinct enzymatic activities that degrade nucleic acids into their component parts, although numerous homologues will exist in different organisms (for example, Exonuclease III). From a detailed literature search, the two most processive exonuclease enzymes are Exonuclease I, encoded by the sbcB gene of *E. coli*, and λ-exonuclease, encoded by the exo gene of bacteriophage λ (Thomas, K. and Olivera, B. (1978) Processivity of DNA exonucleases. Journal of Biological Chemistry. 253, 424-429; and Zagursky, R. and Hays, J. (1983). Expression of the phage lambda recombination genes exo and bet under lacPO control on a multi-copy plasmid. *Gene*. 23, 277-292). In addition, activity of Exonuclease I has been demonstrated in high salt concentrations (Hornblower, B., Coombs, A., Whitaker, R., Kolomeisky, A., Picone, S., Meller, A. Akeson, M. (2007). Single-molecule analysis of DNA-protein complexes using nanopores. *Nature Methods*. 4, 315-317). As λ exonuclease is a trimer the attachment of a functional exonuclease is more challenging so the monomeric enzyme Exonuclease III was also included, as despite its shorter processivity rate it also degrades one strand of dsDNA to yield nucleoside 5' monophosphates. Whilst Exo I degrades ssDNA in a 3'-5' direction RecJ acts 5'-3' and so was also included in this work (Lovett, S. and Kolodner, R. (1989). Identification and purification of a single-stranded-DNA-specific exonuclease encoded by the recJ gene of *Escherichia coli*. *Proceedings of the National Academy of Sciences of the United States of America*. 86, 2627-2631). Both ssDNA exonucleases have been demonstrated to interact and act cooperatively with single stranded binding protein (Genschel, J., Curth, U. and Urbanke, C. (2000) Interaction of *E. coli* single-stranded DNA binding protein (SSB) with exonuclease I. The carboxy terminus of SSB is the recognition site for the nuclease. *Biological Chemistry*. 381, 183-192; and Han, E., Cooper, D., Persky, N., Sutera, V., Whitaker, R., Montello, M. and Lovett, S. (2006). RecJ exonuclease: substrates, products and interaction with SSB. *Nucleic Acids Research*. 34, 1084-1091). The use of these proteins may be required to prevent secondary structure formation of the ssDNA substrate that may enzyme initiation or processivity in high salt concentrations.

Four exonucleases are used in this Example:

1. Exo III from *E. coli*, Monomeric, dsDNA, 3'-5' (SEQ ID NOs: 9 and 10)
2. Exo I from *E. coli*. Monomeric, ssDNA, 3'-5' (SEQ ID NOs: 11 and 12)
3. RecJ from *T. thermophilus*, Monomeric, ssDNA, 5'-3' (SEQ ID NOs: 13 and 14)
4. λ Exo from λ bacteriophage, Trimeric, dsDNA, 5'-3' (the sequence of one monomer is shown in SEQ ID NOs: 15 and 16)

Figure 2:
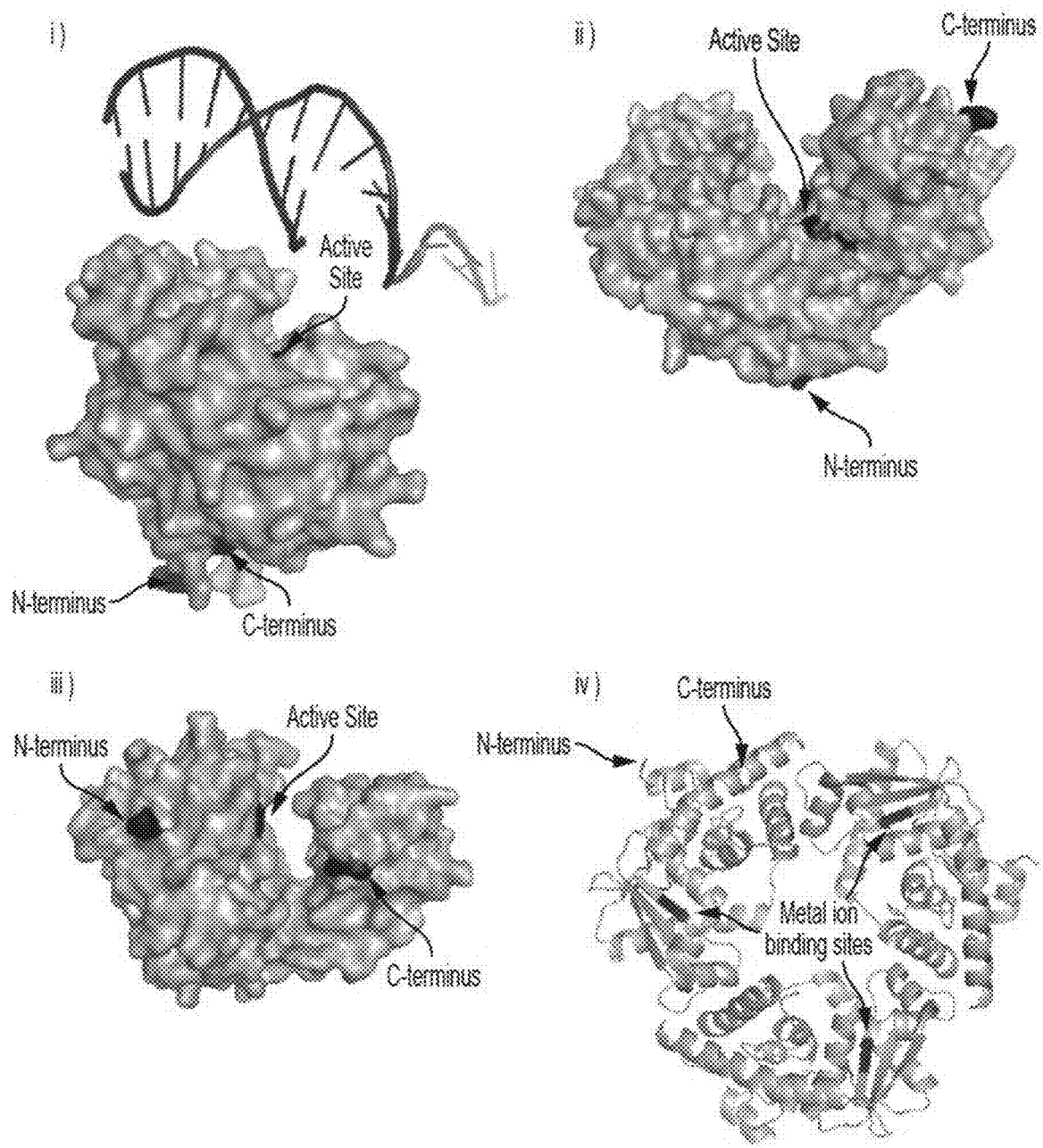
FIG. 2 shows the crystal structures of exonucleases used in the Example, N and C-terminus and active sites are shown for each. i) Adapted form of EcoExoIII; ii) EcoExoI; iii) TthRecJ-cd; and iv) Lambda exo.

High resolution crystal structures are available for all these enzymes (Mol, C., Kuo, C., Thayer, M., Cunningham, R. and Tainer, J. (1995) Structure and function of the multifunctional DNA-repair enzyme exonuclease III. *Nature*. 374, 381-386; Kovall, R. and Matthews, B. (1997). Toroidal structure of lambda-exonuclease. *Science*. 277, 1824-1827; and Busam, R. (2008). Structure of *Escherichia coli* exonuclease I in complex with thymidine 5'-monophosphate. *Acta Crystallographica*. 64, 206-210) and are shown in FIG. 2. The TthRecJ is the enzymes core domain as identified by Yamagata et al. (Yamagata, A., Masui, R., Kakuta, Y., Kuramitsu, S. and Fukuyama, K. (2001).

1.10 Genetic Attachment

Figure 3:
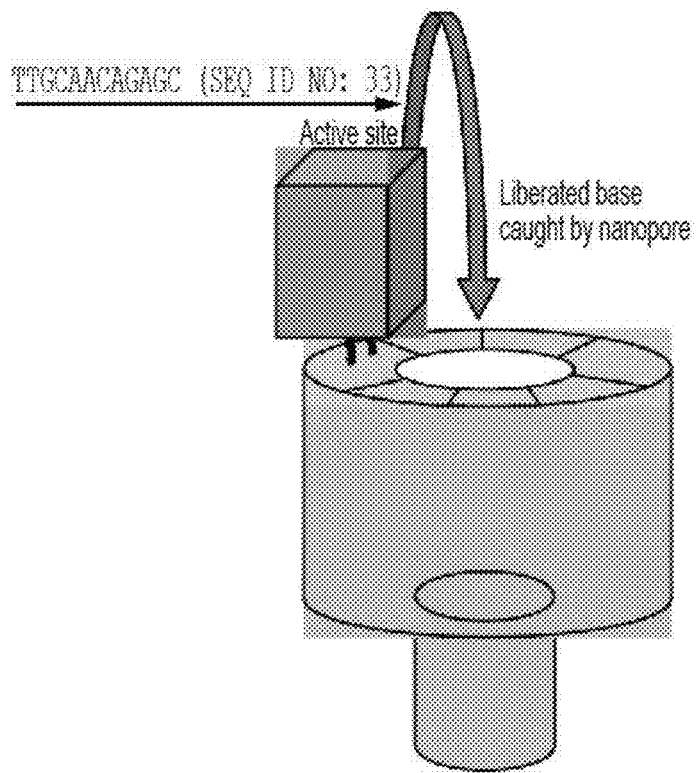
FIG. 3 shows a cartoon of an exonuclease equipped α-HL pore. The exonuclease is genetically fused to one of the seven monomers of the heptamer, with linker arms sufficiently long to enable correct protein folding of the exonuclease moiety and the α-HL moiety.

Taking the characteristics of the exonuclease as detailed above, the work described here was guided by the generation of a hypothetical model in which just one of the seven subunits of the αHL heptamer is modified to carry the exonuclease activity. FIG. 3 is a representation of the fusion construct assembled into a heteroheptamer with the exonuclease attached to a loop on the cis side of the protein. This model satisfies other additional desirable characteristics. An exonuclease fused on the cis side of the αHL heptamer under positive potential should release monophosphate nucleosides or ssDNA that will migrate from the cis to the trans side of the pore. This direction of migration is standard in much of the published literature of nanopore sensing. The genetic attachment of an exonuclease within a loop region also invariably means that the N and C terminal linkers can be designed to limit and constrain the mobility of the exonuclease in relation to the lumen of the pore.

In order to create a genetic fusion of the α-HL and the exonuclease proteins, genetic manipulation of the pre-existing expression plasmid pT7-SC1 carrying the wild-type α-HL gene was made (SEQ ID NO: 3). This plasmid carries the gene encoding the wild-type α-HL (SEQ ID NO: 1) without the benefit of any mutations that have been demonstrated to enhance the capacity of the pore to detect and discriminate monophosphate nucleosides. Unique BspEI restriction endonuclease sites were engineered into the α-HL gene at three specific locations, to enable insertion of the exonuclease gene, detailed below. Three plasmids are thus generated, with each one carrying just a single BspEI site for exonuclease gene infusion.

The first insertion site, L1, is located between residues T18 and T19 of the first loop region (N6-V20) of the α-hemolysin protein (SEQ ID NO: 6). The second insertion site, L2, is located between residues D44 and D45 of the start of the second loop region (D44-K50) of the α-hemolysin protein (SEQ ID NO: 7). The third insertion site, L2b, is located between residues K50 and K51 of the end of the second loop region (D44-K50) of the α-hemolysin protein (SEQ ID NO: 8).

Exonuclease genes were codon optimised for expression in E. coli and synthesised by GenScript Corporation (SEQ ID NOs: 10, 12, 15 and 16). Genes were flanked by regions encoding 10 residues of repeating serine-glycine. Such a protein sequence is believed to be substantially devoid of a defined secondary or tertiary structure. The terminal ends of the linkers were also defined by recognition sequences for the restriction endonuclease BspEI, as this sequence also encodes a serine and glycine that form part of the linker. The recognition site of this enzyme (TCCGGA) was similarly engineered into the three specific locations within the αHL gene to provide a means of inserting the exonuclease genes in frame at these defined locations.

Figure 4:
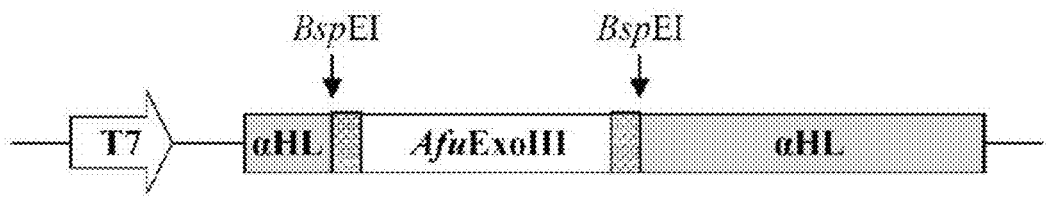
FIG. 4 shows generic image of the protein construct generated shows the BspEI insertion point(s) in the α-HL gene. Ligation AfuExoIII, bounded by two stretches of DNA encoding a (serine/glycine)×5 repeat (shown hatched) generates a fusion protein in which a 64.5 kDa protein will be generated, under the transcriptional control of the T7 promoter shown.

The recombinant gene encodes a fusion protein consisting of: a portion of αHL; a 10 serine-glycine linker region; an exonuclease; a 10 serine-glycine linker region; and the remaining portion of αHL. Once made, the chimeric gene construct was sequenced and verified to be as shown in FIG. 4.

Both the N and C-termini of α-hemolysin are suitable for genetic fusion to an enzyme. It has been shown that the 17 N-terminal residues, which constitute the amino latch, are dispensable for heptamer formation. Whilst it is not possible to delete more than 3 residues from the C-terminus, without effecting oligomerisation, it is already readily presented as a possible attachment point at the back of the cap domain (Walker, B. and Bayley. H. (1995). Key residues for membrane binding, oligomerization and pore-forming activity of Staphylococcal α-hemolysin identified by cysteine scanning mutagenesis and targeted chemical modification. The Journal of Biological Chemistry. 270, 23065-23071).

The attachment of enzymes at the N and C-terminus of α-hemolysin was carried out in a similar manner to that described above. The enzyme and α-hemolysin domains were again mediated by serine-glycine rich linkers to ensure the physical separation necessary for correct folding and spatial separation of each protein domain. The exact details of attachment are however detailed in a later section.

The hemolysin monomers were initially used as a wild-type monomer (wt), however we have shown that a HL-M113R/N139Q monomer shows improved base discrimination and the baseline was changed to this background. Further work showed that the base best resolution was achieved when an adapter molecule was attached to the L135C position, this was added to the hemolysin-exonuclease fusion in later constructs.

In the construct nomenclature, the monomer HL-M113R/N139Q is abbreviated to HL-RQ and the HL-M113R/N139Q/L135C monomer is abbreviated to HL-RQC. Therefore the fusion construct HL-(M113R/N139Q)$_6$(M113R/N139Q/L135C-EcoExoIII-L1-H6)$_1$ is shortened to HL-(RQ)$_6$(RQC-EcoExoIII-L1-H6)$_1$.

2 Results 2.1 Oligomerisation of Loop 1 Fusion Proteins

Water soluble α-hemolysin monomers can bind to and self-assemble on a lipid membrane to form a transmembrane pore of defined structure, via an intermediate heptameric prepore (Walker, B. and Bayley, H. (1995). Key residues for membrane binding, oligomerization and pore-forming activity of Staphylococcal α-hemolysin identified by cysteine scanning mutagenesis and targeted chemical modification. The Journal of Biological Chemistry. 270, 23065-23071). Fully assembled pores can then be isolated and recovered through SDS PAGE, for biophysical characterisation. Radiolabelled α-hemolysin monomers produced through in vitro transcription translation (IVTT) and oligomerised on purified rabbit red blood cell membranes, enable heptamers to be recovered from the gel using the autoradiograph as template. Modified monomers can also be incorporated into the heptamer in any number and at any of the subunit positions (1-7). The modified subunit also typically carries a poly-aspartate tail to allow the differential migration of homo or heteroheptamers on SDS PAGE for ease of purification for each variant (Braha, O., Walker, B., Cheley, S., Kasianowicz, J., Song, L., Gouaux, J. and Bayley, H. (1997). Designed protein pores as components for biosensors. Chemistry and Biology. 4, 497-505). Due to the size of the exonuclease proteins it was not expected that a poly-aspartate tail would be required on the fusion monomers, as the exonuclease alone should cause a significant shift in electrophoretic mobility to enable identification of individual heteroheptamers away from wild-type homoheptamer.

Figure 5:
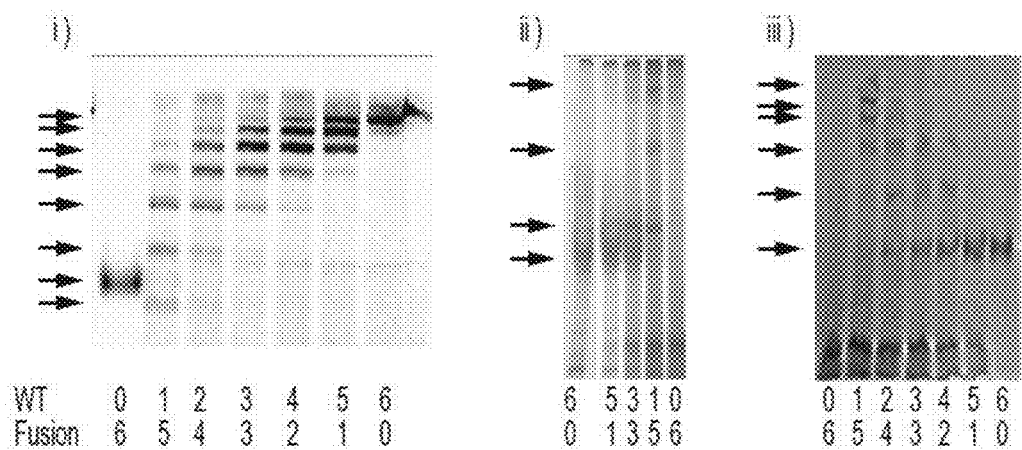
FIG. 5 shows the oligomerisation of α-HL Loop 1 fusion constructs with wild-type α-HL at different protein ratios. i) HL-wt-EcoExoIII-L1-H6; ii) HL-RQC-EcoExoI-L1-H6; and iii) HL-RQC-TthRecJ-L1-H6.

To determine if a mixture of HL-RQ and fusion monomers were able to form heteroheptamers [$^{35}$S]L-methionine labelled HL-RQ and fusion proteins (HL-wt-EcoExoIII-L1-H6 (SEQ ID NO: 18). HL-RQC-EcoExoIII-L1-H6 (SEQ ID NO: 20), HL-RQC-EcoExoI-L1-H6 (SEQ ID NO: 22) and HL-RQC-TthRecJ-L1-H6 (SEQ ID NO: 24) were expressed by IVTT and oligomerised on purified rabbit red blood cell membranes. The autoradiograph of the gel identified several putative heptamer bands of differing size for all enzyme fusions (FIG. 5).

To characterise these heptamer bands and to identify the ratio of subunits within each, proteins were excised from the gel. Heating heptamer at 95° C. for 10 minutes breaks the protein into its constitutive monomers, which can then be visualised on SDS PAGE for densitometry to determine the heptamer subunit composition. The different characteristic heptamer bands can then be identified as homo or heteroheptamers that consist of different ratios of wild-type and fusion α-HL monomers. This characterisation was performed for putative heptamer bands generated using both the HL-wt-EcoExoIII-L1-H6 and HL-RQC-EcoExoI-L1-H6 fusion proteins.

An importance for a sequencing application is that there preferentially be only one exonuclease moiety, ensuring bases are released only from a single DNA stand being processed at any one time. Electrophoretic migration of a 6:1 HL-monomer:HL-Exonuclease species away from other oligomers is therefore desired for ease of purification. Surprisingly, the HL-(RQ)$_6$(wt-EcoExoI-L1-H6)$_1$ heptamer migrates to a position slightly lower down the gel than HL-(RQ)$_7$, despite the presence of a ~36 kDa exonuclease being present on one of the subunits. This band also has a "doublet" appearance, possibly caused by incorrect incorporation of the fusion subunits amino latch due to the downstream insertion of the exonuclease in loop 1 or translation initiating at two points (the start of the fusion protein at hemolysin M1 and also at the first methionine of ExoIII) giving a mixed pool of fusion proteins. The EcoExoIII fusion protein gives formation of all theoretical heteroheptamer varieties and the wild-type and fusion protein homoheptamers. As a significantly smaller protein, ~36 kDa, and with its N and C terminus co-localised it is perhaps unsurprising that EcoExoIII performs better than EcoExoI or TthRecJ as an exonuclease suitable for inserting into loop regions to give good heteroheptamer formation. Both the EcoExoI and TthRecJ fusion proteins give still show formation of heteroheptamers, although with a limited number of fusion monomer subunits, but in contrast the 6:1 heteroheptamer of EcoExoIII these 6:1 heteroheptamers migrate to a position identical to HL-(RQ)$_7$.

Figure 6:
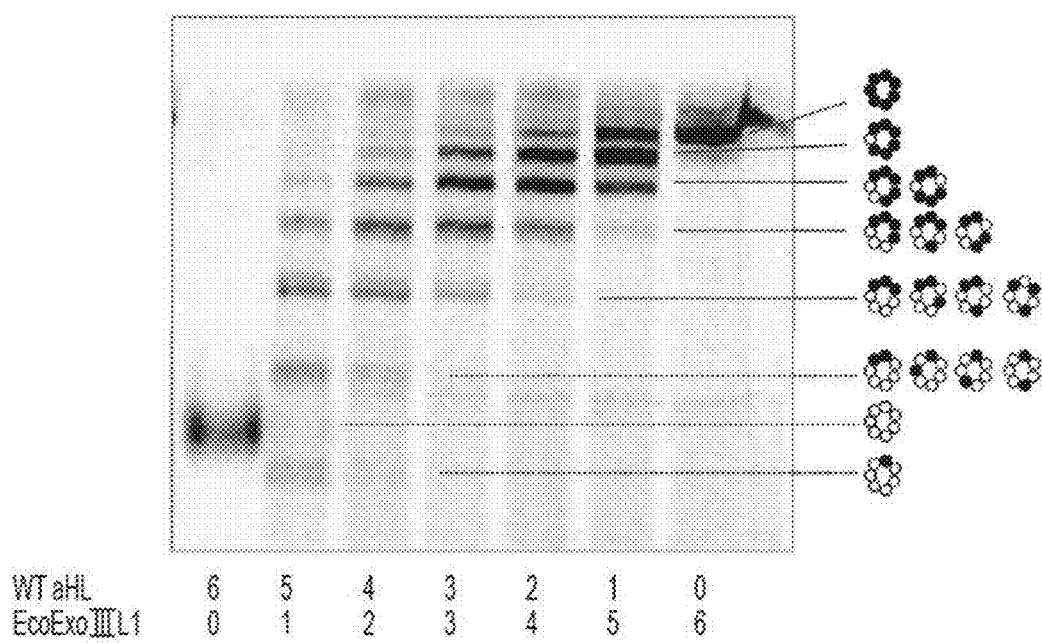
FIG. 6 shows the control of homo and heteroheptamer generation by different monomer ratios. HL-RQ subunits are shown in white and fusion subunits in black. Increasing the ratio of fusion subunits to wild-type subunits increases the generation of 2:5, 1:6 and 0:7 hetero and homo-heptamers. Similarly increasing the concentration of HL-RQ monomer increases the generation of 6:1 and 5:2 heteroheptamers.

It is an important consideration that by varying the ratio of wild-type to fusion monomer different bands corresponding to the different homo and heteroheptamers were observed. This allows the control of homo or heteroheptamer formation based on the molar ratio of different monomer subunits, which is important for the preferential generation of HL-(RQ)$_6$ (RQ-Exonuclease-H6)$_1$ (FIG. 6).

The conditions for the HL-(RQ)$_6$(wt-EcoExoIII-L1-H6)$_1$ heteroheptamer formation were optimised by varying the ratios of monomer proteins. A preferred ratio of 100:1 gives predominately formation of one type of heteroheptamer, HL-(RQ)$_6$(wt-EcoExoIII-L1-H6)$_1$, as well as wild-type homoheptamer, HL-(RQ)$_7$. Affinity purification by the hexa-His tag of the fusion subunit then allows separation of heteroheptamer from HL-RQ homoheptamer.

The HL-(wt-EcoExoIII-L1-H6)$_7$ homoheptamer and the HL-(RQ)$_6$(wt-EcoExoIII-L1-H6)$_1$ heteroheptamer bands were excised from the gel and the protein pores recovered by re-hydration and maceration of the gel slice. These isolated heptamers were both able to insert into planar lipid bilayers to give single channel recordings. The single channel trace for the HL-(wt-EcoExoIII-L1-H6)$_7$ homoheptamer, however, exhibited numerous blocking events at ≥80 mV. This could be attributed to the presence of seven denatured exonuclease peptide chains surrounding the cap domain, as these events were significantly less pronounced with the HL-(RQ)$_6$(wt-EcoExoIII-L1-H6)$_1$ heteroheptamer. The HL-(RQ)$_6$(wt-EcoExoIII-L1-H6) heteroheptamer gave an open pore current of ~160 pA and a heteroheptamer containing the mutations necessary for base discrimination HL-(RQ)$_6$(RQC-EcoExoIII-L1-H6)$_1$ showed covalent attachment of the β-cyclodextrin adapter molecule, which is characterised by an persistent current block to ~90 pA.

The construction of a fusion protein involves the linking of two proteins or domains of proteins by a peptide linker. Linker sequence with regard to length, flexibility and hydrophilicity is important so as not to disturb the functions of the domains. The linker regions of loop 1 fusion constructs were initially designed to be of sufficient length to allow the correct folding of both the exonuclease and α-hemolysin domains of the fusion protein. However, of importance to the release of monophosphate nucleosides in a proximity to the pore lumen is the length and conformation of the linker regions. At some point, however, the linkers will become too short to connect the subunits in their native conformation without strain, which may be particularly detrimental to exonuclease activity and probably oligomerisation. The length of the linkers was therefore reduced to (SG)$_4$, (SG)$_2$ and (SG)$_1$ to determine the effect on oligomerisation efficiency. For oligomerisation the shortened (SG)$_4$ and (SG)$_2$ linkers had no adverse effect on the efficiency of heteroheptamer formation. The effect of these shortened linkers on the enzyme activity was not determined but the (SG)$_4$ fusion protein showed increased expression of soluble protein, which is an indicator of correctly folded proteins.

Figure 7:
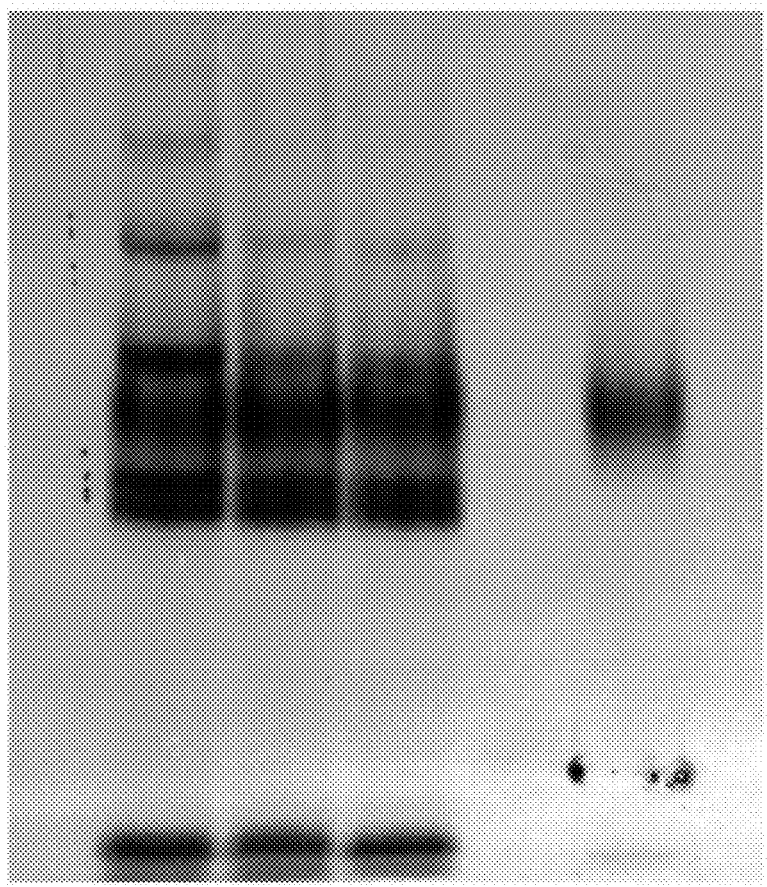
FIG. 7 shows the oligomerisation of HL-RQC-EcoExoIII-L1-H6 fusion proteins that contain a stiff polyproline EcoExoIII C-terminus linker. IVTT expressed proteins mixed in a 5:1 wild-type to fusion protein ratio in the presence of purified rabbit red blood cell membranes. i) HL-RQC-EcoExoIII-L1-{SG}5+{SG}5-H6; ii) HL-RQC-EcoExoIII-L1-{SG}5+5P-H6; iii) HL-RQC-EcoExoIII-L1-4SG+5P-H6; and iv) HL monomers.

The conformational flexibility of these linkers will also have an effect on the exonuclease position in relation to the pore lumen at any given time. While conformational flexibility may be required at the N and C-terminus linker juncture too much flexibility in the rest of the linker may be detrimental to the co-localisation of the exonuclease active site to the pore lumen. The absence of a β-carbon in glycine permits the polypeptide backbone to access dihedral angles that other amino acids cannot. Proline, as a cyclic imino acid, has no amide hydrogen to donate in hydrogen bonding so cannot fit into either α-helix or β-strand secondary structure. Poly-proline regions are therefore stiff with the absence of secondary structure. By in vivo homologous recombination of PCR products the 10 serine-glycine linker was replaced with 5 proline residues. The use of a rigid polyproline "molecular rulers" was the determined for loop 1 EcoExoIII constructs as the linker between the α-terminus of the exonuclease and the N-terminus of α-hemolysin (FIG. 7).

Heteroheptamer formation was not abolished demonstrating the potential use of polyproline as a linker between the C-terminus of EcoExoIII and α-hemolysin T19 for the fusion protein. Although both fusion proteins showed a lower yield of heteroheptamers where the fusion protein is predominant the formation in particular of HL-(RQ)$_6$(RQC-EcoExoIII-L1-H6)$_1$ was unaffected.

The use of different length flexible linkers and alternative rigid linkers for optimising the position and conformational freedom of the exonuclease in relation to the pore lumen, as well as a method for optimising the formation of preferentially 6:1 heteroheptamers, has been demonstrated.

2.2 Mutagenesis and Oligomerisation of Loop 2 Fusion Proteins

Figure 8:
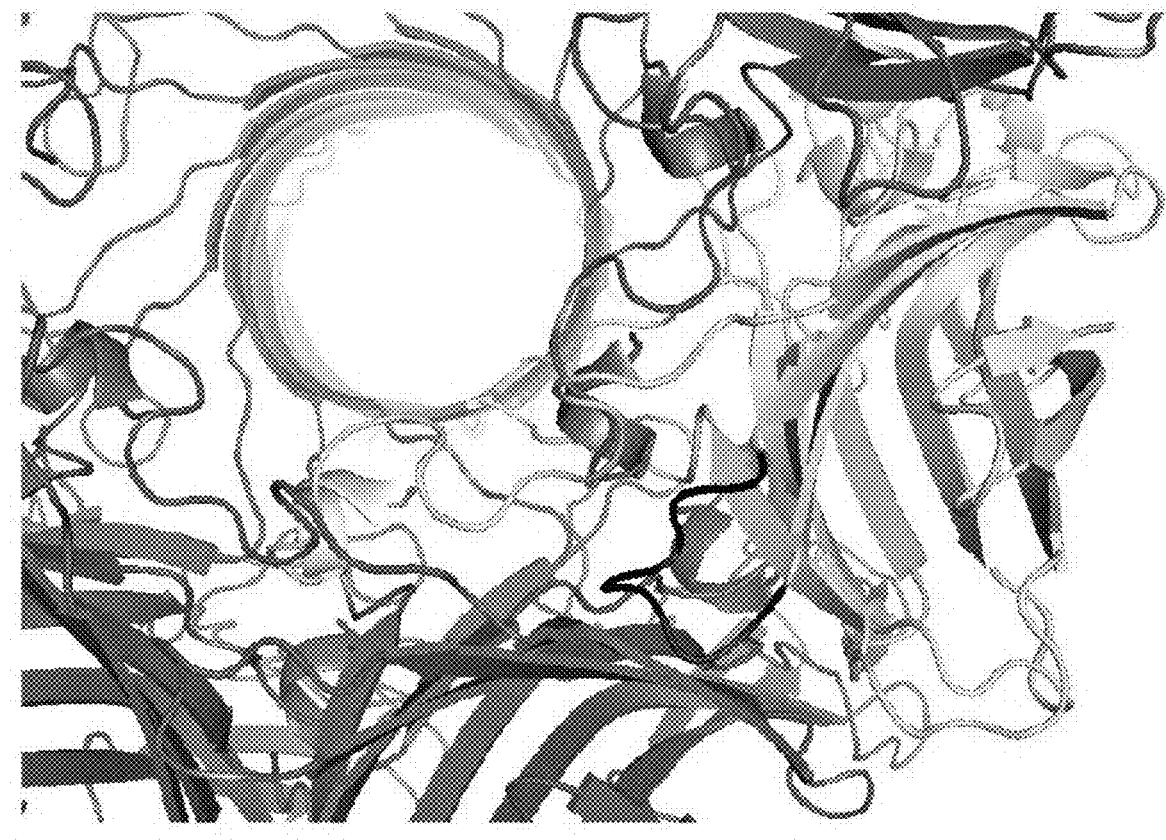
FIG. 8 shows the Loop 2 region of a single α-hemolysin subunit with the mature heptamer. Subunit 1 shown in white, subunits 2-7 shown in grey and the loop 2 region of subunit 1 shown in black.

The high yield of heteroheptamers generated by IVTT proteins for the EcoExoIII in loop 1 gave confidence for insertion of EcoExoIII into other loop regions, in particular both positions within loop 2 (FIG. 8). As this loop region connects two integral beta stands then it is likely that any enzymes that do not have a co-localised N and C-terminus will be too disruptive to the α-hemolysin domain, abolishing the ability of this protomer to oligomerise. Only very long linker regions may enable genetic attachment of EcoExoI or TthRecJ at these positions, due to their N and C-terminus localising to domains at distal ends of the respective enzymes.

The oligomerisation of the HL-RQC-EcoExoIII-L2a-H6 and HL-RQC-EcoExoIII-L2b-H6 fusion proteins was poor and only heptamers with an electrophoretic mobility similar to HL-(RQ)$_7$ and HL-(RQ)$_6$(RQC-EcoExoIII-L1-H6)$_1$ were observed. As oligomerisation of HL-RQC-EcoExoIII-L2a-H6 was slightly improved over the HL-RQC-EcoExoIII-L2b-H6 fusion protein, modification was carried out to improve the formation of heteroheptamer. Deletions of residues around the insertion site were made in an attempt to accommodate the terminal linker residues. In addition certain residues in loop 2 may be important for heptamer self-assembly. Sequence alignment of the α-hemolysin monomer with other β-pore forming toxin monomers, LukS and LukF, indicates loop 2 is a highly conserved region and in particular residue D45, which is the residue immediately after the exonuclease linker juncture. The crystal structure of the α-hemolysin heptamer also indicates that H48 is important to binding the amino latch of the adjoining subunit, at position T22 and D24 (Song, L., Hobaugh, M., Shustak. C., Cheley, S., Bayley, H. and Gouaux, E. (1996). Structure of Staphylococcal α-hemolysin, a heptameric transmembrane pore. Science. 274, 1859-1865). Attempts to modify the insertion point to accommodate and characterise these potentially important interactions were therefore made.

Figure 9:
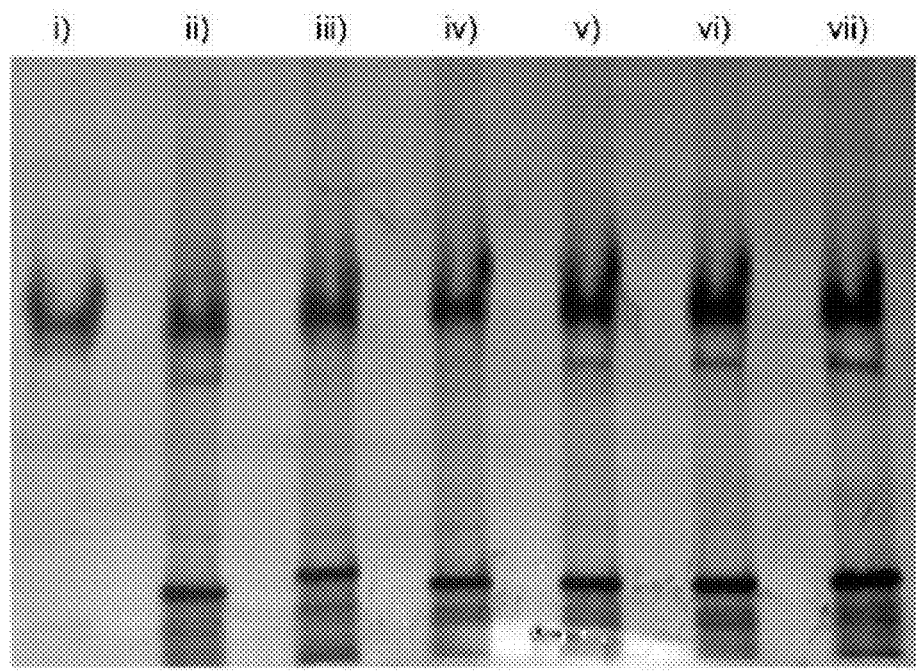
FIG. 9 shows the oligomerisation of alternative Loop 2 EcoExoIII fusion proteins. i) HL-(RQ)$_7$; ii) HL-(RQ)$_6$(RQC-EcoExoIII-L2a-H6)$_1$; iii) HL-(RQ)$_6$(RQC-EcoExoIII-L2a-8P-H6)$_1$; iv) HL-(RQ)$_6$(RQC-EcoExoIII-L2-H48Δ-H6)$_1$; v) HL-(RQ)$_6$(RQC-EcoExoIII-L2-D45Δ-H6)$_1$; vi) HL-(RQ)$_6$(RQC-EcoExoIII-L2-D45-K46Δ-H6)$_1$; and vii) HL-(RQ)$_6$(RQC-EcoExoIII-L2-D45-N47Δ-H6)$_1$.

Around the loop 2a EcoExoIII insertion site (D44-D45) residues D45, K46 and N47 were sequentially deleted by in vivo homologous recombination of PCR products. To determine the importance of H48 the site of insertion was also changed to lie between N47-N49, deleting H48 entirely. As previously stated linker flexibility can have an important effect of interaction of domains within a fusion protein. Therefore the flexible 10 serine glycine linkers were replaced with rigid 8 proline linkers in an attempt to confer greater domain separation. Each loop 2 fusion construct was expressed via IVTT and mixed in a 2.5:1 ratio with wild-type in the presence of purified rabbit red blood cell membranes. Any improvement in oligomerisation was determined by densitometry of the autoradiograph (FIG. 9).

Figure 10:
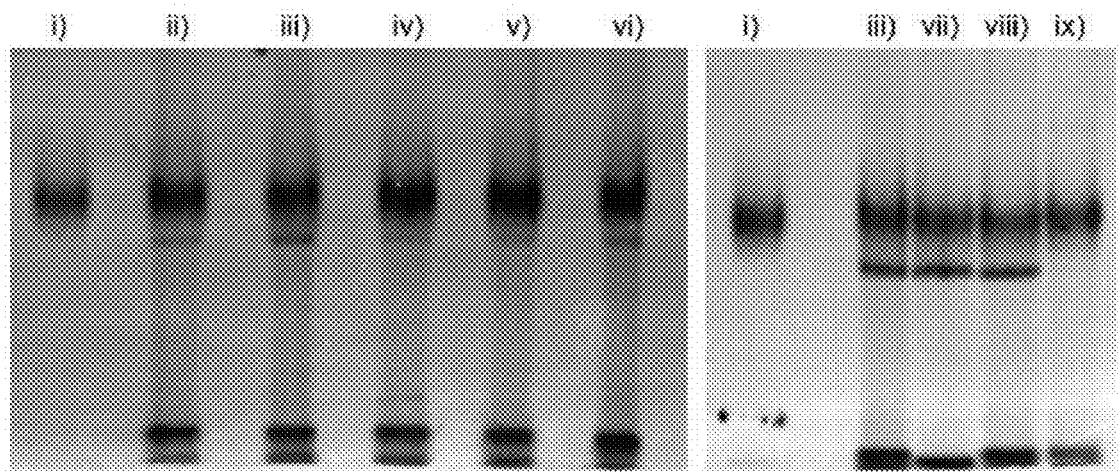
FIG. 10 shows the oligomerisation of alternative Loop 2 EcoExoIII fusion proteins. i) HL-(RQ)$_7$; ii) HL-(RQ)$_6$(RQC-EcoExoIII-L2a-H6)$_1$; iii) HL-(RQ)$_6$(RQC-EcoExoIII-L2-D45-N47Δ-H6)$_1$; iv) HL-(RQ)$_6$(RQC-EcoExoIII-L2-D46-K56Δ-H6)$_1$; v) HL-(RQ)$_6$(RQC-EcoExoIII-L2-D46Δ-H6)$_1$; vi) HL-(RQ)$_6$(RQC-EcoExoIII-L2-D46-N47Δ-H6)$_1$; vii) HL-(RQ)$_6$(RQC-EcoExoIII-L2-A1-S16Δ/D46-N47Δ-H6)$_1$; viii) HL-(RQ)$_6$(RQC-EcoExoIII-L2-F42-D46Δ-H6)$_1$; and ix) HL-(RQ)$_6$(RQC-EcoExoIII-L2-143-D46Δ-H6)$_1$.

Oligomerisation of the L2 fusion protein was abolished when the flexibility of the linker was changed to a more rigid polyproline linker. In addition deletion of H48 and positioning of the exonuclease insertion between N47 and N49 abolished heteroheptamer formation. It appeared that only deletion of residues from around the D44-D45 insertion site improved oligomerisation of the fusion protein. To determine if this could further be improved residue D45 was added back to the loop 2 deletion fusion proteins in a position adjacent to D44, before the EcoExoIII insertion site (FIG. 10).

Heteroheptamer formation was not affected by the position of residue D45 and indeed adding back this residue to all fusion proteins was detrimental to oligomerisation, possibly as it reduced the number of residues deleted to accommodate the exonuclease by one as a consequence. Accommodating the exonuclease is therefore the key to improving the oligomerisation of the loop 2 fusion protein (as in SEQ ID NO: 26). The insertion site was varied further in an attempt to determine how close to the $\beta_2$ strand the insertion site could be. The position within the loop region could be important for the relative positioning of the EcoExoIII active site in relation to the pore lumen and it is predicted the closer to $\beta_2$ the better the presentation of cleaved monophosphate nucleosides. In each fusion construct the insertion site was not only varied but the following three residues of α-hemolysin at the C-terminus of EcoExoIII were deleted in order to accommodate the exonuclease. Oligomerisation of the alternative loop 2 fusion proteins HL-(RQ)$_6$(RQC-EcoExoIII-L2-D45-N47Δ-H6)$_1$, HL-(RQ)$_6$(RQC-EcoExoIII-L2-F42-D46Δ-H6)$_1$ and HL-(RQ)$_6$(RQC-EcoExoIII-L2-I43-D46Δ-H6)$_1$ determined that the insertion point can lie anywhere within the loop region but as soon as it breaks a region of secondary structure all oligomerisation is abolished (FIG. 10).

Whilst the linkers in the loop 2 fusion protein require some degree of flexibility, as determined by the fact that rigid polyproline linkers could not substitute, the length can be reduced. The linker regions were shortened as for the loop 1 EcoExoIII fusion protein to (SG)$_4$, (SG)$_3$, (SG)$_2$ and (SG)$_1$ to determine the effect on oligomerisation efficiency. For oligomerisation the shortened (SG)$_4$, (SG)$_3$ and (SG)$_2$ linkers had no adverse effect on the efficiency of heteroheptamer formation. The effect of these shortened linkers on the enzyme activity was not, however, determined.

2.3 Genetic Attachment at the N and C-Terminus of α-Hemolysin

Figure 11:
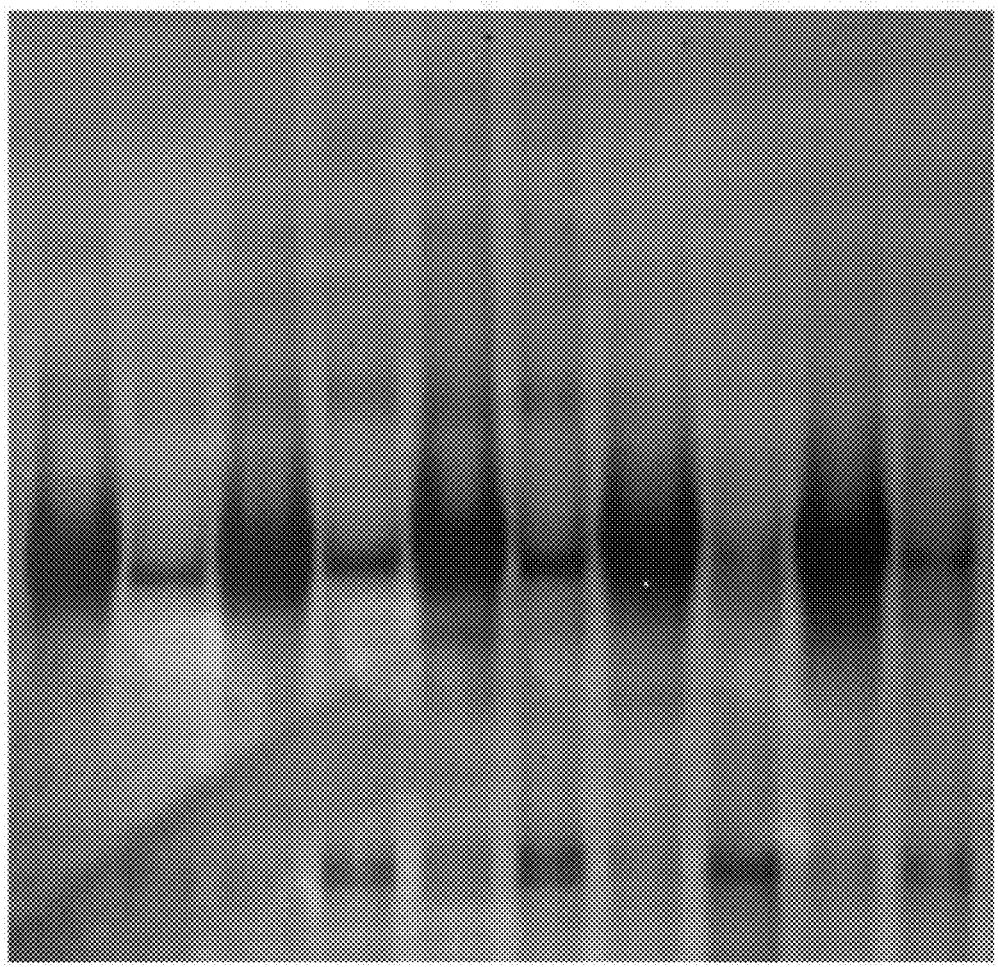
FIG. 11 shows the oligomerisation of EcoExoI C-terminus fusion proteins. a) denotes both hemolysin and enzyme-fusion protein monomers are radiolabelled, b) denotes only the fusion protein monomer is radiolabelled. i) HL-(RQ)$_6$(RQC-EcoExoI-Cter-{SG}8-H6)$_1$; ii) HL-(RQ)$_6$(RQC-EcoExoI-Cter-DG{SG}8-H6)$_1$; iii) HL-(RQ)$_6$(RQC-EcoExoI-Cter-WPV{SG}8-H6)$_1$; iv) HL-(RQ)$_6$(RQC-EcoExoI-Cter-DGS{P}12-H6)$_1$; and v) HL-(RQ)$_6$(RQC-EcoExoI-Cter-WPV{P}12-H6)$_1$.

Genetic attachment of two proteins, typically an enzyme to an antibody, has previously focused on the fusion of one protein's C-terminus to another protein's N-terminus, mediated by a peptide linker. As previously mentioned strategies for the attachment of a DNA handling enzyme to the C or N-terminus of α-hemolysin was considered, in particular the attachment of EcoExoI and the Klenow fragment. Attachment of EcoExoI at the C-terminus was mediated by five different linkers in order to determine the optimum fusion protein for oligomerisation. As the C-terminus is at the back of the α-hemolysin cap domain a turn of approximately 180° was desired. In order to initiate this turn either a Gly-Asp or Trp-Pro-Val motif was added at the start of the linker peptide. Two linker peptides were also used, either a flexible 16 serine-glycine or a 12 polyproline. As early results from the EcoExoI loop 1 fusion protein indicated that the 6:1 heteroheptamer had the same electrophoretic mobility as wild-type homoheptamer then a mixture of radiolabelled and non-radio labelled IVTT monomers were used for oligomerisation. Monomers were mixed in a 1:1 ratio and oligomerised on purified rabbit red blood cell membranes (FIG. 11).

Although the predominant fusion protein produced is the 6:1 heteroheptamer this migrates to the same position as the HL-(RQ)$_7$ homoheptamer. Therefore the proteins corresponding to HL-(RQ)$_5$(RQC-EcoExoI-Cter-{SG}8-H6)$_2$, HL-(RQ)$_5$(RQC-EcoExoI-Cter-DG{SG}8-H6)$_2$ as well as the HL-(RQ)$_5$(RQC-EcoExoI-L1-H6)$_2$ heteroheptamer from an earlier experiment were purified from SDS and the ability to insert into planar lipid bilayers determined. All heteroheptamers were capable of inserting into the lipid bilayer to give single channel recordings.

The success for fusion of the EcoExoI at the C-terminus of α-hemolysin mediated by an (SG)$_8$ and DG(SG)$_8$ peptide linker provides the method for the later attachment of other DNA handling enzymes via genetic fusion, such as the Klenow fragment (SEQ ID NOs: 28 and 30). The advantages of the Klenow fragment are the fact it provides a molecular motor for strand sequencing and also shows some resistance to SDS PAGE (Akeson, Personal Communication).

2.4 Non-SDS PAGE Purification of Heptamers

Figure 12A:
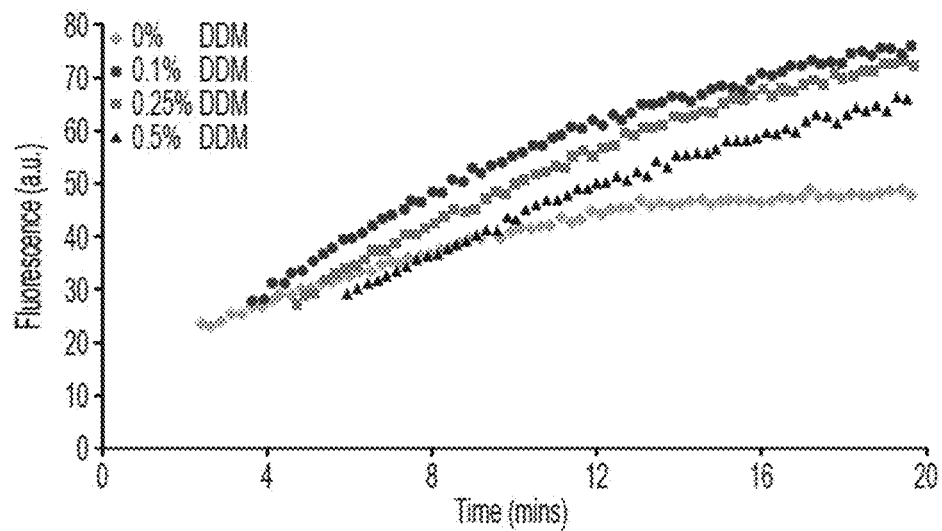
FIGS. 12A and 12B show the effect of different surfactants on EcoExoIII activity. Bottom graph (FIG. 12B)—Sodium dodecyl sulphate (SDS): a; 0%, b; 0.1%, c; 0.5%. Top graph (FIG. 12A)—n-Dodecyl-D-maltopyranoside (DDM): a; 0%, b; 0.1%, c; 0.25%, d; 0.5%.
Figure 12B:
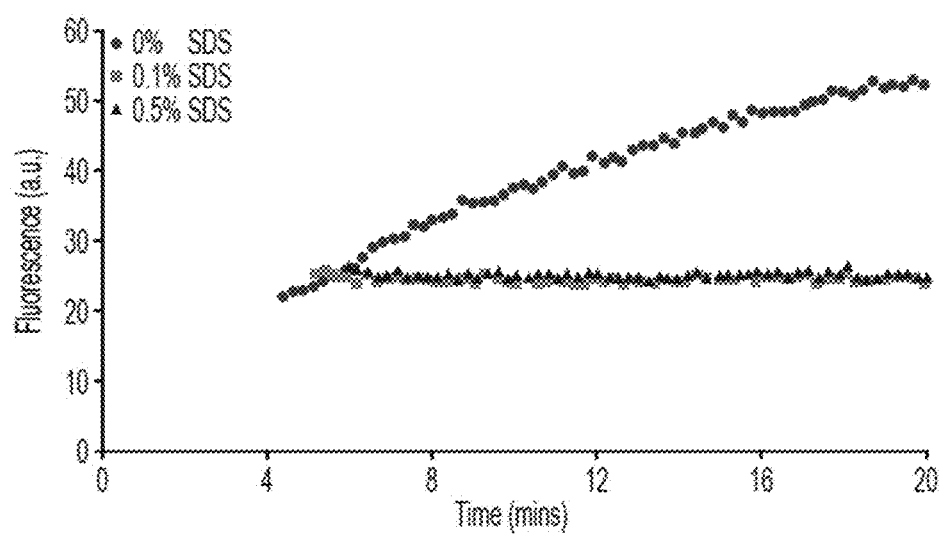

Sodium dodecyl sulphate (SDS) is an anionic surfactant that is highly denaturing to proteins, due to its ability to disrupt non-covalent bonds and bind to the peptide chain. As existing heptamer purification techniques rely on the use of SDS PAGE then the effect of this detergent on EcoExoIII was determined by a fluorescence based activity assay (FIG. 12, left panel).

Even a low concentration of SDS abolished EcoExoIII activity for the native enzyme, making the classical SDS PAGE purification of heptamers denaturing with regard to the exonuclease moiety of a fusion protein heteroheptamer. An alternative purification method was developed therefore using the alternative detergent, n-dodecyl-D-maltopyranoside (DDM). The effect of this surfactant on the EcoExoIII was determined and found to be non-denaturing to the native enzyme (FIG. 12, right panel). Following oligomerisation on rabbit red blood cell membranes instead of purifying heptamers via SDS PAGE the lipid membranes were dissolved by addition of 0.1% DDM for 15 minutes. Heteroheptamers were then purified away from the wild-type homoheptamer by affinity purification to the hexa-His tag on the C-terminus of the fusion protein. A buffer exchange further removed any surfactant and heptamers were then used for single channel recordings. This method does not distinguish entirely between heteroheptamers so the formation of 5:2 was limited by optimising the ratios of monomers mixed.

Purification via DDM extraction produced heptamers that showed an increased number of blocking events and surfactant behaviour on the lipid bilayer in single channel recordings. Whilst the cause of this instability remains undetermined, it is likely to be a result of other membrane proteins released from the rabbit red blood cell membranes, either affecting the lipid bilayer directly or else increasing the protein associated surfactant carryover. Oligomerisation of α-hemolysin monomers is classically facilitated either on purified rabbit red blood cell membranes or deoxycholate micelles. The yield of heptamer from deoxycholate is too poor in this instance to be of use and as previously mentioned the use of purified rabbit red blood cell membranes led to lipid bilayer instability. As an alternative, synthetic lipid vesicles were developed based on the lipid composition of rabbit red blood cell membranes, which lack other the membrane proteins of rabbit red blood cell membranes. These are composed of 30% cholesterol, 30% phosphatidylcholine (PC), 20% phosphatidylethanolamine (PE), 10% sphingomyelin (SM) and 10% phosphatidylserine (PS). The synthetic lipid vesicles developed here give approximately the same efficiency of heptamerisation as observed for rabbit red blood cell membranes. Heptamers purified from these synthetic lipid vesicles by DDM extraction also showed a dramatic decrease in the occurrences of lipid bilayer instability.

Figure 13:
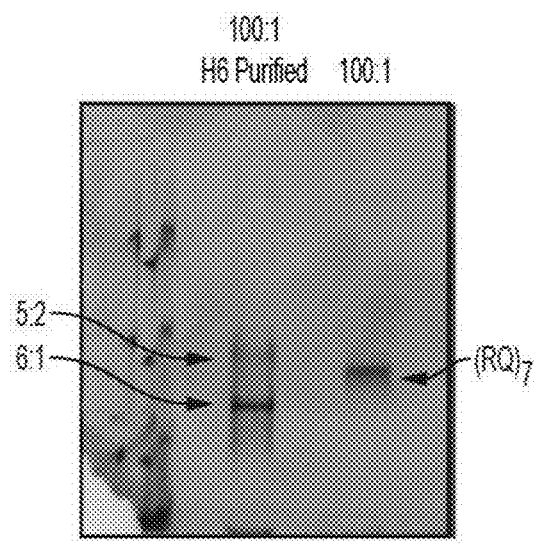
FIG. 13 shows the oligomerisation of E. coli BL21 (DE3) pLysS expressed α-hemolysin monomers for formation and purification of preferentially 6:1 heteroheptamers. His-tag purification is used to select between heteroheptamers and wild-type homoheptamer to give a large excess of 6:1 heteroheptamer.

Oligomerisation and DDM purification of heptamers was also determined for *E. coli* expressed proteins. Expression of wild-type and fusion monomers in *E. coli* gives a concentration sufficient for large scale production of enzyme pores, typically 3 mg ml$^{-1}$ and 1 mg ml$^{-1}$ respectively. Monomers were oligomerised on synthetic lipid vesicles at a ratio of 100:1 (wild-type:fusion) and purified as detailed previously (FIG. 13).

High level *E. coli* expression of monomers that can be oligomerised on synthetic lipid vesicles was achieved. Purification of the 6:1 heteroheptamer was also achieved in conditions that are non-denaturing to enzymes, ensuring activity of the pores exonuclease moiety.

2.5 Enzymatic Activity of Fusion Protein Heptamers

Figure 14:
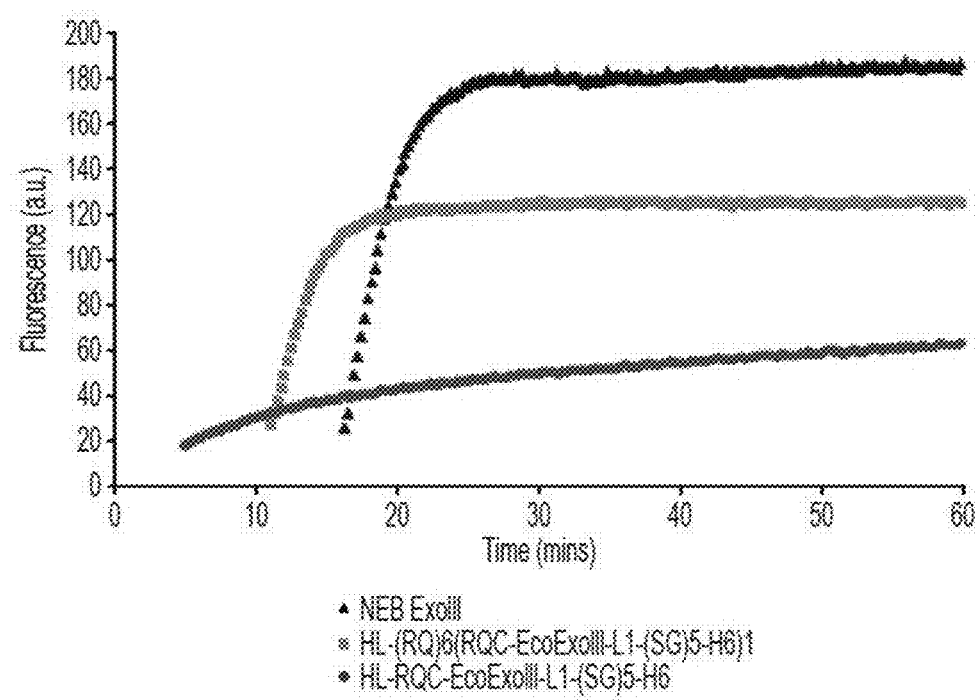
FIG. 14 shows the exonuclease activity of monomer and heteroheptamer fusion proteins. Left graph—Activity of Wild-type and fusion monomers: a, $10^{-2}$ dilution HL-RQC-EcoExoIII-L1-H6; b, $10^{-4}$ dilution HL-RQC-EcoExoIII-L1-H6; c, $10^{-6}$ dilution HL-RQC-EcoExoIII-L1-H6; d, $10^{-2}$ dilution HL-RQ. Right graph—Activity of HL-(RQ)$_6$(RQC-EcoExoIII-L1-H6)$_1$: a, DDM crude extract; b. Ni-NTA purified; c. Ni-NTA purified and buffer exchange.
Figure 15:
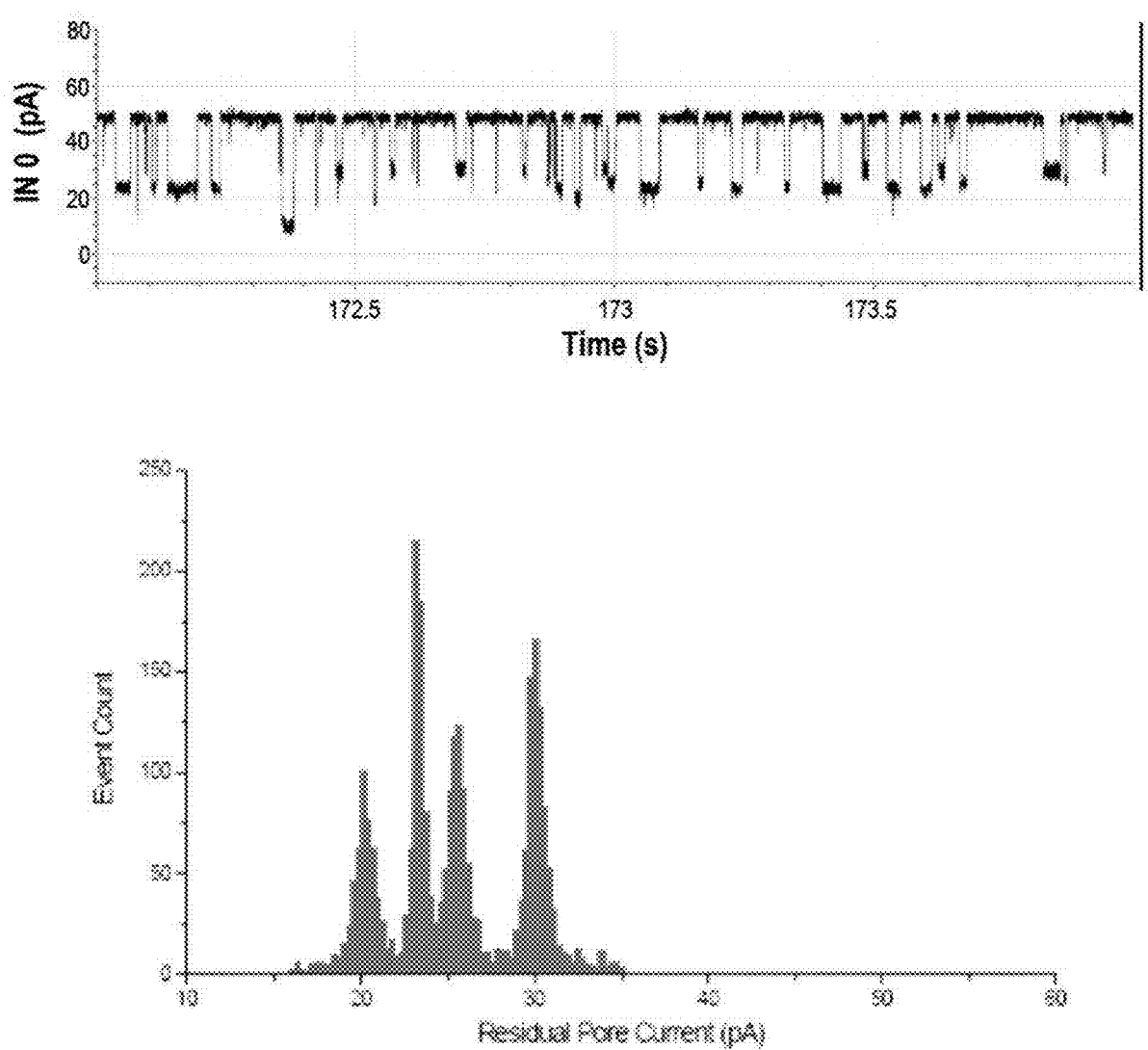
FIG. 15 shows base detection by the HL-(RQ)$_6$(RQC-EcoExoIII-L2-D46-N47Δ-H6) heteroheptamer. The top trace was obtained from a heteroheptamer with a covalently attached am$_6$-amPDP$_1$-βCD adapter molecule. Further blocking events can be seen and ascribed to individual mono-phosphate nucleosides for base discrimination. The bottom graph shows the corresponding histograms of dNMP events from the top trace. Peaks, from left to right, correspond to G, T, A, C respectively. Data acquired at 400/400 mM KCl, 180 mV and 10 µM dNMPs.

As the terminal ends of the enzyme are conformationally constrained within loop regions of the α-hemolysin monomer then the dynamic movements of the exonuclease domains necessary for activity could be impacted. The native enzyme (Exonuclease III, NEB)) was able to cleave nucleotides from the dsDNA substrate to a point where the sense strand was no longer of sufficient length to hybridise to the antisense strand (~8 bp). On dissociation of the DNA strands the fluorophore, at the 5' end of the sense strand, was sufficiently spatially separated from its quencher pair, at the 3' end of the antisense strand, giving a fluorescence increase relative to the enzyme activity. The activity of the native enzyme was also determined in a range of salt concentrations (0-1M KCl). Activity of the native enzyme was demonstrated in concentrations ≤300 mM KCl, which is within the experimental conditions required for single channel recordings and base discrimination. To determine if exonuclease activity of the EcoExoIII moiety on the fusion proteins was maintained after genetic attachment and oligomerisation, its activity was determined in this same fluorescence based DNA degradation assay (FIG. 14).

The EcoExoIII fusion proteins demonstrated retained exonuclease activity but as yet this is a qualitative rather than quantitative indication as amount of fusion protein was not determined. Therefore the effect of genetic fusion of the EcoExoIII to an α-hemolysin monomer on the rate of exonuclease activity cannot be determined as yet.

The exonuclease activity of the fusion protein was checked at all stages of purification and found to retain activity. Following oligomerisation and DDM purification the activity of fully formed pores was also checked and found to show some exonuclease activity. This demonstrates the ability to genetically couple an enzyme to a protein pore and still retain activity of the enzyme after expression and oligomerisation to a fully assembled pore.

2.6 Pore Forming Activity of Fusion Protein Heptamers.

As previously mentioned in the text the ability of a variety of different enzyme pore constructs to insert into lipid bilayers for single channel recordings has been shown. We have demonstrated that changes to the β-barrel of the α-hemolysin protein can enable covalent linkage and stabilisation of an adapter molecule for continuous base detection. For this the pore preferentially requires 6 subunits with mutations M113R/N139Q and 1 subunit with mutations M113R/N139Q/L135C. To determine if the exonuclease domain of the fusion protein within loop regions affected the ability of the pore to discriminate bases the M113R/N39Q/L135C mutations were made in the fusion constructs. As base discrimination preferentially requires a heteroheptamer with only one subunit carrying the L135C mutation and the enzyme pore preferentially one subunit being a fusion protein, the L135C mutation was made in the fusion protein. The wild-type M113R and N139Q construct from previous work was used for the other subunits. *E. coli* expressed HL-RQ and HL-RQC-EcoExoIII-L2-D46-N47Δ-H6 were oligomerised on synthetic lipid vesicles (at a ratio of 100:1) and purified by DDM extraction. The exonuclease activity of the fully formed pore was determined and indicated correct folding of the exonuclease moiety. The protein was also used for electrophysiology to determine firstly pore functionality and secondly if base discrimination was possible (FIG. 19).

The 6:1 heteroheptamer can be inserted into a lipid bilayer and a stable transmembrane current established. This current can be modulated by the introduction of β-cyclodextrin, and is further reduced by the addition of monophosphate nucleosides. The presence of the exonuclease domain appears to have no detrimental effect on current flow or the base discrimination by the pore. Although the work shown is for a heteroheptamer incorporating a fusion protein with the insertion of EcoExoIII at the loop 2 position, similar data was acquired for the loop 1 heteroheptamers.

Sequence listing

```
SEQ ID NO: 1
  1 ATGGCAGATT CTGATATCAA TATTAAAACC GGTACTACAG ATATTGGAAG CAATACTACA GTAAAAACAG
 71 GTGATTTAGT CAGTTATGAT AAAGAAAATG GCATGCACAA AAAAGTATTT TATAGTTTTA TCGATGATAA
141 AAATCACAAT AAAAAACTGC TAGTTATTAG AACAAAAGGT ACCATTGCTG GTCAATATAG AGTTTATAGC
211 GAAGAAGGTG CTAACAAAAG TGGTTTAGCC TGGCCTTCAG CCTTTAAGGT ACAGTTGCAA CTACCTGATA
281 ATGAAGTAGC TCAAATATCT GATTACTATC CAAGAAATTC GATTGATACA AAAGAGTATA TGAGTACTTT
351 AACTTATGGA TTCAAGGGTA ATGTTACTGG TGATGATACA GGAAAAATTG GCGGCCTTAT TCGTGCAAAT
```

```
 421 CTTTCCATTC GTCATACACT GAAATATGTT CAACCTGATT TCAAAACAAT TTTACACACC CCAACTCATA
 491 AAAAAGTAGG CTGGAAAGTG ATATTTAACA ATATGGTGAA TCAAAATTGG GGACCATACG ATCGAGATTC
 561 TTGGAACCCG GTATATGGCA ATCAACTTTT CATGAAAACT AGAAATGTTT CTATGAAAGC ACCAGATAAC
 631 TTCCTTGATC CTAACAAAGC AAGTTCTCTA TTATCTTCAG GGTTTTCACC AGACTTCGCT ACAGTTATTA
 701 CTATGGATAG AAAAGCATCC AAACAACAAA CAAATATAGA TGTAATATAC GAACGAGTTC GTGATGATTA
 771 CCAATTGCAT TGGACTTCAA CAAATTGGAA AGGTACCAAT ACTAAAGATA AATGGACAGA TCGTTCTTCA
 841 GAAAGATATA AATCGATTG GGAAAAAGAA GAAATGACAA AT
```

SEQ ID NO: 2
```
   1 ADSDINIKTG TTDIGSNTTV KTGDLVTYDK ENGMHKKVFY SFIDDKNHNK KLLVIRTKGT IAGQYRVYSE
  71 EGANKSGLAW PSAFKVQLQL PDNEVAQISD YYPRNSIDTK EYMSTLTYGF NGNVTGDDTG KIGGLIGANV
 141 SIGHTLKYVQ PDFKTILESP TDKKVGWKVI FNNMVNQNWG PYDRDSWNPV YGNQLFMKTR NGSMKAADNF
 211 LDPNKASSLL SSGFSPDFAT VITMDRKASK QQTNIDVIYE RVRDDYQLHW TSTNWKGTNT KDKWTDRSSE
 281 RYKIDWEKEE MTN
```

SEQ ID NO: 3
```
   1 ATGGCAGATT CTGATATTAA TATTAAAACC GGTACTACAG ATATTGGAAG CAATACTACA GTAAAAACAG
  71 GTGATTTAGT CACTTATGAT AAAGAAAATG GCATGCACAA AAAAGTATTT TATAGTTTTA TCGATGATAA
 141 AAATCACAAT AAAAAAACTG CTAGTTATTA GAACAAAAGGT ACCATTGCTG GTCAATATAG AGTTTATAGC
 211 GAAGAAGGTG CTAACAAAAG TGGTTTAGCC TGGCCTTTCA CCTTTAAGGT ACAGTTGCAA CTACCTGATA
 281 ATGAAGTAGC TCAAATATCT GATTACTATC CAAGAAATTC GATTGATACA AAAGAGTATA GGAGTACTTT
 351 AACTTATGGA TTCAACGGTA ATGTTACTGG TGATGATACA GGAAAAATTG GCGGCCTTAT TGGTGCACAA
 431 CTTTCCATTC CTCATACACT CAAATATCTT CAACCTCATT TCAAAACAAT TTTACACACC CCAACTCATA
 491 AAAAAGTAGG CTGGAAAGTG ATATTTAACA ATATGGTGAA TCAAAATTGG GGACCATACG ATCGAGATTC
 561 TTGGAACCCG GTATATGGCA ATCAACTTTT CATGAAAACT AGAAATGGTT CTATGAAAGC AGCAGATAAC
 631 TTCCTTGATC CTAACAAAGC AAGTTCTCTA TTATCTTCAG GGTTTTCACC AGACTTCGCT ACAGTTATTA
 701 CTATGGATAG AAAAGCATCC AAACAACAAA CAAATATAGA TGTAATATAC GAACGAGTTC GTGATGATTA
 771 CCAATTGCAT TGGACTTCAA CAAATTGGAA AGCTACCAAT ACTAAAGATA AATGGACACA TCCTTCTTCA
 841 GAAAGATATA AATCGATTG GGAAAAAGAA GAAATGACAA AT
```

SEQ ID NO: 4
```
   1 ADSDINIKTG TTDIGSNTTV KTGDLVTYDK ENGMHKKVFY SFIDDKNHNK KLLVIRTKGT IAGQYRVYSE
  71 EGANKSGLAW PSAFKVQLQL PDNEVAQISD YYPRNSIDTK EYRSTLTYGF NGNVTGDDTG KIGGLIGAQV
 141 SIGHTLKYVQ PDFKTILESP TDKKVGWKVI FNNMVNQNWG PYDRDSWNPV YGNQLFMKTE NGSMKAADNF
 211 LDPNKASSLL SSGFSPDFAT VITMDRKASK QQTNIDVIYE RVRDDYQLHW TSTNWKGTNT KDKWTDRSSE
 281 RYKIDWEKEE MTN
```

SEQ ID NO: 5
```
    1 TTGTTGAAGA CGAAAGGGCC TCGTGATACG CCTATTTTTA TAGGTTAATG TGATGATAAT AATGGTTTCT
   71 TAGACGTCAG GTGGCACTTT TCGGGGAAAT GTGCGCGGAA CCCCTATTTG TTTATTTTTC TAAATACATT
  141 CAAATATGTA TCCGCTCATG AGACAATAAC CCTGATAAAT GCTTCAATAA TATTGAAAAA GGAAGAGTAT
  211 GAGTATTCAA CATTTCCGTG TCGCCCTTAT TCCCTTTTTT GCGGCATTTT GCCTTCCTGT TTTTGCTCAC
  281 CCAGAAACGC TGGTGAAAGT AAAAGATGCT GAAGATCAGT TGGGTGCACG AGTGGGTTAC ATCGAACTGG
  351 ATCTCAACAG CGGTAAGATC CTTGAGAGTT TTCGCCCCGA AGAACGTTTT CCAATGATGA GCACTTTTAA
  421 AGTTCTGCTA TGTGGCGCGG TATTATCCCG TGTTGACGCC GGGCAAGAGC AACTCGGTCG CCGCATACAC
  491 TATTCTCAGA ATGACTTGGT TGAGTACTCA CCAGTCACAG AAAAGCATCT TACGGATGGC ATGACAGTAA
  561 GAGAATTATG CAGTGCTGCC ATAACCATGA GTGATAACAC TGCGGCCAAC TTACTTCTGA CAACGATCGG
  631 AGGACCGAAG GAGCTAACCG CTTTTTTGCA CAACATGGGG GATCATGTAA CTCGCCTTGA TCGTTGGGAA
  701 CCGGAGCTGA ATGAAGCCAT ACCAAACGAC GAGCGTGACA CCACGATGCC TGCAGCAATG GCAACAACGT
  771 TGCGCAAACT ATTAACTGGC GAACTACTTA CTCTAGCTTC CCGGCAACAA TTAATAGACT GGATGGAGGC
  841 GGATAAAGTT GCAGGACCAC TTCTGCGCTC GGCCCTTCCG GCTGGCTGGT TTATTGCTGA TAAATCTGGA
  911 GCCGGTGAGC GTGGGTCTCG CGGTATCATT GCAGCACTGG GGCCAGATGG TAAGCCCTCC CGTATCGTAG
  981 TTATCTACAG ACGGGGAGT CAGGCAACTA TGGATGAACG AAATAGACAG ATCGCTGAGA TAGGTGCCTC
 1051 ACTGATTAAG CATTGGTAAC TGTCAGACCA AGTTTACTCA TATATACTTT AGATTGATTT AAAACTTCAT
 1121 TTTTAATTTA AAAGGATCTA GGTGAAGATC CTTTTTGATA ATCTCATGAC CAAAATCCCT TAACGTGAGT
 1191 TTTCGTTCCA CTGAGCGTCA GACCCCGTAG AAAAGATCAA AGGATCTTCT TGAGATCCTT TTTTTCTGCG
 1261 CGTAATCTGC TGCTTGCAAA CAAAAAAACC ACCGCTACCA GCGGTGGTTT GTTTGCCGGA TCAAGAGCTA
 1331 CCAAGTGTTT TTGCGAAGGT AACTGGCTTC AGCAGAGCGC AGATACCAAA TACTGTCCTT CTAGTGTAGC
 1401 CGTAGTTAGG CCACCACTTC AAGAACTCTG TAGCACCGCC TACATACCTC GCTCTGCTAA TCCTGTTACC
 1471 AGTGGCTGCT GCCAGTGGCG ATAAGTCGTG TCTTACCGGG TTGGACTCAA GACGATAGTT ACCGGATAAG
 1541 GCGCAGCGGT CGGGCTGAAC GGGGGGTTCG TGCACACAGC CCAGCTTGGA GCGAACGACC TACACCGAAC
 1611 TGAGATACCT ACAGCGTGAG CTATGAGAAA GCGCCACGCT TCCCGAAGGG AGAAAGGCGG ACAGGTATCC
 1681 GGTAAGCGGC AGGGTCGGAA CAGGAGAGCG CACGAGGGAG CTTCCAGGGG GAAACGCCTG GTATCTTTAT
 1751 AGTCCTGTCG GGTTTCGCCA CCTCTGACTT GAGCGTCGAT TTTTGTGATG CTCGTCAGGG GGGCGGAGCC
 1821 TATGGAAAAA CGCCAGCAAC GCGGCCTTTT TACGGTTCCT GGCCTTTTGC TGGCCTTTTG CTCACATGTT
 1891 CTTTCCTGCG TTATCCCCTG ATTCTGTGGA TAACCGTATT ACCGCCTTTG AGTGAGCTGA TACCGCTCGC
 1961 CGCAGCCGAA CGACCGAGCG CAGCGAGTCA GTGAGCGAGG AAGCGGAAGA GCGCCTGATG CGGTATTTTC
 2031 TCCTTACCCA TCTCTCCCCT ATTTCACACC CCATATATCC TCCACTCTCA CTACAATCTC CTCTCATCCC
 2101 GCATAGTTAA GCCAGTATAC ACTCCGCTAT CGCTACGTGA CTGGGTCATG GCTGCGCCCC GACACCCGCC
 2171 AACACCCGCT GACGCGCCCT GACGGGCTTG TCTGCTCCCG GCATCCGCTT ACAGACAAGC TGTGACCGTC
 2241 TCCGGGAGCT GCATGTGTCA GAGGTTTTCA CCGTCATCAC CGAAACGCGC GAGGCAGCGC TCTCCCTTAT
 2311 GCGACTCCTG CATTAGGAAG CGACCCAGTA GTAGGTTGAG GCCGTTGAGC ACCGCCGCCG CAAGGAATGG
 2381 TGCATGCAAG GAGATGGCGC CCAACAGTCC CCCGGCCACG GGGCCTGCCA CCATACCCAC GCCGAAACAA
 2451 GCGCTGATGA GCCCGAAGTG GCGAGCCCGA TCTTCCCCAT CGGTGATGTC GGCGATATAG GCGCCAGCAA
 2521 CCGCACCTGT GGCGCCGGTG ATGCCGGCCA CGATGCGTCC GGCGTAGAGG ATCGAGATCT AGCCCGCCTA
 3011 TTACTATCCA AGAAATTCGA TTGATACAAA AGATATATG AGTACTTTAA CTTATGGATT CAACGGTAAT
 3081 GTTACTGGTG ATGATACAGG AAAAATTGGC GGCCTTATTG GTGCAAATGT TTCGATTGGT CATACACTGA
```

```
Sequence listing

3151 AATATGTTCA ACCTGATTTC AAAACAATTT TAGAGAGCCC AACTGATAAA AAAGTAGGCT GGAAAGTGAT
3221 ATTTAACAAT ATCGTGAATC AAAATTGGGG ACCATACGAT CCAGATTCTT CCAACCCCCT ATATCCCAAT
3291 CAACTTTTCA TGAAAACTAG AAATGGTTCT ATGAAAGCAG CAGATAACTT CCTTGATCCT AACAAAGCAA
3361 GTTCTCTATT ATCTTCAGGG TTTTCACCAG ACTTCGCTAC AGTTATTACT ATGGATAGAA AAGCATCCAA
3431 ACAACAAACA AATATAGATG TAATATACGA ACGAGTTCGT GATGATTACC AATTGCATTG GACTTCAACA
3501 AATTGGAAAG GTACCAATAC TAAAGATAAA TGGACAGATC GTTCTTCAGA AAGATATAAA ATCGATTGGG
3571 AAAAAGAAGA AATGACAAAT TAATGTAAAT TATTTGTACA TGTACAAATA AATATAATTT ATAACTTTAG
3641 CCGAAAGCTT GGATCCGGCT GCTAACAAAG CCCGAAAGGA AGCTGAGTTG GCTGCTGCCA CCGCTGAGCA
3711 ATAACTAGCA TAACCCCTTG GGGCCTCTAA ACGGGTCTTG AGGGGTTTTT TGCTGAAAGG AGGAACTATA
3781 TATAATTCGA GCTCGGTACC CACCCCGGTT GATAATCAGA AAAGCCCCAA AACAGGAAG ATTGTATAAG
3851 CAAATATTTA AATTGTAAAC GTTAATATTT TGTTAAAATT CGCGTTAAAT TTTTGTTAAA TCAGCTCATT
3921 GTTGTTCCAG TTTGGAACAA GAGTCCAGTA TTAAAGAACG TGGACTCCAA CGTCAAAGGG CGAAAAACCG
3991 GTTGTTCCAG TTTGGAACAA GAGTCCAGTA TTAAAGAACG TGGACTCCAA CGTCAAAGGG CGAAAAACCG
4061 TCTATCAGGG CGATGGCCCA CTACGTGAAC CATCACCCTA ATCAAGTTTT TTGGGGTCGA GGTGCCGTAA
4131 AGCACTAAAT CGGAACCCTA AAGGGATGCC CCGATTTAGA GCTTGACGGG GAAAGCCGGC GAACGTGGCG
4201 AGAAAGCAAG GGAAGAAAGC CAAAGCAGCG GCCGCTAGCG CGCTCGCAAG TCTACCCCTC ACGCTGCGCG
4271 TAACCACCAC ACCCGCCGCG CTTAATGCGC CGCTACAGGG CGCGTGGGGA TCCTCTAGAG TCGACCTGCA
4341 GGCATGCAAG CTATCCCGCA AGAGGCCCGG CAGTACCGGC ATAACCAAGC CTATGCCTAC AGCATCCAGG
4411 GTGACGGTGC CGAGGATGAC GATGAGCGCA TTGTTAGATT TCATACACGG TGCCTGACTG CGTTAGCAAT
4481 TTAACTGTGA TAAACTACCG CATTAAAGCT AGCTTATCGA TGATAAGCTG TCAAACATGA GAA

SEQ ID NO: 6
   1 ATGGCAGATT CTGATATTAA TATTAAAACC GGTACTACAG ATATTGGAAG CAATACTTCC GGAACAGTAA
  71 AACAGGTGA TTTAGTCACT TATGATAAAG AAATGGCAT GACACAAAAA GTATTTTATA GTTTTATCGA
 141 TGATAAAAAT CACAATAAAA AACTGCTAGT TATTAGAACA AAAGGTACCA TTGCTGGTCA ATATAGAGTT
 211 TATAGCGAAG AAGGTGCTAA CAAAAGTGGT TTAGCCTGGC CTTCAGCCTT TAAGGTACAG TTGCAACTAC
 281 CTGATAATGA AGTACCTCAA ATATCTGATT ACTATCCAAG AAATTCGATT CATACAAAAG AGTATATGAG
 351 TACTTTAACT TATGGATTCA ACGGTAATGT TACTGGTGAT GATACAGGAA AAATTGGCGG CCTTATTGGT
 421 GCAAATGTTT CGATTGGTCA TACACTGAAA TATGTTCAAC CTGATTTCAA AACAATTTTA GAGAGCCCAA
 491 CTGATAAAAA AGTAGGCTGG AAAGTGATAT TTAACAATAT GGTGAATCAA AATTGGGAC CATACGATCG
 561 AGATTCTTGG AACCCGGTAT ATGGCAATCA ACTTTTCATG AAAACTAGAA ATGGTTCTAT GAAAGCAGCA
 631 GATAACTTCC TTGATCCTAA CAAAGCAAGT TCTCTATTAT CTTCAGGGTT TTCACCAGAC TTCGCTACAG
 701 TTATTACTAT GGATAGAAAA GCATCCAAAC AACAAACAAA TATAGATGTA ATATACGAAC GAGTTCGTGA
 771 TGATTACCAA TTGCATTGGA CTTCAACAAA TTGGAAAGGT ACCAATACTA AGATAAATG GACAGATCGT
 841 TCTTCAGAAA GATATAAAAT CGATTGGGAA AAGAAGAAA TGACAAAT

SEQ ID NO: 7
   1 ATGGCAGATT CTCATATTAA TATTAAAACC GGTACTACAG ATATTCGAAG CAATACTACA GTAAAAACAG
  71 GTGATTTAGT CACTTATGAT AAAGAAAATG GCATGCACAA AAAGTATTT TATAGTTTTA TCGATTCCGG
 141 AGATAAAAAT CACAATAAAA AACTGCTAGT TATTAGAACA AAAGGTACCA TTGCTGGTCA ATATAGAGTT
 211 TATAGCGAAG AACCTGCTAA CAAAACTCGT TTACCCTCCC CTTCACCCTT TAAGGTACAC TTGCAACTAC
 281 CTGATAATGA AGTAGCTCAA ATATCTGATT ACTATCCAAG AAATTCGATT GATACAAAAG AGTATATGAG
 351 TACTTTAACT TATGGATTCA ACGGTAATGT TACTGGTGAT GATACAGGAA AAATTGGCGG CCTTATTGGT
 421 GCAAATGTTT CGATTGGTCA TACACTGAAA TATGTTCAAC CTGATTTCAA AACAATTTTA GAGAGCCCAA
 491 CTGATAAAAA AGTAGGCTGG AAAGTGATAT TTAACAATAT GGTGAATCAA AATTGGGAC CATACGATCG
 561 AGATTCTTGG AACCCGGTAT ATGGCAATCA ACTTTTCATG AAAACTAGAA ATGGTTCTAT GAAAGCAGCA
 631 CATAACTTCC TTCATCCTAA CAAAGCAAGT TCTCTATTAT CTTCAGGGTT TTCACCAGAC TTCGCTACAG
 701 TTATTAGTAT GGATAGAAAA GCATCCAAAC AACAAACAAA TATAGATGTA ATATACGAAC GAGTTCGTGA
 771 TGATTACCAA TTGCATTGGA CTTCAACAAA TTGGAAAGGT ACCAATACTA AGATAAATG GACAGATCGT
 841 TCTTCAGAAA GATATAAAAT CGATTGGGAA AAGAAGAAA TGACAAAT

SEQ ID NO: 8
   1 ATGGCAGATT CTGATATTAA TATTAAAACC GGTACTACAG ATATTCGAAG CAATACTACA GTAAAAACAG
  71 GTGATTTAGT CACTTATGAT AAAGAAAATG GCATGCACAA AAAGTATTT TATAGTTTTA TCGATGATAA
 141 AAATCACAAT AAATCCGGAA AACTGCTAGT TATTAGAACA AAAGGTACCA TTGCTGGTCA ATATAGAGTT
 211 TATAGCGAAG AAGGTGCTAA CAAAAGTGGT TTAGCCTGGC CTTCAGCCTT TAAGGTACAG TTGCAACTAC
 281 CTGATAATGA AGTAGCTCAA ATATCTGATT ACTATCCAAG AAATTCGATT GATACAAAAG AGTATATGAG
 351 TACTTTAACT TATCCATTCA ACGGTAATGT TACTGGTCAT CATACACGAA AAATTCGCCG CCTTATTGGT
 421 GCAAATGTTT CGATTGGTCA TACACTGAAA TATGTTCAAC CTGATTTCAA AACAATTTTA GAGAGCCCAA
 491 CTGATAAAAA AGTAGGCTGG AAAGTGATAT TTAACAATAT GGTGAATCAA AATTGGGAC CATACGATCG
 561 AGATTCTTGG AACCCGGTAT ATGGCAATCA ACTTTTCATG AAAACTAGAA ATGGTTCTAT GAAAGCAGCA
 631 GATAACTTCC TTGATCCTAA CAAAGCAAGT TCTCTATTAT CTTCAGGGTT TTCACCAGAC TTCGCTACAG
 701 TTATTACTAT GGATAGAAAA GCATCCAAAC AACAAACAAA TATAGATGTA ATATACGAAC GAGTTCGTGA
 771 TGATTACCAA TTGCATTGGA CTTCAACAAA TTGGAAAGGT ACCAATACTA AGATAAATG GACAGATCGT
 841 TCTTCAGAAA GATATAAAAT CGATTGGGAA AAGAAGAAA TGACAAAT

SEQ ID NO: 9
   1 ATGAAATTTG TCTCTTTTAA TATCAACGGC CTGCGCGCCA GACCTCACCA GCTTGAAGCC ATCGTCGAAA
  71 AGCACCAACG GGATGTGATT GGCCTGCAGG AGACAAAAGT TCATGACGAT ATGTTTCCGC TCGAAGAGGT
 141 GGCGAAGCTC GGCTACAACG TGTTTTATCA CGGGCAGAAA GGCCATTATG GCGTGGCGCT GCTGACCAAA
 211 GAGACGCCGA TTGCCGTGCG TCGCGGCTTT CCCGGTGACA ACGAAGAGGC GCAGCGCGG ATTATTATGG
 281 CGGAAATCCC CTCACTGCTG GGTAATGTCA CCGTGATCAA CGGTTACTTC CGCAGGGTG AAAGCCGCGA
 351 CGATGCGATA AAATTCCCGG CAAAAGCGCA GTTTTATCAG AATCTGCAAA ACTACCTGGA AACCGAACTC
 421 AAACGTGATA ATCCGGTACT GATTATGGGC GATATGAATA TCAGCCCTAC AGATCTGGAT ATCGGCATTG
 491 GCGAAGAAAA CCGTAAGCGC TGGCTGCGTA CCGGTAAATG CTCTTTCCTG CCGGAAGAGC GCGAATGGAT
 561 GGACAGGCTG ATGAGCTGCG GGTTGGTCGA ACCTTCCGC CATGCGAATC CGCAAACAGC AGATCGTTTC
 631 TCATGGTTTG ATTACCGCTC AAAAGGTTTT GACGATAACC GTGGTCTGCG CATCGACCTG CTGCTCGCCA
```

Sequence listing

```
    710 GCCAACCGCT GGCAGAATGT TGCGTAGAAA CCGGCATCGA CTATGAAATC CGCAGCATGG AAAAACCGTC
    771 CGATCACGCC CCCGTCTGCG CGACCTTCCG CCGC

SEQ ID NO: 10
      1 MKPVSFNING LRARPHQLEA IVEKHQPDVI GLQETKVHDD MFPLEEVAKL GYNVFYHGQK GHYGVALLTK
     71 ETPIAVRRGF PGDDEEAQRR IIMAEIPSLL GNVTVINGYF PQGESRDHPI KFPAKAQFYQ NLQNYLETEL
    141 KRDNPVLIMG DMNISPTDLD IGIGEENRKR WLRTGKCSFL PERREWMDRL MSWGLVDTFR HANPQTADRF
    211 SWFDYRSKGF DDNRGLRIDL LLASQPLAEC CVETGIDYEI RSMEKPSDHA PVWATFRR

SEQ ID NO: 11
      1 ATGATGAATG ACGGTAAGCA ACAATCTACC TTTTTGTTTC ACGATTACGA AACCTTTGGC ACGCACCCCG
     71 CGTTAGATCG CCCTGCACAG TTCGCAGCCA TTCGCACCGA TAGCGAATTC AATGTCATCG GCGAACCCGA
    141 AGTCTTTTAC TGCAAGCCCG CTGATGACTA TTTACCCCAG CCAGGAGCCG TATTAATTAC CGGTATTACC
    211 CCGCAGGAAG CACGGGCGAA AGGAGAAAAC GAAGCCGCGT TTGCCGCCCG TATTCACTCG CTTTTTACCG
    281 TACCGAAGAC CTGTATTCTG GGCTACAACA ATGTGCGTTT CGACGACGAA GTCACACGCA ACATTTTTTA
    351 TCGTAATTTC TACGATCCTT ACGCCTGGAG CTGGCAGCAT GATAACTCGC GCTGGGATTT ACTGGATGTT
    421 ATGCGTGCCT GTTATGCCCT GCGCCCGGAA GGAATAAACT GGCCTGAAAA TGATGACGGT CTACCGAGCT
    491 TTCGCCTTGA GCATTTAACC AAAGCGAATG GTATTGAACA TAGCAACGCC CACGATGCGA TGGCTGATGT
    561 GTACGCCACT ATTGCGATGG CAAAGCTGGT AAAAACGCGT CAGCCACGCC TGTTTGATTA TCTCTTTACC
    631 CATCGTAATA AACACAAACT GATGGCGTTG ATTGATGTTC CGCAGATGAA ACCCCTGGTG CACGTTTCCG
    701 GAATGTTTGG AGCATGGCGC GGCAATACCA GCTGGGTGGC ACCGCTGGCG TGGCATCCTG AAAATCGCAA
    771 TCCCGTAATT ATCGTGGATT TGGCACGAGA CATTTCGCCA TTACTGGAAC TGGATAGCGA CACATTGCGC
    841 GAGCGTTTAT ATACCGCAAA AACCGATCTT GGCGATAACG CCGCCGTTCC GGTTAAGCTG GTGCATATCA
    911 ATAAATGTCC GGTGCTGGCC CAGGCGAATA CGCTACGCCC GGAAGATGCC GACCGACTGG GAATTAATCG
    981 TCAGCATTGC CTCGATAACC TGAAAATTCT GCGTGAAAAT CCGCAAGTGC GCGAAAAAGT GGTGGCGATA
   1051 TTCGCGGAAG CCGAACCGTT TACGCCTTCA GATAACGTGG ATGCACAGCT TTATAACGGC TTTTTTCAGTG
   1121 ACGCAGATCG TGCAGCAATG AAAATTGTGC TGGAAACCGA GCCGCGTAAT TTACCGGCAC TGGATATCAC
   1191 TTTTGTTGAT AAACGGATTG AAAAGCTGTT GTTCAATTAT CGGGCACGCA ACTTCCCGGG GACGCTGGAT
   1261 TATGCCGAGC AGCAACGCTG GCTGGAGCAC CGTCGCCAGG TCTTCACGCC AGAGTTTTTG CAGGGTTATG
   1331 CTGATGAATT GCAGATGCTG GTACAACAAT ATGCCGATGA CAAAGAGAAA GCGGCGCTGT TAAAAGCACT
   1401 TTGGCAGTAG GCGGAAGAGA TTGTC

SEQ ID NO: 12
      1 MMNDGKQQST FLFHDYETFG THPALDRPAQ FAAIRTDSEP NVIGEPEVFY CKPADDYLPQ PGAVLITGIT
     71 PQEAPAKGEN EAAFAARIHS LFTVPKTCIL GYNNVRFDDE VTRNIFYRNF YDPYAWSWQH DNSRWDLLDV
    141 MRACYALRPE GINWPENDDG LPSFRLEHLT KANGIEHSNA HDAMADVYAI IAMAKLVKTR QPRLFDYLFT
    211 HRNKHKLMAL IDVPQMKPLV HVSGMFGAWR GNTSWVAPLA WHPENRNAVI MVDLAGDISP LLELDSDTLR
    281 ERLYTAKTDL GDNAAVPVKL VHINKCPVLA QANTLRPEDA DRLGINRQHC LDNLKILREN PQVREKVVAI
    351 FAEAEPFTPS DNVDAQLYNG FFSDADRAAM KIVLETEPRN LPALDITFVD KRIEKLLFNY RARNFDGTLD
    421 YAEQQRWLEH RRQVFTPEFL QGYADELQML VQQYADDKEK VALLKALWQY AEEIV

SEQ ID NO: 13
      1 ATGTTTCGTG GTAAAGAAGA TCTGGATCCG CCGCTGGCAC TGCTGCCGCT GAAAGGCCTG CGCGAAGCCG
     71 CCGCACTCCT GGAAGAAGCC CTGCGTCAAG GTAAACGCAT TCGTGTTCAC GCCGACTATG ATGCCGATGG
    141 CCTGACCGGC ACCGCGATCC TGGTTCGTGG TCTGGCCGGC ATGTTCATCG CTGATGTTCA CCCGTTTATC
    211 CACCGCCTGG AAGAAGGCTA TGGTGTCCTG ATGGAACGCG TCCCGGAACA TCTGGAAGCC TCGGACCTGT
    281 TTCTGACCGT TGACTGCCGC ATTACCAACC ATGCGGAACT GCGCGAACTG CTGGAAAATG GCGTGGAAGT
    351 CATTGTTACC GATCATCATA CGCCGGGCAA AACGCCGCCG CCGGGTCTGG TCGTGCATCC GGCGCTGACG
    421 CCGGATCTGA AAGAAAAACC GACCGGCGCA GGCGTGGCGT TTCTGCTGCT GTGGGCACTG CATGAACGCC
    491 TGGGCCTGCC GCCGCCGCTG GAATACGCGG ACCTGGCAGC CGTTGGCACC ATTGCCGACG TTGCCCCGCT
    561 GTGGGGTTGG AATCGTGCAC TGGTGAAAGA AGGTCTGGCA CGCATCCCGG CTTCATCTTG GGTGGGCCTG
    631 CGTGTGCTGG CTGAAGCCGT GGGCTATACC GGCAAAGCGG TCGAAGTCGC TTTCCGCATC GCGCCGCGCA
    701 TCAATGCCGC TTCCCGCCTG GGCGAAGCGG AAAAGCCCT GCGCCTGCTG CTGACGGATG ATGCGGCAGA
    771 AGCTCAGGCG CTGGTCGGCG AACTGCACCG TCTGAACGCC CGTCGTCAGA CCCTGGAAGA AGCGATGCTG
    841 CGCAAACTGC TGCCGCAGGC CGACCCGGAA GCGAAAGCCA TCGTTCTGCT GGACCCGGAA GGCCATCCGG
    911 GTGTTATGGG TATTGTGGCC TCTCGCATCC TGGAAGCGAC CCTGCGCCCG GTCTTTCTGG TGGCCCAGGG
    981 CAAAGGCACC GTGCGTTCGC TGGCTCCGAT TTCCGCCGTC GAGCTGCGCT CCGCGGAGGA AGATCTGCTG
   1051 CTGCGTTATG GTGGTCATAA AGAAGCGGCG GGTTTCGCAA TGGATGAAGC GCTGTTTCCG GCGTTCAAAG
   1121 CACGCGTTGA AGCGTATGCC GCACGTTTCC CGGATCCGGT TCGTGAAGTG GCACTGCTGG ATCTGCTGCC
   1191 GGAACCGGGC CTGCTGCCGC AGGTGTTCCG TGAACTGGCA CTGCTGGAAC CGTATGGTGA AGGTAACCCG
   1261 GAACCGCTGT TCCTG

SEQ ID NO: 14
      1 MFRRKEDLDP PLALLPLKCL REAAALLEEA LRQCKRIRVH CDYDADCLTC TAILVRCLAA LCADVHPFIP
     71 HRLEEGYGVL MERVPEHLEA SDLFLTVDCG ITNHAELREL LENGVEVIVT DHHTPGKTPP PGLVVHPALT
    141 PDLKERPTGA GVAFLLLWAL HERLGLPPPL EYADLAAVGT IADVAPLWGW NRALVKEGLA RIPASSWVGL
    211 RLLAEAVGYT GKAVEVAFRI APRINAASRL GEAEKALRLL LTDDAAEAQA LVEGLHRLNA RRQTLEEAML
    281 RKLLPQADPE AKAIVLLDPE GHPGVMGIVA SRILEATLRP VFLVAQGKGT VRSLAPISAV EALRSAEDLL
    351 LRYGGHKEAA GFAMDEALFP ARKARVEAYA ARFPDPVREV ALLDLLPEPG LLPQVFRELA LLEPYGEGNP
    421 EPLFL

SEQ ID NO: 15
      1 TCCGGAAGCG GCTCTGGTAG TGGTTCTGGC ATGACACCGG ACATTATCCT GCAGCGTACC GGGATCGATG
     71 TGAGAGCTGT CGAACAGGGG GATGATGCGT GGCACAAATT ACGCTCGGC GTCATCACCG CTTCAGAAGT
    141 TCACAACGTG ATAGCAAAAC CCCGCTCCGG AAAGAAGTGG CCTGACATGA AAATGTCCTA CTTCCACACC
    211 CTGCTTGCTG AGGTTTGCAC CGGTGTGGCT CCGGAAGTTA ACGCTAAAGC ACTGGCCTGG GGAAAACAGT
    281 ACGAGAACGA CGCCAGAACC CTGTTTGAAT TCACTTCCGG CGTGAATGTT ACTGAATCCC CGATCATCTA
```

Sequence listing

```
351 TGGCGACGAA AGTATGCGTA CCGCCTGCTC TCCCGATGGT TTATGCAGTG ACGGCAACGG CCTTGAACTG
421 AAATGCCCGT TTACCTCCCG GGATTTCATG AAGTTCCGGC TCGGTGGTTT CGAGGCCATA AAGTCAGCTT
491 ACATGGCCCA GGTGCAGTAC AGCATGTGGG TGACGCGAAA AAATGCCTSG TACTTTGCCA ACTATGACCG
561 GCGTATGAAG CGTGAAGGCC TGCATTATGT CGTGATTGAG CGGGATGAAA AGTACATGGC GAGTTTTGAC
631 GAGATCGTGC CGGAGTTCAT CGAAAAAATG GACGAGGCAC TGGCTGAAAT TGGTTTTGTA TTTGGGGAGC
701 AATGGCGATC TGGCTCTGGT TCCGGCAGCG GTTCCGGA
```

SEQ ID NO: 16
```
  1 MTPDIILQRT CIDVRAVEQG DDAWHKLRLG VITASEVHNV IAKPRSCKKW PDMKMSYFHT LLAEVCTCVA
 71 PEVNAKALAW GKQYENDART LFEFTSGVNV TESPIIYRDE SMRTACSPDG LCSDGNGLEL KCPFTSRDFM
141 KFRLGGFEAT KSAYMAQVQY SMWVTRKNAW YFANYDPRMK REGLHYVVIE RDEKYMASFD EIVPEFIEKM
211 DEALAEICFV FCEQWR
```

SEQ ID NO: 17
```
   1 ATGGCAGATT CTGATATTAA TATTAAAACC GGTACTACAG ATATTGGAAG CAATACTTCC GGAAGCGGCT
  71 CTGGTAGTGG TTCTGGCATG AAATTTGTTA GCTTCAATAT CAACGGCCTG CGCGCGCGCC CGCATCAGCT
 141 GGAAGCGATT GTGGAAAAAC ATCAGCCGGA TGTTATTGGT CTGCAGGAAA CCAAAGTTCA CGATGATATG
 211 TTTCCGCTGG AAGAAGTGGC GAAACTGGGC TATAACGTCT TTTATCATGG CCAGAAAGGT CATTATGGCG
 281 TGGCCCTGCT GACCAAAGAA ACCCCGATCG CGGTTCGTCG TGGTTTTCCG GGTGATGATG AAGAAGCGCA
 351 GCGTCGTATT ATTATGGCGG AAATTCCGAG CCTGCTGGCA AATGTGACCG TTATTAACGG CTATTTTCCG
 421 CAGGGCCAAA GCCGTGATCA TCCGATTAAA TTTCCGGCCA AAGCGCAGTT CTATCAGAAC CTGCAGAACT
 491 ATCTGGAAAC CGAACTGAAA CGTCATAATC CGGTGCTGAT CATGGGCCAT ATGAACATTA GCCCGACCGA
 561 TCTGGATATT GGCATTGGCG AAGAAAACCG TAAACGCTGG CTGCGTACCG GTAAATGCAG CTTTCTGCCG
 631 GAAGAACGTG AATGGATGGA TCGCCTGATG AGCTGGGGAC TGGTGGATAC CTTTCGTCAT GCGAACCCGC
 701 AGACCGCCGA TCGCTTTAGC TGGTTTGATT ATCGCAGCAA AGGTTTTGAT GATAACCGTG GCCTGCGCAT
 771 TGATCTGCTG CTGGCGAGCC AGCCGCTGGC GGAATGCTGC GTTGAAACCG GTATTGATTA TGAAATTCGC
 841 AGCATGCAAA AACCGAGCGA TCACGCCCCG GTGTGGGCGA CCTTTCGCCG CTCTGGCTCT GGTTCCGGCA
 911 GGGGTTGCGA AACAGTAAAA ACAGGTGATT TAGTCACTTA TGATAAAGAA AATGGCATGC ACAAAAAAGT
 981 ATTTTATAGT TTTATCGATG ATAAAAATCA CAATAAAAAA CTGCTAGTTA TTAGAACAAA AGGTACCATT
1051 GCTGGTCAAT ATAGAGTTTA TAGCGAAGAA GCTGCTAACA AAAGTGGTTT AGCCTGGCCT TCAGCCTTTA
1121 AGGTACAGTT GCAACTACCT GATAATGAAG TAGCTCAAAT ATCTGATTAC TATCCAAGAA ATTCGATTGA
1191 TACAAAAGAG TATATGAGTA CTTTAACTTA TGGATTCAAC GGTAATGTTA CTGGTGATGA TACAGGAAAA
1261 ATTGGCGGCC TTATTGGTGC AAATGTTTCG ATTGGTCATA CACTGAAATA TGTTCAACCT GATTTCAAAA
1331 CAATTTTAGA GAGCCCAACT GATAAAAAAG TAGGCTGGAA AGTGATATTT AACAATATGG TGAATCAAAA
1401 TTGGGGACCA TACGATCGAG ATTCTTGGAA CCCCGGTATA TGGCAATCAAC TTTTCATGAA AACTAGAAAT
1471 CGTTCTATGA AACCAGCACA TAACTTCCTT CATCCTAACA AAGCAAGTTC TCTATTATCT TCACCCTTTT
1541 CACCCAGACTT CGCTACAGTT ATTACTATGG ATAGAAAAGC ATCCAAACAA CAAACAAATA TAGATGTAAT
1611 ATACGAACGA GTTCGTGATG ATTACCAATT GCATTGGACT TCAACAAATT GGAAAGGTAC CAATACTAAA
1681 GATAAATGGA CAGATCGTTC TTCAGAAAGA TATAAAATCG ATTGGGAAAA AGAAGAAATG ACAAATGGTG
1751 GTTCGGGCTC ATCTGGTGGC TCGAGTCACC ATCATCATCA CCAC
```

SEQ ID NO: 18
```
  1 ADSDINIKTG TTDIGSNTSG SGSGSGSGMK FVSFNINGLR ARPHQLEAIV EKHQPDVIGL QETKVHDDMF
 71 PLEEVAKLGY NVFYHGQKGH YGVALLTKET PIAVRRGPPG DDEEAQRRII MAEIPSLLGN VTVINGYFPQ
141 GESRDHPIKF PAKAQFYQNL QNYLETELKR DNPVLIMGDM NISFTDLDIG IGEENRKRWL RTGKCSFLPE
211 EREWMDRLMS WGLVDIFRHA NPQIADRFSW FDYRSKGFDD NRGLRIDLLL ASQPLAECCV EIGIDYEIRS
281 MEKPSDHAPV WATFRRSCSC SGSCSCTVKT GDLVTYDKEN GMHKKVFYSF IDDKNHNKKL LVIRTKGTIA
351 GQYRVYSEEG ANKSGLAWPS AFKVQLQLPD NEVAQISDYY PRNSIDTKEY MSTLTYGFNG NVTGDDTGKI
421 GGLIGANVSI GHTLKYVQPD FKTILESPTD KKVGWKVIFN NMVNQNWGPY DRDSWNPVYG NQLFMKTRNG
491 SMKAADNFLD PNKASSLLSS CFSPDFATVI TMDRKASKQQ TNIDVIYERV RDDYQLHWTS TNWKGTNTKD
561 KWTDRSSERY KIDWEKEEMT NGGSGSSGGS SHHHHHH
```

SEQ ID NO: 19
```
   1 ATGGCAGATT CTGATATTAA TATTAAAACC GGTACTACAG ATATTGGAAG CAATACTTCC GGAAGCGGCT
  71 CTCCTAGTGG TTCTGGCATG AAATTTGTTA GCTTCAATAT CAACGCCCTG CGCGCGCGCC CGCATCAGCT
 141 GGAAGCGATT GTGGAAAAAC ATCAGCCGGA TGTTATTGGT CTGCAGGAAA CCAAAGTTCA CGATGATATG
 211 TTTCCGCTGG AAGAAGTGGC GAAACTGGGC TATAACGTCT TTTATCATGG CCAGAAAGGT CATTATGGCG
 281 TGGCCCTGCT GACCAAAGAA ACCCCGATCG CGGTTCGTCG TGGTTTTCCG GGTGATGATG AAGAAGCGCA
 351 GCGTCGTATT ATTATGGCGG AAATTCCGAG CCTGCTGGGC AATGTGACCG TTATTAACGG CTATTTTCCG
 421 CAGGGCGAAA GCCGTGATCA TCCGATTAAA TTTCCGGCCA AAGCGCAGTT CTATCAGAAC CTGCAGAACT
 491 ATCTGGAAAC CGAACTGAAA CGTGATAATC CGGTGCTGAT CATGGGCGAT ATGAACATTA GCCCGACCGA
 561 TCTGGATATT GGCATTGGCG AAGAAAACCG TAAACGCTGG CTGCGTACCG GTAAATGCAG CTTTCTGCCG
 631 GAAGAACGTG AATGGATGGA TCGCCTGATG AGCTGGGGCC TGGTGGATAC CTTTCGTCAT GCGAACCCGC
 701 AGACCGCCGA TCGCTTTAGC TGGTTTGATT ATCGCAGCAA AGGTTTTGAT GATAACCGTG GCCTGCGCAT
 771 TGATCTGCTG CTGGCGAGCC AGCCGCTGGC GGAATGCTGC GTTGAAACCG GTATTGATTA TGAAATTCGC
 841 AGCATGCAAA AACCGAGCGA TCACGCCCCG GTGTGGGCGA CCTTTCGCCG CTCTGGCTCT GGTTCCGGCA
 911 GCGGTTCCGG AACAGTAAAA ACAGGTGATT TAGTCACTTA TGATAAAGAA AATGGCATGC ACAAAAAAGT
 981 ATTTTATAGT TTTATCGATG ATAAAAATGA CAATAAAAAA CTGCTAGTTA TTAGAACAAA AGGTACCATT
1051 GCTGGTCAAT ATAGAGTTTA TAGCGAAGAA GGTGCTAACA AAAGTGGTTT AGCCTGGCCT TCAGCCTTTA
1121 AGGTACAGTT GCAACTACCT GATAATGAAG TAGCTCAAAT ATCTGATTAC TATCCAAGAA ATTCGATTGA
1191 TACAAAAGAG TATATGAGTA CTTTAACTTA TGGATTCAAC GGTAATGTTA CTGGTGATGA TACAGGAAAA
1261 ATTGGCGGCC GTATTGGTGC ACAAGTTTCG ATTGGTCATA CACTGAAATA TGTTCAACCT GATTTCAAAA
1331 CAATTTTACA CACCCCAACT CATAAAAAAC TACCCTCCAA ACTCATATTT AACAATATCC TCAATCAAAA
1401 TTGGGGACCA TACGATCGAG ATTCTTGGAA CCCCGGTATA TGGCAATCAAC TTTTCATGAA AACTAGAAAT
1471 GGTTCTATGA AGCAGCAGA TAACTTCCTT GATCCTAACA AAGCAAGTTC TCTATTATCT TCAGGGTTTT
1541 CACCAGACTT CGCTACAGTT ATTACTATGG ATAGAAAAGC ATCCAAACAA CAAACAAATA TAGATGTAAT
1611 ATACGAACGA GTTCGTGATG ATTACCAATT GCATTGGACT TCAACAAATT GGAAAGGTAC CAATACTAAA
```

```
                              Sequence listing

1681 GATAAATGGA CAGATCGTTC TTCAGAAAGA TATAAAATCG ATTGGAAAAA AGAAGAAATG ACAAATGGTG
1751 GTTCGGGCTC ATCTGGTGGC TCGAGTCACC ATCATCATCA CCAC

SEQ ID NO: 20
   1 ADSDINIKTG TTDIGSNTSG SGSGSGSGMK FVSFNINGLR ARPHQLEAIV EKHQPDVIGL QETKVHDDMF
  71 PLEEVAKLGY NVFYHGQKGH YGVALLTKET PTAVRRGFPG DDEEAQRRII MAEIPSLLGN VTVINGYFPQ
 141 CESRDHPIKF PAKAQFYQNL QNYLETELKR DNPVLIMCDM NISPTDLDIC ICEENRKRWL RIGKCSFLPE
 211 EREWMDRLMS WGLVDTFRHA NPQTADRFSW FDYRSKGFDD NRFLRIDLLL ASQPLAECCV ETGIDYEIRS
 281 MEKPSDHAPV WATFRRSGSG SGSGSGTVKT GDLVTYDKEN GMHKKVPYSF IDDKNHNKKL LVIRTKGTIA
 351 GQYRVYSEEG ANKSGLAWPS AFKVQLQLPD NEVAQISDYY PRNSIDTKEY RSTLTYGFNG NVTGDDTGKI
 421 GGCIGAQVSI GHTLKYVQPD FKTILESPTD KKVGWKVIFN NMVQNWGPY DRDSWNPVYG NQLFMKTRNG
 491 SMKAADNFLD PNKASSLLSS GFSPDFAIVI TMDRKASKQQ TNIDVIYERV RDDYQLHWTS TNWKGTNTKD
 561 KWTDRSSERY KIDWEKEEMT NGGSGSSGGS SHHHHHH

SEQ ID NO: 21
   1 ATGGCAGATT CTGATATTAA TATTAAAACC GGTACTACAG ATATTGGAAG CAATACTTCC GGAAGCGGCT
  71 CTGGTAGTGG TTCTGGCATG ATGAACGATG GCAAACAGCA GAGCACCTTC CTGTTTCATG ATTATGAAAC
 141 CTTCGGTACC CATCCGGCCC TGGATCCTCC GGCGCAGTTT GCGGCCATTC GCACCGATAG CGAATTCAAT
 211 GTGATTGGCG AACCGGAAGT GTTTTATTGC AAACCGGCCG ATGATTATCT GCCGCAGCCG GGTGCGGTGC
 281 TGATTACCGG TATTACCCCG CAGGAAGCGC GCGCGAAAGG TGAAAACGAA GCGTTTGCGG CCCGCGCCAT
 351 TCATAGCCTG TTTACCGTGC CGAAAACCTG CATTCTGGGC TATAACAATG GCGCTTCGA TGATGAAGTT
 421 ACCCGTAATA TCTTTTATCG TAACTTTTAT GATCCGTATG CGTGGAGCTG GCAGCATGAT AACAGCCGTT
 491 GGGATCTGCT GGATGTGATG CGCGCGTGCT ATGCGCTGCG CCCGGAAGGC ATTAATTGGC CGGAAAACGA
 561 TGATGGCCTG CCGAGCTTTC GTCTGGAACA TCTGACCAAA GCCAACGGCA TTGAACATAG CAATGCCCAT
 631 GATGCGATGG CCGATGTTTA TGCGACCATT GCCATGGCGA AACTGGTTAA AACCCGTCAG CCGCGCCTGT
 701 TTGATTATCT GTTTACCCAC CGTAACAAAC ACAAACTGAT GGCGCTGATT GATGTTCCGC AGATGAAACC
 771 CCTGGTGCAT GTGAGCGGCA TGTTTGGCGC CTGGCGCGGC AACACCAGCT GGGTGGCCCC GCTGGCCTGG
 841 CACCCGGAAA ATCGTAACGC CGTTGATTAT GTTGATCTGG CCGGTGATAT TAGCCCGCTG CTGGAACTGG
 911 ATAGCGATAC CCTGCGTGAA CGCCTGTATA CCGCCAAAAC CGATCTGGGC GATAATGCCG CCGTGCCGGT
 981 GAAACTGGTT CACATTAACA AATGCCCGGT GCTGGCCCAG GCGAACACCC TGCGCCCGGA AGATGCGGAT
1051 CGTCTGGGTA TTAATCGCCA GCATTGTCTG GATAATCTGA AAATCCTGCG TGAAAACCCG CAGGTGCGTG
1121 AAAAAGTGGT GGCGATCTTC GCGGAAGCGG AACCGTTCAC CCCGAGCGAT AACGTGGATG CGCAGCTGTA
1191 TAACGGCTTC TTTAGCGATG CCGATCGCGC GGCGATGAAA ATCGTTCTGG AAACCGAACC GCGCAATCTG
1261 CCGGCGCTGG ATATTACCTT TGTTGATAAA CGTATTGAAA AACTGCTGTT TAATTATCGT GCGCGCAATT
1331 TTCCGGGTAC CCTGGATTAT GCCGAACAGC AGCGTTGGCT GGAACATCGT CGTCAGGTTT TCACCCCGGA
1401 ATTTCTGCAG GGTTATGCGG ATGAACTGCA GATGCTGGTT CAGCAGTATG CCGATGATAA AGAAAAAGTG
1471 GCGCTGCTGA AAGCGCTGTG GCAGTATGCG GAAGAAATCG TTTCTGGCTC TGGTTCCGGC AGCGGTTCCG
1541 GAACAGTAAA AACAGGTGAT TTAGTCACTT ATGATAAAGA AAATGGCATG CACAAAAAAG TATTTTATAG
1611 TTTTATCGAT GATAAAAATC ACAATAAAAA ACTGCTAGTT ATTAGAACAA AAGGTACCAT TGCTGGTCAA
1681 TATAGAGTTT ATAGCGAAGA AGGTGCTAAC AAAAGTGGTT TAGCCTGGCC TTCAGCCTTT AAGGTACAGT
1751 TGCAACTACC TGATAATGAA GTAGCTCAAA TATCGATTA CTATCCAAGA AATTCGATTG ATACAAAAGA
1821 GTATAGGAGT ACTTTAACTT ATGGATTCAA CGGTAATGTT ACTGGTGATG ATACAGGAAA AATTGGCGGC
1891 TGTATTGGTG CACAAGTTTC GATTGGTCAT ACACTGAAAT ATGTTCAACC TGATTTCAAA ACAATTTTAG
1961 AGAGCCCAAC TGATAAAAAA GTAGGCTGGA AAGTGATATT TAACAATATG GTGAATCAAA ATTGGGGACC
2031 ATACGATCGA GATTCTTGGA ACCCGGTATA TGGCAATCAA CTTTTCATGA AAACTAGAAA TGGTTCTATG
2101 AAAGCAGCAG ATAACTTCCT TGATCCTAAC AAAGCAAGTT CTCTATTATC TTCAGGGTTT TCACCAGACT
2171 TCGCTACAGT TATTACTATG GATAGAAAG CATCCAAACA ACAAACAAAT ATAGATGTAA TATACGAACG
2241 AGTTCGTGAT GATTACCAAT TGCATTGGAC TTCAACAAAT TGGAAAGGTA CCAATACTAA AGATAAATGG
2311 ACAGATCGTT CTTCAGAAAG ATATAAAATC GATTGGGAAA AGAAGAAATT GACAAATGGT GGTTCGGGCT
2381 CATCTGGTGG CTCGAGTCAC CATCATCATC ACCAC

SEQ ID NO: 22
   1 ADSDINIKTG TTDIGSNTSG SGSGSGSGMM NDGKQQSTFL FHDYETFGTH PALDRPAQFA AIRTDSEFNV
  71 IGEPEVFYCK PADDYLPQPG AVLITGITPQ EARAKGENEA AFAARIHSLF TVPKTCILGY NNVRFDDEVT
 141 RNIFYRNFYD PYAWSWQHDN SRWDLLDVMR ACYALRPEGI NWPENDDGLP SFRLEHLTKA NGIEHSNAHD
 211 AMADVYATIA MAKLVKTRQP RLFDYLFTHR NKHKLMALID VPQMKPLVHV SGMFGAWRGN TSWVAPLAWH
 281 PENRNAVIMV DLAGDISPLL ELDSDTLRER LYTAKTDLGD NAAVPVKLVH INKCPVLAQA NTLRPEDADR
 351 LGINRQHCLD NLKILRENPQ VREKVVAIFA EAEPFTPSDN VDAQLYNGFF SDADRAAMKI VLETEPRNLP
 421 ALDITFVDKR IEKLLFNYRA RNFPGTLDYA EQQRWLEHRR QVFTPEPLQG YADELQMLVQ QYADDKEKVA
 491 LLKALWQYAE EIVSGSGSGS GSGTVKTGDL VTYDKENGMH KKVFYSFIDD KNHNKKLLVI RTKGTIAGQY
 561 RVYSEEGANK SGLAWPSAFK VQLQLPDNEV AQISDYYPRN SIDTKEYRST LTYGFNGNVT GDDTGKIGGC
 631 IGAQVSIGHT LKYVQPDFKT ILESPTDKKV GWKVIFNNMV NQNWGPYDRD SWNPVYGNQL FMKTRNGSMK
 701 AADNFLDPNK ASSLLSSGFS PDFATVITMD RKASKQQTNI DVIYERVRDD YQLHWTSTNW KGTNTKDKWT
 771 DRSSERYKID WEKEEMTNGG SGSSGGSSHH HHHH

SEQ ID NO: 23
   1 ATGGCAGATT CTGATATTAA TATTAAAACC GGTACTACAG ATATTGGAAG CAATACTTCC GGAAGCGGCT
  71 CTGGTAGTGG TTCTGGCATG TTTCGTCGTA AAGAAGATCT GGATCCGCCG CTGGCACTGC TGCCGCTGAA
 141 AGGCCTGCGC GAAGCGCCG CACTGCTGGA GAAGCGCTG CGTCAAGGTA ACGCATTG TGTTCACGGC
 211 GACTATGATG CGGATGGCCT GACCGGCACC GCGATCCTGG TTCGTGGTCT GGCCGCCCTG GGTGCGGATG
 281 TTCATCCGTT TATCCCGCAC CGCCTGGAAG AAGGCTATGG TGTCCTGATG GAACGCTGCC CGGAACATCT
 351 CGAAGCCTCG CACCTGTTTC TGACCGTTGA CTGCGGCATT ACCAACCATG CGGAACTGCC CGAACTGCTG
 421 GAAAATGGCG TGGAAGTCAT TGTTACCGAT CATCATACGC CGGGCAAAAC GCCGCCGCCG GGTCTGGTCG
 491 TGCATCCGGC GCTGACGCCG GATCTGAAAG AAAAACCGAC CGGCGCAGGC GTGGCGTTTC TGCTGCTGTG
 561 GGCACTGCAT AACGCCTGG CCTGCCGCC GCCGCTGGAA TACGCGGACC TGGCAGCCGT TGGCACCATT
 631 GCCGACGTTG CCCCGCTGTG GGGTTGGAAT CGTGCACTGG TGAAGAAGG TCTGGCACGC ATCCCGGCTT
 701 CATCTTGGGT GGGCCTGCGT CTGCTGGCTG AAGCCGTGGG CTATACCGGC AAAGCGGTCG AAGTCGCTTT
```

```
                            Sequence listing
 771 CCGCATCGCG CCGCGCATCA ATGCGGCTTC CCGCCTGGGC GAAGCGGAAA AAGCCCTGCG CCTGCTGCTG
 841 ACGGATGATG CGGCAGAAGC TCAGGCGCTG GTCGGCGAAC TGCACCGTCT GAACGCCCGT CGTCAGACCC
 911 TGGAAGAAGC GATGCTGCGC AAACTGCTGC CGCAGGCCGA CCCGGAAGCG AAAGCCATCG TTCTGCTGGA
 981 CCCGGAAGGC CATCCGGGTG TTATGGGTAT TGTGGCCTCT CGCATCCTGG AAGCGACCCT GCGCCCGGTC
1051 TTTCTGGTGG CCCAGGGCAA AGGCACCGTG CGTTCGCTGG CTCCGATTTC CGCCGTCGAA GCACTGCGCA
1121 GCGCGGAAGA TCTGCTGCTG CGTTATGGTG GTCATAAAGA AGCGGCGGGT TTCGCAATGG ATGAAGCGCT
1191 GTTTCCGGCG TTCAAAGCAC GCGTTGAAGC GTATGCCGCA CGTTTCCCGG ACCCGGTTCG TGAAGTGGCA
1261 CTGCTGGATC TGCTGCCGGA ACCGGGCCTG CTGCCGCAGG TGTTCCGTGA ACTGGCAGTG CTGGAACCGT
1331 ATGGTGAAGG TAACCCGGAA CCGCTCTTCC TCTCTGGCTC TGGTTCCGGC AGCGGTTCCG GAACACTAAA
1401 AACAGGTGAT TTAGTCACTT ATGATAAAGA AAATGGCATG CACAAAAAAG TATTTTATAG TTTTATCGAT
1471 GATAAAAATC ACAATAAAAA ACTGCTAGTT ATTAGAACAA AAGGTACCAT TGCTGGTCAA TATAGAGTTT
1541 ATAGCGAAGA AGGTGCTAAC AAAAGTGGTT TAGCCTGGCC TTCAGCCTTT AAGGTACAGT TGCAACTACC
1611 TGATAATGAA GTAGCTCAAA TATCTGATTA CTATCCAAGA AATTCGATTG ATACAAAAGA GTATAGGAGT
1681 ACTTTAACTT ATGGATTCAA CGGTAATGTT ACTGGTGATG ATACAGGAAA AATTGGCGGC TGTATTGGTG
1751 CACAAGTTTC GATTGGTCAT ACACTGAAAT ATGTTCAACC TGATTTCAAA ACAATTTTAG AGAGCCCAAC
1821 TGATAAAAAA GTAGGCTGGA AAGTGATATT TAACAATATG GTGAATCAAA ATTGGGGACC ATACGATCGA
1891 GATTCTTGGA ACCCGGTATA TGGCAATCAA CTTTTCATGA AAACTAGAAA TGGTTCTATG AAAGCAGCAG
1961 ATAACTTCCT TGATCCTAAC AAAGCAAGTT CTCTATTATC TTCAGGGTTT TCACCAGACT TCGCTACAGT
2031 TATTACTATG GATAGAAAAG CATCCAAACA ACAAACAAAT ATAGATGTAA TATACGAACG AGTTCGTGAT
2101 GATTACCAAT TGCATTGGAC TTCAACAAAT TGGAAAGGTA CCAATACTAA AGATAAATGG ACAGATCGTT
2171 CTTCAGAAAG ATATAAAATC GATTGGGAAA AGAAGAAAAT GACAAATGGT GGTTCGGGCT CATCTGGTGG
2241 CTCGAGTCAG CATCATCATC ACCAG SEQ ID NO: 24
   1 ADSDINIKTG TTDIGSNTSG SGSGSGSGMF RRKEDLDPPL ALLLPLKGLRE AAALLEEALR QGKRIRVHGD
  71 YDADGLTGTA ILVRGLAALG ADVHPFIPHR LEFGYGVLME RVPEHLEASD LFLTVDCGIT NHAELRELLE
 141 NGVEVIVTDH HTPGKTPPPG LVVHPALTPD LKEKPTGAGV AFLLLWALHE RLGLPPPLEY ADLAAVGTIA
 211 DVAPLWGWNR ALVKEGLARI PASSWVGLRL LAEAVGYTGK AVEVAFRIAP RINAASRLGE AEKALRLLLT
 281 DDAAEAQALV GELHRLNARR QTLEEAMLRK LLPQADPEAK AIVLLDPEGH PGVMGIVASR ILEATLRPVF
 351 LVAQGKGTVR SLAPISAVEA LRSAEDLLLR YGGHKEAAGF AMDEALFPAF KARVEAYAAR FPDPVREVAL
 421 LDLLPEPGLL PQVFRELALL EPYGEGNPEP LFLSGSGSGS GSGTVKTGDL VTYDKENGMH KKVFYSFIDD
 491 KNHNKKLLVI RTKGTIAGQY RVYSEEGANK SGLAWPSAFK VQLQLPDNEV AQISDYYPRN SIDTKEYRST
 561 LTYGFNGNVT GDDTGKIGGC IGAQVSIGHT LKYVQPDFKT ILESPTDKKV GWKVIFNNMV NQNWGPYDRD
 631 SWNPVYGNQL FMKTRNCSMK AADNFLDPNK ASSLLSSCFS PDFATVITMD RKASKQQTNI DVIYERVRDD
 701 YQLHWTSTNW KGTNTKDKWT DRSSERYKID WEKEEMTNGG SGSSGGSSHH HHHH SEQ ID NO: 25
   1 ATGGCAGATT CTGATATTAA TATTAAAACC GGTACTACAG ATATTGGAAG CAATACTACA GTAAAAACAG
  71 GTGATTTAGT CACTTATGAT AAAGAAAATG GCATGCACAA AAAAGTATTT TATAGTTTTA TCGATTCCGG
 141 AAGCGGCTCT GGTAGTGGTT CTGGCATGAA ATTTGTTAGC TTCAATATCA ACGGCCTGCG CGCGCGCCCG
 211 CATCAGCTGG AAGCGATTGT GGAAAAACAT CAGCCGGATG TTATTGGTCT GCAGGAAACC AAAGTTCACG
 281 ATGATATGTT TCCGCTGGAA GAAGTGGCGA AACTGGGCTA TAACGTGTTT TATCATGGCC AGAAAGGTCA
 351 TTATGGCGTG GCCCTGCTGA CCAAAGAAAC CCCGATCGCG GTTCGTCGTG GTTTTCCGGG TGATGATGAA
 421 GAAGCGCAGC GTCGTATTAT TATGGCGGAA ATTCCGAGCC TGCTGGGCAA TGTGACCGTT ATTAACGGCT
 491 ATTTTCCGCA GGGCGAAAGC CGTGATCATC CGATTAAATT TCCGGCCAAA GCGCAGTTCT ATCAGAACCT
 561 GCAGAACTAT CTGGAAACCG AACTGAAACG TGATAATCCG GTGCTGATCA TGGGCGATAT GAACATTAGC
 631 CCGACCGATC TGGATATTGG CATTGGCGAA GAAAACCGTA AACGCTGGCT GCGTACCGGT AAATGCAGCT
 701 TTCTGCCGGA AGAACGTGAA TGGATGGATC GCCTGATGAG CTGGGGCCTG GTGGATACCT TTCGTCATCC
 771 GAACCCGCAG ACCGCCGATC GCTTTAGCTG GTTTGATTAT CGCAGCAAAG GTTTTGATGA TAACCGTGGC
 841 CTGCGCATTG ATCTGCTGCT GGCGAGCCAG CCGCTGGCGG AATGCTGCGT TGAAACCGGT ATTGATTATG
 911 AAATTCCCAG CATGGAAAAA CCGAGCGATC ACGCCCCGGT GTGGGCGACC TTTCGCCGCT CTGGCTCTGG
 981 TTCCGGCAGC GGTTCCGGAC ACAATAAAAA ACTGCTAGTT ATTAGAACAA AAGGTACCAT TGCTGGTCAA
1051 TATAGAGTTT ATAGCGAAGA AGGTGCTAAC AAAAGTGGTT TAGCCTGGCC TTCAGCCTTT AAGGTACAGT
1121 TGCAACTACC TGATAATGAA GTAGCTCAAA TATCTGATTA CTATCCAAGA AATTCGATTG ATACAAAAGA
1191 GTATAGGAGT ACTTTAACTT ATGGATTCAA CGGTAATGTT ACTGGTGATG ATACAGGAAA AATTGGCGGC
1261 TGTATTGGTG CACAAGTTTC GATTGGTCAT ACACTGAAAT ATGTTCAACC TGATTTCAAA ACAATTTTAG
1331 AGAGCCCAAC TGATAAAAAA GTAGGCTGGA AAGTGATATT TAACAATATG GTGAATCAAA ATTGGGGACC
1401 ATACGATCGA GATTCTTGGA ACCCGGTATA TGGCAATCAA CTTTTCATGA AAACTAGAAA TGGTTCTATG
1471 AAAGCAGCAG ATAACTTCCT TGATCCTAAC AAAGCAAGTT CTCTATTATC TTCAGGGTTT TCACCAGACT
1541 TCGCTACAGT TATTACTATG GATAGAAAAG CATCCAAACA ACAAACAAAT ATAGATGTAA TATACGAACG
1611 AGTTCGTGAT GATTACCAAT TGCATTGGAC TTCAACAAAT TGGAAAGGTA CCAATACTAA AGATAAATGG
1681 ACAGATCGTT CTTCAGAAAG ATATAAAATC GATTGGGAAA AGAAGAAAAT GACAAATGGT GGTTCGGGCT
1751 CATCTGGTGG CTCGAGTCAC CATCATCATC ACCAC SEQ ID NO: 26
   1 ADSDINIKTG TTDIGSNTTV KTGDLVTYDK ENGMHKKVFY SFIDSGSGSG SGSGMKFVSP NINGLRARPH
  71 QLEAIVEKHQ PDVIGLQETK VHDDMFPLEE VAKLGYNVFY HGQKGHYGVA LLTKETPIAV RRGFPGDDEE
 141 AQRRIIMAEI PSLLGNVTVI NGYFPQGESR DHPIKFPAKA QFYQNLQNYL ETELKRDNPV LIMGDMNISP
 211 TDLDIGIGEE NRKRWLRTGK CSFLPEEREW MDRLMSWGLV DTFRHANDQT ADRFSWFDYR SKGFDDNRGL
 281 RIDLLLASQP LAECCVEIGI DYEIRSMEKP SDHAPVWATF RRSGSGSGSG SGHNKKLLVI RTKGTIAGQY
 351 RVYSEECANK SCLAWPSAFK VQLQLPDNEV AQISDYYPRN SIDTKEYRST LTYCFNCNVT CDDTCKICCC
 421 IGAQVSIGHT LKYVQPDFKT ILESPTDKKV GWKVIFNNMV NQNWGPYDRD SWNPVYGNQL FMKTRNGSMK
 491 AADNFLDPNK ASSLLSSGFS PDFATVITMD RKASKQQTNI DVIYERVRDD YQLHWTSTNW KGTNTKDKWT
 561 DRSSERYKID WEKEEMTNGG SGSSGGSSHH HHHH
```

Sequence listing

SEQ ID NO: 27
```
   1 ATGGCAGATT CTGATATTAA TATTAAAACC GGTACTACAG ATATTGGAAG CAATACTACA GTAAAAACAG
  71 GTGATTTAGT CACTTATGAT AAAGAAAATG GCATGCACAA AAAAGTATTT TATAGTTTTA TCGATGATAA
 141 AAATCACAAT AAAAAACTGC TAGTTATTAG AACAAAAGGT ACCATTGCTG GTCAATATAG AGTTTATAGC
 211 GAAGAAGGTG CTAACAAAAG TGGTTTAGCC TGGCCTTCAG CCTTTAAGGT ACAGTTGCAA CTACCTGATA
 281 ATGAAGTAGC TCAAATATCT GATTACTATC CAAGAAATTC GATTGATACA AAAGAGTATA GGAGTACTTT
 351 AACTTATGGA TTCAACGGTA ATGTTACTGG TGATGATACA GGAAAAATTG GCGGCTGTAT TGGTGCACAA
 421 GTTTCGATTG TCATACACT GAAATATGTT CAACCTGATT TCAAAACAAT TTTAGAGAGC CCAACTGATA
 491 AAAAAGTAGG CTGGAAAGTG ATATTTAACA ATATGGTGAA TCAAAATTGG GGACCATACG ATCGAGATTC
 561 TTGGAACCCG GTATATGGCA ATCAACTTTT CATGAAAACT AGAATGGTT CTATGAAAGC AGCAGATAAC
 631 TTCCTTGATC CTAACAAAGC AAGTTCTCTA TTATCTTCAG GGTTTTCACC AGACTTCGCT ACAGTTATTA
 701 CTATGGATAG AAAAGCATCC AAACAACAAA CAAATATAGA TGTAATATAC GAACGAGTTC GTGATGATTA
 771 CCAATTGCAT TGGACTTCAA CAAATTGGAA AGGTACCAAT ACTAAAGATA AATGGACAGA TCGTTCTTCA
 841 GAAAGATATA AATCGATTG GAAAAAGAA GAAATGACAA ATTCCGGTAG CGGCTCTGGT TCTGGCTCTG
 911 GTTCCGGCAG CGGTTCCGGA CAGAGCACCT TCCTGTTTCA TGATTATGAA ACCTTCGGTA CCCATCCGGC
 981 CCTGGATCGT CCGGCGCAGT TTGCGGCCAT TCGCACCGAT AGCGAATTCA ATGTGATTGG CGAACCGGAA
1051 GTGTTTTATT GCAAACCGGC CGATGATTAT CTGCCGCAGC CGGGTGCGGT GCTGATTACC GGTATTACCC
1121 CGCAGGAAGC GCGCGCGAAA GGTGAAAACG AAGCGGCGTT TGCCGCGCGC ATTCATAGCC TGTTTACCGT
1191 GCCGAAAACC TGCATTCTGG GCTATAACAA TGTGCGCTTC GATGATGAAG TTACCCGTAA TATCTTTTAT
1261 CGTAACTTTT ATGATCCGTA TGCGTGGAGC TGGCAGCATG ATAACAGCCG TTGGGATCTG CTGGATGTGA
1331 TGCGCGCGTG CTATGCGCTG CGCCCGGAAG GCATTAATTG GCCGGAAAAC GATGATGGCC TGCCGAGCTT
1401 TCGTCTGGAA CATCTGACCA AGGCAACGG CATTGAACAT AGCAATGCCC ATGATGCGAT GGCCGATGTT
1471 TATGCGACCA TTGCGATGGC GAAACTGGTT AAAACCCGTC AGCCGCGCCT GTTTGATTAT CTGTTTACCC
1541 ACCGTAACAA ACACAAACTC ATGGCCCTGA TTGATGTTCC GCACATCAAA CCGCTGCTGC ATGTGAGCGC
1611 CATGTTTGGC GCCTGGCGCG GCAACACCAG CTGGGTGGCC CCGCTGGCCT GGCACCCGGA AAATCGTAAC
1681 GCCGTGATTA TGGTTGATCT GGCCGGTGAT ATTAGCCCGC TGCTGGAACT GGATAGCGAT ACCCTGCGTG
1751 AACGCCTGTA TACCGCCAAA ACCGATCTGG GCGATAATGC CGCCGTGCCG GTGAAACTGG TTCACATTAA
1821 CAAATGCCCG GTGCTGGCCC AGGCGAACAC CCTGCGCCCG GAAGATCGCC TGGGCATCAA TCGTCAGCAT
1891 CAGCATTGTC TGGATAATCT GAAAATCCTG CGTGAAAACC CGCAGGTGCG TGAAAAAGTG GTGGCCGATCT
1961 TGCGGAAGC GGAACCGTTC ACCCCGAGCG ATAACGTGGA TGCGCAGCTG TATAACGGCT TCTTTAGCGA
2031 TGCCGATCGC GCGGCGATGA AAATCGTTCT GGAAACCGAA CCGCGCAATC TGCCGGCGCT GGATATTACC
2101 TTTGTTGATA AAGGTATTGA AAAACTGCTG TTTAATTATC GTGCGCGCAA TTTTCCGGGT ACCCTGGATT
2171 ATGCCGAACA GCAGCGTTGG CTGGAACATC GTCGTCAGGT TTTCACCCCG GAATTTCTGC AGGGGTTATGC
2241 GGATGAACTG CAGATGCTGG TTCAGCAGTA TGCCGATGAT AAAGAAAAAG TGGCGCTGCT GAAAGCGCTG
2311 TGGCAGTATG CGGAAGAAAT CGTTTCTGGC TCTGGTCACC ATCATCATCA CCAC
```

SEQ ID NO: 28
```
   1 ADSDINIKTG TTDIGSNTTV KTGDLVTYDK ENGMHKKVFY SFIDDKNHNK KLLVIRTKGT IAGQYRVYSE
  71 EGANKSGLAW PSAFKVQLQL PDNEVAQISD YYPRNSIDTK EYRSTLTYGF NGNVTGDDTG KIGGCIGAQV
 141 SIGHTLKYVQ PDFKTILESP TDKKVGWKVI FNNMVNQNWG PYDRDSWNPV YGNQLFMKTR NGSMKAADNF
 211 LDDNKASSLL SSGFSPDFAT VITMDRKASK QQTNIDVIYE RVDDYQLHW TSTNWKGTNT KDKWTDRSSE
 281 RYKIDWEKEE MTNSGSGSGS GSGSGSGSGG STFLFHDYET FGTHPALDRP AQFAAIRTDS EFNVIGEPEV
 351 FYCKPADDYL PQPGAVLITG ITPQEARAKG ENEAAFAARI HSLFTVPKTC ILGYNNVRFD DEVTRNIFYR
 421 NFYDPYAWSW QHDNSRWDLL DVMRACYALR PEGINWPEND DGLPSFRLEH LTKANGIEHS NAHDAMADVY
 491 ATIAMAKLVK TRQPRLFDYL FTHRNKHKLM ALIDVPQMKP LVHVSGMFGA WRGNTSWVAP LAWHPENRNA
 561 VIMVDLAGDI SPLLELDSDT LRERLYTAKT DLGDNAAVPV KLVHINKCPV LAQANTLRPE DADRLGINRQ
 631 HGLDNLKILR ENPQVREKVV AIFAEAEPFT PSDNVDAQLY NGFFSDADRA AMKIVLETEP RNLPALDITF
 701 VDKRIEKLLF NYRARNFPGT LDYARQQRWL EHRRQVFTPR FLQGYADELQ MLVQQYADDK EKVALLKALW
 771 QYAEEIVSCS CHHHHHH
```

SEQ ID NO: 29
```
   1 ATGGCAGATT CTGATATTAA TATTAAAACC GGTACTACAG ATATTGGAAG CAATACTACA GTAAAAACAG
  71 GTGATTTAGT CACTTATGAT AAAGAAAATG GCATGCACAA AAAAGTATTT TATAGTTTTA TCGATGATAA
 141 AAATCACAAT AAAAAACTGC TAGTTATTAG AACAAAAGGT ACCATTGCTG GTCAATATAG AGTTTATAGC
 211 GAAGAAGGTG CTAACAAAAG TGGTTTAGCC TGGCCTTCAG CCTTTAAGGT ACAGTTGCAA CTACCTGATA
 281 ATGAAGTAGC TCAAATATCT GATTACTATC CAAGAAATTC GATTGATACA AAAGAGTATA GGAGTACTTT
 351 AACTTATGGA TTCAACGGTA ATGTTACTGG TGATGATACA GGAAAAATTG GCGGCTGTAT TGGTGCACAA
 421 GTTTCGATTG TCATACACT GAAATATGTT CAACCTGATT TCAAAACAAT TTTAGAGAGC CCAACTGATA
 491 AAAAAGTAGG CTGGAAAGTG ATATTTAACA ATATGGTGAA TCAAAATTGG GGACCATACG ATCGAGATTC
 561 TTGGAACCCG GTATATGGCA ATCAACTTTT CATGAAAACT AGAATGGTT CTATGAAAGC AGCAGATAAC
 631 TTCCTTGATC CTAACAAAGC AAGTTCTCTA TTATCTTCAG GGTTTTCACC AGACTTCGCT ACAGTTATTA
 701 CTATGGATAG AAAAGCATCC AAACAACAAA CAAATATAGA TGTAATATAC GAACGAGTTC GTGATGATTA
 771 CCAATTGCAT TGGACTTCAA CAAATTGGAA AGGTACCAAT ACTAAAGATA AATGGACAGA TCGTTCTTCA
 841 GAAAGATATA AATCGATTG GAAAAAGAA GAAATGACAA ATGATGGCTC CGGTAGCGGC TCTGGTTCTG
 911 GCTCTGGTTC CGGCAGCGGT TCCGCACAGA GCACCTTCCT GTTTCATGAT TATGAAACCT TCGGTACCCA
 981 TCCGGCCCTG GATCGTCCGG CGCAGTTTGC GGCCATTCGC ACCGATAGCG AATTCAATGT GATTGGCGAA
1051 CCGGAAGTGT TTTATTGCAA ACCGGCCGAT GATTATCTGC CGCAGCCGGG TGCGGTGCTG ATTACCGGTA
1121 TTACCCCGCA GGAAGCGCGC GCGAAAGGTG AAAACGAACC GGCGTTTGCC CCGCGCATTC ATCCTGTT
1191 TACCGTGCCG AAAACCTGCA TTCTGGGCTA TAACAATGTG CGCTTCGATG ATGAAGTTAC CCGTAATATC
1261 TTTTATCGTA ACTTTTATGA TCCGTATGCG TGGAGCTGGC AGCATGATAA CAGCCGTTGG GATCTGCTGG
1331 ATGTGATGCG CGCGTGCTAT GCGCTGCGCC CGGAAGGCAT TAATTGGCCG GAAAACGATG ATGGCCTGCC
1401 GAGCTTTCGT CTGGAACATC TGACCAAAGC CAACGGCATT GAACATAGCA ATGCCCATGA TGCGATGGCC
1471 GATGTTTATG CGACCATTGC GATGGCGAAA CTGGTTAAAA CCCGTCAGCC GCGCCTGTTT GATTATCTGT
1541 TTACCCACCG TAACAAACAC AAACTGATGG CGCTGATTGA TGTTCCGCAG ATGAAACCGC TGGTGCATGT
1611 GAGCGGCATG TTTGGCGCCT GGCGCGGCAA CACCAGCTGG GTGGCCCCGC TGGCCTGGCA CCCGGAAAAT
1681 CGTAACGCCG TGATTATGGT TGATCTGGCC GGTGATATTA GCCCGCTGCT GGAACTGGAT AGCGATACCC
1751 TGCGTGAACG CCTGTATACC GCCAAAACCG ATCTGGGCGA TAATGCCGCC GTGCCGGTGA AACTGGTTCA
```

-continued

Sequence listing

```
1821 CATTAACAAA TGCCCGGTGC TGGCCCAGGC GAACACCCTG CGCCCGGAAG ATGCGGATCG TCTGGGTATT
1891 AATCGCCAGC ATTGTCTGGA TAATCTGAAA ATCCTGCGTG AAAACCCGCA GGTGCGTGAA AAAGTGGTGG
1961 CGATCTTCGC GGAAGCGGAA CCGTTCACCC CGAGCGATAA CGTGGATGCG CAGCTGTATA ACGGCTTCTT
2031 TAGCGATGCC GATCGCGCGG CGATGAAAAT CGTTCTGGAA ACCGAACCGC GCAATCTGCC GGCGCTGGAT
2101 ATTACCTTTG TTGATAAACG TATTGAAAAA CTGCTGTTTA ATTATCGTGC CCGCAATTTT CCGGGTACCC
2171 TGGATTATGC CGAACAGCAG CGTTGGCTGG AACATCGTCG TCAGGTTTTC ACCCCGGAAT TTCTGCAGGG
2241 TTATGCGGAT GAACTGCAGA TGCTGGTTCA GCAGTATGCC GATGATAAAG AAAAAGTGGC GCTGCTGAAA
2311 GCGCTGTGGC AGTATGCGGA AGAAATCGTT TCTGGCTCTG GTCACCATCA TCATCACCAC
```

```
SEQ ID NO: 30
   1 ADSDINIKTG TTDIGSNTTV KTGDLVTYDK ENGMHKKVFY SFIDDKNHNK KLLVIRTKGT IAGQYRVYSE
  71 EGANKSGLAW PSAFKVQLQL PDNEVAQISD YYPRNSIDTK EYRSTLTYGF NGNVTGDDTG KTGGCTGAQV
 141 SIGHTLKYVQ PDFKTILESP TDKKVGWKVI FNNMVNQNWG PYDRDSWNPV YGNQLFMKTR NGSMKAADNF
 211 LDPNKASSLL SSGFSPDFAT VITMDRKASK QQTNIDVIYE RVRDDYQLHW TSTNWKGTNT KDKWTDRSSE
 281 RYKIDWEKEE MTNDGSGSGS GSGSGSGSGS GQSTFLFHDY ETFGTHPALD RPAQFAAIRT DSEFNVIGEP
 351 EVFYCKPADD YLPQPGAVLI TGITPQEARA KGENEAAFAA RIHSLFTVPK TCILCYNNVR FDDEVTRNIF
 421 YRNFYDPYAW SWQHDNSRWD LLDVMRACYA LRPEGINWPE NDDGLPSFRL EHLTKANGIE HSNAHDAMAD
 491 VYATIAMAKL VKTRQPRLFD YLFTHRNKHK LMALIDVPQM KPLVHVSGMF GAWRGNTSWV APLAWHPENR
 561 NAVIMVDLAC DISPLLELDS DTLRERLYTA KTDLCDNAAV PVKLVHINKC PVLAQANTLR PEDADRLCIN
 631 RQHCLDNLKI LRENPQVREK VVAIFAEAEP FTPSDNVDAQ LYNGFFSDAD RAAMKIVLET EPRNLPALDI
 701 TFVDKRIEKL LFNYRARNFP GTLDYAEQQR WLEHRRQVFT PEFLQGYADE LQMLVQQYAD DKEKVALLKA
 771 LWQYAEEIVS GSGHHHHHH
```

The invention claimed is:

1. A method of attaching an enzyme to a transmembrane protein pore subunit comprising:
   (a) providing a preparation of a first fusion protein, wherein each of the first fusion proteins comprise (i) an enzyme and (ii) a first polypeptide linker, wherein one end of the first polypeptide linker is attached to the carboxyl or amino terminus of the enzyme, and wherein the first polypeptide linker comprises an internal reactive lysine residue;
   (b) providing a preparation of a second fusion protein, wherein each of the second fusion proteins comprise (i) a transmembrane protein pore subunit and (ii) a second polypeptide linker, wherein one end of the second polypeptide linker is attached to the carboxyl or amino terminus of the transmembrane protein pore subunit and wherein the second polypeptide linker comprises an internal reactive amino acid group having a carboxyl group that is specific for the reactive lysine in (a), and an affinity purification tag;
   (c) performing a coupling reaction between the two fusion proteins of (a) and (b) above under suitable conditions such that the internal reactive lysine residue of the first linker covalently attaches to the internal reactive amino acid group of the second linker, thereby generating a population of enzyme-attached transmembrane protein pore subunits; and
   (d) separating the preparation of enzyme-attached transmembrane protein pore subunits from any unreacted first fusion protein and second fusion protein.

2. A method according to claim 1 wherein the first polypeptide linker is attached to the carboxyl terminus of the enzyme.

3. A method according to claim 1 wherein the second polypeptide linker is attached to the carboxyl terminus of the transmembrane protein pore subunit.

4. A method according to claim 1 wherein the first polypeptide linker is attached to the carboxyl terminus of the enzyme and the second polypeptide linker is attached to the carboxyl terminus of the transmembrane protein pore subunit.

5. A method according to claim 1 wherein the enzyme is a nucleic acid handling enzyme.

6. A method according to claim 1 wherein the enzyme is a polymerase, exonuclease, helicase or topoisomerase.

7. A method according to claim 1 wherein the enzyme is capable of catalyzing the synthesis of a polymer.

8. A method according to claim 1 wherein the enzyme is a DNA polymerase or is an RNA polymerase.

9. A method according to claim 1 wherein the transmembrane protein pore subunit is from a β-barrel pore or an α-helix pore.

10. A method according to claim 1 wherein the transmembrane protein pore subunit is from α-hemolysin.

11. A method according to claim 5, wherein the enzyme retains the ability to handle nucleic acids after being attached to the transmembrane protein pore subunit.

12. A method according to claim 7, wherein the enzyme retains the ability to catalyze synthesis of a polymer after being attached to the transmembrane protein pore subunit.

13. A method according to claim 1, wherein the transmembrane protein pore subunit retains its ability to form a pore after being attached to the enzyme.

14. The method of claim 1 further comprising, after step (d):
   (e) combining the preparation of enzyme-attached transmembrane pore subunits with one or more wild-type transmembrane protein pore subunits to produce heteroligomeric transmembrane protein pores having a desired stoichiometry of enzyme-attached transmembrane protein pore subunits to wild-type subunits.

15. The method according to claim 14, wherein the heteroligomeric transmembrane protein pores comprise an α-hemolysin transmembrane protein pore subunit.

16. The method according to claim 14, wherein the enzyme attached to the heteroligomeric transmembrane protein pores is an exonuclease or a polymerase enzyme.

17. The method according to claim 14, wherein the one or more wild-type transmembrane protein pore subunits are 5, 6, 7, or 8 wild-type transmembrane protein pore subunits.

18. The method of claim 14, wherein the enzyme forms part of the cis side of the heteroligomeric transmembrane protein pores.

19. A method of attaching an enzyme to a transmembrane protein pore subunit comprising:
   (a) providing a preparation of a first fusion protein, wherein each of the first fusion proteins comprise (i) transmembrane protein pore subunit and (ii) a first polypeptide linker, wherein one end of the first polypeptide linker is attached to the carboxyl or amino terminus of the transmembrane protein pore subunit, and wherein the first polypeptide linker comprises an internal reactive lysine residue;

(b) providing a preparation of a second fusion protein, wherein each of the second fusion proteins comprise (i) an enzyme and (ii) a second polypeptide linker, wherein one end of the second polypeptide linker is attached to the carboxyl or amino terminus of the enzyme and wherein the second polypeptide linker comprises an internal reactive amino acid group having a carboxyl group that is specific for the internal reactive lysine in (a), and an affinity purification tag;

(c) performing a coupling reaction between the two fusion proteins of (a) and (b) above under suitable conditions such that the internal reactive lysine residue of the first linker covalently attaches to the internal reactive amino acid group of the second linker, thereby generating a population of enzyme-attached transmembrane protein pore subunits; and (d) separating the preparation of enzyme-attached transmembrane protein pore subunits from any unreacted first fusion protein and second fusion protein.

20. The method of claim 19 further comprising, after step (d):

(e) combining the preparation of enzyme-attached transmembrane protein pore subunits with one or more wild-type transmembrane protein pore subunits to produce heteroligomeric transmembrane protein pores having a desired stoichiometry of enzyme-attached transmembrane protein pore subunits to wild-type subunits.

* * * * *

SEQUENCE LISTING

<160> NUMBER OF SEQ ID NOS: 33

<210> SEQ ID NO 1
<211> LENGTH: 882
<212> TYPE: DNA
<213> ORGANISM: Staphylococcus aureus
<220> FEATURE:
<221> NAME/KEY: CDS
<222> LOCATION: (4)..(882)

<400> SEQUENCE: 1

```
atg gca gat tct gat att aat att aaa acc ggt act aca gat att gga      48
    Ala Asp Ser Asp Ile Asn Ile Lys Thr Gly Thr Thr Asp Ile Gly
    1               5                   10                  15 agc aat act aca gta aaa aca ggt gat tta gtc act tat gat aaa gaa      96
Ser Asn Thr Thr Val Lys Thr Gly Asp Leu Val Thr Tyr Asp Lys Glu
                20                  25                  30 aat ggc atg cac aaa aaa gta ttt tat agt ttt atc gat gat aaa aat     144
Asn Gly Met His Lys Lys Val Phe Tyr Ser Phe Ile Asp Asp Lys Asn
            35                  40                  45 cac aat aaa aaa ctg cta gtt att aga aca aaa ggt acc att gct ggt     192
His Asn Lys Lys Leu Leu Val Ile Arg Thr Lys Gly Thr Ile Ala Gly
        50                  55                  60 caa tat aga gtt tat agc gaa gaa ggt gct aac aaa agt ggt tta gcc     240
Gln Tyr Arg Val Tyr Ser Glu Glu Gly Ala Asn Lys Ser Gly Leu Ala
65                  70                  75 tgg cct tca gcc ttt aag gta cag ttg caa cta cct gat aat gaa gta     288
Trp Pro Ser Ala Phe Lys Val Gln Leu Gln Leu Pro Asp Asn Glu Val
80                  85                  90                  95 gct caa ata tct gat tac tat cca aga aat tcg att gat aca aaa gag     336
Ala Gln Ile Ser Asp Tyr Tyr Pro Arg Asn Ser Ile Asp Thr Lys Glu
                100                 105                 110 tat atg agt act tta act tat gga ttc aac ggt aat gtt act ggt gat     384
Tyr Met Ser Thr Leu Thr Tyr Gly Phe Asn Gly Asn Val Thr Gly Asp
            115                 120                 125 gat aca gga aaa att ggc ggc ctt att ggt gca aat gtt tcg att ggt     432
Asp Thr Gly Lys Ile Gly Gly Leu Ile Gly Ala Asn Val Ser Ile Gly
        130                 135                 140
```

```
cat aca ctg aaa tat gtt caa cct gat ttc aaa aca att tta gag agc    480
His Thr Leu Lys Tyr Val Gln Pro Asp Phe Lys Thr Ile Leu Glu Ser
    145                 150                 155 cca act gat aaa aaa gta ggc tgg aaa gtg ata ttt aac aat atg gtg    528
Pro Thr Asp Lys Lys Val Gly Trp Lys Val Ile Phe Asn Asn Met Val
160                 165                 170                 175 aat caa aat tgg gga cca tac gat cga gat tct tgg aac ccg gta tat    576
Asn Gln Asn Trp Gly Pro Tyr Asp Arg Asp Ser Trp Asn Pro Val Tyr
                180                 185                 190 ggc aat caa ctt ttc atg aaa act aga aat ggt tct atg aaa gca gca    624
Gly Asn Gln Leu Phe Met Lys Thr Arg Asn Gly Ser Met Lys Ala Ala
            195                 200                 205 gat aac ttc ctt gat cct aac aaa gca agt tct cta tta tct tca ggg    672
Asp Asn Phe Leu Asp Pro Asn Lys Ala Ser Ser Leu Leu Ser Ser Gly
        210                 215                 220 ttt tca cca gac ttc gct aca gtt att act atg gat aga aaa gca tcc    720
Phe Ser Pro Asp Phe Ala Thr Val Ile Thr Met Asp Arg Lys Ala Ser
    225                 230                 235 aaa caa caa aca aat ata gat gta ata tac gaa cga gtt cgt gat gat    768
Lys Gln Gln Thr Asn Ile Asp Val Ile Tyr Glu Arg Val Arg Asp Asp
240                 245                 250                 255 tac caa ttg cat tgg act tca aca aat tgg aaa ggt acc aat act aaa    816
Tyr Gln Leu His Trp Thr Ser Thr Asn Trp Lys Gly Thr Asn Thr Lys
                260                 265                 270 gat aaa tgg aca gat cgt tct tca gaa aga tat aaa atc gat tgg gaa    864
Asp Lys Trp Thr Asp Arg Ser Ser Glu Arg Tyr Lys Ile Asp Trp Glu
            275                 280                 285 aaa gaa gaa atg aca aat                                            882
Lys Glu Glu Met Thr Asn
            290

<210> SEQ ID NO 2
<211> LENGTH: 293
<212> TYPE: PRT
<213> ORGANISM: Staphylococcus aureus

<400> SEQUENCE: 2

Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
            20                  25                  30

Gly Met His Lys Lys Val Phe Tyr Ser Phe Ile Asp Asp Lys Asn His
        35                  40                  45

Asn Lys Lys Leu Leu Val Ile Arg Thr Lys Gly Thr Ile Ala Gly Gln
    50                  55                  60

Tyr Arg Val Tyr Ser Glu Glu Gly Ala Asn Lys Ser Gly Leu Ala Trp
65                  70                  75                  80

Pro Ser Ala Phe Lys Val Gln Leu Gln Leu Pro Asp Asn Glu Val Ala
                85                  90                  95

Gln Ile Ser Asp Tyr Tyr Pro Arg Asn Ser Ile Asp Thr Lys Glu Tyr
            100                 105                 110

Met Ser Thr Leu Thr Tyr Gly Phe Asn Gly Asn Val Thr Gly Asp Asp
        115                 120                 125

Thr Gly Lys Ile Gly Gly Leu Ile Gly Ala Asn Val Ser Ile Gly His
    130                 135                 140

Thr Leu Lys Tyr Val Gln Pro Asp Phe Lys Thr Ile Leu Glu Ser Pro
145                 150                 155                 160
```

```
Thr Asp Lys Lys Val Gly Trp Lys Val Ile Phe Asn Asn Met Val Asn
            165                 170                 175

Gln Asn Trp Gly Pro Tyr Asp Arg Asp Ser Trp Asn Pro Val Tyr Gly
        180                 185                 190

Asn Gln Leu Phe Met Lys Thr Arg Asn Gly Ser Met Lys Ala Ala Asp
    195                 200                 205

Asn Phe Leu Asp Pro Asn Lys Ala Ser Ser Leu Leu Ser Ser Gly Phe
210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Thr Asn Trp Lys Gly Thr Asn Thr Lys Asp
            260                 265                 270

Lys Trp Thr Asp Arg Ser Ser Glu Arg Tyr Lys Ile Asp Trp Glu Lys
        275                 280                 285

Glu Glu Met Thr Asn
    290

<210> SEQ ID NO 3
<211> LENGTH: 882
<212> TYPE: DNA
<213> ORGANISM: Artificial sequence
<220> FEATURE:
<223> OTHER INFORMATION: DNA Sequence encoding one subunit of alpha-HL
      M113R/N139Q
<220> FEATURE:
<221> NAME/KEY: CDS
<222> LOCATION: (4)..(882)

<400> SEQUENCE: 3 atg gca gat tct gat att aat att aaa acc ggt act aca gat att gga      48
    Ala Asp Ser Asp Ile Asn Ile Lys Thr Gly Thr Thr Asp Ile Gly
    1               5                   10                  15 agc aat act aca gta aaa aca ggt gat tta gtc act tat gat aaa gaa      96
Ser Asn Thr Thr Val Lys Thr Gly Asp Leu Val Thr Tyr Asp Lys Glu
                20                  25                  30 aat ggc atg cac aaa aaa gta ttt tat agt ttt atc gat gat aaa aat     144
Asn Gly Met His Lys Lys Val Phe Tyr Ser Phe Ile Asp Asp Lys Asn
            35                  40                  45 cac aat aaa aaa ctg cta gtt att aga aca aaa ggt acc att gct ggt     192
His Asn Lys Lys Leu Leu Val Ile Arg Thr Lys Gly Thr Ile Ala Gly
        50                  55                  60 caa tat aga gtt tat agc gaa gaa ggt gct aac aaa agt ggt tta gcc     240
Gln Tyr Arg Val Tyr Ser Glu Glu Gly Ala Asn Lys Ser Gly Leu Ala
65                  70                  75 tgg cct tca gcc ttt aag gta cag ttg caa cta cct gat aat gaa gta     288
Trp Pro Ser Ala Phe Lys Val Gln Leu Gln Leu Pro Asp Asn Glu Val
80                  85                  90                  95 gct caa ata tct gat tac tat cca aga aat tcg att gat aca aaa gag     336
Ala Gln Ile Ser Asp Tyr Tyr Pro Arg Asn Ser Ile Asp Thr Lys Glu
                100                 105                 110 tat agg agt act tta act tat gga ttc aac ggt aat gtt act ggt gat     384
Tyr Arg Ser Thr Leu Thr Tyr Gly Phe Asn Gly Asn Val Thr Gly Asp
            115                 120                 125 gat aca gga aaa att ggc ggc ctt att ggt gca caa gtt tcg att ggt     432
Asp Thr Gly Lys Ile Gly Gly Leu Ile Gly Ala Gln Val Ser Ile Gly
        130                 135                 140
```

```
cat aca ctg aaa tat gtt caa cct gat ttc aaa aca att tta gag agc      480
His Thr Leu Lys Tyr Val Gln Pro Asp Phe Lys Thr Ile Leu Glu Ser
    145                 150                 155 cca act gat aaa aaa gta ggc tgg aaa gtg ata ttt aac aat atg gtg      528
Pro Thr Asp Lys Lys Val Gly Trp Lys Val Ile Phe Asn Asn Met Val
160                 165                 170                 175 aat caa aat tgg gga cca tac gat cga gat tct tgg aac ccg gta tat      576
Asn Gln Asn Trp Gly Pro Tyr Asp Arg Asp Ser Trp Asn Pro Val Tyr
                180                 185                 190 ggc aat caa ctt ttc atg aaa act aga aat ggt tct atg aaa gca gca      624
Gly Asn Gln Leu Phe Met Lys Thr Arg Asn Gly Ser Met Lys Ala Ala
            195                 200                 205 gat aac ttc ctt gat cct aac aaa gca agt tct cta tta tct tca ggg      672
Asp Asn Phe Leu Asp Pro Asn Lys Ala Ser Ser Leu Leu Ser Ser Gly
        210                 215                 220 ttt tca cca gac ttc gct aca gtt att act atg gat aga aaa gca tcc      720
Phe Ser Pro Asp Phe Ala Thr Val Ile Thr Met Asp Arg Lys Ala Ser
    225                 230                 235 aaa caa caa aca aat ata gat gta ata tac gaa cga gtt cgt gat gat      768
Lys Gln Gln Thr Asn Ile Asp Val Ile Tyr Glu Arg Val Arg Asp Asp
240                 245                 250                 255 tac caa ttg cat tgg act tca aca aat tgg aaa ggt acc aat act aaa      816
Tyr Gln Leu His Trp Thr Ser Thr Asn Trp Lys Gly Thr Asn Thr Lys
                260                 265                 270 gat aaa tgg aca gat cgt tct tca gaa aga tat aaa atc gat tgg gaa      864
Asp Lys Trp Thr Asp Arg Ser Ser Glu Arg Tyr Lys Ile Asp Trp Glu
            275                 280                 285 aaa gaa gaa atg aca aat                                              882
Lys Glu Glu Met Thr Asn
        290

<210> SEQ ID NO 4
<211> LENGTH: 293
<212> TYPE: PRT
<213> ORGANISM: Artificial sequence
<220> FEATURE:
<223> OTHER INFORMATION: Synthetic Construct

<400> SEQUENCE: 4

Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
                20                  25                  30

Gly Met His Lys Lys Val Phe Tyr Ser Phe Ile Asp Asp Lys Asn His
            35                  40                  45

Asn Lys Lys Leu Leu Val Ile Arg Thr Lys Gly Thr Ile Ala Gly Gln
        50                  55                  60

Tyr Arg Val Tyr Ser Glu Glu Gly Ala Asn Lys Ser Gly Leu Ala Trp
65                  70                  75                  80

Pro Ser Ala Phe Lys Val Gln Leu Gln Leu Pro Asp Asn Glu Val Ala
                85                  90                  95

Gln Ile Ser Asp Tyr Tyr Pro Arg Asn Ser Ile Asp Thr Lys Glu Tyr
            100                 105                 110

Arg Ser Thr Leu Thr Tyr Gly Phe Asn Gly Asn Val Thr Gly Asp Asp
        115                 120                 125

Thr Gly Lys Ile Gly Gly Leu Ile Gly Ala Gln Val Ser Ile Gly His
    130                 135                 140

Thr Leu Lys Tyr Val Gln Pro Asp Phe Lys Thr Ile Leu Glu Ser Pro
145                 150                 155                 160
```

```
Thr Asp Lys Lys Val Gly Trp Lys Val Ile Phe Asn Asn Met Val Asn
            165                 170                 175
Gln Asn Trp Gly Pro Tyr Asp Arg Asp Ser Trp Asn Pro Val Tyr Gly
        180                 185                 190
Asn Gln Leu Phe Met Lys Thr Arg Asn Gly Ser Met Lys Ala Ala Asp
            195                 200                 205
Asn Phe Leu Asp Pro Asn Lys Ala Ser Ser Leu Leu Ser Ser Gly Phe
        210                 215                 220
Ser Pro Asp Phe Ala Thr Val Ile Thr Met Asp Arg Lys Ala Ser Lys
225                 230                 235                 240
Gln Gln Thr Asn Ile Asp Val Ile Tyr Glu Arg Val Arg Asp Asp Tyr
            245                 250                 255
Gln Leu His Trp Thr Ser Thr Asn Trp Lys Gly Thr Asn Thr Lys Asp
            260                 265                 270
Lys Trp Thr Asp Arg Ser Ser Glu Arg Tyr Lys Ile Asp Trp Glu Lys
        275                 280                 285
Glu Glu Met Thr Asn
    290

<210> SEQ ID NO 5
<211> LENGTH: 4543
<212> TYPE: DNA
<213> ORGANISM: Artificial sequence
<220> FEATURE:
<223> OTHER INFORMATION: DNA Sequence encoding pT7-SC1_BspEI-KO

<400> SEQUENCE: 5
ttcttgaaga cgaaagggcc tcgtgatacg cctatttta taggttaatg tcatgataat     60
aatggtttct tagacgtcag gtggcacttt tcggggaaat gtgcgcggaa ccccctatttg    120 tttatttttc taaatacatt caaatatgta tccgctcatg agacaataac cctgataaat    180
gcttcaataa tattgaaaaa ggaagagtat gagtattcaa catttccgtg tcgcccttat    240 tcccttttt gcggcatttt gccttcctgt ttttgctcac ccagaaacgc tggtgaaagt    300
aaaagatgct gaagatcagt tgggtgcacg agtgggttac atcgaactgg atctcaacag    360
cggtaagatc cttgagagtt tcgccccga gaacgttttt ccaatgatga gcacttttaa    420
agttctgcta tgtggcgcgg tattatcccg tgttgacgcc gggcaagagc aactcggtcg    480
ccgcatacac tattctcaga atgacttggt tgagtactca ccagtcacag aaaagcatct    540
tacggatggc atgacagtaa gagaattatg cagtgctgcc ataaccatga gtgataacac    600
tgcggccaac ttacttctga acgatcgg aggaccgaag gagctaaccg ctttttgca    660 caacatgggg gatcatgtaa ctcgccttga tcgttgggaa ccggagctga atgaagccat    720
accaaacgac gagcgtgaca ccacgatgcc tgcagcaatg gcaacaacgt tgcgcaaact    780
attaactggc gaactactta ctctagcttc ccggcaacaa ttaatagact ggatggaggc    840
ggataaagtt gcaggaccac ttctgcgctc ggcccttccg gctggctggt ttattgctga    900
taaatctgga gccggtgagc gtgggtctcg cggtatcatt gcagcactgg ggccagatgg    960
taagccctcc cgtatcgtag ttatctacac gacgggagt caggcaacta tggatgaacg   1020
aaatagacag atcgctgaga taggtgcctc actgattaag cattggtaac tgtcagacca   1080
agtttactca tatatacttt agattgattt aaaacttcat ttttaattta aaaggatcta   1140
ggtgaagatc cttttgata atctcatgac caaaatccct taacgtgagt ttcgttcca    1200 ctgagcgtca gaccccgtag aaaagatcaa aggatcttct tgagatcctt ttttctgcg   1260
```

```
cgtaatctgc tgcttgcaaa caaaaaaacc accgctacca gcggtggttt gtttgccgga    1320
tcaagagcta ccaactcttt ttccgaaggt aactggcttc agcagagcgc agataccaaa    1380
tactgtcctt ctagtgtagc cgtagttagg ccaccacttc aagaactctg tagcaccgcc    1440 tacataccte gctctgctaa tcctgttacc agtggctgct gccagtggcg ataagtcgtg    1500
tcttaccggg ttggactcaa gacgatagtt accggataag cgcagcggt cgggctgaac     1560 ggggggttcg tgcacacagc ccagcttgga gcgaacgacc tacaccgaac tgagatacct    1620
acagcgtgag ctatgagaaa gcgccacgct tcccgaaggg agaaaggcgg acaggtatcc    1680
ggtaagcggc agggtcggaa caggagagcg cacgagggag cttccagggg gaaacgcctg    1740
gtatctttat agtcctgtcg ggtttcgcca cctctgactt gagcgtcgat ttttgtgatg    1800
ctcgtcaggg gggcggagcc tatggaaaaa cgccagcaac gcggccttttt tacggttcct    1860 ggccttttgc tggccttttg ctcacatgtt ctttcctgcg ttatcccctg attctgtgga    1920
taaccgtatt accgcctttg agtgagctga taccgctcgc cgcagccgaa cgaccgagcg    1980
cagcgagtca gtgagcgagg aagcggaaga gcgcctgatg cggtattttc tccttacgca    2040
tctgtgcggt atttcacacc gcatatatgg tgcactctca gtacaatctg ctctgatgcc    2100
gcatagttaa gccagtatac actccgctat cgctacgtga ctgggtcatg gctgcgcccc    2160
gacacccgcc aacacccgct gacgcgccct gacgggcttg tctgctcccg gcatccgctt    2220
acagacaagc tgtgaccgtc tccgggagct gcatgtgtca gaggttttca ccgtcatcac    2280
cgaaacgcgc gaggcagcgc tctcccttat gcgactcctg cattaggaag cagcccagta    2340
gtaggttgag gccgttgagc accgccgccg caaggaatgg tgcatgcaag gagatggcgc    2400
ccaacagtcc cccggccacg gggcctgcca ccatacccac gccgaaacaa gcgctcatga    2460
gcccgaagtg gcgagcccga tcttccccat cggtgatgtc ggcgatatag gcgccagcaa    2520
ccgcacctgt ggcgccggtg atgccggcca cgatgcgtcc ggcgtagagg atcgagatct    2580
agcccgccta atgagcgggc ttttttttag atctcgatcc cgcgaaatta atacgactca    2640 ctataggag accacaacgg tttccctcta gaaataattt tgtttaactt taagaaggag    2700
atatacatat ggcagattct gatattaata ttaaaaccgg tactacagat attggaagca    2760
atactacagt aaaaacaggt gatttagtca cttatgataa agaaaatggc atgcacaaaa    2820
aagtatttta tagtttatc gatgataaaa atcacaataa aaaactgcta gttattagaa    2880
caaaaggtac cattgctggt caatatagag tttatagcga agaaggtgct aacaaaagtg    2940
gtttagcctg gccttcagcc tttaaggtac agttgcaact acctgataat gaagtagctc    3000
aaatatctga ttactatcca agaaattcga ttgatacaaa agagtatatg agtactttaa    3060
cttatggatt caacggtaat gttactggtg atgatacagg aaaaattggc ggccttattg    3120
gtgcaaatgt ttcgattggt catacactga atatgttca acctgatttc aaaacaattt    3180
tagagagccc aactgataaa aagtaggct ggaaagtgat atttaacaat atggtgaatc    3240
aaaattgggg accatacgat cgagattctt ggaacccggt atatggcaat caacttttca    3300
tgaaaactag aaatggttct atgaaagcag cagataactt ccttgatcct aacaaagcaa    3360
gttctctatt atcttcaggg ttttcaccag acttcgctac agttattact atggatagaa    3420
aagcatccaa acaacaaaca aatatagatg taatatacga acgagttcgt gatgattacc    3480
aattgcattg gacttcaaca aattggaaag gtaccaatac taaagataaa tggacagatc    3540
gttcttcaga aagatataaa atcgattggg aaaaagaaga aatgacaaat taatgtaaat    3600
tatttgtaca tgtacaaata aatataattt ataactttag ccgaaagctt ggatccggct    3660
```

```
gctaacaaag cccgaaagga agctgagttg gctgctgcca ccgctgagca ataactagca   3720
taacccettg gggcctctaa acgggtcttg aggggttttt tgctgaaagg aggaactata   3780
tataattcga gctcggtacc caccccggtt gataatcaga aaagccccaa aaacaggaag   3840
attgtataag caaatattta aattgtaaac gttaatattt tgttaaaatt cgcgttaaat   3900
ttttgttaaa tcagctcatt ttttaaccaa taggccgaaa tcggcaaaat cccttataaa   3960
tcaaaagaat agaccgagat agggttgagt gttgttccag tttggaacaa gagtccagta   4020
ttaaagaacg tggactccaa cgtcaaaggg cgaaaaaccg tctatcaggg cgatggccca   4080
ctacgtgaac catcacccta atcaagtttt tggggtcga ggtgccgtaa agcactaaat    4140
cggaacccta aagggatgcc ccgatttaga gcttgacggg gaaagccggc gaacgtggcg   4200
agaaaggaag ggaagaaagc gaaggagcg ggcgctaggg cgctggcaag tgtagcggtc    4260
acgctgcgcg taaccaccac acccgccgcg cttaatgcgc cgctacaggg cgcgtgggga   4320
tcctctagag tcgacctgca ggcatgcaag ctatcccgca agaggccgg cagtaccggc    4380
ataaccaagc ctatgcctac agcatccagg gtgacggtgc cgaggatgac gatgagcgca   4440
ttgttagatt tcatacacgg tgcctgactg cgttagcaat ttaactgtga taaactaccg   4500
cattaaagct agcttatcga tgataagctg tcaaacatga gaa                    4543
```

<210> SEQ ID NO 6
<211> LENGTH: 888
<212> TYPE: DNA
<213> ORGANISM: Artificial sequence
<220> FEATURE:
<223> OTHER INFORMATION: DNA Sequence encoding one subunit of a
  wild-type alpha-hemolysin containing a BspEI cloning site at
  position 1 (L1)

<400> SEQUENCE: 6

```
atggcagatt ctgatattaa tattaaaacc ggtactacag atattggaag caatacttcc     60
ggaacagtaa aacaggtga tttagtcact tatgataaag aaaatggcat gcacaaaaaa    120
gtattttata gttttatcga tgataaaaat cacaataaaa aactgctagt tattagaaca    180
aaaggtacca ttgctggtca atatagagtt tatagcgaag aaggtgctaa caaagtggt    240
ttagcctggc cttcagcctt aaggtacag ttgcaactac ctgataatga agtagctcaa     300
atatctgatt actatccaag aaattcgatt gatacaaaag agtatatgag tactttaact    360
tatggattca acggtaatgt tactggtgat gatacaggaa aaattggcgg ccttattggt    420
gcaaatgttt cgattggtca tacactgaaa tatgttcaac ctgatttcaa aacaattta    480
gagagcccaa ctgataaaaa agtaggctgg aaagtgatat taacaatat ggtgaatcaa    540
aattggggac catacgatcg agattcttgg aacccggtat atggcaatca acttttcatg    600
aaaactagaa atggttctat gaaagcagca gataacttcc ttgatcctaa caaagcaagt    660
tctctattat cttcagggtt ttcaccagac ttcgctacag ttattactat ggatagaaaa    720
gcatccaaac aacaaacaaa tatagatgta atatacgaac gagttcgtga tgattaccaa    780
ttgcattgga cttcaacaaa ttggaaaggt accaatacta aagataaatg gacagatcgt    840
tcttcagaaa gatataaaat cgattgggaa aaagaagaaa tgacaaat                888
```

<210> SEQ ID NO 7
<211> LENGTH: 888
<212> TYPE: DNA
<213> ORGANISM: Artificial sequence
<220> FEATURE:
<223> OTHER INFORMATION: DNA Sequence encoding one subunit of a
      wild-type alpha-hemolysin containing a BspEI cloning site at
      position 2 (L2a)

<400> SEQUENCE: 7

| | | | | | |
|---|---|---|---|---|---|
| atggcagatt | ctgatattaa | tattaaaacc | ggtactacag | atattggaag | caatactaca | 60 |
| gtaaaaacag | gtgatttagt | cacttatgat | aaagaaaatg | gcatgcacaa | aaaagtattt | 120 |
| tatagttttta | tcgattccgg | agataaaaat | cacaataaaa | aactgctagt | tattagaaca | 180 |
| aaaggtacca | ttgctggtca | atatagagtt | tatagcgaag | aaggtgctaa | caaaagtggt | 240 |
| ttagcctggc | cttcagcctt | taaggtacag | ttgcaactac | ctgataatga | agtagctcaa | 300 |
| atatctgatt | actatccaag | aaattcgatt | gatacaaaag | agtatatgag | tactttaact | 360 |
| tatggattca | acggtaatgt | tactggtgat | gatacaggaa | aaattggcgg | ccttattggt | 420 |
| gcaaatgttt | cgattggtca | tacactgaaa | tatgttcaac | ctgatttcaa | aacaatttta | 480 |
| gagagcccaa | ctgataaaaa | agtaggctgg | aaagtgatat | taacaatat | ggtgaatcaa | 540 |
| aattggggac | atacgatcg | agattcttgg | aacccggtat | atggcaatca | acttttcatg | 600 |
| aaaactagaa | atggttctat | gaaagcagca | gataacttcc | ttgatcctaa | caaagcaagt | 660 |
| tctctattat | cttcagggtt | ttcaccagac | ttcgctacag | ttattactat | ggatagaaaa | 720 |
| gcatccaaac | aacaaacaaa | tatagatgta | atatacgaac | gagttcgtga | tgattaccaa | 780 |
| ttgcattgga | cttcaacaaa | ttggaaaggt | accaatacta | aagataaatg | gacagatcgt | 840 |
| tcttcagaaa | gatataaaat | cgattgggaa | aaagaagaaa | tgacaaat | | 888 |

<210> SEQ ID NO 8
<211> LENGTH: 888
<212> TYPE: DNA
<213> ORGANISM: Artificial sequence
<220> FEATURE:
<223> OTHER INFORMATION: DNA Sequence encoding one subunit of a
      wild-type alpha-hemolysin containing a BspEI cloning site at
      position 2 (L2b)

<400> SEQUENCE: 8

| | | | | | |
|---|---|---|---|---|---|
| atggcagatt | ctgatattaa | tattaaaacc | ggtactacag | atattggaag | caatactaca | 60 |
| gtaaaaacag | gtgatttagt | cacttatgat | aaagaaaatg | gcatgcacaa | aaaagtattt | 120 |
| tatagttttta | tcgatgataa | aaatcacaat | aaatccggaa | aactgctagt | tattagaaca | 180 |
| aaaggtacca | ttgctggtca | atatagagtt | tatagcgaag | aaggtgctaa | caaaagtggt | 240 |
| ttagcctggc | cttcagcctt | taaggtacag | ttgcaactac | ctgataatga | agtagctcaa | 300 |
| atatctgatt | actatccaag | aaattcgatt | gatacaaaag | agtatatgag | tactttaact | 360 |
| tatggattca | acggtaatgt | tactggtgat | gatacaggaa | aaattggcgg | ccttattggt | 420 |
| gcaaatgttt | cgattggtca | tacactgaaa | tatgttcaac | ctgatttcaa | aacaatttta | 480 |
| gagagcccaa | ctgataaaaa | agtaggctgg | aaagtgatat | taacaatat | ggtgaatcaa | 540 |
| aattggggac | atacgatcg | agattcttgg | aacccggtat | atggcaatca | acttttcatg | 600 |
| aaaactagaa | atggttctat | gaaagcagca | gataacttcc | ttgatcctaa | caaagcaagt | 660 |
| tctctattat | cttcagggtt | ttcaccagac | ttcgctacag | ttattactat | ggatagaaaa | 720 |
| gcatccaaac | aacaaacaaa | tatagatgta | atatacgaac | gagttcgtga | tgattaccaa | 780 |
| ttgcattgga | cttcaacaaa | ttggaaaggt | accaatacta | aagataaatg | gacagatcgt | 840 |
| tcttcagaaa | gatataaaat | cgattgggaa | aaagaagaaa | tgacaaat | | 888 |

<210> SEQ ID NO 9
<211> LENGTH: 804
<212> TYPE: DNA
<213> ORGANISM: Escherichia coli
<220> FEATURE:
<221> NAME/KEY: CDS
<222> LOCATION: (1)..(804)

<400> SEQUENCE: 9

| | | |
|---|---|---|
| atg aaa ttt gtc tct ttt aat atc aac ggc ctg cgc gcc aga cct cac<br>Met Lys Phe Val Ser Phe Asn Ile Asn Gly Leu Arg Ala Arg Pro His<br>1                       5                    10                15 | 48 |
| cag ctt gaa gcc atc gtc gaa aag cac caa ccg gat gtg att ggc ctg<br>Gln Leu Glu Ala Ile Val Glu Lys His Gln Pro Asp Val Ile Gly Leu<br>                  20                    25                    30 | 96 |
| cag gag aca aaa gtt cat gac gat atg ttt ccg ctc gaa gag gtg gcg<br>Gln Glu Thr Lys Val His Asp Asp Met Phe Pro Leu Glu Glu Val Ala<br>        35                    40                    45 | 144 |
| aag ctc ggc tac aac gtg ttt tat cac ggg cag aaa ggc cat tat ggc<br>Lys Leu Gly Tyr Asn Val Phe Tyr His Gly Gln Lys Gly His Tyr Gly<br>50                      55                    60 | 192 |
| gtg gcg ctg ctg acc aaa gag acg ccg att gcc gtg cgt cgc ggc ttt<br>Val Ala Leu Leu Thr Lys Glu Thr Pro Ile Ala Val Arg Arg Gly Phe<br>65                      70                    75                80 | 240 |
| ccc ggt gac gac gaa gag gcg cag cgg cgg att att atg gcg gaa atc<br>Pro Gly Asp Asp Glu Glu Ala Gln Arg Arg Ile Ile Met Ala Glu Ile<br>                  85                    90                    95 | 288 |
| ccc tca ctg ctg ggt aat gtc acc gtg atc aac ggt tac ttc ccg cag<br>Pro Ser Leu Leu Gly Asn Val Thr Val Ile Asn Gly Tyr Phe Pro Gln<br>                  100                 105               110 | 336 |
| ggt gaa agc cgc gac cat ccg ata aaa ttc ccg gca aaa gcg cag ttt<br>Gly Glu Ser Arg Asp His Pro Ile Lys Phe Pro Ala Lys Ala Gln Phe<br>              115                 120               125 | 384 |
| tat cag aat ctg caa aac tac ctg gaa acc gaa ctc aaa cgt gat aat<br>Tyr Gln Asn Leu Gln Asn Tyr Leu Glu Thr Glu Leu Lys Arg Asp Asn<br>130                     135                 140 | 432 |
| ccg gta ctg att atg ggc gat atg aat atc agc cct aca gat ctg gat<br>Pro Val Leu Ile Met Gly Asp Met Asn Ile Ser Pro Thr Asp Leu Asp<br>145                     150                 155               160 | 480 |
| atc ggc att ggc gaa gaa aac cgt aag cgc tgg ctg cgt acc ggt aaa<br>Ile Gly Ile Gly Glu Glu Asn Arg Lys Arg Trp Leu Arg Thr Gly Lys<br>                  165                 170               175 | 528 |
| tgc tct ttc ctg ccg gaa gag cgc gaa tgg atg gac agg ctg atg agc<br>Cys Ser Phe Leu Pro Glu Glu Arg Glu Trp Met Asp Arg Leu Met Ser<br>              180                 185               190 | 576 |
| tgg ggg ttg gtc gat acc ttc cgc cat gcg aat ccg caa aca gca gat<br>Trp Gly Leu Val Asp Thr Phe Arg His Ala Asn Pro Gln Thr Ala Asp<br>              195                 200               205 | 624 |
| cgt ttc tca tgg ttt gat tac cgc tca aaa ggt ttt gac gat aac cgt<br>Arg Phe Ser Trp Phe Asp Tyr Arg Ser Lys Gly Phe Asp Asp Asn Arg<br>210                     215                 220 | 672 |
| ggt ctg cgc atc gac ctg ctc gcc agc caa ccg ctg gca gaa tgt<br>Gly Leu Arg Ile Asp Leu Leu Ala Ser Gln Pro Leu Ala Glu Cys<br>225                     230                 235               240 | 720 |
| tgc gta gaa acc ggc atc gac tat gaa atc cgc agc atg gaa aaa ccg<br>Cys Val Glu Thr Gly Ile Asp Tyr Glu Ile Arg Ser Met Glu Lys Pro<br>                  245                 250               255 | 768 |
| tcc gat cac gcc ccc gtc tgg gcg acc ttc cgc cgc<br>Ser Asp His Ala Pro Val Trp Ala Thr Phe Arg Arg<br>              260                 265 | 804 |

```
<210> SEQ ID NO 10
<211> LENGTH: 268
<212> TYPE: PRT
<213> ORGANISM: Escherichia coli

<400> SEQUENCE: 10

Met Lys Phe Val Ser Phe Asn Ile Asn Gly Leu Arg Ala Arg Pro His
 1               5                  10                  15

Gln Leu Glu Ala Ile Val Glu Lys His Gln Pro Asp Val Ile Gly Leu
            20                  25                  30

Gln Glu Thr Lys Val His Asp Asp Met Phe Pro Leu Glu Glu Val Ala
        35                  40                  45

Lys Leu Gly Tyr Asn Val Phe Tyr His Gly Gln Lys Gly His Tyr Gly
    50                  55                  60

Val Ala Leu Leu Thr Lys Glu Thr Pro Ile Ala Val Arg Arg Gly Phe
65                  70                  75                  80

Pro Gly Asp Asp Glu Glu Ala Gln Arg Arg Ile Ile Met Ala Glu Ile
                85                  90                  95

Pro Ser Leu Leu Gly Asn Val Thr Val Ile Asn Gly Tyr Phe Pro Gln
            100                 105                 110

Gly Glu Ser Arg Asp His Pro Ile Lys Phe Pro Ala Lys Ala Gln Phe
        115                 120                 125

Tyr Gln Asn Leu Gln Asn Tyr Leu Glu Thr Glu Leu Lys Arg Asp Asn
    130                 135                 140

Pro Val Leu Ile Met Gly Asp Met Asn Ile Ser Pro Thr Asp Leu Asp
145                 150                 155                 160

Ile Gly Ile Gly Glu Glu Asn Arg Lys Arg Trp Leu Arg Thr Gly Lys
                165                 170                 175

Cys Ser Phe Leu Pro Glu Glu Arg Glu Trp Met Asp Arg Leu Met Ser
            180                 185                 190

Trp Gly Leu Val Asp Thr Phe Arg His Ala Asn Pro Gln Thr Ala Asp
        195                 200                 205

Arg Phe Ser Trp Phe Asp Tyr Arg Ser Lys Gly Phe Asp Asp Asn Arg
    210                 215                 220

Gly Leu Arg Ile Asp Leu Leu Leu Ala Ser Gln Pro Leu Ala Glu Cys
225                 230                 235                 240

Cys Val Glu Thr Gly Ile Asp Tyr Glu Ile Arg Ser Met Glu Lys Pro
                245                 250                 255

Ser Asp His Ala Pro Val Trp Ala Thr Phe Arg Arg
            260                 265

<210> SEQ ID NO 11
<211> LENGTH: 1425
<212> TYPE: DNA
<213> ORGANISM: Escherichia coli
<220> FEATURE:
<221> NAME/KEY: CDS
<222> LOCATION: (1)..(1425)

<400> SEQUENCE: 11 atg atg aat gac ggt aag caa caa tct acc ttt ttg ttt cac gat tac      48
Met Met Asn Asp Gly Lys Gln Gln Ser Thr Phe Leu Phe His Asp Tyr
 1               5                  10                  15 gaa acc ttt ggc acg cac ccc gcg tta gat cgc cct gca cag ttc gca      96
Glu Thr Phe Gly Thr His Pro Ala Leu Asp Arg Pro Ala Gln Phe Ala
            20                  25                  30
```

```
gcc att cgc acc gat agc gaa ttc aat gtc atc ggc gaa ccc gaa gtc      144
Ala Ile Arg Thr Asp Ser Glu Phe Asn Val Ile Gly Glu Pro Glu Val
        35                  40                  45 ttt tac tgc aag ccc gct gat gac tat tta ccc cag cca gga gcc gta      192
Phe Tyr Cys Lys Pro Ala Asp Asp Tyr Leu Pro Gln Pro Gly Ala Val
 50                  55                  60 tta att acc ggt att acc ccg cag gaa gca cgg gcg aaa gga gaa aac      240
Leu Ile Thr Gly Ile Thr Pro Gln Glu Ala Arg Ala Lys Gly Glu Asn
65                  70                  75                  80 gaa gcc gcg ttt gcc gcc cgt att cac tcg ctt ttt acc gta ccg aag      288
Glu Ala Ala Phe Ala Ala Arg Ile His Ser Leu Phe Thr Val Pro Lys
                85                  90                  95 acc tgt att ctg ggc tac aac aat gtg cgt ttc gac gac gaa gtc aca      336
Thr Cys Ile Leu Gly Tyr Asn Asn Val Arg Phe Asp Asp Glu Val Thr
            100                 105                 110 cgc aac att ttt tat cgt aat ttc tac gat cct tac gcc tgg agc tgg      384
Arg Asn Ile Phe Tyr Arg Asn Phe Tyr Asp Pro Tyr Ala Trp Ser Trp
        115                 120                 125 cag cat gat aac tcg cgc tgg gat tta ctg gat gtt atg cgt gcc tgt      432
Gln His Asp Asn Ser Arg Trp Asp Leu Leu Asp Val Met Arg Ala Cys
130                 135                 140 tat gcc ctg cgc ccg gaa gga ata aac tgg cct gaa aat gat gac ggt      480
Tyr Ala Leu Arg Pro Glu Gly Ile Asn Trp Pro Glu Asn Asp Asp Gly
145                 150                 155                 160 cta ccg agc ttt cgc ctt gag cat tta acc aaa gcg aat ggt att gaa      528
Leu Pro Ser Phe Arg Leu Glu His Leu Thr Lys Ala Asn Gly Ile Glu
                165                 170                 175 cat agc aac gcc cac gat gcg atg gct gat gtg tac gcc act att gcg      576
His Ser Asn Ala His Asp Ala Met Ala Asp Val Tyr Ala Thr Ile Ala
            180                 185                 190 atg gca aag ctg gta aaa acg cgt cag cca cgc ctg ttt gat tat ctc      624
Met Ala Lys Leu Val Lys Thr Arg Gln Pro Arg Leu Phe Asp Tyr Leu
        195                 200                 205 ttt acc cat cgt aat aaa cac aaa ctg atg gcg ttg att gat gtt ccg      672
Phe Thr His Arg Asn Lys His Lys Leu Met Ala Leu Ile Asp Val Pro
210                 215                 220 cag atg aaa ccc ctg gtg cac gtt tcc gga atg ttt gga gca tgg cgc      720
Gln Met Lys Pro Leu Val His Val Ser Gly Met Phe Gly Ala Trp Arg
225                 230                 235                 240 ggc aat acc agc tgg gtg gca ccg ctg gcg tgg cat cct gaa aat cgc      768
Gly Asn Thr Ser Trp Val Ala Pro Leu Ala Trp His Pro Glu Asn Arg
                245                 250                 255 aat gcc gta att atg gtg gat ttg gca gga gac att tcg cca tta ctg      816
Asn Ala Val Ile Met Val Asp Leu Ala Gly Asp Ile Ser Pro Leu Leu
            260                 265                 270 gaa ctg gat agc gac aca ttg cgc gag cgt tta tat acc gca aaa acc      864
Glu Leu Asp Ser Asp Thr Leu Arg Glu Arg Leu Tyr Thr Ala Lys Thr
        275                 280                 285 gat ctt ggc gat aac gcc gcc gtt ccg gtt aag ctg gtg cat atc aat      912
Asp Leu Gly Asp Asn Ala Ala Val Pro Val Lys Leu Val His Ile Asn
290                 295                 300 aaa tgt ccg gtg ctg gcc cag gcg aat acg cta cgc ccg gaa gat gcc      960
Lys Cys Pro Val Leu Ala Gln Ala Asn Thr Leu Arg Pro Glu Asp Ala
305                 310                 315                 320 gac cga ctg gga att aat cgt cag cat tgc ctc gat aac ctg aaa att     1008
Asp Arg Leu Gly Ile Asn Arg Gln His Cys Leu Asp Asn Leu Lys Ile
                325                 330                 335 ctg cgt gaa aat ccg caa gtg cgc gaa aaa gtg gtg gcg ata ttc gcg     1056
Leu Arg Glu Asn Pro Gln Val Arg Glu Lys Val Val Ala Ile Phe Ala
            340                 345                 350
```

```
gaa gcc gaa ccg ttt acg cct tca gat aac gtg gat gca cag ctt tat      1104
Glu Ala Glu Pro Phe Thr Pro Ser Asp Asn Val Asp Ala Gln Leu Tyr
        355                 360                 365 aac ggc ttt ttc agt gac gca gat cgt gca gca atg aaa att gtg ctg      1152
Asn Gly Phe Phe Ser Asp Ala Asp Arg Ala Ala Met Lys Ile Val Leu
    370                 375                 380 gaa acc gag ccg cgt aat tta ccg gca ctg gat atc act ttt gtt gat      1200
Glu Thr Glu Pro Arg Asn Leu Pro Ala Leu Asp Ile Thr Phe Val Asp
385                 390                 395                 400 aaa cgg att gaa aag ctg ttg ttc aat tat cgg gca cgc aac ttc ccg      1248
Lys Arg Ile Glu Lys Leu Leu Phe Asn Tyr Arg Ala Arg Asn Phe Pro
                405                 410                 415 ggg acg ctg gat tat gcc gag cag caa cgc tgg ctg gag cac cgt cgc      1296
Gly Thr Leu Asp Tyr Ala Glu Gln Gln Arg Trp Leu Glu His Arg Arg
            420                 425                 430 cag gtc ttc acg cca gag ttt ttg cag ggt tat gct gat gaa ttg cag      1344
Gln Val Phe Thr Pro Glu Phe Leu Gln Gly Tyr Ala Asp Glu Leu Gln
        435                 440                 445 atg ctg gta caa caa tat gcc gat gac aaa gag aaa gtg gcg ctg tta      1392
Met Leu Val Gln Gln Tyr Ala Asp Asp Lys Glu Lys Val Ala Leu Leu
    450                 455                 460 aaa gca ctt tgg cag tac gcg gaa gag att gtc                          1425
Lys Ala Leu Trp Gln Tyr Ala Glu Glu Ile Val
465                 470                 475

<210> SEQ ID NO 12
<211> LENGTH: 475
<212> TYPE: PRT
<213> ORGANISM: Escherichia coli

<400> SEQUENCE: 12

Met Met Asn Asp Gly Lys Gln Gln Ser Thr Phe Leu Phe His Asp Tyr
1               5                   10                  15

Glu Thr Phe Gly Thr His Pro Ala Leu Asp Arg Pro Ala Gln Phe Ala
            20                  25                  30

Ala Ile Arg Thr Asp Ser Glu Phe Asn Val Ile Gly Glu Pro Glu Val
        35                  40                  45

Phe Tyr Cys Lys Pro Ala Asp Asp Tyr Leu Pro Gln Pro Gly Ala Val
    50                  55                  60

Leu Ile Thr Gly Ile Thr Pro Gln Glu Ala Arg Ala Lys Gly Glu Asn
65                  70                  75                  80

Glu Ala Ala Phe Ala Ala Arg Ile His Ser Leu Phe Thr Val Pro Lys
                85                  90                  95

Thr Cys Ile Leu Gly Tyr Asn Asn Val Arg Phe Asp Asp Glu Val Thr
            100                 105                 110

Arg Asn Ile Phe Tyr Arg Asn Phe Tyr Asp Pro Tyr Ala Trp Ser Trp
        115                 120                 125

Gln His Asp Asn Ser Arg Trp Asp Leu Leu Asp Val Met Arg Ala Cys
    130                 135                 140

Tyr Ala Leu Arg Pro Glu Gly Ile Asn Trp Pro Glu Asn Asp Asp Gly
145                 150                 155                 160

Leu Pro Ser Phe Arg Leu Glu His Leu Thr Lys Ala Asn Gly Ile Glu
                165                 170                 175

His Ser Asn Ala His Asp Ala Met Ala Asp Val Tyr Ala Thr Ile Ala
            180                 185                 190

Met Ala Lys Leu Val Lys Thr Arg Gln Pro Arg Leu Phe Asp Tyr Leu
        195                 200                 205
```

-continued

```
Phe Thr His Arg Asn Lys His Lys Leu Met Ala Leu Ile Asp Val Pro
    210                 215                 220

Gln Met Lys Pro Leu Val His Val Ser Gly Met Phe Gly Ala Trp Arg
225                 230                 235                 240

Gly Asn Thr Ser Trp Val Ala Pro Leu Ala Trp His Pro Glu Asn Arg
                    245                 250                 255

Asn Ala Val Ile Met Val Asp Leu Ala Gly Asp Ile Ser Pro Leu Leu
                260                 265                 270

Glu Leu Asp Ser Asp Thr Leu Arg Glu Arg Leu Tyr Thr Ala Lys Thr
            275                 280                 285

Asp Leu Gly Asp Asn Ala Ala Val Pro Val Lys Leu Val His Ile Asn
        290                 295                 300

Lys Cys Pro Val Leu Ala Gln Ala Asn Thr Leu Arg Pro Glu Asp Ala
305                 310                 315                 320

Asp Arg Leu Gly Ile Asn Arg Gln His Cys Leu Asp Asn Leu Lys Ile
                    325                 330                 335

Leu Arg Glu Asn Pro Gln Val Arg Glu Lys Val Val Ala Ile Phe Ala
                340                 345                 350

Glu Ala Glu Pro Phe Thr Pro Ser Asp Asn Val Asp Ala Gln Leu Tyr
            355                 360                 365

Asn Gly Phe Phe Ser Asp Ala Asp Arg Ala Ala Met Lys Ile Val Leu
        370                 375                 380

Glu Thr Glu Pro Arg Asn Leu Pro Ala Leu Asp Ile Thr Phe Val Asp
385                 390                 395                 400

Lys Arg Ile Glu Lys Leu Leu Phe Asn Tyr Arg Ala Arg Asn Phe Pro
                    405                 410                 415

Gly Thr Leu Asp Tyr Ala Glu Gln Gln Arg Trp Leu Glu His Arg Arg
                420                 425                 430

Gln Val Phe Thr Pro Glu Phe Leu Gln Gly Tyr Ala Asp Glu Leu Gln
            435                 440                 445

Met Leu Val Gln Gln Tyr Ala Asp Asp Lys Glu Lys Val Ala Leu Leu
        450                 455                 460

Lys Ala Leu Trp Gln Tyr Ala Glu Glu Ile Val
465                 470                 475

<210> SEQ ID NO 13
<211> LENGTH: 1275
<212> TYPE: DNA
<213> ORGANISM: Thermus thermophilus
<220> FEATURE:
<221> NAME/KEY: CDS
<222> LOCATION: (1)..(1275)

<400> SEQUENCE: 13 atg ttt cgt cgt aaa gaa gat ctg gat ccg ccg ctg gca ctg ctg ccg    48
Met Phe Arg Arg Lys Glu Asp Leu Asp Pro Pro Leu Ala Leu Leu Pro
1               5                   10                  15 ctg aaa ggc ctg cgc gaa gcc gcc gca ctg ctg gaa gaa gcg ctg cgt    96
Leu Lys Gly Leu Arg Glu Ala Ala Ala Leu Leu Glu Glu Ala Leu Arg
            20                  25                  30 caa ggt aaa cgc att cgt gtt cac ggc gac tat gat gcg gat ggc ctg   144
Gln Gly Lys Arg Ile Arg Val His Gly Asp Tyr Asp Ala Asp Gly Leu
        35                  40                  45 acc ggc acc gcg atc ctg gtt cgt ggt ctg gcc gcc ctg ggt gcg gat   192
Thr Gly Thr Ala Ile Leu Val Arg Gly Leu Ala Ala Leu Gly Ala Asp
    50                  55                  60
```

| | |
|---|---|
| gtt cat ccg ttt atc ccg cac cgc ctg gaa gaa ggc tat ggt gtc ctg<br>Val His Pro Phe Ile Pro His Arg Leu Glu Glu Gly Tyr Gly Val Leu<br>65      70        75        80 | 240 |
| atg gaa cgc gtc ccg gaa cat ctg gaa gcc tcg gac ctg ttt ctg acc<br>Met Glu Arg Val Pro Glu His Leu Glu Ala Ser Asp Leu Phe Leu Thr<br>      85        90        95 | 288 |
| gtt gac tgc ggc att acc aac cat gcg gaa ctg cgc gaa ctg ctg gaa<br>Val Asp Cys Gly Ile Thr Asn His Ala Glu Leu Arg Glu Leu Leu Glu<br>    100        105        110 | 336 |
| aat ggc gtg gaa gtc att gtt acc gat cat cat acg ccg ggc aaa acg<br>Asn Gly Val Glu Val Ile Val Thr Asp His His Thr Pro Gly Lys Thr<br>115        120        125 | 384 |
| ccg ccg ccg ggt ctg gtc gtg cat ccg gcg ctg acg ccg gat ctg aaa<br>Pro Pro Pro Gly Leu Val Val His Pro Ala Leu Thr Pro Asp Leu Lys<br>130        135        140 | 432 |
| gaa aaa ccg acc ggc gca ggc gtg gcg ttt ctg ctg ctg tgg gca ctg<br>Glu Lys Pro Thr Gly Ala Gly Val Ala Phe Leu Leu Leu Trp Ala Leu<br>145        150        155        160 | 480 |
| cat gaa cgc ctg ggc ctg ccg ccg ctg gaa tac gcg gac ctg gca<br>His Glu Arg Leu Gly Leu Pro Pro Leu Glu Tyr Ala Asp Leu Ala<br>        165        170        175 | 528 |
| gcc gtt ggc acc att gcc gac gtt gcc ccg ctg tgg ggt tgg aat cgt<br>Ala Val Gly Thr Ile Ala Asp Val Ala Pro Leu Trp Gly Trp Asn Arg<br>    180        185        190 | 576 |
| gca ctg gtg aaa gaa ggt ctg gca cgc atc ccg gct tca tct tgg gtg<br>Ala Leu Val Lys Glu Gly Leu Ala Arg Ile Pro Ala Ser Ser Trp Val<br>195        200        205 | 624 |
| ggc ctg cgt ctg ctg gct gaa gcc gtg ggc tat acc ggc aaa gcg gtc<br>Gly Leu Arg Leu Leu Ala Glu Ala Val Gly Tyr Thr Gly Lys Ala Val<br>210        215        220 | 672 |
| gaa gtc gct ttc cgc atc gcg ccg cgc atc aat gcg gct tcc cgc ctg<br>Glu Val Ala Phe Arg Ile Ala Pro Arg Ile Asn Ala Ala Ser Arg Leu<br>225        230        235        240 | 720 |
| ggc gaa gcg gaa aaa gcc ctg cgc ctg ctg ctg acg gat gat gcg gca<br>Gly Glu Ala Glu Lys Ala Leu Arg Leu Leu Leu Thr Asp Asp Ala Ala<br>        245        250        255 | 768 |
| gaa gct cag gcg ctg gtc ggc gaa ctg cac cgt ctg aac gcc cgt cgt<br>Glu Ala Gln Ala Leu Val Gly Glu Leu His Arg Leu Asn Ala Arg Arg<br>    260        265        270 | 816 |
| cag acc ctg gaa gaa gcg atg ctg cgc aaa ctg ctg ccg cag gcc gac<br>Gln Thr Leu Glu Glu Ala Met Leu Arg Lys Leu Leu Pro Gln Ala Asp<br>275        280        285 | 864 |
| ccg gaa gcg aaa gcc atc gtt ctg ctg gac ccg gaa ggc cat ccg ggt<br>Pro Glu Ala Lys Ala Ile Val Leu Leu Asp Pro Glu Gly His Pro Gly<br>290        295        300 | 912 |
| gtt atg ggt att gtg gcc tct cgc atc ctg gaa gcg acc ctg cgc ccg<br>Val Met Gly Ile Val Ala Ser Arg Ile Leu Glu Ala Thr Leu Arg Pro<br>305        310        315        320 | 960 |
| gtc ttt ctg gtg gcc cag ggc aaa ggc acc gtg cgt tcg ctg gct ccg<br>Val Phe Leu Val Ala Gln Gly Lys Gly Thr Val Arg Ser Leu Ala Pro<br>        325        330        335 | 1008 |
| att tcc gcc gtc gaa gca ctg cgc agc gcg gaa gat ctg ctg ctg cgt<br>Ile Ser Ala Val Glu Ala Leu Arg Ser Ala Glu Asp Leu Leu Leu Arg<br>    340        345        350 | 1056 |
| tat ggt ggt cat aaa gaa gcg gcg ggt ttc gca atg gat gaa gcg ctg<br>Tyr Gly Gly His Lys Glu Ala Ala Gly Phe Ala Met Asp Glu Ala Leu<br>355        360        365 | 1104 |
| ttt ccg gcg ttc aaa gca cgc gtt gaa gcg tat gcc gca cgt ttc ccg<br>Phe Pro Ala Phe Lys Ala Arg Val Glu Ala Tyr Ala Ala Arg Phe Pro<br>370        375        380 | 1152 |

```
gat  ccg  gtt  cgt  gaa  gtg  gca  ctg  ctg  gat  ctg  ctg  ccg  gaa  ccg  ggc       1200
Asp  Pro  Val  Arg  Glu  Val  Ala  Leu  Leu  Asp  Leu  Leu  Pro  Glu  Pro  Gly
385                 390                      395                      400 ctg  ctg  ccg  cag  gtg  ttc  cgt  gaa  ctg  gca  ctg  ctg  gaa  ccg  tat  ggt       1248
Leu  Leu  Pro  Gln  Val  Phe  Arg  Glu  Leu  Ala  Leu  Leu  Glu  Pro  Tyr  Gly
                    405                      410                      415 gaa  ggt  aac  ccg  gaa  ccg  ctg  ttc  ctg                                           1275
Glu  Gly  Asn  Pro  Glu  Pro  Leu  Phe  Leu
               420                 425

<210> SEQ ID NO 14
<211> LENGTH: 425
<212> TYPE: PRT
<213> ORGANISM: Thermus thermophilus

<400> SEQUENCE: 14

Met Phe Arg Arg Lys Glu Asp Leu Asp Pro Pro Leu Ala Leu Leu Pro
1               5                   10                  15

Leu Lys Gly Leu Arg Glu Ala Ala Ala Leu Leu Glu Glu Ala Leu Arg
            20                  25                  30

Gln Gly Lys Arg Ile Arg Val His Gly Asp Tyr Asp Ala Asp Gly Leu
        35                  40                  45

Thr Gly Thr Ala Ile Leu Val Arg Gly Leu Ala Ala Leu Gly Ala Asp
50                  55                  60

Val His Pro Phe Ile Pro His Arg Leu Glu Glu Gly Tyr Gly Val Leu
65                  70                  75                  80

Met Glu Arg Val Pro Glu His Leu Glu Ala Ser Asp Leu Phe Leu Thr
                85                  90                  95

Val Asp Cys Gly Ile Thr Asn His Ala Glu Leu Arg Glu Leu Leu Glu
            100                 105                 110

Asn Gly Val Glu Val Ile Val Thr Asp His His Thr Pro Gly Lys Thr
        115                 120                 125

Pro Pro Pro Gly Leu Val Val His Pro Ala Leu Thr Pro Asp Leu Lys
130                 135                 140

Glu Lys Pro Thr Gly Ala Gly Val Ala Phe Leu Leu Leu Trp Ala Leu
145                 150                 155                 160

His Glu Arg Leu Gly Leu Pro Pro Leu Glu Tyr Ala Asp Leu Ala
                165                 170                 175

Ala Val Gly Thr Ile Ala Asp Val Ala Pro Leu Trp Gly Trp Asn Arg
            180                 185                 190

Ala Leu Val Lys Glu Gly Leu Ala Arg Ile Pro Ala Ser Ser Trp Val
        195                 200                 205

Gly Leu Arg Leu Leu Ala Glu Ala Val Gly Tyr Thr Gly Lys Ala Val
210                 215                 220

Glu Val Ala Phe Arg Ile Ala Pro Arg Ile Asn Ala Ala Ser Arg Leu
225                 230                 235                 240

Gly Glu Ala Glu Lys Ala Leu Arg Leu Leu Thr Asp Asp Ala Ala
                245                 250                 255

Glu Ala Gln Ala Leu Val Gly Glu Leu His Arg Leu Asn Ala Arg Arg
            260                 265                 270

Gln Thr Leu Glu Glu Ala Met Leu Arg Lys Leu Leu Pro Gln Ala Asp
        275                 280                 285

Pro Glu Ala Lys Ala Ile Val Leu Leu Asp Pro Glu Gly His Pro Gly
290                 295                 300

Val Met Gly Ile Val Ala Ser Arg Ile Leu Glu Ala Thr Leu Arg Pro
305                 310                 315                 320
```

```
Val Phe Leu Val Ala Gln Gly Lys Gly Thr Val Arg Ser Leu Ala Pro
                325                 330                 335

Ile Ser Ala Val Glu Ala Leu Arg Ser Ala Glu Asp Leu Leu Leu Arg
            340                 345                 350

Tyr Gly Gly His Lys Glu Ala Ala Gly Phe Ala Met Asp Glu Ala Leu
        355                 360                 365

Phe Pro Ala Phe Lys Ala Arg Val Glu Ala Tyr Ala Ala Arg Phe Pro
370                 375                 380

Asp Pro Val Arg Glu Val Ala Leu Leu Asp Leu Leu Pro Glu Pro Gly
385                 390                 395                 400

Leu Leu Pro Gln Val Phe Arg Glu Leu Ala Leu Leu Glu Pro Tyr Gly
                405                 410                 415

Glu Gly Asn Pro Glu Pro Leu Phe Leu
                420                 425

<210> SEQ ID NO 15
<211> LENGTH: 738
<212> TYPE: DNA
<213> ORGANISM: Bacteriophage lambda
<220> FEATURE:
<221> NAME/KEY: CDS
<222> LOCATION: (31)..(708)

<400> SEQUENCE: 15
tccggaagcg gctctggtag tggttctggc atg aca ccg gac att atc ctg cag      54
                                 Met Thr Pro Asp Ile Ile Leu Gln
                                  1               5 cgt acc ggg atc gat gtg aga gct gtc gaa cag ggg gat gat gcg tgg     102
Arg Thr Gly Ile Asp Val Arg Ala Val Glu Gln Gly Asp Asp Ala Trp
 10              15                  20 cac aaa tta cgg ctc ggc gtc atc acc gct tca gaa gtt cac aac gtg     150
His Lys Leu Arg Leu Gly Val Ile Thr Ala Ser Glu Val His Asn Val
 25                  30                  35                  40 ata gca aaa ccc cgc tcc gga aag aag tgg cct gac atg aaa atg tcc     198
Ile Ala Lys Pro Arg Ser Gly Lys Lys Trp Pro Asp Met Lys Met Ser
                 45                  50                  55 tac ttc cac acc ctg ctt gct gag gtt tgc acc ggt gtg gct ccg gaa     246
Tyr Phe His Thr Leu Leu Ala Glu Val Cys Thr Gly Val Ala Pro Glu
             60                  65                  70 gtt aac gct aaa gca ctg gcc tgg gga aaa cag tac gag aac gac gcc     294
Val Asn Ala Lys Ala Leu Ala Trp Gly Lys Gln Tyr Glu Asn Asp Ala
 75                  80                  85 aga acc ctg ttt gaa ttc act tcc ggc gtg aat gtt act gaa tcc ccg     342
Arg Thr Leu Phe Glu Phe Thr Ser Gly Val Asn Val Thr Glu Ser Pro
 90                  95                 100 atc atc tat cgc gac gaa agt atg cgt acc gcc tgc tct ccc gat ggt     390
Ile Ile Tyr Arg Asp Glu Ser Met Arg Thr Ala Cys Ser Pro Asp Gly
105                 110                 115                 120 tta tgc agt gac ggc aac ggc ctt gaa ctg aaa tgc ccg ttt acc tcc     438
Leu Cys Ser Asp Gly Asn Gly Leu Glu Leu Lys Cys Pro Phe Thr Ser
                125                 130                 135 cgg gat ttc atg aag ttc cgg ctc ggt ggt ttc gag gcc ata aag tca     486
Arg Asp Phe Met Lys Phe Arg Leu Gly Gly Phe Glu Ala Ile Lys Ser
            140                 145                 150 gct tac atg gcc cag gtg cag tac agc atg tgg gtg acg cga aaa aat     534
Ala Tyr Met Ala Gln Val Gln Tyr Ser Met Trp Val Thr Arg Lys Asn
        155                 160                 165 gcc tgg tac ttt gcc aac tat gac ccg cgt atg aag cgt gaa ggc ctg     582
Ala Trp Tyr Phe Ala Asn Tyr Asp Pro Arg Met Lys Arg Glu Gly Leu
170                 175                 180
```

```
cat tat gtc gtg att gag cgg gat gaa aag tac atg gcg agt ttt gac         630
His Tyr Val Val Ile Glu Arg Asp Glu Lys Tyr Met Ala Ser Phe Asp
185             190                 195                 200 gag atc gtg ccg gag ttc atc gaa aaa atg gac gag gca ctg gct gaa         678
Glu Ile Val Pro Glu Phe Ile Glu Lys Met Asp Glu Ala Leu Ala Glu
            205                 210                 215 att ggt ttt gta ttt ggg gag caa tgg cga tctggctctg gttccggcag          728
Ile Gly Phe Val Phe Gly Glu Gln Trp Arg
        220                 225 cggttccgga                                                              738
```

<210> SEQ ID NO 16
<211> LENGTH: 226
<212> TYPE: PRT
<213> ORGANISM: Bacteriophage lambda

<400> SEQUENCE: 16

```
Met Thr Pro Asp Ile Ile Leu Gln Arg Thr Gly Ile Asp Val Arg Ala
1               5                   10                  15

Val Glu Gln Gly Asp Asp Ala Trp His Lys Leu Arg Leu Gly Val Ile
            20                  25                  30

Thr Ala Ser Glu Val His Asn Val Ile Ala Lys Pro Arg Ser Gly Lys
        35                  40                  45

Lys Trp Pro Asp Met Lys Met Ser Tyr Phe His Thr Leu Leu Ala Glu
    50                  55                  60

Val Cys Thr Gly Val Ala Pro Glu Val Asn Ala Lys Ala Leu Ala Trp
65                  70                  75                  80

Gly Lys Gln Tyr Glu Asn Asp Ala Arg Thr Leu Phe Glu Phe Thr Ser
                85                  90                  95

Gly Val Asn Val Thr Glu Ser Pro Ile Ile Tyr Arg Asp Glu Ser Met
            100                 105                 110

Arg Thr Ala Cys Ser Pro Asp Gly Leu Cys Ser Asp Gly Asn Gly Leu
        115                 120                 125

Glu Leu Lys Cys Pro Phe Thr Ser Arg Asp Phe Met Lys Phe Arg Leu
    130                 135                 140

Gly Gly Phe Glu Ala Ile Lys Ser Ala Tyr Met Ala Gln Val Gln Tyr
145                 150                 155                 160

Ser Met Trp Val Thr Arg Lys Asn Ala Trp Tyr Phe Ala Asn Tyr Asp
                165                 170                 175

Pro Arg Met Lys Arg Glu Gly Leu His Tyr Val Val Ile Glu Arg Asp
            180                 185                 190

Glu Lys Tyr Met Ala Ser Phe Asp Glu Ile Val Pro Glu Phe Ile Glu
        195                 200                 205

Lys Met Asp Glu Ala Leu Ala Glu Ile Gly Phe Val Phe Gly Glu Gln
    210                 215                 220

Trp Arg
225
```

<210> SEQ ID NO 17
<211> LENGTH: 1794
<212> TYPE: DNA
<213> ORGANISM: Artificial sequence
<220> FEATURE:
<223> OTHER INFORMATION: DNA Sequence encoding HL-wt-EcoExoIII-L1-H6
<220> FEATURE:
<221> NAME/KEY: CDS
<222> LOCATION: (4)..(1794)

<400> SEQUENCE: 17

| | | | | | | | | | | | | | | | | |
|---|---|---|---|---|---|---|---|---|---|---|---|---|---|---|---|---|
| atg | gca | gat | tct | gat | att | aat | att | aaa | acc | ggt | act | aca | gat | att | gga | 48 |
| | Ala | Asp | Ser | Asp | Ile | Asn | Ile | Lys | Thr | Gly | Thr | Thr | Asp | Ile | Gly | |
| | 1 | | | | 5 | | | | | 10 | | | | | 15 | |

| | | | | | | | | | | | | | | | | |
|---|---|---|---|---|---|---|---|---|---|---|---|---|---|---|---|---|
| agc | aat | act | tcc | gga | agc | ggc | tct | ggt | agt | ggt | tct | ggc | atg | aaa | ttt | 96 |
| Ser | Asn | Thr | Ser | Gly | Ser | Gly | Ser | Gly | Ser | Gly | Ser | Gly | Met | Lys | Phe | |
| | | | | 20 | | | | | 25 | | | | | 30 | | |

| | | | | | | | | | | | | | | | | |
|---|---|---|---|---|---|---|---|---|---|---|---|---|---|---|---|---|
| gtt | agc | ttc | aat | atc | aac | ggc | ctg | cgc | gcg | cgc | ccg | cat | cag | ctg | gaa | 144 |
| Val | Ser | Phe | Asn | Ile | Asn | Gly | Leu | Arg | Ala | Arg | Pro | His | Gln | Leu | Glu | |
| | | | 35 | | | | | 40 | | | | | 45 | | | |

| | | | | | | | | | | | | | | | | |
|---|---|---|---|---|---|---|---|---|---|---|---|---|---|---|---|---|
| gcg | att | gtg | gaa | aaa | cat | cag | ccg | gat | gtt | att | ggt | ctg | cag | gaa | acc | 192 |
| Ala | Ile | Val | Glu | Lys | His | Gln | Pro | Asp | Val | Ile | Gly | Leu | Gln | Glu | Thr | |
| | | 50 | | | | | 55 | | | | | 60 | | | | |

| | | | | | | | | | | | | | | | | |
|---|---|---|---|---|---|---|---|---|---|---|---|---|---|---|---|---|
| aaa | gtt | cac | gat | gat | atg | ttt | ccg | ctg | gaa | gaa | gtg | gcg | aaa | ctg | ggc | 240 |
| Lys | Val | His | Asp | Asp | Met | Phe | Pro | Leu | Glu | Glu | Val | Ala | Lys | Leu | Gly | |
| 65 | | | | | 70 | | | | | 75 | | | | | | |

| | | | | | | | | | | | | | | | | |
|---|---|---|---|---|---|---|---|---|---|---|---|---|---|---|---|---|
| tat | aac | gtg | ttt | tat | cat | ggc | cag | aaa | ggt | cat | tat | ggc | gtg | gcc | ctg | 288 |
| Tyr | Asn | Val | Phe | Tyr | His | Gly | Gln | Lys | Gly | His | Tyr | Gly | Val | Ala | Leu | |
| 80 | | | | | 85 | | | | | 90 | | | | | 95 | |

| | | | | | | | | | | | | | | | | |
|---|---|---|---|---|---|---|---|---|---|---|---|---|---|---|---|---|
| ctg | acc | aaa | gaa | acc | ccg | atc | gcg | gtt | cgt | cgt | ggt | ttt | ccg | ggt | gat | 336 |
| Leu | Thr | Lys | Glu | Thr | Pro | Ile | Ala | Val | Arg | Arg | Gly | Phe | Pro | Gly | Asp | |
| | | | | 100 | | | | | 105 | | | | | 110 | | |

| | | | | | | | | | | | | | | | | |
|---|---|---|---|---|---|---|---|---|---|---|---|---|---|---|---|---|
| gat | gaa | gaa | gcg | cag | cgt | cgt | att | att | atg | gcg | gaa | att | ccg | agc | ctg | 384 |
| Asp | Glu | Glu | Ala | Gln | Arg | Arg | Ile | Ile | Met | Ala | Glu | Ile | Pro | Ser | Leu | |
| | | | | 115 | | | | | 120 | | | | | 125 | | |

| | | | | | | | | | | | | | | | | |
|---|---|---|---|---|---|---|---|---|---|---|---|---|---|---|---|---|
| ctg | ggc | aat | gtg | acc | gtt | att | aac | ggc | tat | ttt | ccg | cag | ggc | gaa | agc | 432 |
| Leu | Gly | Asn | Val | Thr | Val | Ile | Asn | Gly | Tyr | Phe | Pro | Gln | Gly | Glu | Ser | |
| | | 130 | | | | | 135 | | | | | 140 | | | | |

| | | | | | | | | | | | | | | | | |
|---|---|---|---|---|---|---|---|---|---|---|---|---|---|---|---|---|
| cgt | gat | cat | ccg | att | aaa | ttt | ccg | gcc | aaa | gcg | cag | ttc | tat | cag | aac | 480 |
| Arg | Asp | His | Pro | Ile | Lys | Phe | Pro | Ala | Lys | Ala | Gln | Phe | Tyr | Gln | Asn | |
| 145 | | | | | 150 | | | | | 155 | | | | | | |

| | | | | | | | | | | | | | | | | |
|---|---|---|---|---|---|---|---|---|---|---|---|---|---|---|---|---|
| ctg | cag | aac | tat | ctg | gaa | acc | gaa | ctg | aaa | cgt | gat | aat | ccg | gtg | ctg | 528 |
| Leu | Gln | Asn | Tyr | Leu | Glu | Thr | Glu | Leu | Lys | Arg | Asp | Asn | Pro | Val | Leu | |
| 160 | | | | | 165 | | | | | 170 | | | | | 175 | |

| | | | | | | | | | | | | | | | | |
|---|---|---|---|---|---|---|---|---|---|---|---|---|---|---|---|---|
| atc | atg | ggc | gat | atg | aac | att | agc | ccg | acc | gat | ctg | gat | att | ggc | att | 576 |
| Ile | Met | Gly | Asp | Met | Asn | Ile | Ser | Pro | Thr | Asp | Leu | Asp | Ile | Gly | Ile | |
| | | | | 180 | | | | | 185 | | | | | 190 | | |

| | | | | | | | | | | | | | | | | |
|---|---|---|---|---|---|---|---|---|---|---|---|---|---|---|---|---|
| ggc | gaa | gaa | aac | cgt | aaa | cgc | tgg | ctg | cgt | acc | ggt | aaa | tgc | agc | ttt | 624 |
| Gly | Glu | Glu | Asn | Arg | Lys | Arg | Trp | Leu | Arg | Thr | Gly | Lys | Cys | Ser | Phe | |
| | | | | 195 | | | | | 200 | | | | | 205 | | |

| | | | | | | | | | | | | | | | | |
|---|---|---|---|---|---|---|---|---|---|---|---|---|---|---|---|---|
| ctg | ccg | gaa | gaa | cgt | gaa | tgg | atg | gat | cgc | ctg | atg | agc | tgg | ggc | ctg | 672 |
| Leu | Pro | Glu | Glu | Arg | Glu | Trp | Met | Asp | Arg | Leu | Met | Ser | Trp | Gly | Leu | |
| | | | | 210 | | | | | 215 | | | | | 220 | | |

| | | | | | | | | | | | | | | | | |
|---|---|---|---|---|---|---|---|---|---|---|---|---|---|---|---|---|
| gtg | gat | acc | ttt | cgt | cat | gcg | aac | ccg | cag | acc | gcc | gat | cgc | ttt | agc | 720 |
| Val | Asp | Thr | Phe | Arg | His | Ala | Asn | Pro | Gln | Thr | Ala | Asp | Arg | Phe | Ser | |
| | 225 | | | | | 230 | | | | | 235 | | | | | |

| | | | | | | | | | | | | | | | | |
|---|---|---|---|---|---|---|---|---|---|---|---|---|---|---|---|---|
| tgg | ttt | gat | tat | cgc | agc | aaa | ggt | ttt | gat | gat | aac | cgt | ggc | ctg | cgc | 768 |
| Trp | Phe | Asp | Tyr | Arg | Ser | Lys | Gly | Phe | Asp | Asp | Asn | Arg | Gly | Leu | Arg | |
| 240 | | | | 245 | | | | | 250 | | | | | 255 | | |

| | | | | | | | | | | | | | | | | |
|---|---|---|---|---|---|---|---|---|---|---|---|---|---|---|---|---|
| att | gat | ctg | ctg | ctg | gcg | agc | cag | ccg | ctg | gcg | gaa | tgc | tgc | gtt | gaa | 816 |
| Ile | Asp | Leu | Leu | Leu | Ala | Ser | Gln | Pro | Leu | Ala | Glu | Cys | Cys | Val | Glu | |
| | | | | 260 | | | | | 265 | | | | | 270 | | |

| | | | | | | | | | | | | | | | | |
|---|---|---|---|---|---|---|---|---|---|---|---|---|---|---|---|---|
| acc | ggt | att | gat | tat | gaa | att | cgc | agc | atg | gaa | aaa | ccg | agc | gat | cac | 864 |
| Thr | Gly | Ile | Asp | Tyr | Glu | Ile | Arg | Ser | Met | Glu | Lys | Pro | Ser | Asp | His | |
| | | 275 | | | | | 280 | | | | | 285 | | | | |

| | | | | | | | | | | | | | | | | |
|---|---|---|---|---|---|---|---|---|---|---|---|---|---|---|---|---|
| gcc | ccg | gtg | tgg | gcg | acc | ttt | cgc | cgc | tct | ggc | tct | ggt | tcc | ggc | agc | 912 |
| Ala | Pro | Val | Trp | Ala | Thr | Phe | Arg | Arg | Ser | Gly | Ser | Gly | Ser | Gly | Ser | |
| | | 290 | | | | | 295 | | | | | 300 | | | | |

```
ggt tcc gga aca gta aaa aca ggt gat tta gtc act tat gat aaa gaa      960
Gly Ser Gly Thr Val Lys Thr Gly Asp Leu Val Thr Tyr Asp Lys Glu
        305                 310                 315 aat ggc atg cac aaa aaa gta ttt tat agt ttt atc gat gat aaa aat     1008
Asn Gly Met His Lys Lys Val Phe Tyr Ser Phe Ile Asp Asp Lys Asn
320                 325                 330                 335 cac aat aaa aaa ctg cta gtt att aga aca aaa ggt acc att gct ggt     1056
His Asn Lys Lys Leu Leu Val Ile Arg Thr Lys Gly Thr Ile Ala Gly
                340                 345                 350 caa tat aga gtt tat agc gaa gaa ggt gct aac aaa agt ggt tta gcc     1104
Gln Tyr Arg Val Tyr Ser Glu Glu Gly Ala Asn Lys Ser Gly Leu Ala
            355                 360                 365 tgg cct tca gcc ttt aag gta cag ttg caa cta cct gat aat gaa gta     1152
Trp Pro Ser Ala Phe Lys Val Gln Leu Gln Leu Pro Asp Asn Glu Val
        370                 375                 380 gct caa ata tct gat tac tat cca aga aat tcg att gat aca aaa gag     1200
Ala Gln Ile Ser Asp Tyr Tyr Pro Arg Asn Ser Ile Asp Thr Lys Glu
385                 390                 395 tat atg agt act tta act tat gga ttc aac ggt aat gtt act ggt gat     1248
Tyr Met Ser Thr Leu Thr Tyr Gly Phe Asn Gly Asn Val Thr Gly Asp
400                 405                 410                 415 gat aca gga aaa att ggc ggc ctt att ggt gca aat gtt tcg att ggt     1296
Asp Thr Gly Lys Ile Gly Gly Leu Ile Gly Ala Asn Val Ser Ile Gly
                420                 425                 430 cat aca ctg aaa tat gtt caa cct gat ttc aaa aca att tta gag agc     1344
His Thr Leu Lys Tyr Val Gln Pro Asp Phe Lys Thr Ile Leu Glu Ser
            435                 440                 445 cca act gat aaa aaa gta ggc tgg aaa gtg ata ttt aac aat atg gtg     1392
Pro Thr Asp Lys Lys Val Gly Trp Lys Val Ile Phe Asn Asn Met Val
        450                 455                 460 aat caa aat tgg gga cca tac gat cga gat tct tgg aac ccg gta tat     1440
Asn Gln Asn Trp Gly Pro Tyr Asp Arg Asp Ser Trp Asn Pro Val Tyr
465                 470                 475 ggc aat caa ctt ttc atg aaa act aga aat ggt tct atg aaa gca gca     1488
Gly Asn Gln Leu Phe Met Lys Thr Arg Asn Gly Ser Met Lys Ala Ala
480                 485                 490                 495 gat aac ttc ctt gat cct aac aaa gca agt tct cta tta tct tca ggg     1536
Asp Asn Phe Leu Asp Pro Asn Lys Ala Ser Ser Leu Leu Ser Ser Gly
                500                 505                 510 ttt tca cca gac ttc gct aca gtt att act atg gat aga aaa gca tcc     1584
Phe Ser Pro Asp Phe Ala Thr Val Ile Thr Met Asp Arg Lys Ala Ser
            515                 520                 525 aaa caa caa aca aat ata gat gta ata tac gaa cga gtt cgt gat gat     1632
Lys Gln Gln Thr Asn Ile Asp Val Ile Tyr Glu Arg Val Arg Asp Asp
        530                 535                 540 tac caa ttg cat tgg act tca aca aat tgg aaa ggt acc aat act aaa     1680
Tyr Gln Leu His Trp Thr Ser Thr Asn Trp Lys Gly Thr Asn Thr Lys
545                 550                 555 gat aaa tgg aca gat cgt tct tca gaa aga tat aaa atc gat tgg gaa     1728
Asp Lys Trp Thr Asp Arg Ser Ser Glu Arg Tyr Lys Ile Asp Trp Glu
560                 565                 570                 575 aaa gaa gaa atg aca aat ggt ggt tcg ggc tca tct ggt ggc tcg agt     1776
Lys Glu Glu Met Thr Asn Gly Gly Ser Gly Ser Ser Gly Gly Ser Ser
                580                 585                 590 cac cat cat cat cac cac                                             1794
His His His His His His
            595
```

```
<210> SEQ ID NO 18
<211> LENGTH: 597
<212> TYPE: PRT
<213> ORGANISM: Artificial sequence
<220> FEATURE:
<223> OTHER INFORMATION: Synthetic Construct

<400> SEQUENCE: 18

Ala Asp Ser Asp Ile Asn Ile Lys Thr Gly Thr Thr Asp Ile Gly Ser
1               5                   10                  15

Asn Thr Ser Gly Ser Gly Ser Gly Ser Gly Met Lys Phe Val
                20                  25                  30

Ser Phe Asn Ile Asn Gly Leu Arg Ala Arg Pro His Gln Leu Glu Ala
            35                  40                  45

Ile Val Glu Lys His Gln Pro Asp Val Ile Gly Leu Gln Glu Thr Lys
        50                  55                  60

Val His Asp Asp Met Phe Pro Leu Glu Glu Val Ala Lys Leu Gly Tyr
65                  70                  75                  80

Asn Val Phe Tyr His Gly Gln Lys Gly His Tyr Gly Val Ala Leu Leu
                85                  90                  95

Thr Lys Glu Thr Pro Ile Ala Val Arg Arg Gly Phe Pro Gly Asp Asp
            100                 105                 110

Glu Glu Ala Gln Arg Arg Ile Ile Met Ala Glu Ile Pro Ser Leu Leu
        115                 120                 125

Gly Asn Val Thr Val Ile Asn Gly Tyr Phe Pro Gln Gly Glu Ser Arg
    130                 135                 140

Asp His Pro Ile Lys Phe Pro Ala Lys Ala Gln Phe Tyr Gln Asn Leu
145                 150                 155                 160

Gln Asn Tyr Leu Glu Thr Glu Leu Lys Arg Asp Asn Pro Val Leu Ile
                165                 170                 175

Met Gly Asp Met Asn Ile Ser Pro Thr Asp Leu Asp Ile Gly Ile Gly
            180                 185                 190

Glu Glu Asn Arg Lys Arg Trp Leu Arg Thr Gly Lys Cys Ser Phe Leu
        195                 200                 205

Pro Glu Glu Arg Glu Trp Met Asp Arg Leu Met Ser Trp Gly Leu Val
    210                 215                 220

Asp Thr Phe Arg His Ala Asn Pro Gln Thr Ala Asp Arg Phe Ser Trp
225                 230                 235                 240

Phe Asp Tyr Arg Ser Lys Gly Phe Asp Asp Asn Arg Gly Leu Arg Ile
                245                 250                 255

Asp Leu Leu Leu Ala Ser Gln Pro Leu Ala Glu Cys Cys Val Glu Thr
            260                 265                 270

Gly Ile Asp Tyr Glu Ile Arg Ser Met Glu Lys Pro Ser Asp His Ala
        275                 280                 285

Pro Val Trp Ala Thr Phe Arg Arg Ser Gly Ser Gly Ser Gly Ser Gly
    290                 295                 300

Ser Gly Thr Val Lys Thr Gly Asp Leu Val Thr Tyr Asp Lys Glu Asn
305                 310                 315                 320

Gly Met His Lys Lys Val Phe Tyr Ser Phe Ile Asp Asp Lys Asn His
                325                 330                 335

Asn Lys Lys Leu Leu Val Ile Arg Thr Lys Gly Thr Ile Ala Gly Gln
            340                 345                 350

Tyr Arg Val Tyr Ser Glu Glu Gly Ala Asn Lys Ser Gly Leu Ala Trp
        355                 360                 365
```

```
Pro Ser Ala Phe Lys Val Gln Leu Gln Leu Pro Asp Asn Glu Val Ala
    370                 375                 380

Gln Ile Ser Asp Tyr Tyr Pro Arg Asn Ser Ile Asp Thr Lys Glu Tyr
385                 390                 395                 400

Met Ser Thr Leu Thr Tyr Gly Phe Asn Gly Asn Val Thr Gly Asp Asp
                405                 410                 415

Thr Gly Lys Ile Gly Gly Leu Ile Gly Ala Asn Val Ser Ile Gly His
            420                 425                 430

Thr Leu Lys Tyr Val Gln Pro Asp Phe Lys Thr Ile Leu Glu Ser Pro
        435                 440                 445

Thr Asp Lys Lys Val Gly Trp Lys Val Ile Phe Asn Asn Met Val Asn
    450                 455                 460

Gln Asn Trp Gly Pro Tyr Asp Arg Asp Ser Trp Asn Pro Val Tyr Gly
465                 470                 475                 480

Asn Gln Leu Phe Met Lys Thr Arg Asn Gly Ser Met Lys Ala Ala Asp
                485                 490                 495

Asn Phe Leu Asp Pro Asn Lys Ala Ser Ser Leu Leu Ser Ser Gly Phe
            500                 505                 510

Ser Pro Asp Phe Ala Thr Val Ile Thr Met Asp Arg Lys Ala Ser Lys
        515                 520                 525

Gln Gln Thr Asn Ile Asp Val Ile Tyr Glu Arg Val Arg Asp Asp Tyr
    530                 535                 540

Gln Leu His Trp Thr Ser Thr Asn Trp Lys Gly Thr Asn Thr Lys Asp
545                 550                 555                 560

Lys Trp Thr Asp Arg Ser Ser Glu Arg Tyr Lys Ile Asp Trp Glu Lys
                565                 570                 575

Glu Glu Met Thr Asn Gly Gly Ser Gly Ser Ser Gly Ser Ser His
            580                 585                 590

His His His His His
        595

<210> SEQ ID NO 19
<211> LENGTH: 1794
<212> TYPE: DNA
<213> ORGANISM: Artificial sequence
<220> FEATURE:
<223> OTHER INFORMATION: DNA Sequence encoding HL-RQC-EcoExoIII-L1-H6
<220> FEATURE:
<221> NAME/KEY: CDS
<222> LOCATION: (4)..(1794)

<400> SEQUENCE: 19 atg gca gat tct gat att aat att aaa acc ggt act aca gat att gga        48
    Ala Asp Ser Asp Ile Asn Ile Lys Thr Gly Thr Thr Asp Ile Gly
    1               5                   10                  15 agc aat act tcc gga agc ggc tct ggt agt ggt tct ggc atg aaa ttt        96
Ser Asn Thr Ser Gly Ser Gly Ser Gly Ser Gly Ser Gly Met Lys Phe
                20                  25                  30 gtt agc ttc aat atc aac ggc ctg cgc gcg cgc ccg cat cag ctg gaa       144
Val Ser Phe Asn Ile Asn Gly Leu Arg Ala Arg Pro His Gln Leu Glu
            35                  40                  45 gcg att gtg gaa aaa cat cag ccg gat gtt att ggt ctg cag gaa acc       192
Ala Ile Val Glu Lys His Gln Pro Asp Val Ile Gly Leu Gln Glu Thr
        50                  55                  60 aaa gtt cac gat gat atg ttt ccg ctg gaa gaa gtg gcg aaa ctg ggc       240
Lys Val His Asp Asp Met Phe Pro Leu Glu Glu Val Ala Lys Leu Gly
    65                  70                  75
```

```
tat aac gtg ttt tat cat ggc cag aaa ggt cat tat ggc gtg gcc ctg      288
Tyr Asn Val Phe Tyr His Gly Gln Lys Gly His Tyr Gly Val Ala Leu
80              85                  90                  95 ctg acc aaa gaa acc ccg atc gcg gtt cgt cgt ggt ttt ccg ggt gat      336
Leu Thr Lys Glu Thr Pro Ile Ala Val Arg Arg Gly Phe Pro Gly Asp
                100                 105                 110 gat gaa gaa gcg cag cgt cgt att att atg gcg gaa att ccg agc ctg      384
Asp Glu Glu Ala Gln Arg Arg Ile Ile Met Ala Glu Ile Pro Ser Leu
            115                 120                 125 ctg ggc aat gtg acc gtt att aac ggc tat ttt ccg cag ggc gaa agc      432
Leu Gly Asn Val Thr Val Ile Asn Gly Tyr Phe Pro Gln Gly Glu Ser
        130                 135                 140 cgt gat cat ccg att aaa ttt ccg gcc aaa gcg cag ttc tat cag aac      480
Arg Asp His Pro Ile Lys Phe Pro Ala Lys Ala Gln Phe Tyr Gln Asn
    145                 150                 155 ctg cag aac tat ctg gaa acc gaa ctg aaa cgt gat aat ccg gtg ctg      528
Leu Gln Asn Tyr Leu Glu Thr Glu Leu Lys Arg Asp Asn Pro Val Leu
160                 165                 170                 175 atc atg ggc gat atg aac att agc ccg acc gat ctg gat att ggc att      576
Ile Met Gly Asp Met Asn Ile Ser Pro Thr Asp Leu Asp Ile Gly Ile
                180                 185                 190 ggc gaa gaa aac cgt aaa cgc tgg ctg cgt acc ggt aaa tgc agc ttt      624
Gly Glu Glu Asn Arg Lys Arg Trp Leu Arg Thr Gly Lys Cys Ser Phe
            195                 200                 205 ctg ccg gaa gaa cgt gaa tgg atg gat cgc ctg atg agc tgg ggc ctg      672
Leu Pro Glu Glu Arg Glu Trp Met Asp Arg Leu Met Ser Trp Gly Leu
        210                 215                 220 gtg gat acc ttt cgt cat gcg aac ccg cag acc gcc gat cgc ttt agc      720
Val Asp Thr Phe Arg His Ala Asn Pro Gln Thr Ala Asp Arg Phe Ser
    225                 230                 235 tgg ttt gat tat cgc agc aaa ggt ttt gat gat aac cgt ggc ctg cgc      768
Trp Phe Asp Tyr Arg Ser Lys Gly Phe Asp Asp Asn Arg Gly Leu Arg
240                 245                 250                 255 att gat ctg ctg ctg gcg agc cag ccg ctg gcg gaa tgc tgc gtt gaa      816
Ile Asp Leu Leu Leu Ala Ser Gln Pro Leu Ala Glu Cys Cys Val Glu
                260                 265                 270 acc ggt att gat tat gaa att cgc agc atg gaa aaa ccg agc gat cac      864
Thr Gly Ile Asp Tyr Glu Ile Arg Ser Met Glu Lys Pro Ser Asp His
            275                 280                 285 gcc ccg gtg tgg gcg acc ttt cgc cgc tct ggc tct ggt tcc ggc agc      912
Ala Pro Val Trp Ala Thr Phe Arg Arg Ser Gly Ser Gly Ser Gly Ser
        290                 295                 300 ggt tcc gga aca gta aaa aca ggt gat tta gtc act tat gat aaa gaa      960
Gly Ser Gly Thr Val Lys Thr Gly Asp Leu Val Thr Tyr Asp Lys Glu
305                 310                 315 aat ggc atg cac aaa aaa gta ttt tat agt ttt atc gat gat aaa aat     1008
Asn Gly Met His Lys Lys Val Phe Tyr Ser Phe Ile Asp Asp Lys Asn
320                 325                 330                 335 cac aat aaa aaa ctg cta gtt att aga aca aaa ggt acc att gct ggt     1056
His Asn Lys Lys Leu Leu Val Ile Arg Thr Lys Gly Thr Ile Ala Gly
                340                 345                 350 caa tat aga gtt tat agc gaa gaa ggt gct aac aaa agt ggt tta gcc     1104
Gln Tyr Arg Val Tyr Ser Glu Glu Gly Ala Asn Lys Ser Gly Leu Ala
            355                 360                 365 tgg cct tca gcc ttt aag gta cag ttg caa cta cct gat aat gaa gta     1152
Trp Pro Ser Ala Phe Lys Val Gln Leu Gln Leu Pro Asp Asn Glu Val
        370                 375                 380 gct caa ata tct gat tac tat cca aga aat tcg att gat aca aaa gag     1200
Ala Gln Ile Ser Asp Tyr Tyr Pro Arg Asn Ser Ile Asp Thr Lys Glu
    385                 390                 395
```

| | | |
|---|---|---|
| tat agg agt act tta act tat gga ttc aac ggt aat gtt act ggt gat<br>Tyr Arg Ser Thr Leu Thr Tyr Gly Phe Asn Gly Asn Val Thr Gly Asp<br>400 405 410 415 | | 1248 |
| gat aca gga aaa att ggc ggc tgt att ggt gca caa gtt tcg att ggt<br>Asp Thr Gly Lys Ile Gly Gly Cys Ile Gly Ala Gln Val Ser Ile Gly<br>420 425 430 | | 1296 |
| cat aca ctg aaa tat gtt caa cct gat ttc aaa aca att tta gag agc<br>His Thr Leu Lys Tyr Val Gln Pro Asp Phe Lys Thr Ile Leu Glu Ser<br>435 440 445 | | 1344 |
| cca act gat aaa aaa gta ggc tgg aaa gtg ata ttt aac aat atg gtg<br>Pro Thr Asp Lys Lys Val Gly Trp Lys Val Ile Phe Asn Asn Met Val<br>450 455 460 | | 1392 |
| aat caa aat tgg gga cca tac gat cga gat tct tgg aac ccg gta tat<br>Asn Gln Asn Trp Gly Pro Tyr Asp Arg Asp Ser Trp Asn Pro Val Tyr<br>465 470 475 | | 1440 |
| ggc aat caa ctt ttc atg aaa act aga aat ggt tct atg aaa gca gca<br>Gly Asn Gln Leu Phe Met Lys Thr Arg Asn Gly Ser Met Lys Ala Ala<br>480 485 490 495 | | 1488 |
| gat aac ttc ctt gat cct aac aaa gca agt tct cta tta tct tca ggg<br>Asp Asn Phe Leu Asp Pro Asn Lys Ala Ser Ser Leu Leu Ser Ser Gly<br>500 505 510 | | 1536 |
| ttt tca cca gac ttc gct aca gtt att act atg gat aga aaa gca tcc<br>Phe Ser Pro Asp Phe Ala Thr Val Ile Thr Met Asp Arg Lys Ala Ser<br>515 520 525 | | 1584 |
| aaa caa caa aca aat ata gat gta ata tac gaa cga gtt cgt gat gat<br>Lys Gln Gln Thr Asn Ile Asp Val Ile Tyr Glu Arg Val Arg Asp Asp<br>530 535 540 | | 1632 |
| tac caa ttg cat tgg act tca aca aat tgg aaa ggt acc aat act aaa<br>Tyr Gln Leu His Trp Thr Ser Thr Asn Trp Lys Gly Thr Asn Thr Lys<br>545 550 555 | | 1680 |
| gat aaa tgg aca gat cgt tct tca gaa aga tat aaa atc gat tgg gaa<br>Asp Lys Trp Thr Asp Arg Ser Ser Glu Arg Tyr Lys Ile Asp Trp Glu<br>560 565 570 575 | | 1728 |
| aaa gaa gaa atg aca aat ggt ggt tcg ggc tca tct ggt ggc tcg agt<br>Lys Glu Glu Met Thr Asn Gly Gly Ser Gly Ser Ser Gly Gly Ser Ser<br>580 585 590 | | 1776 |
| cac cat cat cat cac cac<br>His His His His His His<br>595 | | 1794 |

<210> SEQ ID NO 20
<211> LENGTH: 597
<212> TYPE: PRT
<213> ORGANISM: Artificial sequence
<220> FEATURE:
<223> OTHER INFORMATION: Synthetic Construct

<400> SEQUENCE: 20

Ala Asp Ser Asp Ile Asn Ile Lys Thr Gly Thr Thr Asp Ile Gly Ser
1               5                   10                  15

Asn Thr Ser Gly Ser Gly Ser Gly Ser Gly Met Lys Phe Val
            20                  25                  30

Ser Phe Asn Ile Asn Gly Leu Arg Ala Arg Pro His Gln Leu Glu Ala
        35                  40                  45

Ile Val Glu Lys His Gln Pro Asp Val Ile Gly Leu Gln Glu Thr Lys
    50                  55                  60

Val His Asp Asp Met Phe Pro Leu Glu Glu Val Ala Lys Leu Gly Tyr
65                  70                  75                  80

Asn Val Phe Tyr His Gly Gln Lys Gly His Tyr Gly Val Ala Leu Leu
                85                  90                  95

```
Thr Lys Glu Thr Pro Ile Ala Val Arg Arg Gly Phe Pro Gly Asp Asp
            100                 105                 110

Glu Glu Ala Gln Arg Arg Ile Ile Met Ala Glu Ile Pro Ser Leu Leu
        115                 120                 125

Gly Asn Val Thr Val Ile Asn Gly Tyr Phe Pro Gln Gly Glu Ser Arg
    130                 135                 140

Asp His Pro Ile Lys Phe Pro Ala Lys Ala Gln Phe Tyr Gln Asn Leu
145                 150                 155                 160

Gln Asn Tyr Leu Glu Thr Glu Leu Lys Arg Asp Asn Pro Val Leu Ile
                165                 170                 175

Met Gly Asp Met Asn Ile Ser Pro Thr Asp Leu Asp Ile Gly Ile Gly
            180                 185                 190

Glu Glu Asn Arg Lys Arg Trp Leu Arg Thr Gly Lys Cys Ser Phe Leu
        195                 200                 205

Pro Glu Glu Arg Glu Trp Met Asp Arg Leu Met Ser Trp Gly Leu Val
    210                 215                 220

Asp Thr Phe Arg His Ala Asn Pro Gln Thr Ala Asp Arg Phe Ser Trp
225                 230                 235                 240

Phe Asp Tyr Arg Ser Lys Gly Phe Asp Asp Asn Arg Gly Leu Arg Ile
                245                 250                 255

Asp Leu Leu Leu Ala Ser Gln Pro Leu Ala Glu Cys Cys Val Glu Thr
            260                 265                 270

Gly Ile Asp Tyr Glu Ile Arg Ser Met Glu Lys Pro Ser Asp His Ala
        275                 280                 285

Pro Val Trp Ala Thr Phe Arg Arg Ser Gly Ser Gly Ser Gly Ser Gly
    290                 295                 300

Ser Gly Thr Val Lys Thr Gly Asp Leu Val Thr Tyr Asp Lys Glu Asn
305                 310                 315                 320

Gly Met His Lys Lys Val Phe Tyr Ser Phe Ile Asp Asp Lys Asn His
                325                 330                 335

Asn Lys Lys Leu Leu Val Ile Arg Thr Lys Gly Thr Ile Ala Gly Gln
            340                 345                 350

Tyr Arg Val Tyr Ser Glu Glu Gly Ala Asn Lys Ser Gly Leu Ala Trp
        355                 360                 365

Pro Ser Ala Phe Lys Val Gln Leu Gln Leu Pro Asp Asn Glu Val Ala
    370                 375                 380

Gln Ile Ser Asp Tyr Tyr Pro Arg Asn Ser Ile Asp Thr Lys Glu Tyr
385                 390                 395                 400

Arg Ser Thr Leu Thr Tyr Gly Phe Asn Gly Asn Val Thr Gly Asp Asp
                405                 410                 415

Thr Gly Lys Ile Gly Gly Cys Ile Gly Ala Gln Val Ser Ile Gly His
            420                 425                 430

Thr Leu Lys Tyr Val Gln Pro Asp Phe Lys Thr Ile Leu Glu Ser Pro
        435                 440                 445

Thr Asp Lys Lys Val Gly Trp Lys Val Ile Phe Asn Asn Met Val Asn
    450                 455                 460

Gln Asn Trp Gly Pro Tyr Asp Arg Asp Ser Trp Asn Pro Val Tyr Gly
465                 470                 475                 480

Asn Gln Leu Phe Met Lys Thr Arg Asn Gly Ser Met Lys Ala Ala Asp
                485                 490                 495

Asn Phe Leu Asp Pro Asn Lys Ala Ser Ser Leu Leu Ser Ser Gly Phe
            500                 505                 510
```

```
Ser Pro Asp Phe Ala Thr Val Ile Thr Met Asp Arg Lys Ala Ser Lys
            515                 520                 525

Gln Gln Thr Asn Ile Asp Val Ile Tyr Glu Arg Val Arg Asp Asp Tyr
    530                 535                 540

Gln Leu His Trp Thr Ser Thr Asn Trp Lys Gly Thr Asn Thr Lys Asp
545                 550                 555                 560

Lys Trp Thr Asp Arg Ser Ser Glu Arg Tyr Lys Ile Asp Trp Glu Lys
                565                 570                 575

Glu Glu Met Thr Asn Gly Gly Ser Gly Ser Ser Gly Gly Ser Ser His
            580                 585                 590

His His His His His
            595

<210> SEQ ID NO 21
<211> LENGTH: 2415
<212> TYPE: DNA
<213> ORGANISM: Artificial sequence
<220> FEATURE:
<223> OTHER INFORMATION: DNA Sequence encoding HL-RQC-EcoExoI-L1-H6
<220> FEATURE:
<221> NAME/KEY: CDS
<222> LOCATION: (4)..(2415)

<400> SEQUENCE: 21
```

| | | | | | | | | | | | | | | | | |
|---|---|---|---|---|---|---|---|---|---|---|---|---|---|---|---|---|
| atg gca gat tct gat att aat att aaa acc ggt act aca gat att gga | | | | | | | | | | | | | | | | 48 |
| | Ala | Asp | Ser | Asp | Ile | Asn | Ile | Lys | Thr | Gly | Thr | Thr | Asp | Ile | Gly | |
| | 1 | | | | 5 | | | | | 10 | | | | | 15 | |
| agc aat act tcc gga agc ggc tct ggt agt ggt tct ggc atg atg aac | | | | | | | | | | | | | | | | 96 |
| Ser | Asn | Thr | Ser | Gly | Ser | Gly | Ser | Gly | Ser | Gly | Ser | Gly | Met | Met | Asn | |
| | | | 20 | | | | | 25 | | | | | 30 | | | |
| gat ggc aaa cag cag agc acc ttc ctg ttt cat gat tat gaa acc ttc | | | | | | | | | | | | | | | | 144 |
| Asp | Gly | Lys | Gln | Gln | Ser | Thr | Phe | Leu | Phe | His | Asp | Tyr | Glu | Thr | Phe | |
| | | | 35 | | | | | 40 | | | | | 45 | | | |
| ggt acc cat ccg gcc ctg gat cgt ccg gcg cag ttt gcg gcc att cgc | | | | | | | | | | | | | | | | 192 |
| Gly | Thr | His | Pro | Ala | Leu | Asp | Arg | Pro | Ala | Gln | Phe | Ala | Ala | Ile | Arg | |
| | | 50 | | | | | 55 | | | | | 60 | | | | |
| acc gat agc gaa ttc aat gtg att ggc gaa ccg gaa gtg ttt tat tgc | | | | | | | | | | | | | | | | 240 |
| Thr | Asp | Ser | Glu | Phe | Asn | Val | Ile | Gly | Glu | Pro | Glu | Val | Phe | Tyr | Cys | |
| 65 | | | | | 70 | | | | | 75 | | | | | | |
| aaa ccg gcc gat gat tat ctg ccg cag ccg ggt gcg gtg ctg att acc | | | | | | | | | | | | | | | | 288 |
| Lys | Pro | Ala | Asp | Asp | Tyr | Leu | Pro | Gln | Pro | Gly | Ala | Val | Leu | Ile | Thr | |
| 80 | | | | 85 | | | | | 90 | | | | | 95 | | |
| ggt att acc ccg cag gaa gcg cgc gcg aaa ggt gaa aac gaa gcg gcg | | | | | | | | | | | | | | | | 336 |
| Gly | Ile | Thr | Pro | Gln | Glu | Ala | Arg | Ala | Lys | Gly | Glu | Asn | Glu | Ala | Ala | |
| | | | | 100 | | | | | 105 | | | | | 110 | | |
| ttt gcc gcg cgc att cat agc ctg ttt acc gtg ccg aaa acc tgc att | | | | | | | | | | | | | | | | 384 |
| Phe | Ala | Ala | Arg | Ile | His | Ser | Leu | Phe | Thr | Val | Pro | Lys | Thr | Cys | Ile | |
| | | | 115 | | | | | 120 | | | | | 125 | | | |
| ctg ggc tat aac aat gtg cgc ttc gat gat gaa gtt acc cgt aat atc | | | | | | | | | | | | | | | | 432 |
| Leu | Gly | Tyr | Asn | Asn | Val | Arg | Phe | Asp | Asp | Glu | Val | Thr | Arg | Asn | Ile | |
| | | | 130 | | | | | 135 | | | | | 140 | | | |
| ttt tat cgt aac ttt tat gat ccg tat gcg tgg agc tgg cag cat gat | | | | | | | | | | | | | | | | 480 |
| Phe | Tyr | Arg | Asn | Phe | Tyr | Asp | Pro | Tyr | Ala | Trp | Ser | Trp | Gln | His | Asp | |
| | | 145 | | | | | 150 | | | | | 155 | | | | |
| aac agc cgt tgg gat ctg ctg gat gtg atg cgc gcg tgc tat gcg ctg | | | | | | | | | | | | | | | | 528 |
| Asn | Ser | Arg | Trp | Asp | Leu | Leu | Asp | Val | Met | Arg | Ala | Cys | Tyr | Ala | Leu | |
| 160 | | | | | 165 | | | | | 170 | | | | | 175 | |
| cgc ccg gaa ggc att aat tgg ccg gaa aac gat gat ggc ctg ccg agc | | | | | | | | | | | | | | | | 576 |
| Arg | Pro | Glu | Gly | Ile | Asn | Trp | Pro | Glu | Asn | Asp | Asp | Gly | Leu | Pro | Ser | |
| | | | | 180 | | | | | 185 | | | | | 190 | | |

-continued

| | | |
|---|---|---|
| ttt cgt ctg gaa cat ctg acc aaa gcc aac ggc att gaa cat agc aat<br>Phe Arg Leu Glu His Leu Thr Lys Ala Asn Gly Ile Glu His Ser Asn<br>195 200 205 | | 624 |
| gcc cat gat gcg atg gcc gat gtt tat gcg acc att gcg atg gcg aaa<br>Ala His Asp Ala Met Ala Asp Val Tyr Ala Thr Ile Ala Met Ala Lys<br>210 215 220 | | 672 |
| ctg gtt aaa acc cgt cag ccg cgc ctg ttt gat tat ctg ttt acc cac<br>Leu Val Lys Thr Arg Gln Pro Arg Leu Phe Asp Tyr Leu Phe Thr His<br>225 230 235 | | 720 |
| cgt aac aaa cac aaa ctg atg gcg ctg att gat gtt ccg cag atg aaa<br>Arg Asn Lys His Lys Leu Met Ala Leu Ile Asp Val Pro Gln Met Lys<br>240 245 250 255 | | 768 |
| ccg ctg gtg cat gtg agc ggc atg ttt ggc gcc tgg cgc ggc aac acc<br>Pro Leu Val His Val Ser Gly Met Phe Gly Ala Trp Arg Gly Asn Thr<br>260 265 270 | | 816 |
| agc tgg gtg gcc ccg ctg gcc tgg cac ccg gaa aat cgt aac gcc gtg<br>Ser Trp Val Ala Pro Leu Ala Trp His Pro Glu Asn Arg Asn Ala Val<br>275 280 285 | | 864 |
| att atg gtt gat ctg gcc ggt gat att agc ccg ctg ctg gaa ctg gat<br>Ile Met Val Asp Leu Ala Gly Asp Ile Ser Pro Leu Leu Glu Leu Asp<br>290 295 300 | | 912 |
| agc gat acc ctg cgt gaa cgc ctg tat acc gcc aaa acc gat ctg ggc<br>Ser Asp Thr Leu Arg Glu Arg Leu Tyr Thr Ala Lys Thr Asp Leu Gly<br>305 310 315 | | 960 |
| gat aat gcc gcc gtg ccg gtg aaa ctg gtt cac att aac aaa tgc ccg<br>Asp Asn Ala Ala Val Pro Val Lys Leu Val His Ile Asn Lys Cys Pro<br>320 325 330 335 | | 1008 |
| gtg ctg gcc cag gcg aac acc ctg cgc ccg gaa gat gcg gat cgt ctg<br>Val Leu Ala Gln Ala Asn Thr Leu Arg Pro Glu Asp Ala Asp Arg Leu<br>340 345 350 | | 1056 |
| ggt att aat cgc cag cat tgt ctg gat aat ctg aaa atc ctg cgt gaa<br>Gly Ile Asn Arg Gln His Cys Leu Asp Asn Leu Lys Ile Leu Arg Glu<br>355 360 365 | | 1104 |
| aac ccg cag gtg cgt gaa aaa gtg gtg gcg atc ttc gcg gaa gcg gaa<br>Asn Pro Gln Val Arg Glu Lys Val Val Ala Ile Phe Ala Glu Ala Glu<br>370 375 380 | | 1152 |
| ccg ttc acc ccg agc gat aac gtg gat gcg cag ctg tat aac ggc ttc<br>Pro Phe Thr Pro Ser Asp Asn Val Asp Ala Gln Leu Tyr Asn Gly Phe<br>385 390 395 | | 1200 |
| ttt agc gat gcc gat cgc gcg gcg atg aaa atc gtt ctg gaa acc gaa<br>Phe Ser Asp Ala Asp Arg Ala Ala Met Lys Ile Val Leu Glu Thr Glu<br>400 405 410 415 | | 1248 |
| ccg cgc aat ctg ccg gcg ctg gat att acc ttt gtt gat aaa cgt att<br>Pro Arg Asn Leu Pro Ala Leu Asp Ile Thr Phe Val Asp Lys Arg Ile<br>420 425 430 | | 1296 |
| gaa aaa ctg ctg ttt aat tat cgt gcg cgc aat ttt ccg ggt acc ctg<br>Glu Lys Leu Leu Phe Asn Tyr Arg Ala Arg Asn Phe Pro Gly Thr Leu<br>435 440 445 | | 1344 |
| gat tat gcc gaa cag cag cgt tgg ctg gaa cat cgt cgt cag gtt ttc<br>Asp Tyr Ala Glu Gln Gln Arg Trp Leu Glu His Arg Arg Gln Val Phe<br>450 455 460 | | 1392 |
| acc ccg gaa ttt ctg cag ggt tat gcg gat gaa ctg cag atg ctg gtt<br>Thr Pro Glu Phe Leu Gln Gly Tyr Ala Asp Glu Leu Gln Met Leu Val<br>465 470 475 | | 1440 |
| cag cag tat gcc gat gat aaa gaa aaa gtg gcg ctg ctg aaa gcg ctg<br>Gln Gln Tyr Ala Asp Asp Lys Glu Lys Val Ala Leu Leu Lys Ala Leu<br>480 485 490 495 | | 1488 |
| tgg cag tat gcg gaa gaa atc gtt tct ggc tct ggt tcc ggc agc ggt<br>Trp Gln Tyr Ala Glu Glu Ile Val Ser Gly Ser Gly Ser Gly Ser Gly<br>500 505 510 | | 1536 |

| | | |
|---|---|---|
| tcc gga aca gta aaa aca ggt gat tta gtc act tat gat aaa gaa aat<br>Ser Gly Thr Val Lys Thr Gly Asp Leu Val Thr Tyr Asp Lys Glu Asn<br>515 520 525 | | 1584 |
| ggc atg cac aaa aaa gta ttt tat agt ttt atc gat gat aaa aat cac<br>Gly Met His Lys Lys Val Phe Tyr Ser Phe Ile Asp Asp Lys Asn His<br>530 535 540 | | 1632 |
| aat aaa aaa ctg cta gtt att aga aca aaa ggt acc att gct ggt caa<br>Asn Lys Lys Leu Leu Val Ile Arg Thr Lys Gly Thr Ile Ala Gly Gln<br>545 550 555 | | 1680 |
| tat aga gtt tat agc gaa gaa ggt gct aac aaa agt ggt tta gcc tgg<br>Tyr Arg Val Tyr Ser Glu Glu Gly Ala Asn Lys Ser Gly Leu Ala Trp<br>560 565 570 575 | | 1728 |
| cct tca gcc ttt aag gta cag ttg caa cta cct gat aat gaa gta gct<br>Pro Ser Ala Phe Lys Val Gln Leu Gln Leu Pro Asp Asn Glu Val Ala<br>580 585 590 | | 1776 |
| caa ata tct gat tac tat cca aga aat tcg att gat aca aaa gag tat<br>Gln Ile Ser Asp Tyr Tyr Pro Arg Asn Ser Ile Asp Thr Lys Glu Tyr<br>595 600 605 | | 1824 |
| agg agt act tta act tat gga ttc aac ggt aat gtt act ggt gat gat<br>Arg Ser Thr Leu Thr Tyr Gly Phe Asn Gly Asn Val Thr Gly Asp Asp<br>610 615 620 | | 1872 |
| aca gga aaa att ggc ggc tgt att ggt gca caa gtt tcg att ggt cat<br>Thr Gly Lys Ile Gly Gly Cys Ile Gly Ala Gln Val Ser Ile Gly His<br>625 630 635 | | 1920 |
| aca ctg aaa tat gtt caa cct gat ttc aaa aca att tta gag agc cca<br>Thr Leu Lys Tyr Val Gln Pro Asp Phe Lys Thr Ile Leu Glu Ser Pro<br>640 645 650 655 | | 1968 |
| act gat aaa aaa gta ggc tgg aaa gtg ata ttt aac aat atg gtg aat<br>Thr Asp Lys Lys Val Gly Trp Lys Val Ile Phe Asn Asn Met Val Asn<br>660 665 670 | | 2016 |
| caa aat tgg gga cca tac gat cga gat tct tgg aac ccg gta tat ggc<br>Gln Asn Trp Gly Pro Tyr Asp Arg Asp Ser Trp Asn Pro Val Tyr Gly<br>675 680 685 | | 2064 |
| aat caa ctt ttc atg aaa act aga aat ggt tct atg aaa gca gca gat<br>Asn Gln Leu Phe Met Lys Thr Arg Asn Gly Ser Met Lys Ala Ala Asp<br>690 695 700 | | 2112 |
| aac ttc ctt gat cct aac aaa gca agt tct cta tta tct tca ggg ttt<br>Asn Phe Leu Asp Pro Asn Lys Ala Ser Ser Leu Leu Ser Ser Gly Phe<br>705 710 715 | | 2160 |
| tca cca gac ttc gct aca gtt att act atg gat aga aaa gca tcc aaa<br>Ser Pro Asp Phe Ala Thr Val Ile Thr Met Asp Arg Lys Ala Ser Lys<br>720 725 730 735 | | 2208 |
| caa caa aca aat ata gat gta ata tac gaa cga gtt cgt gat gat tac<br>Gln Gln Thr Asn Ile Asp Val Ile Tyr Glu Arg Val Arg Asp Asp Tyr<br>740 745 750 | | 2256 |
| caa ttg cat tgg act tca aca aat tgg aaa ggt acc aat act aaa gat<br>Gln Leu His Trp Thr Ser Thr Asn Trp Lys Gly Thr Asn Thr Lys Asp<br>755 760 765 | | 2304 |
| aaa tgg aca gat cgt tct tca gaa aga tat aaa atc gat tgg gaa aaa<br>Lys Trp Thr Asp Arg Ser Ser Glu Arg Tyr Lys Ile Asp Trp Glu Lys<br>770 775 780 | | 2352 |
| gaa gaa atg aca aat ggt ggt tcg ggc tca tct ggt ggc tcg agt cac<br>Glu Glu Met Thr Asn Gly Gly Ser Gly Ser Ser Gly Gly Ser Ser His<br>785 790 795 | | 2400 |
| cat cat cat cac cac<br>His His His His His<br>800 | | 2415 |

```
<210> SEQ ID NO 22
<211> LENGTH: 804
<212> TYPE: PRT
<213> ORGANISM: Artificial sequence
<220> FEATURE:
<223> OTHER INFORMATION: Synthetic Construct

<400> SEQUENCE: 22

Ala Asp Ser Asp Ile Asn Ile Lys Thr Gly Thr Thr Asp Ile Gly Ser
1               5                   10                  15

Asn Thr Ser Gly Ser Gly Ser Gly Ser Gly Met Met Asn Asp
            20                  25                  30

Gly Lys Gln Gln Ser Thr Phe Leu Phe His Asp Tyr Glu Thr Phe Gly
        35                  40                  45

Thr His Pro Ala Leu Asp Arg Pro Ala Gln Phe Ala Ala Ile Arg Thr
    50                  55                  60

Asp Ser Glu Phe Asn Val Ile Gly Glu Pro Glu Val Phe Tyr Cys Lys
65                  70                  75                  80

Pro Ala Asp Asp Tyr Leu Pro Gln Pro Gly Ala Val Leu Ile Thr Gly
                85                  90                  95

Ile Thr Pro Gln Glu Ala Arg Ala Lys Gly Glu Asn Glu Ala Ala Phe
            100                 105                 110

Ala Ala Arg Ile His Ser Leu Phe Thr Val Pro Lys Thr Cys Ile Leu
        115                 120                 125

Gly Tyr Asn Asn Val Arg Phe Asp Asp Glu Val Thr Arg Asn Ile Phe
    130                 135                 140

Tyr Arg Asn Phe Tyr Asp Pro Tyr Ala Trp Ser Trp Gln His Asp Asn
145                 150                 155                 160

Ser Arg Trp Asp Leu Leu Asp Val Met Arg Ala Cys Tyr Ala Leu Arg
                165                 170                 175

Pro Glu Gly Ile Asn Trp Pro Glu Asn Asp Asp Gly Leu Pro Ser Phe
            180                 185                 190

Arg Leu Glu His Leu Thr Lys Ala Asn Gly Ile Glu His Ser Asn Ala
        195                 200                 205

His Asp Ala Met Ala Asp Val Tyr Ala Thr Ile Ala Met Ala Lys Leu
    210                 215                 220

Val Lys Thr Arg Gln Pro Arg Leu Phe Asp Tyr Leu Phe Thr His Arg
225                 230                 235                 240

Asn Lys His Lys Leu Met Ala Leu Ile Asp Val Pro Gln Met Lys Pro
                245                 250                 255

Leu Val His Val Ser Gly Met Phe Gly Ala Trp Arg Gly Asn Thr Ser
            260                 265                 270

Trp Val Ala Pro Leu Ala Trp His Pro Glu Asn Arg Asn Ala Val Ile
        275                 280                 285

Met Val Asp Leu Ala Gly Asp Ile Ser Pro Leu Leu Glu Leu Asp Ser
    290                 295                 300

Asp Thr Leu Arg Glu Arg Leu Tyr Thr Ala Lys Thr Asp Leu Gly Asp
305                 310                 315                 320

Asn Ala Ala Val Pro Val Lys Leu Val His Ile Asn Lys Cys Pro Val
                325                 330                 335

Leu Ala Gln Ala Asn Thr Leu Arg Pro Glu Asp Ala Asp Arg Leu Gly
            340                 345                 350

Ile Asn Arg Gln His Cys Leu Asp Asn Leu Lys Ile Leu Arg Glu Asn
        355                 360                 365
```

```
Pro Gln Val Arg Glu Lys Val Val Ala Ile Phe Ala Glu Ala Glu Pro
    370             375                 380
Phe Thr Pro Ser Asp Asn Val Asp Ala Gln Leu Tyr Asn Gly Phe Phe
385             390                 395                 400
Ser Asp Ala Asp Arg Ala Ala Met Lys Ile Val Leu Glu Thr Glu Pro
                405                 410                 415
Arg Asn Leu Pro Ala Leu Asp Ile Thr Phe Val Asp Lys Arg Ile Glu
            420                 425                 430
Lys Leu Leu Phe Asn Tyr Arg Arg Asn Phe Pro Gly Thr Leu Asp
        435                 440                 445
Tyr Ala Glu Gln Gln Arg Trp Leu Glu His Arg Arg Gln Val Phe Thr
    450                 455                 460
Pro Glu Phe Leu Gln Gly Tyr Ala Asp Glu Leu Gln Met Leu Val Gln
465             470                 475                 480
Gln Tyr Ala Asp Asp Lys Glu Lys Val Ala Leu Leu Lys Ala Leu Trp
                485                 490                 495
Gln Tyr Ala Glu Glu Ile Val Ser Gly Ser Gly Ser Gly Ser
            500                 505                 510
Gly Thr Val Lys Thr Gly Asp Leu Val Thr Tyr Asp Lys Glu Asn Gly
        515                 520                 525
Met His Lys Lys Val Phe Tyr Ser Phe Ile Asp Lys Asn His Asn
    530                 535                 540
Lys Lys Leu Leu Val Ile Arg Thr Lys Gly Thr Ile Ala Gly Gln Tyr
545                 550                 555                 560
Arg Val Tyr Ser Glu Glu Gly Ala Asn Lys Ser Gly Leu Ala Trp Pro
                565                 570                 575
Ser Ala Phe Lys Val Gln Leu Gln Leu Pro Asp Asn Glu Val Ala Gln
            580                 585                 590
Ile Ser Asp Tyr Tyr Pro Arg Asn Ser Ile Asp Thr Lys Glu Tyr Arg
        595                 600                 605
Ser Thr Leu Thr Tyr Gly Phe Asn Gly Asn Val Thr Gly Asp Asp Thr
    610                 615                 620
Gly Lys Ile Gly Gly Cys Ile Gly Ala Gln Val Ser Ile Gly His Thr
625                 630                 635                 640
Leu Lys Tyr Val Gln Pro Asp Phe Lys Thr Ile Leu Glu Ser Pro Thr
                645                 650                 655
Asp Lys Lys Val Gly Trp Lys Val Ile Phe Asn Asn Met Val Asn Gln
            660                 665                 670
Asn Trp Gly Pro Tyr Asp Arg Asp Ser Trp Asn Pro Val Tyr Gly Asn
        675                 680                 685
Gln Leu Phe Met Lys Thr Arg Asn Gly Ser Met Lys Ala Ala Asp Asn
    690                 695                 700
Phe Leu Asp Pro Asn Lys Ala Ser Ser Leu Leu Ser Ser Gly Phe Ser
705             710                 715                 720
Pro Asp Phe Ala Thr Val Ile Thr Met Asp Arg Lys Ala Ser Lys Gln
                725                 730                 735
Gln Thr Asn Ile Asp Val Ile Tyr Glu Arg Val Arg Asp Tyr Gln
            740                 745                 750
Leu His Trp Thr Ser Thr Asn Trp Lys Gly Thr Asn Thr Lys Asp Lys
        755                 760                 765
Trp Thr Asp Arg Ser Ser Glu Arg Tyr Lys Ile Asp Trp Glu Lys Glu
    770                 775                 780
```

```
                Glu Met Thr Asn Gly Gly Ser Gly Ser Ser Gly Ser Ser His His
                785                 790                 795                 800

His His His His

<210> SEQ ID NO 23
<211> LENGTH: 2265
<212> TYPE: DNA
<213> ORGANISM: Artificial sequence
<220> FEATURE:
<223> OTHER INFORMATION: DNA Sequence encoding HL-RQC-TthRecJ-L1-H6
<220> FEATURE:
<221> NAME/KEY: CDS
<222> LOCATION: (4)..(2265)

<400> SEQUENCE: 23 atg gca gat tct gat att aat att aaa acc ggt act aca gat att gga        48
    Ala Asp Ser Asp Ile Asn Ile Lys Thr Gly Thr Thr Asp Ile Gly
    1               5                   10                  15 agc aat act tcc gga agc ggc tct ggt agt ggt tct ggc atg ttt cgt        96
Ser Asn Thr Ser Gly Ser Gly Ser Gly Ser Gly Ser Gly Met Phe Arg
                20                  25                  30 cgt aaa gaa gat ctg gat ccg ccg ctg gca ctg ctg ccg ctg aaa ggc       144
Arg Lys Glu Asp Leu Asp Pro Pro Leu Ala Leu Leu Pro Leu Lys Gly
            35                  40                  45 ctg cgc gaa gcc gcc gca ctg ctg gaa gaa gcg ctg cgt caa ggt aaa       192
Leu Arg Glu Ala Ala Ala Leu Leu Glu Glu Ala Leu Arg Gln Gly Lys
        50                  55                  60 cgc att cgt gtt cac ggc gac tat gat gcg gat ggc ctg acc ggc acc       240
Arg Ile Arg Val His Gly Asp Tyr Asp Ala Asp Gly Leu Thr Gly Thr
    65                  70                  75 gcg atc ctg gtt cgt ggt ctg gcc gcc ctg ggt gcg gat gtt cat ccg       288
Ala Ile Leu Val Arg Gly Leu Ala Ala Leu Gly Ala Asp Val His Pro
80                  85                  90                  95 ttt atc ccg cac cgc ctg gaa gaa ggc tat ggt gtc ctg atg gaa cgc       336
Phe Ile Pro His Arg Leu Glu Glu Gly Tyr Gly Val Leu Met Glu Arg
                100                 105                 110 gtc ccg gaa cat ctg gaa gcc tcg gac ctg ttt ctg acc gtt gac tgc       384
Val Pro Glu His Leu Glu Ala Ser Asp Leu Phe Leu Thr Val Asp Cys
            115                 120                 125 ggc att acc aac cat gcg gaa ctg cgc gaa ctg ctg gaa aat ggc gtg       432
Gly Ile Thr Asn His Ala Glu Leu Arg Glu Leu Leu Glu Asn Gly Val
        130                 135                 140 gaa gtc att gtt acc gat cat cat acg ccg ggc aaa acg ccg ccg ccg       480
Glu Val Ile Val Thr Asp His His Thr Pro Gly Lys Thr Pro Pro Pro
    145                 150                 155 ggt ctg gtc gtg cat ccg gcg ctg acg ccg gat ctg aaa gaa aaa ccg       528
Gly Leu Val Val His Pro Ala Leu Thr Pro Asp Leu Lys Glu Lys Pro
160                 165                 170                 175 acc ggc gca ggc gtg gcg ttt ctg ctg ctg tgg gca ctg cat gaa cgc       576
Thr Gly Ala Gly Val Ala Phe Leu Leu Leu Trp Ala Leu His Glu Arg
                180                 185                 190 ctg ggc ctg ccg ccg ccg ctg gaa tac gcg gac ctg gca gcc gtt ggc       624
Leu Gly Leu Pro Pro Pro Leu Glu Tyr Ala Asp Leu Ala Ala Val Gly
            195                 200                 205 acc att gcc gac gtt gcc ccg ctg tgg ggt tgg aat cgt gca ctg gtg       672
Thr Ile Ala Asp Val Ala Pro Leu Trp Gly Trp Asn Arg Ala Leu Val
        210                 215                 220 aaa gaa ggt ctg gca cgc atc ccg gct tca tct tgg gtg ggc ctg cgt       720
Lys Glu Gly Leu Ala Arg Ile Pro Ala Ser Ser Trp Val Gly Leu Arg
    225                 230                 235
```

```
ctg ctg gct gaa gcc gtg ggc tat acc ggc aaa gcg gtc gaa gtc gct        768
Leu Leu Ala Glu Ala Val Gly Tyr Thr Gly Lys Ala Val Glu Val Ala
240                 245                 250                 255 ttc cgc atc gcg ccg cgc atc aat gcg gct tcc cgc ctg ggc gaa gcg        816
Phe Arg Ile Ala Pro Arg Ile Asn Ala Ala Ser Arg Leu Gly Glu Ala
                260                 265                 270 gaa aaa gcc ctg cgc ctg ctg ctg acg gat gat gcg gca gaa gct cag        864
Glu Lys Ala Leu Arg Leu Leu Leu Thr Asp Asp Ala Ala Glu Ala Gln
            275                 280                 285 gcg ctg gtc ggc gaa ctg cac cgt ctg aac gcc cgt cgt cag acc ctg        912
Ala Leu Val Gly Glu Leu His Arg Leu Asn Ala Arg Arg Gln Thr Leu
        290                 295                 300 gaa gaa gcg atg ctg cgc aaa ctg ctg ccg cag gcc gac ccg gaa gcg        960
Glu Glu Ala Met Leu Arg Lys Leu Leu Pro Gln Ala Asp Pro Glu Ala
    305                 310                 315 aaa gcc atc gtt ctg ctg gac ccg gaa ggc cat ccg ggt gtt atg ggt       1008
Lys Ala Ile Val Leu Leu Asp Pro Glu Gly His Pro Gly Val Met Gly
320                 325                 330                 335 att gtg gcc tct cgc atc ctg gaa gcg acc ctg cgc ccg gtc ttt ctg       1056
Ile Val Ala Ser Arg Ile Leu Glu Ala Thr Leu Arg Pro Val Phe Leu
                340                 345                 350 gtg gcc cag ggc aaa ggc acc gtg cgt tcg ctg gct ccg att tcc gcc       1104
Val Ala Gln Gly Lys Gly Thr Val Arg Ser Leu Ala Pro Ile Ser Ala
            355                 360                 365 gtc gaa gca ctg cgc agc gcg gaa gat ctg ctg ctg cgt tat ggt ggt       1152
Val Glu Ala Leu Arg Ser Ala Glu Asp Leu Leu Leu Arg Tyr Gly Gly
        370                 375                 380 cat aaa gaa gcg gcg ggt ttc gca atg gat gaa gcg ctg ttt ccg gcg       1200
His Lys Glu Ala Ala Gly Phe Ala Met Asp Glu Ala Leu Phe Pro Ala
    385                 390                 395 ttc aaa gca cgc gtt gaa gcg tat gcc gca cgt ttc ccg gat ccg gtt       1248
Phe Lys Ala Arg Val Glu Ala Tyr Ala Ala Arg Phe Pro Asp Pro Val
400                 405                 410                 415 cgt gaa gtg gca ctg ctg gat ctg ctg ccg gaa ccg ggc ctg ctg ccg       1296
Arg Glu Val Ala Leu Leu Asp Leu Leu Pro Glu Pro Gly Leu Leu Pro
                420                 425                 430 cag gtg ttc cgt gaa ctg gca ctg ctg gaa ccg tat ggt gaa ggt aac       1344
Gln Val Phe Arg Glu Leu Ala Leu Leu Glu Pro Tyr Gly Glu Gly Asn
            435                 440                 445 ccg gaa ccg ctg ttc ctg tct ggc tct ggt tcc ggc agc ggt tcc gga       1392
Pro Glu Pro Leu Phe Leu Ser Gly Ser Gly Ser Gly Ser Gly Ser Gly
        450                 455                 460 aca gta aaa aca ggt gat tta gtc act tat gat aaa gaa aat ggc atg       1440
Thr Val Lys Thr Gly Asp Leu Val Thr Tyr Asp Lys Glu Asn Gly Met
    465                 470                 475 cac aaa aaa gta ttt tat agt ttt atc gat gat aaa aat cac aat aaa       1488
His Lys Lys Val Phe Tyr Ser Phe Ile Asp Asp Lys Asn His Asn Lys
480                 485                 490                 495 aaa ctg cta gtt att aga aca aaa ggt acc att gct ggt caa tat aga       1536
Lys Leu Leu Val Ile Arg Thr Lys Gly Thr Ile Ala Gly Gln Tyr Arg
                500                 505                 510 gtt tat agc gaa gaa ggt gct aac aaa agt ggt tta gcc tgg cct tca       1584
Val Tyr Ser Glu Glu Gly Ala Asn Lys Ser Gly Leu Ala Trp Pro Ser
            515                 520                 525 gcc ttt aag gta cag ttg caa cta cct gat aat gaa gta gct caa ata       1632
Ala Phe Lys Val Gln Leu Gln Leu Pro Asp Asn Glu Val Ala Gln Ile
        530                 535                 540 tct gat tac tat cca aga aat tcg att gat aca aaa gag tat agg agt       1680
Ser Asp Tyr Tyr Pro Arg Asn Ser Ile Asp Thr Lys Glu Tyr Arg Ser
    545                 550                 555
```

-continued

| | | |
|---|---|---|
| act tta act tat gga ttc aac ggt aat gtt act ggt gat gat aca gga<br>Thr Leu Thr Tyr Gly Phe Asn Gly Asn Val Thr Gly Asp Asp Thr Gly<br>560                    565                    570                    575 | 1728 |
| aaa att ggc ggc tgt att ggt gca caa gtt tcg att ggt cat aca ctg<br>Lys Ile Gly Gly Cys Ile Gly Ala Gln Val Ser Ile Gly His Thr Leu<br>                    580                    585                    590 | 1776 |
| aaa tat gtt caa cct gat ttc aaa aca att tta gag agc cca act gat<br>Lys Tyr Val Gln Pro Asp Phe Lys Thr Ile Leu Glu Ser Pro Thr Asp<br>                  595                    600                    605 | 1824 |
| aaa aaa gta ggc tgg aaa gtg ata ttt aac aat atg gtg aat caa aat<br>Lys Lys Val Gly Trp Lys Val Ile Phe Asn Asn Met Val Asn Gln Asn<br>610                    615                    620 | 1872 |
| tgg gga cca tac gat cga gat tct tgg aac ccg gta tat ggc aat caa<br>Trp Gly Pro Tyr Asp Arg Asp Ser Trp Asn Pro Val Tyr Gly Asn Gln<br>625                    630                    635 | 1920 |
| ctt ttc atg aaa act aga aat ggt tct atg aaa gca gca gat aac ttc<br>Leu Phe Met Lys Thr Arg Asn Gly Ser Met Lys Ala Ala Asp Asn Phe<br>640                    645                    650                    655 | 1968 |
| ctt gat cct aac aaa gca agt tct cta tta tct tca ggg ttt tca cca<br>Leu Asp Pro Asn Lys Ala Ser Ser Leu Leu Ser Ser Gly Phe Ser Pro<br>                    660                    665                    670 | 2016 |
| gac ttc gct aca gtt att act atg gat aga aaa gca tcc aaa caa caa<br>Asp Phe Ala Thr Val Ile Thr Met Asp Arg Lys Ala Ser Lys Gln Gln<br>                  675                    680                    685 | 2064 |
| aca aat ata gat gta ata tac gaa cga gtt cgt gat gat tac caa ttg<br>Thr Asn Ile Asp Val Ile Tyr Glu Arg Val Arg Asp Asp Tyr Gln Leu<br>                    690                    695                    700 | 2112 |
| cat tgg act tca aca aat tgg aaa ggt acc aat act aaa gat aaa tgg<br>His Trp Thr Ser Thr Asn Trp Lys Gly Thr Asn Thr Lys Asp Lys Trp<br>705                    710                    715 | 2160 |
| aca gat cgt tct tca gaa aga tat aaa atc gat tgg gaa aaa gaa gaa<br>Thr Asp Arg Ser Ser Glu Arg Tyr Lys Ile Asp Trp Glu Lys Glu Glu<br>720                    725                    730                    735 | 2208 |
| atg aca aat ggt ggt tcg ggc tca tct ggt ggc tcg agt cac cat cat<br>Met Thr Asn Gly Gly Ser Gly Ser Ser Gly Gly Ser Ser His His His<br>                    740                    745                    750 | 2256 |
| cat cac cac<br>His His His | 2265 |

<210> SEQ ID NO 24
<211> LENGTH: 754
<212> TYPE: PRT
<213> ORGANISM: Artificial sequence
<220> FEATURE:
<223> OTHER INFORMATION: Synthetic Construct

<400> SEQUENCE: 24

Ala Asp Ser Asp Ile Asn Ile Lys Thr Gly Thr Thr Asp Ile Gly Ser
1                    5                        10                    15

Asn Thr Ser Gly Ser Gly Ser Gly Ser Gly Met Phe Arg Arg
                    20                        25                    30

Lys Glu Asp Leu Asp Pro Pro Leu Ala Leu Leu Pro Leu Lys Gly Leu
              35                    40                    45

Arg Glu Ala Ala Ala Leu Leu Glu Glu Ala Leu Arg Gln Gly Lys Arg
        50                    55                    60

Ile Arg Val His Gly Asp Tyr Asp Ala Asp Gly Leu Thr Gly Thr Ala
65                    70                    75                    80

Ile Leu Val Arg Gly Leu Ala Ala Leu Gly Ala Asp Val His Pro Phe
              85                    90                    95

```
Ile Pro His Arg Leu Glu Glu Gly Tyr Gly Val Leu Met Glu Arg Val
                100                 105                 110
Pro Glu His Leu Glu Ala Ser Asp Leu Phe Leu Thr Val Asp Cys Gly
            115                 120                 125
Ile Thr Asn His Ala Glu Leu Arg Glu Leu Leu Glu Asn Gly Val Glu
        130                 135                 140
Val Ile Val Thr Asp His His Thr Pro Gly Lys Thr Pro Pro Gly
145                 150                 155                 160
Leu Val Val His Pro Ala Leu Thr Pro Asp Leu Lys Glu Lys Pro Thr
                165                 170                 175
Gly Ala Gly Val Ala Phe Leu Leu Leu Trp Ala Leu His Glu Arg Leu
            180                 185                 190
Gly Leu Pro Pro Leu Glu Tyr Ala Asp Leu Ala Ala Val Gly Thr
        195                 200                 205
Ile Ala Asp Val Ala Pro Leu Trp Gly Trp Asn Arg Ala Leu Val Lys
210                 215                 220
Glu Gly Leu Ala Arg Ile Pro Ala Ser Ser Trp Val Gly Leu Arg Leu
225                 230                 235                 240
Leu Ala Glu Ala Val Gly Tyr Thr Gly Lys Ala Val Glu Val Ala Phe
                245                 250                 255
Arg Ile Ala Pro Arg Ile Asn Ala Ala Ser Arg Leu Gly Glu Ala Glu
            260                 265                 270
Lys Ala Leu Arg Leu Leu Leu Thr Asp Asp Ala Ala Glu Ala Gln Ala
        275                 280                 285
Leu Val Gly Glu Leu His Arg Leu Asn Ala Arg Arg Gln Thr Leu Glu
290                 295                 300
Glu Ala Met Leu Arg Lys Leu Leu Pro Gln Ala Asp Pro Glu Ala Lys
305                 310                 315                 320
Ala Ile Val Leu Leu Asp Pro Glu Gly His Pro Gly Val Met Gly Ile
                325                 330                 335
Val Ala Ser Arg Ile Leu Glu Ala Thr Leu Arg Pro Val Phe Leu Val
            340                 345                 350
Ala Gln Gly Lys Gly Thr Val Arg Ser Leu Ala Pro Ile Ser Ala Val
        355                 360                 365
Glu Ala Leu Arg Ser Ala Glu Asp Leu Leu Leu Arg Tyr Gly Gly His
370                 375                 380
Lys Glu Ala Ala Gly Phe Ala Met Asp Glu Ala Leu Phe Pro Ala Phe
385                 390                 395                 400
Lys Ala Arg Val Glu Ala Tyr Ala Ala Arg Phe Pro Asp Pro Val Arg
                405                 410                 415
Glu Val Ala Leu Leu Asp Leu Leu Pro Glu Pro Gly Leu Leu Pro Gln
            420                 425                 430
Val Phe Arg Glu Leu Ala Leu Leu Glu Pro Tyr Gly Glu Gly Asn Pro
        435                 440                 445
Glu Pro Leu Phe Leu Ser Gly Ser Gly Ser Gly Ser Gly Thr
    450                 455                 460
Val Lys Thr Gly Asp Leu Val Thr Tyr Asp Lys Glu Asn Gly Met His
465                 470                 475                 480
Lys Lys Val Phe Tyr Ser Phe Ile Asp Asp Lys Asn His Asn Lys Lys
                485                 490                 495
Leu Leu Val Ile Arg Thr Lys Gly Thr Ile Ala Gly Gln Tyr Arg Val
            500                 505                 510
```

-continued

```
Tyr Ser Glu Glu Gly Ala Asn Lys Ser Gly Leu Ala Trp Pro Ser Ala
            515                 520                 525

Phe Lys Val Gln Leu Gln Leu Pro Asp Asn Glu Val Ala Gln Ile Ser
530                 535                 540

Asp Tyr Tyr Pro Arg Asn Ser Ile Asp Thr Lys Glu Tyr Arg Ser Thr
545                 550                 555                 560

Leu Thr Tyr Gly Phe Asn Gly Asn Val Thr Gly Asp Thr Gly Lys
                565                 570                 575

Ile Gly Gly Cys Ile Gly Ala Gln Val Ser Ile Gly His Thr Leu Lys
            580                 585                 590

Tyr Val Gln Pro Asp Phe Lys Thr Ile Leu Glu Ser Pro Thr Asp Lys
            595                 600                 605

Lys Val Gly Trp Lys Val Ile Phe Asn Asn Met Val Asn Gln Asn Trp
            610                 615                 620

Gly Pro Tyr Asp Arg Asp Ser Trp Asn Pro Val Tyr Gly Asn Gln Leu
625                 630                 635                 640

Phe Met Lys Thr Arg Asn Gly Ser Met Lys Ala Ala Asp Asn Phe Leu
                645                 650                 655

Asp Pro Asn Lys Ala Ser Ser Leu Leu Ser Ser Gly Phe Ser Pro Asp
            660                 665                 670

Phe Ala Thr Val Ile Thr Met Asp Arg Lys Ala Ser Lys Gln Gln Thr
            675                 680                 685

Asn Ile Asp Val Ile Tyr Glu Arg Val Arg Asp Tyr Gln Leu His
            690                 695                 700

Trp Thr Ser Thr Asn Trp Lys Gly Thr Asn Thr Lys Asp Lys Trp Thr
705                 710                 715                 720

Asp Arg Ser Ser Glu Arg Tyr Lys Ile Asp Trp Lys Glu Met
                725                 730                 735

Thr Asn Gly Gly Ser Gly Ser Ser Gly Gly Ser His His His His
            740                 745                 750

His His

<210> SEQ ID NO 25
<211> LENGTH: 1785
<212> TYPE: DNA
<213> ORGANISM: Artificial sequence
<220> FEATURE:
<223> OTHER INFORMATION: DNA Sequence encoding
      HL-RQC-EcoExoIII-L2-D45-N47delta-H6
<220> FEATURE:
<221> NAME/KEY: CDS
<222> LOCATION: (4)..(1785)

<400> SEQUENCE: 25 atg gca gat tct gat att aat att aaa acc ggt act aca gat att gga     48
    Ala Asp Ser Asp Ile Asn Ile Lys Thr Gly Thr Thr Asp Ile Gly
    1               5                   10                  15 agc aat act aca gta aaa aca ggt gat tta gtc act tat gat aaa gaa     96
Ser Asn Thr Thr Val Lys Thr Gly Asp Leu Val Thr Tyr Asp Lys Glu
                20                  25                  30 aat ggc atg cac aaa aaa gta ttt tat agt ttt atc gat tcc gga agc    144
Asn Gly Met His Lys Lys Val Phe Tyr Ser Phe Ile Asp Ser Gly Ser
            35                  40                  45 ggc tct ggt agt ggt tct ggc atg aaa ttt gtt agc ttc aat atc aac    192
Gly Ser Gly Ser Gly Ser Gly Met Lys Phe Val Ser Phe Asn Ile Asn
        50                  55                  60
```

```
ggc ctg cgc gcg cgc ccg cat cag ctg gaa gcg att gtg gaa aaa cat        240
Gly Leu Arg Ala Arg Pro His Gln Leu Glu Ala Ile Val Glu Lys His
         65                  70                  75 cag ccg gat gtt att ggt ctg cag gaa acc aaa gtt cac gat gat atg        288
Gln Pro Asp Val Ile Gly Leu Gln Glu Thr Lys Val His Asp Asp Met
 80                  85                  90                  95 ttt ccg ctg gaa gaa gtg gcg aaa ctg ggc tat aac gtg ttt tat cat        336
Phe Pro Leu Glu Glu Val Ala Lys Leu Gly Tyr Asn Val Phe Tyr His
                    100                 105                 110 ggc cag aaa ggt cat tat ggc gtg gcc ctg ctg acc aaa gaa acc ccg        384
Gly Gln Lys Gly His Tyr Gly Val Ala Leu Leu Thr Lys Glu Thr Pro
             115                 120                 125 atc gcg gtt cgt cgt ggt ttt ccg ggt gat gat gaa gaa gcg cag cgt        432
Ile Ala Val Arg Arg Gly Phe Pro Gly Asp Asp Glu Glu Ala Gln Arg
             130                 135                 140 cgt att att atg gcg gaa att ccg agc ctg ctg ggc aat gtg acc gtt        480
Arg Ile Ile Met Ala Glu Ile Pro Ser Leu Leu Gly Asn Val Thr Val
145                 150                 155 att aac ggc tat ttt ccg cag ggc gaa agc cgt gat cat ccg att aaa        528
Ile Asn Gly Tyr Phe Pro Gln Gly Glu Ser Arg Asp His Pro Ile Lys
160                 165                 170                 175 ttt ccg gcc aaa gcg cag ttc tat cag aac ctg cag aac tat ctg gaa        576
Phe Pro Ala Lys Ala Gln Phe Tyr Gln Asn Leu Gln Asn Tyr Leu Glu
                180                 185                 190 acc gaa ctg aaa cgt gat aat ccg gtg ctg atc atg ggc gat atg aac        624
Thr Glu Leu Lys Arg Asp Asn Pro Val Leu Ile Met Gly Asp Met Asn
             195                 200                 205 att agc ccg acc gat ctg gat att ggc att ggc gaa gaa aac cgt aaa        672
Ile Ser Pro Thr Asp Leu Asp Ile Gly Ile Gly Glu Glu Asn Arg Lys
             210                 215                 220 cgc tgg ctg cgt acc ggt aaa tgc agc ttt ctg ccg gaa gaa cgt gaa        720
Arg Trp Leu Arg Thr Gly Lys Cys Ser Phe Leu Pro Glu Glu Arg Glu
225                 230                 235 tgg atg gat cgc ctg atg agc tgg ggc ctg gtg gat acc ttt cgt cat        768
Trp Met Asp Arg Leu Met Ser Trp Gly Leu Val Asp Thr Phe Arg His
240                 245                 250                 255 gcg aac ccg cag acc gcc gat cgc ttt agc tgg ttt gat tat cgc agc        816
Ala Asn Pro Gln Thr Ala Asp Arg Phe Ser Trp Phe Asp Tyr Arg Ser
                260                 265                 270 aaa ggt ttt gat gat aac cgt ggc ctg cgc att gat ctg ctg ctg gcg        864
Lys Gly Phe Asp Asp Asn Arg Gly Leu Arg Ile Asp Leu Leu Leu Ala
             275                 280                 285 agc cag ccg ctg gcg gaa tgc tgc gtt gaa acc ggt att gat tat gaa        912
Ser Gln Pro Leu Ala Glu Cys Cys Val Glu Thr Gly Ile Asp Tyr Glu
             290                 295                 300 att cgc agc atg gaa aaa ccg agc gat cac gcc ccg gtg tgg gcg acc        960
Ile Arg Ser Met Glu Lys Pro Ser Asp His Ala Pro Val Trp Ala Thr
305                 310                 315 ttt cgc cgc tct ggc tct ggt tcc ggc agc ggt tcc gga cac aat aaa       1008
Phe Arg Arg Ser Gly Ser Gly Ser Gly Ser Gly Ser Gly His Asn Lys
320                 325                 330                 335 aaa ctg cta gtt att aga aca aaa ggt acc att gct ggt caa tat aga       1056
Lys Leu Leu Val Ile Arg Thr Lys Gly Thr Ile Ala Gly Gln Tyr Arg
                340                 345                 350 gtt tat agc gaa gaa ggt gct aac aaa agt ggt tta gcc tgg cct tca       1104
Val Tyr Ser Glu Glu Gly Ala Asn Lys Ser Gly Leu Ala Trp Pro Ser
             355                 360                 365 gcc ttt aag gta cag ttg caa cta cct gat aat gaa gta gct caa ata       1152
Ala Phe Lys Val Gln Leu Gln Leu Pro Asp Asn Glu Val Ala Gln Ile
             370                 375                 380
```

| | | | | | | | | | | | | | | | | |
|---|---|---|---|---|---|---|---|---|---|---|---|---|---|---|---|---|
| tct | gat | tac | tat | cca | aga | aat | tcg | att | gat | aca | aaa | gag | tat | agg | agt | 1200 |
| Ser | Asp | Tyr | Tyr | Pro | Arg | Asn | Ser | Ile | Asp | Thr | Lys | Glu | Tyr | Arg | Ser | |
| | 385 | | | | 390 | | | | | 395 | | | | | | |

| | | | | | | | | | | | | | | | | |
|---|---|---|---|---|---|---|---|---|---|---|---|---|---|---|---|---|
| act | tta | act | tat | gga | ttc | aac | ggt | aat | gtt | act | ggt | gat | gat | aca | gga | 1248 |
| Thr | Leu | Thr | Tyr | Gly | Phe | Asn | Gly | Asn | Val | Thr | Gly | Asp | Asp | Thr | Gly | |
| 400 | | | | | 405 | | | | | 410 | | | | | 415 | |

| | | | | | | | | | | | | | | | | |
|---|---|---|---|---|---|---|---|---|---|---|---|---|---|---|---|---|
| aaa | att | ggc | ggc | tgt | att | ggt | gca | caa | gtt | tcg | att | ggt | cat | aca | ctg | 1296 |
| Lys | Ile | Gly | Gly | Cys | Ile | Gly | Ala | Gln | Val | Ser | Ile | Gly | His | Thr | Leu | |
| | | | | 420 | | | | | 425 | | | | | 430 | | |

| | | | | | | | | | | | | | | | | |
|---|---|---|---|---|---|---|---|---|---|---|---|---|---|---|---|---|
| aaa | tat | gtt | caa | cct | gat | ttc | aaa | aca | att | tta | gag | agc | cca | act | gat | 1344 |
| Lys | Tyr | Val | Gln | Pro | Asp | Phe | Lys | Thr | Ile | Leu | Glu | Ser | Pro | Thr | Asp | |
| | | | 435 | | | | | 440 | | | | | 445 | | | |

| | | | | | | | | | | | | | | | | |
|---|---|---|---|---|---|---|---|---|---|---|---|---|---|---|---|---|
| aaa | aaa | gta | ggc | tgg | aaa | gtg | ata | ttt | aac | aat | atg | gtg | aat | caa | aat | 1392 |
| Lys | Lys | Val | Gly | Trp | Lys | Val | Ile | Phe | Asn | Asn | Met | Val | Asn | Gln | Asn | |
| | | 450 | | | | | 455 | | | | | 460 | | | | |

| | | | | | | | | | | | | | | | | |
|---|---|---|---|---|---|---|---|---|---|---|---|---|---|---|---|---|
| tgg | gga | cca | tac | gat | cga | gat | tct | tgg | aac | ccg | gta | tat | ggc | aat | caa | 1440 |
| Trp | Gly | Pro | Tyr | Asp | Arg | Asp | Ser | Trp | Asn | Pro | Val | Tyr | Gly | Asn | Gln | |
| | 465 | | | | | 470 | | | | | 475 | | | | | |

| | | | | | | | | | | | | | | | | |
|---|---|---|---|---|---|---|---|---|---|---|---|---|---|---|---|---|
| ctt | ttc | atg | aaa | act | aga | aat | ggt | tct | atg | aaa | gca | gca | gat | aac | ttc | 1488 |
| Leu | Phe | Met | Lys | Thr | Arg | Asn | Gly | Ser | Met | Lys | Ala | Ala | Asp | Asn | Phe | |
| 480 | | | | | 485 | | | | | 490 | | | | | 495 | |

| | | | | | | | | | | | | | | | | |
|---|---|---|---|---|---|---|---|---|---|---|---|---|---|---|---|---|
| ctt | gat | cct | aac | aaa | gca | agt | tct | cta | tta | tct | tca | ggg | ttt | tca | cca | 1536 |
| Leu | Asp | Pro | Asn | Lys | Ala | Ser | Ser | Leu | Leu | Ser | Ser | Gly | Phe | Ser | Pro | |
| | | | | 500 | | | | | 505 | | | | | 510 | | |

| | | | | | | | | | | | | | | | | |
|---|---|---|---|---|---|---|---|---|---|---|---|---|---|---|---|---|
| gac | ttc | gct | aca | gtt | att | act | atg | gat | aga | aaa | gca | tcc | aaa | caa | caa | 1584 |
| Asp | Phe | Ala | Thr | Val | Ile | Thr | Met | Asp | Arg | Lys | Ala | Ser | Lys | Gln | Gln | |
| | | | 515 | | | | | 520 | | | | | 525 | | | |

| | | | | | | | | | | | | | | | | |
|---|---|---|---|---|---|---|---|---|---|---|---|---|---|---|---|---|
| aca | aat | ata | gat | gta | ata | tac | gaa | cga | gtt | cgt | gat | gat | tac | caa | ttg | 1632 |
| Thr | Asn | Ile | Asp | Val | Ile | Tyr | Glu | Arg | Val | Arg | Asp | Asp | Tyr | Gln | Leu | |
| | | 530 | | | | | 535 | | | | | 540 | | | | |

| | | | | | | | | | | | | | | | | |
|---|---|---|---|---|---|---|---|---|---|---|---|---|---|---|---|---|
| cat | tgg | act | tca | aca | aat | tgg | aaa | ggt | acc | aat | act | aaa | gat | aaa | tgg | 1680 |
| His | Trp | Thr | Ser | Thr | Asn | Trp | Lys | Gly | Thr | Asn | Thr | Lys | Asp | Lys | Trp | |
| | 545 | | | | | 550 | | | | | 555 | | | | | |

| | | | | | | | | | | | | | | | | |
|---|---|---|---|---|---|---|---|---|---|---|---|---|---|---|---|---|
| aca | gat | cgt | tct | tca | gaa | aga | tat | aaa | atc | gat | tgg | gaa | aaa | gaa | gaa | 1728 |
| Thr | Asp | Arg | Ser | Ser | Glu | Arg | Tyr | Lys | Ile | Asp | Trp | Glu | Lys | Glu | Glu | |
| 560 | | | | | 565 | | | | | 570 | | | | | 575 | |

| | | | | | | | | | | | | | | | | |
|---|---|---|---|---|---|---|---|---|---|---|---|---|---|---|---|---|
| atg | aca | aat | ggt | ggt | tcg | ggc | tca | tct | ggt | ggc | tcg | agt | cac | cat | cat | 1776 |
| Met | Thr | Asn | Gly | Gly | Ser | Gly | Ser | Ser | Gly | Gly | Ser | Ser | His | His | His | |
| | | | 580 | | | | | 585 | | | | | 590 | | | |

| | | | |
|---|---|---|---|
| cat | cac | cac | 1785 |
| His | His | His | |

<210> SEQ ID NO 26
<211> LENGTH: 594
<212> TYPE: PRT
<213> ORGANISM: Artificial sequence
<220> FEATURE:
<223> OTHER INFORMATION: Synthetic Construct

<400> SEQUENCE: 26

| | | | | | | | | | | | | | | |
|---|---|---|---|---|---|---|---|---|---|---|---|---|---|---|
| Ala | Asp | Ser | Asp | Ile | Asn | Ile | Lys | Thr | Gly | Thr | Thr | Asp | Ile | Gly | Ser |
| 1 | | | | 5 | | | | | 10 | | | | | 15 |

| | | | | | | | | | | | | | | |
|---|---|---|---|---|---|---|---|---|---|---|---|---|---|---|
| Asn | Thr | Thr | Val | Lys | Thr | Gly | Asp | Leu | Val | Thr | Tyr | Asp | Lys | Glu | Asn |
| | | 20 | | | | | 25 | | | | | 30 | | |

| | | | | | | | | | | | | | | |
|---|---|---|---|---|---|---|---|---|---|---|---|---|---|---|
| Gly | Met | His | Lys | Lys | Val | Phe | Tyr | Ser | Phe | Ile | Asp | Ser | Gly | Ser | Gly |
| | | 35 | | | | | 40 | | | | | 45 | | |

| | | | | | | | | | | | | | | |
|---|---|---|---|---|---|---|---|---|---|---|---|---|---|---|
| Ser | Gly | Ser | Gly | Ser | Gly | Met | Lys | Phe | Val | Ser | Phe | Asn | Ile | Asn | Gly |
| | 50 | | | | | 55 | | | | | 60 | | | |

| | | | | | | | | | | | | | | |
|---|---|---|---|---|---|---|---|---|---|---|---|---|---|---|
| Leu | Arg | Ala | Arg | Pro | His | Gln | Leu | Glu | Ala | Ile | Val | Glu | Lys | His | Gln |
| 65 | | | | | 70 | | | | | 75 | | | | | 80 |

```
Pro Asp Val Ile Gly Leu Gln Glu Thr Lys Val His Asp Asp Met Phe
                85                  90                  95
Pro Leu Glu Glu Val Ala Lys Leu Gly Tyr Asn Val Phe Tyr His Gly
            100                 105                 110
Gln Lys Gly His Tyr Gly Val Ala Leu Leu Thr Lys Glu Thr Pro Ile
        115                 120                 125
Ala Val Arg Arg Gly Phe Pro Gly Asp Asp Glu Ala Gln Arg Arg
130                 135                 140
Ile Ile Met Ala Glu Ile Pro Ser Leu Leu Gly Asn Val Thr Val Ile
145                 150                 155                 160
Asn Gly Tyr Phe Pro Gln Gly Glu Ser Arg Asp His Pro Ile Lys Phe
                165                 170                 175
Pro Ala Lys Ala Gln Phe Tyr Gln Asn Leu Gln Asn Tyr Leu Glu Thr
            180                 185                 190
Glu Leu Lys Arg Asp Asn Pro Val Leu Ile Met Gly Asp Met Asn Ile
        195                 200                 205
Ser Pro Thr Asp Leu Asp Ile Gly Ile Gly Glu Asn Arg Lys Arg
210                 215                 220
Trp Leu Arg Thr Gly Lys Cys Ser Phe Leu Pro Glu Glu Arg Glu Trp
225                 230                 235                 240
Met Asp Arg Leu Met Ser Trp Gly Leu Val Asp Thr Phe Arg His Ala
                245                 250                 255
Asn Pro Gln Thr Ala Asp Arg Phe Ser Trp Phe Asp Tyr Arg Ser Lys
            260                 265                 270
Gly Phe Asp Asp Asn Arg Gly Leu Arg Ile Asp Leu Leu Leu Ala Ser
        275                 280                 285
Gln Pro Leu Ala Glu Cys Cys Val Glu Thr Gly Ile Asp Tyr Glu Ile
290                 295                 300
Arg Ser Met Glu Lys Pro Ser Asp His Ala Pro Val Trp Ala Thr Phe
305                 310                 315                 320
Arg Arg Ser Gly Ser Gly Ser Gly Ser Gly His Asn Lys Lys
                325                 330                 335
Leu Leu Val Ile Arg Thr Lys Gly Thr Ile Ala Gly Gln Tyr Arg Val
            340                 345                 350
Tyr Ser Glu Glu Gly Ala Asn Lys Ser Gly Leu Ala Trp Pro Ser Ala
        355                 360                 365
Phe Lys Val Gln Leu Gln Leu Pro Asp Asn Glu Val Ala Gln Ile Ser
        370                 375                 380
Asp Tyr Tyr Pro Arg Asn Ser Ile Asp Thr Lys Glu Tyr Arg Ser Thr
385                 390                 395                 400
Leu Thr Tyr Gly Phe Asn Gly Asn Val Thr Gly Asp Asp Thr Gly Lys
                405                 410                 415
Ile Gly Gly Cys Ile Gly Ala Gln Val Ser Ile Gly His Thr Leu Lys
            420                 425                 430
Tyr Val Gln Pro Asp Phe Lys Thr Ile Leu Glu Ser Pro Thr Asp Lys
        435                 440                 445
Lys Val Gly Trp Lys Val Ile Phe Asn Asn Met Val Asn Gln Asn Trp
        450                 455                 460
Gly Pro Tyr Asp Arg Asp Ser Trp Asn Pro Val Tyr Gly Asn Gln Leu
465                 470                 475                 480
Phe Met Lys Thr Arg Asn Gly Ser Met Lys Ala Ala Asp Asn Phe Leu
                485                 490                 495
```

```
                 Asp Pro Asn Lys Ala Ser Ser Leu Leu Ser Ser Gly Phe Ser Pro Asp
                                 500                 505                 510

Phe Ala Thr Val Ile Thr Met Asp Arg Lys Ala Ser Lys Gln Gln Thr
                     515                 520                 525

Asn Ile Asp Val Ile Tyr Glu Arg Val Arg Asp Asp Tyr Gln Leu His
                 530                 535                 540

Trp Thr Ser Thr Asn Trp Lys Gly Thr Asn Thr Lys Asp Lys Trp Thr
                 545                 550                 555                 560

Asp Arg Ser Ser Glu Arg Tyr Lys Ile Asp Trp Glu Lys Glu Met
                                 565                 570                 575

Thr Asn Gly Gly Ser Gly Ser Ser Gly Gly Ser Ser His His His His
                                 580                 585                 590

His His

<210> SEQ ID NO 27
<211> LENGTH: 2364
<212> TYPE: DNA
<213> ORGANISM: Artificial sequence
<220> FEATURE:
<223> OTHER INFORMATION: DNA Sequence encoding
      HL-RQC-EcoExoI-Cter-
8-H6
<220> FEATURE:
<221> NAME/KEY: CDS
<222> LOCATION: (4)..(2364)

<400> SEQUENCE: 27
```

| | | | | | | | | | | | | | | | | |
|---|---|---|---|---|---|---|---|---|---|---|---|---|---|---|---|---|
| atg | gca | gat | tct | gat | att | aat | att | aaa | acc | ggt | act | aca | gat | att | gga | 48 |
| | Ala | Asp | Ser | Asp | Ile | Asn | Ile | Lys | Thr | Gly | Thr | Thr | Asp | Ile | Gly | |
| | 1 | | | 5 | | | | | 10 | | | | | 15 | | |
| agc | aat | act | aca | gta | aaa | aca | ggt | gat | tta | gtc | act | tat | gat | aaa | gaa | 96 |
| Ser | Asn | Thr | Thr | Val | Lys | Thr | Gly | Asp | Leu | Val | Thr | Tyr | Asp | Lys | Glu | |
| | | | | 20 | | | | | 25 | | | | | 30 | | |
| aat | ggc | atg | cac | aaa | aaa | gta | ttt | tat | agt | ttt | atc | gat | gat | aaa | aat | 144 |
| Asn | Gly | Met | His | Lys | Lys | Val | Phe | Tyr | Ser | Phe | Ile | Asp | Asp | Lys | Asn | |
| | | | 35 | | | | | 40 | | | | | 45 | | | |
| cac | aat | aaa | aaa | ctg | cta | gtt | att | aga | aca | aaa | ggt | acc | att | gct | ggt | 192 |
| His | Asn | Lys | Lys | Leu | Leu | Val | Ile | Arg | Thr | Lys | Gly | Thr | Ile | Ala | Gly | |
| | 50 | | | | | 55 | | | | | 60 | | | | | |
| caa | tat | aga | gtt | tat | agc | gaa | gaa | ggt | gct | aac | aaa | agt | ggt | tta | gcc | 240 |
| Gln | Tyr | Arg | Val | Tyr | Ser | Glu | Glu | Gly | Ala | Asn | Lys | Ser | Gly | Leu | Ala | |
| | 65 | | | | | 70 | | | | | 75 | | | | | |
| tgg | cct | tca | gcc | ttt | aag | gta | cag | ttg | caa | cta | cct | gat | aat | gaa | gta | 288 |
| Trp | Pro | Ser | Ala | Phe | Lys | Val | Gln | Leu | Gln | Leu | Pro | Asp | Asn | Glu | Val | |
| 80 | | | | | 85 | | | | | 90 | | | | | 95 | |
| gct | caa | ata | tct | gat | tac | tat | cca | aga | aat | tcg | att | gat | aca | aaa | gag | 336 |
| Ala | Gln | Ile | Ser | Asp | Tyr | Tyr | Pro | Arg | Asn | Ser | Ile | Asp | Thr | Lys | Glu | |
| | | | | 100 | | | | | 105 | | | | | 110 | | |
| tat | agg | agt | act | tta | act | tat | gga | ttc | aac | ggt | aat | gtt | act | ggt | gat | 384 |
| Tyr | Arg | Ser | Thr | Leu | Thr | Tyr | Gly | Phe | Asn | Gly | Asn | Val | Thr | Gly | Asp | |
| | | | 115 | | | | | 120 | | | | | 125 | | | |
| gat | aca | gga | aaa | att | ggc | ggc | tgt | att | ggt | gca | caa | gtt | tcg | att | ggt | 432 |
| Asp | Thr | Gly | Lys | Ile | Gly | Gly | Cys | Ile | Gly | Ala | Gln | Val | Ser | Ile | Gly | |
| | | 130 | | | | | 135 | | | | | 140 | | | | |
| cat | aca | ctg | aaa | tat | gtt | caa | cct | gat | ttc | aaa | aca | att | tta | gag | agc | 480 |
| His | Thr | Leu | Lys | Tyr | Val | Gln | Pro | Asp | Phe | Lys | Thr | Ile | Leu | Glu | Ser | |
| | 145 | | | | | 150 | | | | | 155 | | | | | |
| cca | act | gat | aaa | aaa | gta | ggc | tgg | aaa | gtg | ata | ttt | aac | aat | atg | gtg | 528 |
| Pro | Thr | Asp | Lys | Lys | Val | Gly | Trp | Lys | Val | Ile | Phe | Asn | Asn | Met | Val | |
| 160 | | | | | 165 | | | | | 170 | | | | | 175 | |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| aat | caa | aat | tgg | gga | cca | tac | gat | cga | gat | tct | tgg | aac | ccg | gta | tat | 576  |
| Asn | Gln | Asn | Trp | Gly | Pro | Tyr | Asp | Arg | Asp | Ser | Trp | Asn | Pro | Val | Tyr |      |
|     |     |     | 180 |     |     |     |     | 185 |     |     |     |     | 190 |     |     |      |
| ggc | aat | caa | ctt | ttc | atg | aaa | act | aga | aat | ggt | tct | atg | aaa | gca | gca | 624  |
| Gly | Asn | Gln | Leu | Phe | Met | Lys | Thr | Arg | Asn | Gly | Ser | Met | Lys | Ala | Ala |      |
|     |     |     | 195 |     |     |     |     | 200 |     |     |     |     | 205 |     |     |      |
| gat | aac | ttc | ctt | gat | cct | aac | aaa | gca | agt | tct | cta | tta | tct | tca | ggg | 672  |
| Asp | Asn | Phe | Leu | Asp | Pro | Asn | Lys | Ala | Ser | Ser | Leu | Leu | Ser | Ser | Gly |      |
|     |     |     | 210 |     |     |     |     | 215 |     |     |     |     | 220 |     |     |      |
| ttt | tca | cca | gac | ttc | gct | aca | gtt | att | act | atg | gat | aga | aaa | gca | tcc | 720  |
| Phe | Ser | Pro | Asp | Phe | Ala | Thr | Val | Ile | Thr | Met | Asp | Arg | Lys | Ala | Ser |      |
|     |     | 225 |     |     |     |     | 230 |     |     |     |     | 235 |     |     |     |      |
| aaa | caa | caa | aca | aat | ata | gat | gta | ata | tac | gaa | cga | gtt | cgt | gat | gat | 768  |
| Lys | Gln | Gln | Thr | Asn | Ile | Asp | Val | Ile | Tyr | Glu | Arg | Val | Arg | Asp | Asp |      |
| 240 |     |     |     |     | 245 |     |     |     |     | 250 |     |     |     |     | 255 |      |
| tac | caa | ttg | cat | tgg | act | tca | aca | aat | tgg | aaa | ggt | acc | aat | act | aaa | 816  |
| Tyr | Gln | Leu | His | Trp | Thr | Ser | Thr | Asn | Trp | Lys | Gly | Thr | Asn | Thr | Lys |      |
|     |     |     |     | 260 |     |     |     |     | 265 |     |     |     |     | 270 |     |      |
| gat | aaa | tgg | aca | gat | cgt | tct | tca | gaa | aga | tat | aaa | atc | gat | tgg | gaa | 864  |
| Asp | Lys | Trp | Thr | Asp | Arg | Ser | Ser | Glu | Arg | Tyr | Lys | Ile | Asp | Trp | Glu |      |
|     |     |     | 275 |     |     |     |     | 280 |     |     |     |     | 285 |     |     |      |
| aaa | gaa | gaa | atg | aca | aat | tcc | ggt | agc | ggc | tct | ggt | tct | ggc | tct | ggt | 912  |
| Lys | Glu | Glu | Met | Thr | Asn | Ser | Gly | Ser | Gly | Ser | Gly | Ser | Gly | Ser | Gly |      |
|     |     |     | 290 |     |     |     |     | 295 |     |     |     |     | 300 |     |     |      |
| tcc | ggc | agc | ggt | tcc | gga | cag | agc | acc | ttc | ctg | ttt | cat | gat | tat | gaa | 960  |
| Ser | Gly | Ser | Gly | Ser | Gly | Gln | Ser | Thr | Phe | Leu | Phe | His | Asp | Tyr | Glu |      |
|     |     | 305 |     |     |     |     | 310 |     |     |     |     | 315 |     |     |     |      |
| acc | ttc | ggt | acc | cat | ccg | gcc | ctg | gat | cgt | ccg | gcg | cag | ttt | gcg | gcc | 1008 |
| Thr | Phe | Gly | Thr | His | Pro | Ala | Leu | Asp | Arg | Pro | Ala | Gln | Phe | Ala | Ala |      |
| 320 |     |     |     |     | 325 |     |     |     |     | 330 |     |     |     |     | 335 |      |
| att | cgc | acc | gat | agc | gaa | ttc | aat | gtg | att | ggc | gaa | ccg | gaa | gtg | ttt | 1056 |
| Ile | Arg | Thr | Asp | Ser | Glu | Phe | Asn | Val | Ile | Gly | Glu | Pro | Glu | Val | Phe |      |
|     |     |     |     | 340 |     |     |     |     | 345 |     |     |     |     | 350 |     |      |
| tat | tgc | aaa | ccg | gcc | gat | gat | tat | ctg | ccg | cag | ccg | ggt | gcg | gtg | ctg | 1104 |
| Tyr | Cys | Lys | Pro | Ala | Asp | Asp | Tyr | Leu | Pro | Gln | Pro | Gly | Ala | Val | Leu |      |
|     |     |     | 355 |     |     |     |     | 360 |     |     |     |     | 365 |     |     |      |
| att | acc | ggt | att | acc | ccg | cag | gaa | gcg | cgc | gcg | aaa | ggt | gaa | aac | gaa | 1152 |
| Ile | Thr | Gly | Ile | Thr | Pro | Gln | Glu | Ala | Arg | Ala | Lys | Gly | Glu | Asn | Glu |      |
|     |     | 370 |     |     |     |     | 375 |     |     |     |     | 380 |     |     |     |      |
| gcg | gcg | ttt | gcc | gcg | cgc | att | cat | agc | ctg | ttt | acc | gtg | cca | aaa | acc | 1200 |
| Ala | Ala | Phe | Ala | Ala | Arg | Ile | His | Ser | Leu | Phe | Thr | Val | Pro | Lys | Thr |      |
| 385 |     |     |     |     | 390 |     |     |     |     | 395 |     |     |     |     |     |      |
| tgc | att | ctg | ggc | tat | aac | aat | gtg | cgc | ttc | gat | gat | gaa | gtt | acc | cgt | 1248 |
| Cys | Ile | Leu | Gly | Tyr | Asn | Asn | Val | Arg | Phe | Asp | Asp | Glu | Val | Thr | Arg |      |
| 400 |     |     |     |     | 405 |     |     |     |     | 410 |     |     |     |     | 415 |      |
| aat | atc | ttt | tat | cgt | aac | ttt | tat | gat | ccg | tat | gcg | tgg | agc | tgg | cag | 1296 |
| Asn | Ile | Phe | Tyr | Arg | Asn | Phe | Tyr | Asp | Pro | Tyr | Ala | Trp | Ser | Trp | Gln |      |
|     |     |     |     | 420 |     |     |     |     | 425 |     |     |     |     | 430 |     |      |
| cat | gat | aac | agc | cgt | tgg | gat | ctg | ctg | gat | gtg | atg | cgc | gcg | tgc | tat | 1344 |
| His | Asp | Asn | Ser | Arg | Trp | Asp | Leu | Leu | Asp | Val | Met | Arg | Ala | Cys | Tyr |      |
|     |     |     | 435 |     |     |     |     | 440 |     |     |     |     | 445 |     |     |      |
| gcg | ctg | cgc | ccg | gaa | ggc | att | aat | tgg | ccg | gaa | aac | gat | gat | ggc | ctg | 1392 |
| Ala | Leu | Arg | Pro | Glu | Gly | Ile | Asn | Trp | Pro | Glu | Asn | Asp | Asp | Gly | Leu |      |
|     |     | 450 |     |     |     |     | 455 |     |     |     |     | 460 |     |     |     |      |
| ccg | agc | ttt | cgt | ctg | gaa | cat | ctg | acc | aaa | gcc | aac | ggc | att | gaa | cat | 1440 |
| Pro | Ser | Phe | Arg | Leu | Glu | His | Leu | Thr | Lys | Ala | Asn | Gly | Ile | Glu | His |      |
|     | 465 |     |     |     |     | 470 |     |     |     |     | 475 |     |     |     |     |      |
| agc | aat | gcc | cat | gat | gcg | atg | gcc | gat | gtt | tat | gcg | acc | att | gcg | atg | 1488 |
| Ser | Asn | Ala | His | Asp | Ala | Met | Ala | Asp | Val | Tyr | Ala | Thr | Ile | Ala | Met |      |
| 480 |     |     |     |     | 485 |     |     |     |     | 490 |     |     |     |     | 495 |      |

```
gcg aaa ctg gtt aaa acc cgt cag ccg cgc ctg ttt gat tat ctg ttt    1536
Ala Lys Leu Val Lys Thr Arg Gln Pro Arg Leu Phe Asp Tyr Leu Phe
            500                 505                 510 acc cac cgt aac aaa cac aaa ctg atg gcg ctg att gat gtt ccg cag    1584
Thr His Arg Asn Lys His Lys Leu Met Ala Leu Ile Asp Val Pro Gln
            515                 520                 525 atg aaa ccg ctg gtg cat gtg agc ggc atg ttt ggc gcc tgg cgc ggc    1632
Met Lys Pro Leu Val His Val Ser Gly Met Phe Gly Ala Trp Arg Gly
            530                 535                 540 aac acc agc tgg gtg gcc ccg ctg gcc tgg cac ccg gaa aat cgt aac    1680
Asn Thr Ser Trp Val Ala Pro Leu Ala Trp His Pro Glu Asn Arg Asn
        545                 550                 555 gcc gtg att atg gtt gat ctg gcc ggt gat att agc ccg ctg ctg gaa    1728
Ala Val Ile Met Val Asp Leu Ala Gly Asp Ile Ser Pro Leu Leu Glu
560                 565                 570                 575 ctg gat agc gat acc ctg cgt gaa cgc ctg tat acc gcc aaa acc gat    1776
Leu Asp Ser Asp Thr Leu Arg Glu Arg Leu Tyr Thr Ala Lys Thr Asp
            580                 585                 590 ctg ggc gat aat gcc gcc gtg ccg gtg aaa ctg gtt cac att aac aaa    1824
Leu Gly Asp Asn Ala Ala Val Pro Val Lys Leu Val His Ile Asn Lys
            595                 600                 605 tgc ccg gtg ctg gcc cag gcg aac acc ctg cgc ccg gaa gat gcg gat    1872
Cys Pro Val Leu Ala Gln Ala Asn Thr Leu Arg Pro Glu Asp Ala Asp
            610                 615                 620 cgt ctg ggt att aat cgc cag cat tgt ctg gat aat ctg aaa atc ctg    1920
Arg Leu Gly Ile Asn Arg Gln His Cys Leu Asp Asn Leu Lys Ile Leu
            625                 630                 635 cgt gaa aac ccg cag gtg cgt gaa aaa gtg gtg gcg atc ttc gcg gaa    1968
Arg Glu Asn Pro Gln Val Arg Glu Lys Val Val Ala Ile Phe Ala Glu
640                 645                 650                 655 gcg gaa ccg ttc acc ccg agc gat aac gtg gat gcg cag ctg tat aac    2016
Ala Glu Pro Phe Thr Pro Ser Asp Asn Val Asp Ala Gln Leu Tyr Asn
            660                 665                 670 ggc ttc ttt agc gat gcc gat cgc gcg gcg atg aaa atc gtt ctg gaa    2064
Gly Phe Phe Ser Asp Ala Asp Arg Ala Ala Met Lys Ile Val Leu Glu
            675                 680                 685 acc gaa ccg cgc aat ctg ccg gcg ctg gat att acc ttt gtt gat aaa    2112
Thr Glu Pro Arg Asn Leu Pro Ala Leu Asp Ile Thr Phe Val Asp Lys
            690                 695                 700 cgt att gaa aaa ctg ctg ttt aat tat cgt gcg cgc aat ttt ccg ggt    2160
Arg Ile Glu Lys Leu Leu Phe Asn Tyr Arg Ala Arg Asn Phe Pro Gly
            705                 710                 715 acc ctg gat tat gcc gaa cag cag cgt tgg ctg gaa cat cgt cgt cag    2208
Thr Leu Asp Tyr Ala Glu Gln Gln Arg Trp Leu Glu His Arg Arg Gln
720                 725                 730                 735 gtt ttc acc ccg gaa ttt ctg cag ggt tat gcg gat gaa ctg cag atg    2256
Val Phe Thr Pro Glu Phe Leu Gln Gly Tyr Ala Asp Glu Leu Gln Met
            740                 745                 750 ctg gtt cag cag tat gcc gat gat aaa gaa aaa gtg gcg ctg ctg aaa    2304
Leu Val Gln Gln Tyr Ala Asp Asp Lys Glu Lys Val Ala Leu Leu Lys
            755                 760                 765 gcg ctg tgg cag tat gcg gaa gaa atc gtt tct ggc tct ggt cac cat    2352
Ala Leu Trp Gln Tyr Ala Glu Glu Ile Val Ser Gly Ser Gly His His
            770                 775                 780 cat cat cac cac                                                    2364
His His His His
    785
```

```
<210> SEQ ID NO 28
<211> LENGTH: 787
<212> TYPE: PRT
<213> ORGANISM: Artificial sequence
<220> FEATURE:
<223> OTHER INFORMATION: Synthetic Construct

<400> SEQUENCE: 28

Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
                20                  25                  30

Gly Met His Lys Lys Val Phe Tyr Ser Phe Ile Asp Asp Lys Asn His
            35                  40                  45

Asn Lys Lys Leu Leu Val Ile Arg Thr Lys Gly Thr Ile Ala Gly Gln
    50                  55                  60

Tyr Arg Val Tyr Ser Glu Glu Gly Ala Asn Lys Ser Gly Leu Ala Trp
65                  70                  75                  80

Pro Ser Ala Phe Lys Val Gln Leu Gln Leu Pro Asp Asn Glu Val Ala
                85                  90                  95

Gln Ile Ser Asp Tyr Tyr Pro Arg Asn Ser Ile Asp Thr Lys Glu Tyr
            100                 105                 110

Arg Ser Thr Leu Thr Tyr Gly Phe Asn Gly Asn Val Thr Gly Asp Asp
        115                 120                 125

Thr Gly Lys Ile Gly Gly Cys Ile Gly Ala Gln Val Ser Ile Gly His
    130                 135                 140

Thr Leu Lys Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
            180                 185                 190

Asn Gln Leu Phe Met Lys Thr Arg Asn Gly Ser Met Lys Ala Ala Asp
        195                 200                 205

Asn Phe Leu Asp Pro Asn Lys Ala Ser Ser Leu Leu Ser Ser Gly Phe
    210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Thr Asn Trp Lys Gly Thr Asn Thr Lys Asp
            260                 265                 270

Lys Trp Thr Asp Arg Ser Ser Glu Arg Tyr Lys Ile Asp Trp Glu Lys
        275                 280                 285

Glu Glu Met Thr Asn Ser Gly Ser Gly Ser Gly Ser Gly Ser Gly Ser
    290                 295                 300

Gly Ser Gly Ser Gly Gln Ser Thr Phe Leu Phe His Asp Tyr Glu Thr
305                 310                 315                 320

Phe Gly Thr His Pro Ala Leu Asp Arg Pro Ala Gln Phe Ala Ala Ile
                325                 330                 335

Arg Thr Asp Ser Glu Phe Asn Val Ile Gly Glu Pro Glu Val Phe Tyr
            340                 345                 350

Cys Lys Pro Ala Asp Asp Tyr Leu Pro Gln Pro Gly Ala Val Leu Ile
        355                 360                 365
```

-continued

Thr Gly Ile Thr Pro Gln Glu Ala Arg Ala Lys Gly Glu Asn Glu Ala
370                 375                 380

Ala Phe Ala Ala Arg Ile His Ser Leu Phe Thr Val Pro Lys Thr Cys
385                 390                 395                 400

Ile Leu Gly Tyr Asn Asn Val Arg Phe Asp Asp Glu Val Thr Arg Asn
                405                 410                 415

Ile Phe Tyr Arg Asn Phe Tyr Asp Pro Tyr Ala Trp Ser Trp Gln His
                420                 425                 430

Asp Asn Ser Arg Trp Asp Leu Leu Asp Val Met Arg Ala Cys Tyr Ala
            435                 440                 445

Leu Arg Pro Glu Gly Ile Asn Trp Pro Glu Asn Asp Gly Leu Pro
450                 455                 460

Ser Phe Arg Leu Glu His Leu Thr Lys Ala Asn Gly Ile Glu His Ser
465                 470                 475                 480

Asn Ala His Asp Ala Met Ala Asp Val Tyr Ala Thr Ile Ala Met Ala
                485                 490                 495

Lys Leu Val Lys Thr Arg Gln Pro Arg Leu Phe Asp Tyr Leu Phe Thr
            500                 505                 510

His Arg Asn Lys His Lys Leu Met Ala Leu Ile Asp Val Pro Gln Met
            515                 520                 525

Lys Pro Leu Val His Val Ser Gly Met Phe Gly Ala Trp Arg Gly Asn
530                 535                 540

Thr Ser Trp Val Ala Pro Leu Ala Trp His Pro Glu Asn Arg Asn Ala
545                 550                 555                 560

Val Ile Met Val Asp Leu Ala Gly Asp Ile Ser Pro Leu Leu Glu Leu
                565                 570                 575

Asp Ser Asp Thr Leu Arg Glu Arg Leu Tyr Thr Ala Lys Thr Asp Leu
            580                 585                 590

Gly Asp Asn Ala Ala Val Pro Val Lys Leu Val His Ile Asn Lys Cys
            595                 600                 605

Pro Val Leu Ala Gln Ala Asn Thr Leu Arg Pro Glu Asp Ala Asp Arg
610                 615                 620

Leu Gly Ile Asn Arg Gln His Cys Leu Asp Asn Leu Lys Ile Leu Arg
625                 630                 635                 640

Glu Asn Pro Gln Val Arg Glu Lys Val Val Ala Ile Phe Ala Glu Ala
                645                 650                 655

Glu Pro Phe Thr Pro Ser Asp Asn Val Asp Ala Gln Leu Tyr Asn Gly
            660                 665                 670

Phe Phe Ser Asp Ala Asp Arg Ala Ala Met Lys Ile Val Leu Glu Thr
            675                 680                 685

Glu Pro Arg Asn Leu Pro Ala Leu Asp Ile Thr Phe Val Asp Lys Arg
690                 695                 700

Ile Glu Lys Leu Leu Phe Asn Tyr Arg Ala Arg Asn Phe Pro Gly Thr
705                 710                 715                 720

Leu Asp Tyr Ala Glu Gln Gln Arg Trp Leu Glu His Arg Arg Gln Val
                725                 730                 735

Phe Thr Pro Glu Phe Leu Gln Gly Tyr Ala Asp Glu Leu Gln Met Leu
            740                 745                 750

Val Gln Gln Tyr Ala Asp Asp Lys Glu Lys Val Ala Leu Leu Lys Ala
            755                 760                 765

| | | | | | | | | | | | | | | | | |
|---|---|---|---|---|---|---|---|---|---|---|---|---|---|---|---|---|
| Leu | Trp | Gln | Tyr | Ala | Glu | Glu | Ile | Val | Ser | Gly | Ser | Gly | His | His | His | |
| | 770 | | | | 775 | | | | | 780 | | | | | | |
| His | His | His | | | | | | | | | | | | | | |
| 785 | | | | | | | | | | | | | | | | |

<210> SEQ ID NO 29
<211> LENGTH: 2370
<212> TYPE: DNA
<213> ORGANISM: Artificial sequence
<220> FEATURE:
<223> OTHER INFORMATION: DNA Sequence encoding HL-RQC-EcoExoI-Cter-DG8-H6
<220> FEATURE:
<221> NAME/KEY: CDS
<222> LOCATION: (4)..(2370)

<400> SEQUENCE: 29

| atg | gca | gat | tct | gat | att | aat | att | aaa | acc | ggt | act | aca | gat | att | gga | 48 |
|---|---|---|---|---|---|---|---|---|---|---|---|---|---|---|---|---|
| | Ala | Asp | Ser | Asp | Ile | Asn | Ile | Lys | Thr | Gly | Thr | Thr | Asp | Ile | Gly | |
| | 1 | | | | 5 | | | | | 10 | | | | | 15 | |

| agc | aat | act | aca | gta | aaa | aca | ggt | gat | tta | gtc | act | tat | gat | aaa | gaa | 96 |
|---|---|---|---|---|---|---|---|---|---|---|---|---|---|---|---|---|
| Ser | Asn | Thr | Thr | Val | Lys | Thr | Gly | Asp | Leu | Val | Thr | Tyr | Asp | Lys | Glu | |
| | | | 20 | | | | | 25 | | | | | 30 | | | |

| aat | ggc | atg | cac | aaa | aaa | gta | ttt | tat | agt | ttt | atc | gat | gat | aaa | aat | 144 |
|---|---|---|---|---|---|---|---|---|---|---|---|---|---|---|---|---|
| Asn | Gly | Met | His | Lys | Lys | Val | Phe | Tyr | Ser | Phe | Ile | Asp | Asp | Lys | Asn | |
| | | 35 | | | | | 40 | | | | | 45 | | | | |

| cac | aat | aaa | aaa | ctg | cta | gtt | att | aga | aca | aaa | ggt | acc | att | gct | ggt | 192 |
|---|---|---|---|---|---|---|---|---|---|---|---|---|---|---|---|---|
| His | Asn | Lys | Lys | Leu | Leu | Val | Ile | Arg | Thr | Lys | Gly | Thr | Ile | Ala | Gly | |
| 50 | | | | | 55 | | | | | 60 | | | | | | |

| caa | tat | aga | gtt | tat | agc | gaa | gaa | ggt | gct | aac | aaa | agt | ggt | tta | gcc | 240 |
|---|---|---|---|---|---|---|---|---|---|---|---|---|---|---|---|---|
| Gln | Tyr | Arg | Val | Tyr | Ser | Glu | Glu | Gly | Ala | Asn | Lys | Ser | Gly | Leu | Ala | |
| 65 | | | | | 70 | | | | | 75 | | | | | | |

| tgg | cct | tca | gcc | ttt | aag | gta | cag | ttg | caa | cta | cct | gat | aat | gaa | gta | 288 |
|---|---|---|---|---|---|---|---|---|---|---|---|---|---|---|---|---|
| Trp | Pro | Ser | Ala | Phe | Lys | Val | Gln | Leu | Gln | Leu | Pro | Asp | Asn | Glu | Val | |
| 80 | | | | 85 | | | | | 90 | | | | | 95 | | |

| gct | caa | ata | tct | gat | tac | tat | cca | aga | aat | tcg | att | gat | aca | aaa | gag | 336 |
|---|---|---|---|---|---|---|---|---|---|---|---|---|---|---|---|---|
| Ala | Gln | Ile | Ser | Asp | Tyr | Tyr | Pro | Arg | Asn | Ser | Ile | Asp | Thr | Lys | Glu | |
| | | | 100 | | | | | 105 | | | | | 110 | | | |

| tat | agg | agt | act | tta | act | tat | gga | ttc | aac | ggt | aat | gtt | act | ggt | gat | 384 |
|---|---|---|---|---|---|---|---|---|---|---|---|---|---|---|---|---|
| Tyr | Arg | Ser | Thr | Leu | Thr | Tyr | Gly | Phe | Asn | Gly | Asn | Val | Thr | Gly | Asp | |
| | | | 115 | | | | | 120 | | | | | 125 | | | |

| gat | aca | gga | aaa | att | ggc | ggc | tgt | att | ggt | gca | caa | gtt | tcg | att | ggt | 432 |
|---|---|---|---|---|---|---|---|---|---|---|---|---|---|---|---|---|
| Asp | Thr | Gly | Lys | Ile | Gly | Gly | Cys | Ile | Gly | Ala | Gln | Val | Ser | Ile | Gly | |
| | | 130 | | | | | 135 | | | | | 140 | | | | |

| cat | aca | ctg | aaa | tat | gtt | caa | cct | gat | ttc | aaa | aca | att | tta | gag | agc | 480 |
|---|---|---|---|---|---|---|---|---|---|---|---|---|---|---|---|---|
| His | Thr | Leu | Lys | Tyr | Val | Gln | Pro | Asp | Phe | Lys | Thr | Ile | Leu | Glu | Ser | |
| 145 | | | | | 150 | | | | | 155 | | | | | | |

| cca | act | gat | aaa | aaa | gta | ggc | tgg | aaa | gtg | ata | ttt | aac | aat | atg | gtg | 528 |
|---|---|---|---|---|---|---|---|---|---|---|---|---|---|---|---|---|
| Pro | Thr | Asp | Lys | Lys | Val | Gly | Trp | Lys | Val | Ile | Phe | Asn | Asn | Met | Val | |
| 160 | | | | 165 | | | | | 170 | | | | | 175 | | |

| aat | caa | aat | tgg | gga | cca | tac | gat | cga | gat | tct | tgg | aac | ccg | gta | tat | 576 |
|---|---|---|---|---|---|---|---|---|---|---|---|---|---|---|---|---|
| Asn | Gln | Asn | Trp | Gly | Pro | Tyr | Asp | Arg | Asp | Ser | Trp | Asn | Pro | Val | Tyr | |
| | | | 180 | | | | | 185 | | | | | 190 | | | |

| ggc | aat | caa | ctt | ttc | atg | aaa | act | aga | aat | ggt | tct | atg | aaa | gca | gca | 624 |
|---|---|---|---|---|---|---|---|---|---|---|---|---|---|---|---|---|
| Gly | Asn | Gln | Leu | Phe | Met | Lys | Thr | Arg | Asn | Gly | Ser | Met | Lys | Ala | Ala | |
| | | | 195 | | | | | 200 | | | | | 205 | | | |

| gat | aac | ttc | ctt | gat | cct | aac | aaa | gca | agt | tct | cta | tta | tct | tca | ggg | 672 |
|---|---|---|---|---|---|---|---|---|---|---|---|---|---|---|---|---|
| Asp | Asn | Phe | Leu | Asp | Pro | Asn | Lys | Ala | Ser | Ser | Leu | Leu | Ser | Ser | Gly | |
| | | 210 | | | | | 215 | | | | | 220 | | | | |

| ttt | tca | cca | gac | ttc | gct | aca | gtt | att | act | atg | gat | aga | aaa | gca | tcc | 720 |
|---|---|---|---|---|---|---|---|---|---|---|---|---|---|---|---|---|
| Phe | Ser | Pro | Asp | Phe | Ala | Thr | Val | Ile | Thr | Met | Asp | Arg | Lys | Ala | Ser | |
| 225 | | | | | 230 | | | | | 235 | | | | | | |

| | | | | | | | | | | | | | | | | |
|---|---|---|---|---|---|---|---|---|---|---|---|---|---|---|---|---|
| aaa | caa | caa | aca | aat | ata | gat | gta | ata | tac | gaa | cga | gtt | cgt | gat | gat | 768 |
| Lys | Gln | Gln | Thr | Asn | Ile | Asp | Val | Ile | Tyr | Glu | Arg | Val | Arg | Asp | Asp | |
| 240 | | | | | 245 | | | | | 250 | | | | | 255 | |

| | | | | | | | | | | | | | | | | |
|---|---|---|---|---|---|---|---|---|---|---|---|---|---|---|---|---|
| tac | caa | ttg | cat | tgg | act | tca | aca | aat | tgg | aaa | ggt | acc | aat | act | aaa | 816 |
| Tyr | Gln | Leu | His | Trp | Thr | Ser | Thr | Asn | Trp | Lys | Gly | Thr | Asn | Thr | Lys | |
| | | | 260 | | | | | 265 | | | | | 270 | | | |

| | | | | | | | | | | | | | | | | |
|---|---|---|---|---|---|---|---|---|---|---|---|---|---|---|---|---|
| gat | aaa | tgg | aca | gat | cgt | tct | tca | gaa | aga | tat | aaa | atc | gat | tgg | gaa | 864 |
| Asp | Lys | Trp | Thr | Asp | Arg | Ser | Ser | Glu | Arg | Tyr | Lys | Ile | Asp | Trp | Glu | |
| | | | 275 | | | | | 280 | | | | | 285 | | | |

| | | | | | | | | | | | | | | | | |
|---|---|---|---|---|---|---|---|---|---|---|---|---|---|---|---|---|
| aaa | gaa | gaa | atg | aca | aat | gat | ggc | tcc | ggt | agc | ggc | tct | ggt | tct | ggc | 912 |
| Lys | Glu | Glu | Met | Thr | Asn | Asp | Gly | Ser | Gly | Ser | Gly | Ser | Gly | Ser | Gly | |
| | | 290 | | | | | 295 | | | | | 300 | | | | |

| | | | | | | | | | | | | | | | | |
|---|---|---|---|---|---|---|---|---|---|---|---|---|---|---|---|---|
| tct | ggt | tcc | ggc | agc | ggt | tcc | gga | cag | agc | acc | ttc | ctg | ttt | cat | gat | 960 |
| Ser | Gly | Ser | Gly | Ser | Gly | Ser | Gly | Gln | Ser | Thr | Phe | Leu | Phe | His | Asp | |
| 305 | | | | | 310 | | | | | 315 | | | | | | |

| | | | | | | | | | | | | | | | | |
|---|---|---|---|---|---|---|---|---|---|---|---|---|---|---|---|---|
| tat | gaa | acc | ttc | ggt | acc | cat | ccg | gcc | ctg | gat | cgt | ccg | gcg | cag | ttt | 1008 |
| Tyr | Glu | Thr | Phe | Gly | Thr | His | Pro | Ala | Leu | Asp | Arg | Pro | Ala | Gln | Phe | |
| 320 | | | | | 325 | | | | | 330 | | | | | 335 | |

| | | | | | | | | | | | | | | | | |
|---|---|---|---|---|---|---|---|---|---|---|---|---|---|---|---|---|
| gcg | gcc | att | cgc | acc | gat | agc | gaa | ttc | aat | gtg | att | ggc | gaa | ccg | gaa | 1056 |
| Ala | Ala | Ile | Arg | Thr | Asp | Ser | Glu | Phe | Asn | Val | Ile | Gly | Glu | Pro | Glu | |
| | | | | 340 | | | | | 345 | | | | | 350 | | |

| | | | | | | | | | | | | | | | | |
|---|---|---|---|---|---|---|---|---|---|---|---|---|---|---|---|---|
| gtg | ttt | tat | tgc | aaa | ccg | gcc | gat | gat | tat | ctg | ccg | cag | ccg | ggt | gcg | 1104 |
| Val | Phe | Tyr | Cys | Lys | Pro | Ala | Asp | Asp | Tyr | Leu | Pro | Gln | Pro | Gly | Ala | |
| | | | 355 | | | | | 360 | | | | | 365 | | | |

| | | | | | | | | | | | | | | | | |
|---|---|---|---|---|---|---|---|---|---|---|---|---|---|---|---|---|
| gtg | ctg | att | acc | ggt | att | acc | ccg | cag | gaa | gcg | cgc | gcg | aaa | ggt | gaa | 1152 |
| Val | Leu | Ile | Thr | Gly | Ile | Thr | Pro | Gln | Glu | Ala | Arg | Ala | Lys | Gly | Glu | |
| | | | 370 | | | | | 375 | | | | | 380 | | | |

| | | | | | | | | | | | | | | | | |
|---|---|---|---|---|---|---|---|---|---|---|---|---|---|---|---|---|
| aac | gaa | gcg | gcg | ttt | gcc | gcg | cgc | att | cat | agc | ctg | ttt | acc | gtg | ccg | 1200 |
| Asn | Glu | Ala | Ala | Phe | Ala | Ala | Arg | Ile | His | Ser | Leu | Phe | Thr | Val | Pro | |
| 385 | | | | | 390 | | | | | 395 | | | | | | |

| | | | | | | | | | | | | | | | | |
|---|---|---|---|---|---|---|---|---|---|---|---|---|---|---|---|---|
| aaa | acc | tgc | att | ctg | ggc | tat | aac | aat | gtg | cgc | ttc | gat | gat | gaa | gtt | 1248 |
| Lys | Thr | Cys | Ile | Leu | Gly | Tyr | Asn | Asn | Val | Arg | Phe | Asp | Asp | Glu | Val | |
| 400 | | | | | 405 | | | | | 410 | | | | | 415 | |

| | | | | | | | | | | | | | | | | |
|---|---|---|---|---|---|---|---|---|---|---|---|---|---|---|---|---|
| acc | cgt | aat | atc | ttt | tat | cgt | aac | ttt | tat | gat | ccg | tat | gcg | tgg | agc | 1296 |
| Thr | Arg | Asn | Ile | Phe | Tyr | Arg | Asn | Phe | Tyr | Asp | Pro | Tyr | Ala | Trp | Ser | |
| | | | | 420 | | | | | 425 | | | | | 430 | | |

| | | | | | | | | | | | | | | | | |
|---|---|---|---|---|---|---|---|---|---|---|---|---|---|---|---|---|
| tgg | cag | cat | gat | aac | agc | cgt | tgg | gat | ctg | ctg | gat | gtg | atg | cgc | gcg | 1344 |
| Trp | Gln | His | Asp | Asn | Ser | Arg | Trp | Asp | Leu | Leu | Asp | Val | Met | Arg | Ala | |
| | | | 435 | | | | | 440 | | | | | 445 | | | |

| | | | | | | | | | | | | | | | | |
|---|---|---|---|---|---|---|---|---|---|---|---|---|---|---|---|---|
| tgc | tat | gcg | ctg | cgc | ccg | gaa | ggc | att | aat | tgg | ccg | gaa | aac | gat | gat | 1392 |
| Cys | Tyr | Ala | Leu | Arg | Pro | Glu | Gly | Ile | Asn | Trp | Pro | Glu | Asn | Asp | Asp | |
| | | 450 | | | | | 455 | | | | | 460 | | | | |

| | | | | | | | | | | | | | | | | |
|---|---|---|---|---|---|---|---|---|---|---|---|---|---|---|---|---|
| ggc | ctg | ccg | agc | ttt | cgt | ctg | gaa | cat | ctg | acc | aaa | gcc | aac | ggc | att | 1440 |
| Gly | Leu | Pro | Ser | Phe | Arg | Leu | Glu | His | Leu | Thr | Lys | Ala | Asn | Gly | Ile | |
| 465 | | | | | 470 | | | | | 475 | | | | | | |

| | | | | | | | | | | | | | | | | |
|---|---|---|---|---|---|---|---|---|---|---|---|---|---|---|---|---|
| gaa | cat | agc | aat | gcc | cat | gat | gcg | atg | gcc | gat | gtt | tat | gcg | acc | att | 1488 |
| Glu | His | Ser | Asn | Ala | His | Asp | Ala | Met | Ala | Asp | Val | Tyr | Ala | Thr | Ile | |
| 480 | | | | | 485 | | | | | 490 | | | | | 495 | |

| | | | | | | | | | | | | | | | | |
|---|---|---|---|---|---|---|---|---|---|---|---|---|---|---|---|---|
| gcg | atg | gcg | aaa | ctg | gtt | aaa | acc | cgt | cag | ccg | cgc | ctg | ttt | gat | tat | 1536 |
| Ala | Met | Ala | Lys | Leu | Val | Lys | Thr | Arg | Gln | Pro | Arg | Leu | Phe | Asp | Tyr | |
| | | | | 500 | | | | | 505 | | | | | 510 | | |

| | | | | | | | | | | | | | | | | |
|---|---|---|---|---|---|---|---|---|---|---|---|---|---|---|---|---|
| ctg | ttt | acc | cac | cgt | aac | aaa | cac | aaa | ctg | atg | gcg | ctg | att | gat | gtt | 1584 |
| Leu | Phe | Thr | His | Arg | Asn | Lys | His | Lys | Leu | Met | Ala | Leu | Ile | Asp | Val | |
| | | | | 515 | | | | | 520 | | | | | 525 | | |

| | | | | | | | | | | | | | | | | |
|---|---|---|---|---|---|---|---|---|---|---|---|---|---|---|---|---|
| ccg | cag | atg | aaa | ccg | ctg | gtg | cat | gtg | agc | ggc | atg | ttt | ggc | gcc | tgg | 1632 |
| Pro | Gln | Met | Lys | Pro | Leu | Val | His | Val | Ser | Gly | Met | Phe | Gly | Ala | Trp | |
| | | 530 | | | | | 535 | | | | | 540 | | | | |

| | | | | | | | | | | | | | | | | |
|---|---|---|---|---|---|---|---|---|---|---|---|---|---|---|---|---|
| cgc | ggc | aac | acc | agc | tgg | gtg | gcc | ccg | ctg | gcc | tgg | cac | ccg | gaa | aat | 1680 |
| Arg | Gly | Asn | Thr | Ser | Trp | Val | Ala | Pro | Leu | Ala | Trp | His | Pro | Glu | Asn | |
| 545 | | | | | 550 | | | | | 555 | | | | | | |

```
cgt aac gcc gtg att atg gtt gat ctg gcc ggt gat att agc ccg ctg      1728
Arg Asn Ala Val Ile Met Val Asp Leu Ala Gly Asp Ile Ser Pro Leu
560                 565                 570                 575 ctg gaa ctg gat agc gat acc ctg cgt gaa cgc ctg tat acc gcc aaa      1776
Leu Glu Leu Asp Ser Asp Thr Leu Arg Glu Arg Leu Tyr Thr Ala Lys
            580                 585                 590 acc gat ctg ggc gat aat gcc gcc gtg ccg gtg aaa ctg gtt cac att      1824
Thr Asp Leu Gly Asp Asn Ala Ala Val Pro Val Lys Leu Val His Ile
        595                 600                 605 aac aaa tgc ccg gtg ctg gcc cag gcg aac acc ctg cgc ccg gaa gat      1872
Asn Lys Cys Pro Val Leu Ala Gln Ala Asn Thr Leu Arg Pro Glu Asp
    610                 615                 620 gcg gat cgt ctg ggt att aat cgc cag cat tgt ctg gat aat ctg aaa      1920
Ala Asp Arg Leu Gly Ile Asn Arg Gln His Cys Leu Asp Asn Leu Lys
625                 630                 635 atc ctg cgt gaa aac ccg cag gtg cgt gaa aaa gtg gtg gcg atc ttc      1968
Ile Leu Arg Glu Asn Pro Gln Val Arg Glu Lys Val Val Ala Ile Phe
640                 645                 650                 655 gcg gaa gcg gaa ccg ttc acc ccg agc gat aac gtg gat gcg cag ctg      2016
Ala Glu Ala Glu Pro Phe Thr Pro Ser Asp Asn Val Asp Ala Gln Leu
                660                 665                 670 tat aac ggc ttc ttt agc gat gcc gat cgc gcg gcg atg aaa atc gtt      2064
Tyr Asn Gly Phe Phe Ser Asp Ala Asp Arg Ala Ala Met Lys Ile Val
            675                 680                 685 ctg gaa acc gaa ccg cgc aat ctg ccg gcg ctg gat att acc ttt gtt      2112
Leu Glu Thr Glu Pro Arg Asn Leu Pro Ala Leu Asp Ile Thr Phe Val
        690                 695                 700 gat aaa cgt att gaa aaa ctg ctg ttt aat tat cgt gcg cgc aat ttt      2160
Asp Lys Arg Ile Glu Lys Leu Leu Phe Asn Tyr Arg Ala Arg Asn Phe
705                 710                 715 ccg ggt acc ctg gat tat gcc gaa cag cag cgt tgg ctg gaa cat cgt      2208
Pro Gly Thr Leu Asp Tyr Ala Glu Gln Gln Arg Trp Leu Glu His Arg
720                 725                 730                 735 cgt cag gtt ttc acc ccg gaa ttt ctg cag ggt tat gcg gat gaa ctg      2256
Arg Gln Val Phe Thr Pro Glu Phe Leu Gln Gly Tyr Ala Asp Glu Leu
                740                 745                 750 cag atg ctg gtt cag cag tat gcc gat gat aaa gaa aaa gtg gcg ctg      2304
Gln Met Leu Val Gln Gln Tyr Ala Asp Asp Lys Glu Lys Val Ala Leu
            755                 760                 765 ctg aaa gcg ctg tgg cag tat gcg gaa gaa atc gtt tct ggc tct ggt      2352
Leu Lys Ala Leu Trp Gln Tyr Ala Glu Glu Ile Val Ser Gly Ser Gly
        770                 775                 780 cac cat cat cat cac cac                                              2370
His His His His His His
    785
```

<210> SEQ ID NO 30
<211> LENGTH: 789
<212> TYPE: PRT
<213> ORGANISM: Artificial sequence
<220> FEATURE:
<223> OTHER INFORMATION: Synthetic Construct

<400> SEQUENCE: 30

```
Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
            20                  25                  30

Gly Met His Lys Lys Val Phe Tyr Ser Phe Ile Asp Asp Lys Asn His
        35                  40                  45
```

```
Asn Lys Lys Leu Leu Val Ile Arg Thr Lys Gly Thr Ile Ala Gly Gln
    50                  55                  60

Tyr Arg Val Tyr Ser Glu Glu Gly Ala Asn Lys Ser Gly Leu Ala Trp
65                  70                  75                  80

Pro Ser Ala Phe Lys Val Gln Leu Gln Leu Pro Asp Asn Glu Val Ala
                85                  90                  95

Gln Ile Ser Asp Tyr Tyr Pro Arg Asn Ser Ile Asp Thr Lys Glu Tyr
                100                 105                 110

Arg Ser Thr Leu Thr Tyr Gly Phe Asn Gly Asn Val Thr Gly Asp Asp
                115                 120                 125

Thr Gly Lys Ile Gly Gly Cys Ile Gly Ala Gln Val Ser Ile Gly His
130                 135                 140

Thr Leu Lys Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
                180                 185                 190

Asn Gln Leu Phe Met Lys Thr Arg Asn Gly Ser Met Lys Ala Ala Asp
                195                 200                 205

Asn Phe Leu Asp Pro Asn Lys Ala Ser Ser Leu Leu Ser Ser Gly Phe
210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Thr Asn Trp Lys Gly Thr Asn Thr Lys Asp
                260                 265                 270

Lys Trp Thr Asp Arg Ser Ser Glu Arg Tyr Lys Ile Asp Trp Glu Lys
                275                 280                 285

Glu Glu Met Thr Asn Asp Gly Ser Gly Ser Gly Ser Gly Ser Gly Ser
                290                 295                 300

Gly Ser Gly Ser Gly Ser Gly Gln Ser Thr Phe Leu Phe His Asp Tyr
305                 310                 315                 320

Glu Thr Phe Gly Thr His Pro Ala Leu Asp Arg Pro Ala Gln Phe Ala
                325                 330                 335

Ala Ile Arg Thr Asp Ser Glu Phe Asn Val Ile Gly Glu Pro Glu Val
                340                 345                 350

Phe Tyr Cys Lys Pro Ala Asp Asp Tyr Leu Pro Gln Pro Gly Ala Val
                355                 360                 365

Leu Ile Thr Gly Ile Thr Pro Gln Glu Ala Arg Ala Lys Gly Glu Asn
370                 375                 380

Glu Ala Ala Phe Ala Ala Arg Ile His Ser Leu Phe Thr Val Pro Lys
385                 390                 395                 400

Thr Cys Ile Leu Gly Tyr Asn Asn Val Arg Phe Asp Asp Glu Val Thr
                405                 410                 415

Arg Asn Ile Phe Tyr Arg Asn Phe Tyr Asp Pro Tyr Ala Trp Ser Trp
                420                 425                 430

Gln His Asp Asn Ser Arg Trp Asp Leu Leu Asp Val Met Arg Ala Cys
                435                 440                 445

Tyr Ala Leu Arg Pro Glu Gly Ile Asn Trp Pro Glu Asn Asp Asp Gly
450                 455                 460
```

Leu Pro Ser Phe Arg Leu Glu His Leu Thr Lys Ala Asn Gly Ile Glu
465                 470                 475                 480

His Ser Asn Ala His Asp Ala Met Ala Asp Val Tyr Ala Thr Ile Ala
                485                 490                 495

Met Ala Lys Leu Val Lys Thr Arg Gln Pro Arg Leu Phe Asp Tyr Leu
            500                 505                 510

Phe Thr His Arg Asn Lys His Lys Leu Met Ala Leu Ile Asp Val Pro
        515                 520                 525

Gln Met Lys Pro Leu Val His Val Ser Gly Met Phe Gly Ala Trp Arg
    530                 535                 540

Gly Asn Thr Ser Trp Val Ala Pro Leu Ala Trp His Pro Glu Asn Arg
545                 550                 555                 560

Asn Ala Val Ile Met Val Asp Leu Ala Gly Asp Ile Ser Pro Leu Leu
                565                 570                 575

Glu Leu Asp Ser Asp Thr Leu Arg Glu Arg Leu Tyr Thr Ala Lys Thr
            580                 585                 590

Asp Leu Gly Asp Asn Ala Ala Val Pro Val Lys Leu Val His Ile Asn
        595                 600                 605

Lys Cys Pro Val Leu Ala Gln Ala Asn Thr Leu Arg Pro Glu Asp Ala
    610                 615                 620

Asp Arg Leu Gly Ile Asn Arg Gln His Cys Leu Asp Asn Leu Lys Ile
625                 630                 635                 640

Leu Arg Glu Asn Pro Gln Val Arg Glu Lys Val Val Ala Ile Phe Ala
                645                 650                 655

Glu Ala Glu Pro Phe Thr Pro Ser Asp Asn Val Asp Ala Gln Leu Tyr
            660                 665                 670

Asn Gly Phe Phe Ser Asp Ala Asp Arg Ala Ala Met Lys Ile Val Leu
        675                 680                 685

Glu Thr Glu Pro Arg Asn Leu Pro Ala Leu Asp Ile Thr Phe Val Asp
    690                 695                 700

Lys Arg Ile Glu Lys Leu Leu Phe Asn Tyr Arg Ala Arg Asn Phe Pro
705                 710                 715                 720

Gly Thr Leu Asp Tyr Ala Glu Gln Arg Trp Leu Glu His Arg Arg
                725                 730                 735

Gln Val Phe Thr Pro Glu Phe Leu Gln Gly Tyr Ala Asp Glu Leu Gln
            740                 745                 750

Met Leu Val Gln Gln Tyr Ala Asp Asp Lys Glu Lys Val Ala Leu Leu
        755                 760                 765

Lys Ala Leu Trp Gln Tyr Ala Glu Glu Ile Val Ser Gly Ser Gly His
    770                 775                 780

His His His His His
785

<210> SEQ ID NO 31
<211> LENGTH: 50
<212> TYPE: DNA
<213> ORGANISM: Artificial sequence
<220> FEATURE:
<223> OTHER INFORMATION: DNA oligonucleotide for exonuclease assay

<400> SEQUENCE: 31
gcaacagagc tgatggatca aatgcattag gtaaacatgt tacgtcgtaa            50

```
<210> SEQ ID NO 32
<211> LENGTH: 55
<212> TYPE: DNA
<213> ORGANISM: Artificial sequence
<220> FEATURE:
<223> OTHER INFORMATION: DNA oligonucleotide for exonuclease assay

<400> SEQUENCE: 32
cgatcttacg acgtaacatg tttacctaat gcatttgatc catcagctct gttgc          55

<210> SEQ ID NO 33
<211> LENGTH: 12
<212> TYPE: DNA
<213> ORGANISM: Artificial Sequence
<220> FEATURE:
<223> OTHER INFORMATION: Synthetic polynucleotide

<400> SEQUENCE: 33
ttgcaacaga gc                                                         12
```